United States Patent
Wang et al.

(10) Patent No.: US 10,494,364 B2
(45) Date of Patent: Dec. 3, 2019

(54) CATHEPSIN K INHIBITORS AND APPLICATION THEREOF

(71) Applicant: SUNSHINE LAKE PHARMA CO., LTD., Dongguan, Guangdong (CN)

(72) Inventors: Xiaojun Wang, Dongguan (CN); Pingjian Zhou, Dongguan (CN); Chuanwen Yang, Dongguan (CN); Changwei Huang, Dongguan (CN); Shaohui Xiong, Dongguan (CN); Yingjun Zhang, Dongguan (CN); Jiancun Zhang, Dongguan (CN)

(73) Assignees: SUNSHIN LAKE PHARMA CO., LTD, Dongguan, Guangdong (CN); NORTH & SOUTH BROTHER PHARMACY INVESTMENT COMPANY LIMITED, Wanchai (HK)

( * ) Notice: Subject to any disclaimer, the term of this patent is extended or adjusted under 35 U.S.C. 154(b) by 0 days.

(21) Appl. No.: 15/751,163

(22) PCT Filed: Aug. 26, 2016

(86) PCT No.: PCT/CN2016/096882
§ 371 (c)(1),
(2) Date: Feb. 7, 2018

(87) PCT Pub. No.: WO2017/036357
PCT Pub. Date: Mar. 9, 2017

(65) Prior Publication Data
US 2018/0230138 A1 Aug. 16, 2018

(30) Foreign Application Priority Data
Aug. 29, 2015 (CN) .......................... 2015 1 0548889

(51) Int. Cl.

| | | |
|---|---|---|
| C07D 407/10 | (2006.01) |
| A61K 31/343 | (2006.01) |
| A61K 31/351 | (2006.01) |
| A61K 31/357 | (2006.01) |
| A61K 31/36 | (2006.01) |
| A61K 31/38 | (2006.01) |
| A61K 31/381 | (2006.01) |
| A61K 31/382 | (2006.01) |
| A61K 31/39 | (2006.01) |
| A61K 31/397 | (2006.01) |
| A61K 31/41 | (2006.01) |
| A61K 31/4178 | (2006.01) |
| A61K 31/4192 | (2006.01) |
| A61K 31/4196 | (2006.01) |
| A61K 31/422 | (2006.01) |
| A61K 31/423 | (2006.01) |

(Continued)

(52) U.S. Cl.
CPC .......... *C07D 407/10* (2013.01); *A61K 31/343* (2013.01); *A61K 31/351* (2013.01); *A61K 31/357* (2013.01); *A61K 31/36* (2013.01); *A61K 31/38* (2013.01); *A61K 31/381* (2013.01); *A61K 31/382* (2013.01); *A61K 31/39* (2013.01); *A61K 31/397* (2013.01); *A61K 31/41* (2013.01); *A61K 31/4178* (2013.01); *A61K 31/4192* (2013.01); *A61K 31/4196* (2013.01); *A61K 31/422* (2013.01); *A61K 31/423* (2013.01); *A61K 31/427* (2013.01); *A61K 31/4245* (2013.01); *A61K 31/437* (2013.01); *A61K 31/4355* (2013.01); *A61K 31/443* (2013.01); *A61K 31/5377* (2013.01); *A61K 31/541* (2013.01); *A61K 45/06* (2013.01); *C07D 307/85* (2013.01); *C07D 405/10* (2013.01); *C07D 407/12* (2013.01); *C07D 407/14* (2013.01); *C07D 409/10* (2013.01); *C07D 411/10* (2013.01); *C07D 413/10* (2013.01); *C07D 413/14* (2013.01); *C07D 417/10* (2013.01); *C07D 417/14* (2013.01); *C07D 471/04* (2013.01); *C07D 493/04* (2013.01)

(58) Field of Classification Search
None
See application file for complete search history.

(56) References Cited

U.S. PATENT DOCUMENTS

| | | |
|---|---|---|
| 6,353,017 B1 | 3/2002 | Altmann et al. |
| 7,012,075 B2 | 3/2006 | Prasit et al. |

(Continued)

OTHER PUBLICATIONS

Wu et al., Toxicology, 236, pp. 1-6, (Year: 2007).*
International Search Report of PCT/CN2016/096882 (2016).
Written Opinion of PCT/CN2016/096882 (2016).

*Primary Examiner* — Zinna Northington Davis
(74) *Attorney, Agent, or Firm* — Kam Wah Law

(57) ABSTRACT

The invention relates to capthepsin K inhibitors and uses thereof, specifically relates to a class of compounds having the formula (I) which are used for treating or preventing cathepsin dependent diseases or conditions, specifically, wherein the cathepsin is capthepsin K. The compounds and compositions thereof can be used as bone resorption inhibitors for the treatment of associated diseases.

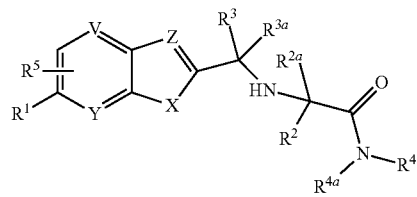

Formula (I)

12 Claims, No Drawings

(51) Int. Cl.
*A61K 31/4245* (2006.01)
*A61K 31/427* (2006.01)
*A61K 31/4355* (2006.01)
*A61K 31/437* (2006.01)
*A61K 31/443* (2006.01)
*A61K 31/5377* (2006.01)
*A61K 31/541* (2006.01)
*A61K 45/06* (2006.01)
*C07D 307/85* (2006.01)
*C07D 405/10* (2006.01)
*C07D 407/12* (2006.01)
*C07D 407/14* (2006.01)
*C07D 409/10* (2006.01)
*C07D 411/10* (2006.01)
*C07D 413/10* (2006.01)
*C07D 413/14* (2006.01)
*C07D 417/10* (2006.01)
*C07D 417/14* (2006.01)
*C07D 471/04* (2006.01)
*C07D 493/04* (2006.01)

(56) References Cited

U.S. PATENT DOCUMENTS

| | | |
|---|---|---|
| 7,312,353 B2 | 12/2007 | Gauthier et al. |
| 7,375,134 B2 | 5/2008 | Bayly et al. |
| 7,547,701 B2 | 6/2009 | Link et al. |
| 7,737,166 B2 * | 6/2010 | Kawakami ............ C07D 263/56 514/210.21 |
| 7,737,300 B2 | 6/2010 | Li |
| 7,973,037 B2 | 7/2011 | Bayly et al. |
| 8,318,748 B2 | 11/2012 | Bayly et al. |
| 8,772,336 B2 | 7/2014 | Bayly et al. |
| 2003/0232863 A1 | 12/2003 | Bayly |
| 2004/0029814 A1 | 2/2004 | Altmann |
| 2004/0110806 A1 | 6/2004 | Altmann |
| 2006/0235220 A1 | 10/2006 | Missbach |
| 2007/0088001 A1 | 4/2007 | Link |
| 2008/0027060 A1 | 1/2008 | Altmann |
| 2009/0005323 A1 | 1/2009 | Percival |
| 2014/0256743 A1 | 9/2014 | Bayly et al. |

* cited by examiner

CATHEPSIN K INHIBITORS AND APPLICATION THEREOF

CROSS-REFERENCE TO RELATED APPLICATIONS

This is a U.S. national stage application of the International Patent Application No. PCT/CN2016/096882, filed Aug. 26, 2016, which claims priority to Chinese Patent Application No. 201510548889.1, filed Aug. 29, 2015, both of which are incorporated herein by reference in their entirety.

FIELD OF THE INVENTION

The present invention pertains to the field of pharmacy. The present invention relates to a class of compounds used for treating or preventing cathepsin dependent diseases or conditions, including but not limited to capthepsin K inhibitors. These compounds and compositions thereof can be used as medicaments which are bone-resorption inhibitors for treating relevant disorders.

BACKGROUND

Osteoporosis is a common disease and frequently-occurring disease in old people, especially in women during or after menopause. With the change of the contemporary disease, WHO lists osteoporosis as one of the three diseases which happens in middle aged and elderly people, ranking NO.7 in the common diseases. About 50% of women over the age of 50 and 20% of men suffer fractures caused by osteoporosis. The current common drug for the treatment of osteoporosis are drugs of anti-bone resorption, drugs of promoting bone formation, drugs having the dual role of the former two drugs, biological drugs, or other drugs, but most of them have side effects, and new drugs for treatment are in urgent need.

Cathepsin is a principal member of the cysteine proteases family, more than 20 species of which have been found in the biosphere, and 11 species mainly exist in human body, which closely associates with many kinds of major diseases such as human tumor, osteoporosis, arthritis, and so on. The subtype of cathepsin consists of cathepsin B, F, H, L, K, S, W and Z. Cathepsin S mainly expresses in antigen-presenting cell, which is an important target for regulating immune reaction because of regulating antigen-presenting. Cathepsin L participates in many special physiological processes, such as activation of prohomone, antigen-presentation, development of tissues and organs, etc. Cathepsin B distributes in liver, spleen, kidney, bone, nerve cells, interstitial fibroblasts, macrophages, etc, and stores in the form of zymogen in lysosome, which participates in many special physiological processes, such as activation of prohomone, antigen-presentation, development of tissues and organs, etc.

Cathepsin K (cat K) has been variously denoted as cathepsin O and cathepsin O2. Cathepsin K selectively expresses in osteoclast in great quantities, its substrate in physiological action is type I collagen of up to 95% content in organic matrix of bone. In addition, cathepsin K can degrade the osteopontin and osteoneckin of bone matrix, which is a cysteine protease that has highest expression and strongest osteolytic activity in osteoclast. The ability of degration to osteogenesis collagen for cathepsin K is more higher than any other enzymes, and athepsin K is a key enzyme in the process of bone resorption, which is also a hot point in the osteoporosis research in recent years. In the present, the FDA has not approved any anti-cathepsin K inhibitor, but some related organization protease inhibitors are in clinical studies.

Merck's odanacatib is in faster research progress, but because of some troubling signs of side effects in clinical studies, it is still in the clinical stage. The effect of cathepsin K is very important and very complicated on physiological processes in body. In order to avoid a broad-spectrum inhibition causing other than clinical side effects, the design and synthesis of efficient selective inhibitors is extremely urgent.

SUMMARY OF THE INVENTION

The invention relates to a class of compounds or pharmaceutical compositions thereof used for treating or preventing cathepsin dependence conditions or diseases. The compounds of the invention have good inhibitory activity against cathepsin K, and the $IC_{50}$ values are in the level of nanomole, while the $IC_{50}$ values of compounds against other sub-type cathepsin such as B, L and S are in the level of micromole. The compounds have high selectivity on cathepsin K. Cathepsin K is a hot target in the osteoporosis research in recent years, which is a key enzyme in the process of bone resorption. Because of the exist of various subtype of cathepsin, especially cathepsin B, L and S having high homology with cathepsin K and playing an important physiological role in body, cathepsin K inhibitor in the human body is easy to cause off-target effect and serious side effects, and thus developing selective cathepsin K inhibitors is a challenge. The compounds of the invention have good inhibitory activity against cathepsin K, and also have higher selectivity on cathepsin B, L and S, reduce the off-target side effect which results from the selectivity of the compounds, and increase the ability of developing cathepsin K inhibitor as medicaments for treating osteoporosis.

The invention provides a class of high selective cathepsin K inhibitors, which have Formula (I) or a stereoisomer, a tautomer, a geometric isomer, an N-oxide, a prodrug or a pharmaceutically acceptable salt thereof, Formula (I)

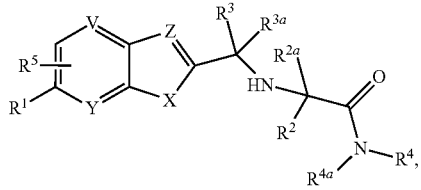

wherein, $R^{4a}$ is H, $C_{1-6}$ alkyl or $C_{2-6}$ alkenyl, wherein each of the $C_{1-6}$ alkyl and $C_{2-6}$ alkenyl is optionally and independently substituted with 1, 2, 3, 4, 5 or 6 substituents selected from halogen, $C_{3-6}$ cycloalkyl, cyano, $C_{6-10}$ aryl, $C_{1-9}$ heteroaryl or $C_{2-9}$ heterocyclyl;

$R^4$ is $C_{1-6}$ alkyl, —C($R^7$)($R^{7a}$)—$R^8$, $C_{3-9}$ heterocyclyl or $C_{2-6}$ alkenyl, wherein each of the $C_{1-6}$ alkyl and $C_{2-6}$ alkenyl is independently and optionally substituted with 1, 2, 3, 4, 5 or 6 substituents selected from halogen, $C_{3-6}$ cycloalkyl, cyano, $C_{6-10}$ aryl, $C_{1-9}$ heteroaryl and $C_{3-9}$ heterocyclyl;

or, $R^4$ and $R^{4a}$, together with the nitrogen atom to which they are attached, form a $C_{3-9}$ heterocyclyl group containing nitrogen, wherein the $C_{3-9}$ heterocyclyl is optionally substituted with 1, 2, 3, 4 or 5 substituents selected from $C_{1-6}$ alkyl, $C_{1-6}$ hydroxyalkyl, cyano, —$C(R^{10})(R^{10a})$—C(=O)—$N(R^{12})(R^{12a})$, —C(=O)—$OR^{8a}$, oxo (=O), $C_{1-6}$ haloalkyl and halogen:

each of $R^7$ and $R^{7a}$ is independently H, $C_{1-6}$ alkyl, —$C(R^{10})(R^{10a})$—C(=O)—$N(R^{12})(R^{12a})$, —C(=O)—$OR^{8a}$, $C_{2-9}$ heterocyclyl or $C_{2-6}$ alkenyl;

or, $R^7$ and $R^{7a}$, together with the carbon atom to which they are attached, form a $C_{3-6}$ carbocyclic ring or $C_{2-6}$ heterocyclic ring, wherein each of the $C_{3-6}$ carbocyclic ring and $C_{2-6}$ heterocyclic ring is independently and optionally substituted with 1, 2, 3, 4, 5 or 6 substituents selected from $C_{1-6}$ alkyl, $C_{1-6}$ hydroxyalkyl, $C_{1-6}$ haloalkyl, oxo (=O), cyano, —C(=O)—$OR^{8a}$ and halogen;

$R^8$ is H, $C_{1-6}$ alkyl, cyano, —$N(R^{12})(R^{12a})$, —C(=O)—C(=O)—$N(R^{12})(R^{12a})$, —C(=O)—$N(R^{12})(R^{12a})$, —C(=O)—$OR^{8a}$, $C_{3-6}$ heterocyclyl or $C_{2-6}$ alkenyl;

each $R^6$, $R^{6a}$, $R^3$, $R^{3a}$, $R^2$, $R^{2a}$, $R^{8a}$, $R^{10}$, $R^{10a}$, $R^{12}$ and $R^{12a}$ is independently H or $C_{1-6}$ alkyl, wherein the $C_{1-6}$ alkyl is optionally substituted with 1, 2, 3, 4, 5 or 6 substituents selected from halogen, hydroxy, amino, carboxy, cyano, $C_{3-6}$ cycloalkyl, $C_{6-10}$ aryl, $C_{1-9}$ heteroaryl and $C_{2-9}$ heterocyclyl;

or, $R^2$ and $R^{2a}$, together with the carbon atom to which they are attached, form a $C_{3-9}$ carbocyclic ring or $C_{2-9}$ heterocyclic ring, wherein each of the $C_{3-9}$ carbocyclic ring and $C_{2-9}$ heterocyclic ring is independently and optionally substituted with 1, 2, 3, 4, 5 or 6 substituents selected from $C_{1-6}$ alkyl, $C_{2-6}$ alkenyl, $C_{1-6}$ hydroxyalkyl, $C_{1-6}$ haloalkyl, hydroxy, amino, carboxy, cyano and halogen;

or, $R^3$ and $R^{3a}$, together with the carbon atom to which they are attached, form a >C(=O), $C_{3-9}$ carbocyclic ring or $C_{2-9}$ heterocyclic ring, wherein each of the $C_{3-9}$ carbocyclic ring and $C_{2-9}$ heterocyclic ring is independently and optionally substituted with 1, 2, 3, 4, 5 or 6 substituents selected from $C_{1-6}$ alkyl, $C_{2-6}$ alkenyl, $C_{1-6}$ hydroxyalkyl, $C_{1-6}$ haloalkyl, hydroxy, amino, carboxy, cyano and halogen;

X is —O—, —S—, or —NH—;

each of V, Z and Y is independently $C(R^9)$ or N;

each $R^9$ is independently H, halogen, cyano, hydroxy, $C_{1-4}$ alkoxy, —$N(R^6)(R^{6a})$, $C_{1-4}$ haloalkyl or $C_{1-4}$ alkyl, wherein each of the $C_{1-4}$ alkyl is optionally substituted with 1, 2, 3, 4, 5 or 6 substituents selected from halogen, $C_{3-6}$ cycloalkyl, $C_{6-10}$ aryl, $C_{1-9}$ heteroaryl and $C_{2-9}$ heterocyclyl;

$R^5$ is H, $C_{1-4}$ alkyl, $C_{2-6}$ alkenyl, $C_{2-6}$ alkynyl, $C_{1-6}$ alkoxy, F, Cl, Br, nitro, cyano, —$N(R^6)(R^{6a})$ or $C_{1-4}$ haloalkyl;

$R^1$ is $C_{6-10}$ aryl, $C_{1-9}$ heteroaryl, $C_{3-12}$ cycloalkyl or $C_{2-12}$ heterocyclyl, wherein each of the $R^1$ is independently and optionally substituted with 1, 2, 3, 4 or 5 $R^{1a}$ which are the same or different;

each $R^{1a}$ is independently H, $C_{1-6}$ alkyl, $C_{1-6}$ haloalkyl, halogen, cyano, oxo (=O), $C_{1-6}$ alkoxy, $C_{6-10}$ aryl, $C_{1-9}$ heteroaryl, $C_{3-12}$ cycloalkyl, $C_{2-12}$ heterocyclyl, —$SR^{14}$, —$OR^{14}$, —$SO_2$—$N(R^{13})(R^{13a})$, —$N(R^{13a})$—$SO_2$—$R^{14}$, —$N(R^{13})(R^{13a})$, —C(=O)—C(=O)—$N(R^{13})(R^{13a})$, —C(=O)—$N(R^{13})(R^{13a})$, —C(=N—OH)$(R^{14a})$, —$N(R^{13})$—C(=O)$R^{14a}$, —C(=O)—$OR^{14}$, —C(=O)—$R^{14a}$ or —$SO_2R^{14}$, wherein each of the $R^{1a}$ is independently and optionally substituted with 1, 2, 3, 4 or 5 $R^{1b}$ which are the same or different;

each $R^{1b}$ is independently H, $C_{1-6}$ alkyl, $C_{1-6}$ haloalkyl, $C_{2-6}$ alkenyl, $C_{2-6}$ alkynyl, $C_{1-6}$ alkoxy, halogen, nitro, cyano, hydroxy, oxo (=O), —$OR^{15}$, —$SO_2R^{15}$, —$N(R^{16})(R^{16a})$, —C(=O)—$N(R^{16})(R^{16a})$, $C_{6-10}$ aryl, $C_{1-9}$ heteroaryl, $C_{3-12}$ cycloalkyl or $C_{2-12}$ heterocyclyl, wherein each of the $R^{1b}$ is independently and optionally substituted with 1, 2, 3, 4 or 5 substituents selected from hydroxy, nitro, cyano, $C_{1-6}$ alkyl, $C_{1-6}$ haloalkyl, halogen, oxo (=O), $C_{1-6}$ alkoxy, $C_{6-10}$ aryl, $C_{1-9}$ heteroaryl, $C_{3-12}$ cycloalkyl, $C_{2-12}$ heterocyclyl and amino;

each $R^{16}$ and $R^{16a}$ is independently H, $C_{1-4}$ alkyl, $C_{2-6}$ alkenyl, $C_{2-6}$ alkynyl, $C_{6-10}$ aryl, $C_{1-9}$ heteroaryl, $C_{3-6}$ cycloalkyl, —$SO_2R^{17}$, —$N(R^{18})(R^{18a})$, $C_{1-4}$ haloalkyl or $C_{2-9}$ heterocyclyl;

each $R^{15}$, $R^{13}$, $R^{13a}$, $R^{14}$, $R^{14a}$, $R^{17}$, $R^{18}$ and $R^{18a}$ is independently H, $C_{1-4}$ alkyl, $C_{1-4}$ haloalkyl, $C_{2-6}$ alkenyl, $C_{2-6}$ alkynyl, phenyl, 5- to 6-membered heteroaryl, $C_{3-6}$ cycloalkyl or 4- to 7-membered heterocyclyl, wherein each of the phenyl, 5- to 6-membered heteroaryl, $C_{3-6}$ cycloalkyl and 4- to 7-membered heterocyclyl is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, $R^{4a}$ is H, methyl, ethyl, n-propyl, or isopropyl:

$R^4$ is methyl, ethyl, n-propyl, isopropyl, —$C(R^7)(R^{7a})$—$R^8$, 5- to 6-membered heterocyclyl or vinyl, wherein each of the methyl, ethyl, n-propyl, isopropyl and vinyl is optionally substituted with 1, 2, 3, 4 or 5 substituents independently selected from halogen, $C_{3-6}$ cycloalkyl and cyano;

or, $R^4$ and $R^{4a}$, together with the nitrogen atom to which they are attached, form one of the following sub-formulae:

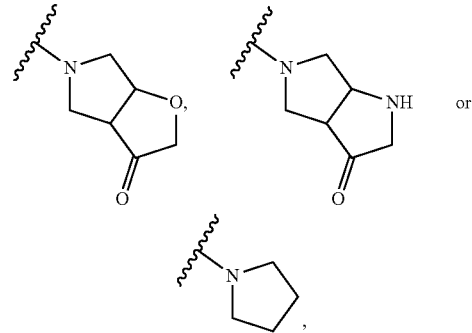

wherein each sub-formula is independently and optionally substituted with 1, 2, 3, 4 or 5 substituents selected from $C_{1-4}$ alkyl, $C_{1-4}$ hydroxyalkyl, oxo (=O), cyano, —$C(R^{10})(R^{10a})$—C(=O)—$N(R^{12})(R^{12a})$, —C(=O)—$OR^{8a}$, $C_{1-4}$ haloalkyl and halogen;

each of $R^7$ and $R^{7a}$ is independently H, $C_{1-4}$ alkyl, —$C(R^{10})(R^{10a})$—C(=O)—$N(R^{12})(R^{12a})$, —C(=O)—$OR^{8a}$, $C_{2-6}$ heterocyclyl or $C_{2-6}$ alkenyl:

or, $R^7$ and $R^{7a}$, together with the carbon atom to which they are attached, form a cyclopropyl, cyclopentyl, cyclobutyl, cyclohexyl, morpholinyl, piperidyl or pyrrolyl group, wherein each of the cyclopropyl, cyclopentyl, cyclobutyl, cyclohexyl, morpholinyl, piperidyl and pyrrolyl is independently and optionally substituted with 1, 2, 3, 4 or 5 substituents selected from $C_{1-4}$ alkyl, $C_{1-4}$ hydroxyalkyl, $C_{1-4}$ haloalkyl, oxo (=O), cyano, —C(=O)—$OR^{8a}$ and halogen;

$R^8$ is H, $C_{1-4}$alkyl, cyano, —$N(R^{12})(R^{12a})$, —C(=O)—C(=O)—$N(R^{12})(R^{12a})$, —C(=O)—$N(R^{12})(R^{12a})$, —C(=O)—$OR^{8a}$, $C_{3-6}$ heterocyclyl or $C_{2-6}$ alkenyl:

wherein $R^{8a}$, $R^{10}$, $R^{10a}$, $R^{12}$ and $R^{12a}$ are as defined herein.

In some embodiments, each $R^6$, $R^{6a}$, $R^3$, $R^{3a}$, $R^2$, $R^{2a}$, $R^{8a}$, $R^{10}$, $R^{10a}$, $R^{12}$ and $R^{12a}$ is independently H, methyl, ethyl, n-propyl, isopropyl, 1-methylpropyl, 2-methylpropyl or tert-butyl, wherein each of the methyl, ethyl, n-propyl, isopropyl, 1-methylpropyl, 2-methylpropyl and tert-butyl is independently and optionally substituted with 1, 2, 3, 4, 5 or 6 substituents selected from F, Cl, Br, hydroxy, amino, carboxy, cyano, cyclohexyl, cyclopentyl, cyclobutyl, cyclopropyl, phenyl, pyridyl, thiazolyl, diazolyl, triazolyl, piperidyl, furyl, tetrahydrofuryl, azetanyl, oxetanyl and morpholinyl;

or, $R^2$ and $R^{2a}$, together with the carbon atom to which they are attached, form a cyclohexyl, cyclopentyl, cyclobutyl, cyclopropyl, cycloheptyl, piperidyl, pyrrolidyl, piperazinyl, tetrahydropyranyl, morpholinyl or tetrahydrofuryl group, wherein each of the cyclohexyl, cyclopentyl, cyclobutyl, cyclopropyl, cycloheptyl, piperidyl, pyrrolidyl, piperazinyl, tetrahydropyranyl, morpholinyl and tetrahydrofuryl is independently and optionally substituted with 1, 2, 3, 4 or 5 substituents selected from $C_{1-4}$ alkyl, $C_{1-4}$ alkenyl, $C_{1-4}$ hydroxyalkyl, $C_{1-4}$ haloalkyl, hydroxy, amino, carboxy, cyano, F, Cl and Br;

or, $R^3$ and $R^{3a}$, together with the carbon atom to which they are attached, form a >C(=O), cyclohexyl, cyclopentyl, cyclobutyl, cyclopropyl, cycloheptyl, piperidyl, pyrrolidyl, piperazinyl, tetrahydropyranyl, morpholinyl or tetrahydrofuryl group, wherein each of the cyclohexyl, cyclopentyl, cyclobutyl, cyclopropyl, cycloheptyl, piperidyl, pyrrolidyl, piperazinyl, tetrahydropyranyl, morpholinyl and tetrahydrofuryl is independently and optionally substituted with 1, 2, 3, 4 or 5 substituents selected from $C_{1-4}$ alkyl, $C_{1-4}$ hydroxyalkyl, $C_{1-4}$ haloalkyl, hydroxy, amino, carboxy, cyano and halogen.

In some embodiments, $R^1$ is one of the following sub-formulae:

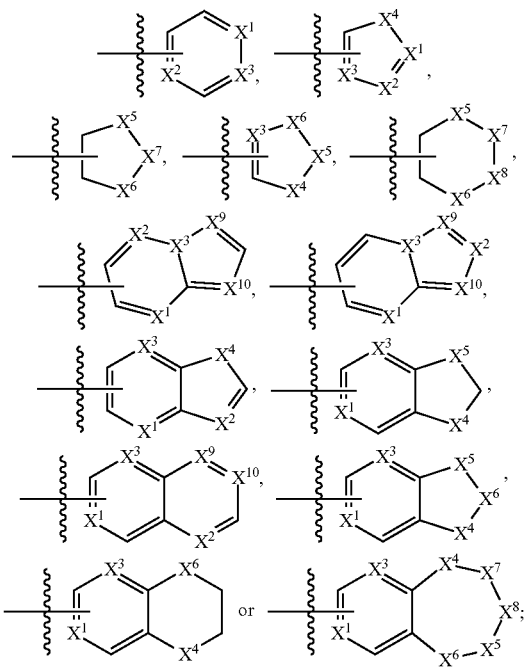

wherein, each $X^1$, $X^2$, $X^3$, $X^9$ and $X^{10}$ is independently CH or N;

each $X^4$, $X^5$, $X^6$, $X^7$ and $X^8$ is independently —CH$_2$—, —C(O)-, —O—, —S—, —S(O)—, —S(O)$_2$— or —NH—;

$R^1$ is independently and optionally substituted with 1, 2, 3, 4 or 5 $R^{1a}$ which are the same or different;

each $R^{1a}$ is independently H, $C_{1-4}$ alkyl, $C_{1-4}$ haloalkyl, halogen, cyano oxo (=O), $C_{1-4}$ alkoxy, —SR$^{14}$, —OR$^{14}$, —SO$_2$—N(R$^{13}$)(R$^{13a}$), —N(R$^{13a}$)—SO$_2$—R$^{14}$, —N(R$^{13}$)(R$^{13a}$), —C(=O)—C(=O)—N(R$^{13}$)(R$^{13a}$), —C(=N—OH)(R$^{14a}$), —C(=O)—N(R$^{13}$)(R$^{13a}$), —N(R$^{13}$)—C(=O)R$^{14a}$, —C(=O)—OR$^{14}$, —C(=O)—R$^{14a}$ or —SO$_2$R$^{14}$, or one of the following sub-formulae:

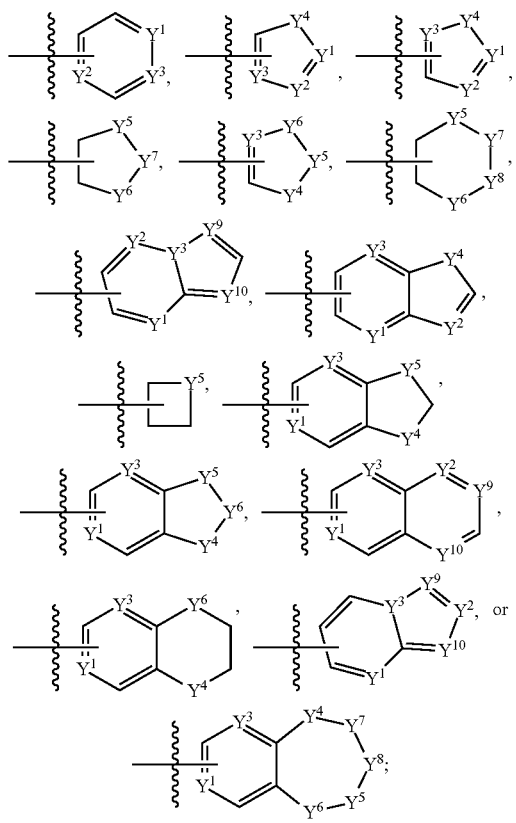

wherein, each $Y^1$, $Y^2$, $Y^3$, $Y^9$ and $Y^{10}$ is independently CH or N;

each $Y^4$, $Y^5$, $Y^6$, $Y^7$ and $Y^8$ is independently —CH$_2$—, —C(=O)—, —O—, —S—, —S(=O)—, —S(=O)$_2$— or —NH—;

each $R^{1a}$ in independently and optionally substituted with 1, 2, 3, 4 or 5 $R^{1b}$ which are the same or different:

each $R^{1b}$ is independently H, $C_{1-4}$ alkyl, $C_{1-4}$ haloalkyl, $C_{2-6}$ alkenyl, $C_{2-6}$ alkynyl, $C_{1-4}$ alkoxy, halogen, nitro, cyano, hydroxy, oxo (=O), —OR$^{15}$, —SO$_2$R$^{15}$, —N(R$^{16}$)(R$^{16a}$), —C(=O)—N(R$^{16}$)(R$^{16a}$), or one of the following sub-formulae:

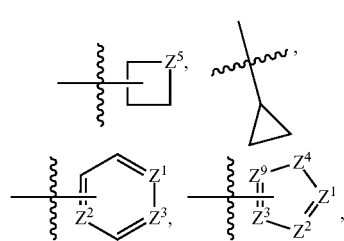

-continued

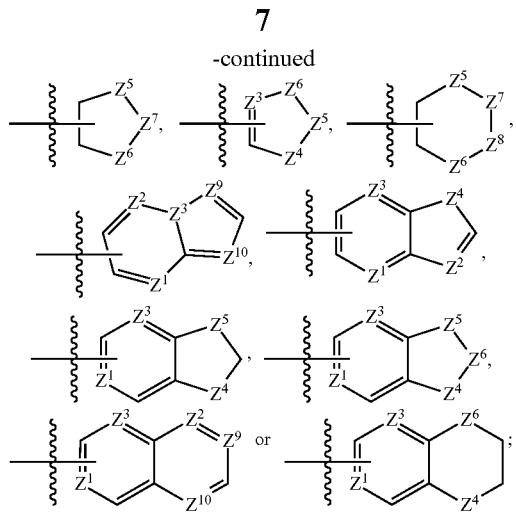

wherein, each $Z^1$, $Z^2$, $Z^3$, $Z^9$ and $Z^{10}$ is independently CH or N;

each $Z^1$, $Z^5$, $Z^6$, $Z^7$ and $Z^8$ is independently —$CH_2$—, —C(=O)—, —O—, —S—, —S(=O)—, —S(=O)$_2$— or —NH—;

each $R^{1b}$ is independently and optionally substituted with 1, 2, 3, 4 or 5 substituents selected from hydroxy, nitro, cyano, $C_{1-4}$ alkyl, $C_{1-4}$ haloalkyl, halogen, oxo (=O), $C_{1-4}$ alkoxy, phenyl, 5- to 6-membered heteroaryl, 4- to 7-membered cycloalkyl, 4- to 7-membered heterocyclyl and amino;

each $R^{16}$ and $R^{16a}$ is independently H, $C_{1-4}$ alkyl, $C_{2-6}$ alkenyl, $C_{2-6}$ alkynyl, $C_{6-10}$ aryl, $C_{1-9}$ heteroaryl, $C_{3-6}$ cycloalkyl, —$SO_2R^{17}$, —$N(R^{18})(R^{18a})$, $C_{1-4}$ haloalkyl or $C_{2-6}$ heterocyclyl;

each $R^{15}$, $R^{13}$, $R^{13a}$, $R^{14}$, $R^{14a}$, $R^{17}$, $R^{18}$ and $R^{18a}$ is independently H, $C_{1-4}$ alkyl, $C_{1-4}$ haloalkyl, $C_{2-6}$ alkenyl, $C_{2-6}$ alkynyl, phenyl, 5- to 6-membered heteroaryl, $C_{3-6}$ cycloalkyl or 4- to 6-membered heterocyclyl, wherein each of the phenyl, 5- to 6-membered heteroaryl, $C_{3-6}$ cycloalkyl and 4- to 6-membered heterocyclyl is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, $R^1$ is one of the following sub-formulae:

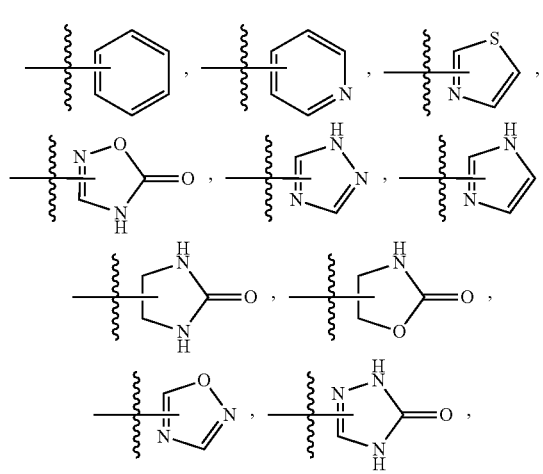

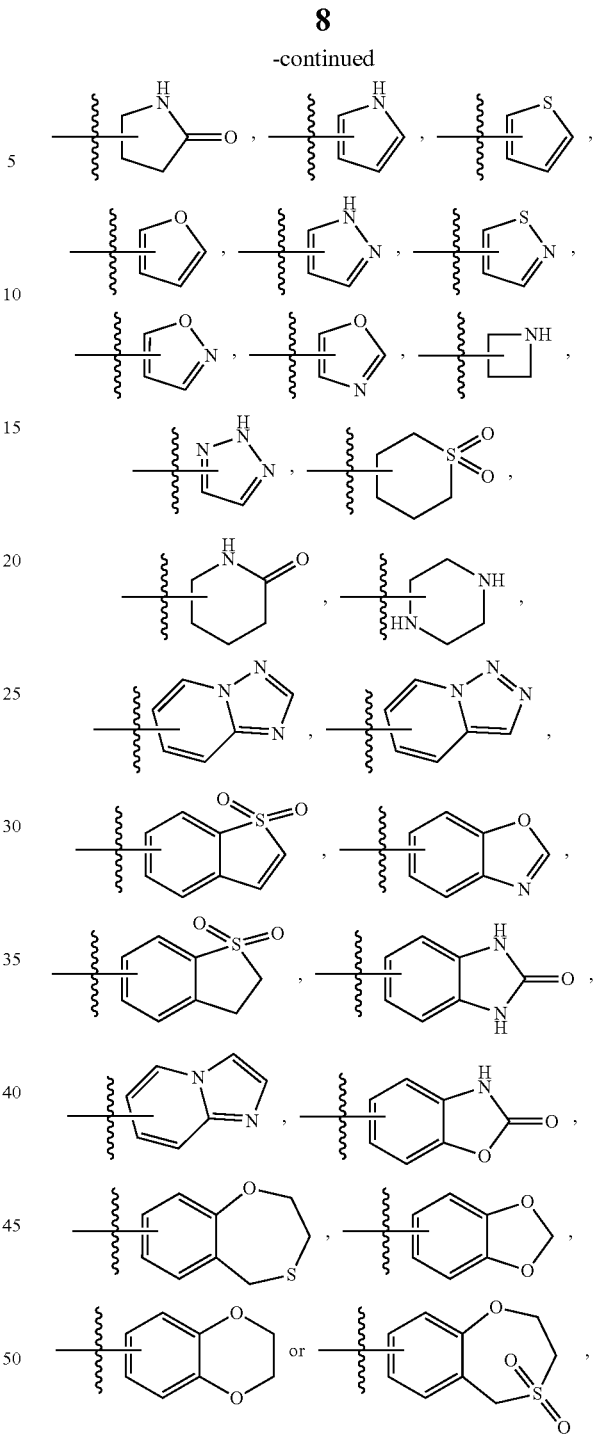

wherein each $R^1$ is independently and optionally substituted with 1, 2, 3, 4 or 5 $R^{1a}$ which are the same or different;

each $R^{1a}$ is independently H, ethyl, methyl, n-propyl, i-propyl, n-butyl, t-butyl, cyano, trifluoromethyl, 2,2-difluoroethyl, 3,3,3-trifluoropropyl, F, Cl, Br, oxo (=O), methoxy, n-propoxy, ethoxy, t-butoxy, 2-methylpropoxy, i-propoxy, —$SR^{14}$, —$OR^{14}$, —$SO_2$—$N(R^{13})(R^{13a})$, —$N(R^{13a})$—$SO_2$—$R^{14}$, —$N(R^{13})(R^{13a})$, —C(=O)—C(=O)—$N(R^{13})(R^{13a})$, —C(=O)—$N(R^{13})(R^{13a})$, —C(=N—OH)($R^{14a}$), —$N(R^{13})$—C(=O)$R^{14a}$, —C(=O)—$OR^{14a}$, —C(=O)—$R^{14a}$, —$SO_2R^{14}$, or one of the following sub-formulae:

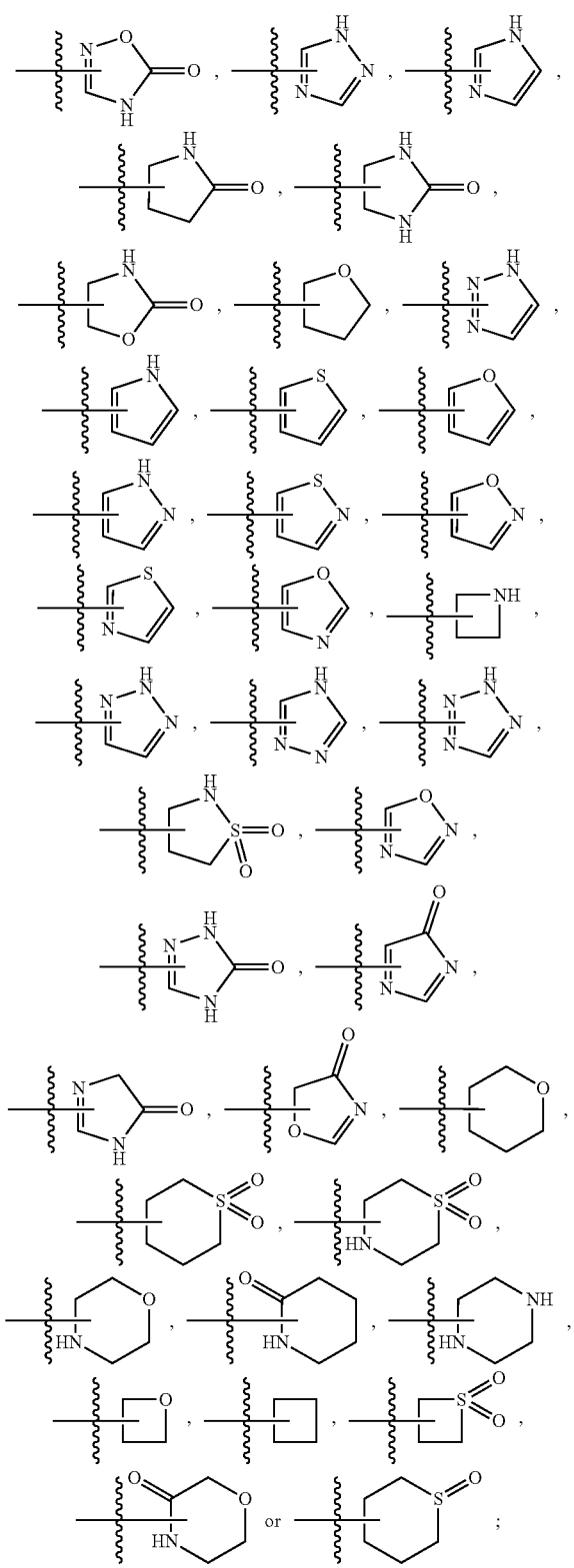

—OR$^{15}$, —SO$_2$R$^{15}$, —N(R$^{16}$)(R$^{16a}$), —C(=O)—N(R$^{16}$)(R$^{16a}$), or one of the following sub-formula:

wherein each R$^{1b}$ is independently and optionally substituted with 1, 2, 3, 4 or 5 substituents selected from hydroxy, nitro, cyano, methyl, ethyl, n-propyl, i-propyl, n-butyl, t-butyl, C$_{1-4}$ haloalkyl, F, Cl, Br, oxo (=O), C$_{1-4}$ alkoxy, phenyl, pyridyl, thiazolyl, thienyl, diazolyl, triazolyl, tetrazolyl, epoxypropyl, tetrahydrofuryl, tetrahydropyranyl, morpholinyl, piperdyl, cyclobutyl, cyclopentyl, dioxanyl, cyclohexyl and amino;

each R$^{16}$ and R$^{16a}$ is independently H, C$_{1-4}$ alkyl, C$_{2-6}$ alkenyl, C$_{2-6}$ alkynyl, phenyl, —SO$_2$R$^{17}$, —N(R$^{18}$)(R$^{18a}$), C$_{1-4}$ haloalkyl, cyclopropyl, cyclohexyl, wherein each R$^{1a}$ is independently and optionally substituted with 1, 2, 3, 4 or 5 R$^{1b}$ which are the same or different;

each R$^{1b}$ is independently H, methyl, ethyl, n-propyl, i-propyl, n-butyl, t-butyl, cyclobutyl, cyclopropyl, cyclohexyl, cyclopentyl, C$_{1-4}$ haloalkyl, C$_{2-6}$ alkenyl, C$_{2-6}$ alkynyl, methoxy, F, Cl, Br, nitro, cyano, hydroxy, oxo (=O),

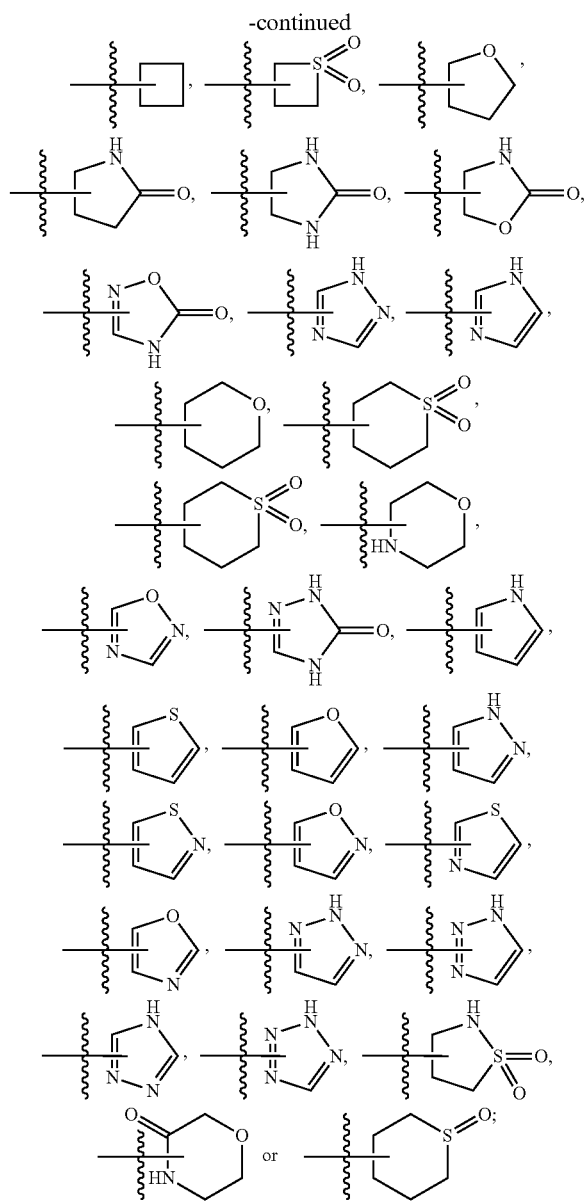

each $R^{15}$, $R^{13}$, $R^{13a}$, $R^{14}$, $R^{14a}$, $R^{17}$, $R^{18}$ and $R^{18a}$ is independently H, methyl, ethyl, n-propyl, i-propyl, n-butyl, 2-methylpropyl, t-butyl, trifluoromethyl, difluoromethyl, 2,2-difluoroethyl, 3,3,3-trifluoropropyl, phenyl, cyclopropyl, cyclohexyl, wherein each sub-formula is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, the compound of the invention has Formula (II) or a stereoisomer, a tautomer, a geometric isomer, an N-oxide or a pharmaceutically acceptable salt thereof, Formula (II)

wherein X, Z, Y, $R^{7a}$, $R^{7}$, $R^{2a}$, $R^{2}$, $R^{3a}$, $R^{3}$, $R^{1}$ and $R^{5}$ are as defined herein.

In some embodiments, the compound of the invention has Formula (III) or a stereoisomer, a tautomer, a geometric isomer, an N-oxide or a pharmaceutically acceptable salt thereof, Formula (III)

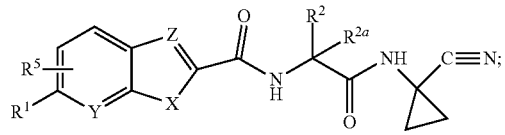

wherein X, Z, Y, $R^{2a}$, $R^2$, $R^1$ and $R^5$ are as defined herein.

In one aspect, the invention provides a pharmaceutical composition comprising the compound of the invention and a pharmaceutically acceptable carrier, excipient, diluent, adjuvant, vehicle, or a combination thereof.

In some embodiments, the pharmaceutical composition of the invention further comprises an organic bisphosphonic acid compound (such as alendronate), an estrogen receptor modulator (such as raloxifene), an estrogen receptor beta modulator (such as estradiol, conjugated estrogens), an androgen receptor modulator, an inhibitor of osteoclast proton ATPase, an inhibitor of HMG-CoA reductase, an integrin receptor antagonist, or an osteoblast anabolic agent, a non-steroidal anti-inflammatory drug, a selective cyclooxygenase-2 inhibitor, an interleukin-1β inhibitor, a LOX/COX inhibitor, activated vitamin D (such as 1α-hydroxy vitamin D (alphacalcidol), 1,25-dihydroxyvitamin D (calcitriol)), phytoestrogen (such as eprazinone), calcitonin (such as miacalcic), strontium ranelate, odanacatib, ONO5334, MIV-711, MIV-710, and a pharmaceutically acceptable salt and a combination thereof.

In one aspect, the invention provides the use of the compound or the pharmaceutical composition of the invention in the manufacture a medicament for inhibiting the activity of cathepsin or treating cathepsin dependent diseases, wherein inhibiting the activity of cathepsin is inhibiting the activity of cathepsin K.

In some embodiments, the invention provides the use of the compound or the pharmaceutical composition of the invention in the manufacture a medicament, wherein the medicament is used for treating, preventing, lessening or relieving osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, serious high calcium in blood, multiple myeloma, multiple sclerosis, myasthenia gravis, psoriasis, pemphigus vulgaris, exophthalmic goiter, systemic lupus erythematosus, asthma, pain, atherosclerosis, bone loss, abnormally increased bone turnover, hypercalcemia of malignancy, obesity or bone metastasis in a patient.

"Cathepsin dependent diseases or conditions" refer to pathological conditions which dependent upon one or more protease activities. "Cathepsin K dependent disease or condition" refers to a pathological condition which dependents upon cathepsin K activity. The disease which associates with cathepsin K activity consists of osteoporosis, glucocorticoid induced bone osteoporosis, Paget's disease, abnormally increased bone turnover, periodontal disease, tooth loss, bone fracture, rheumatoid arthritis, osteoarthritis, periprosthetic osteolysis, osteogenesis imperfecta, metastatic bone disease, hypercalcemia of malignancy and multiple myeloma. When the compound of the invention is used for treating these diseases, the therapeutic amount of the compound varies with the specific disease, and it is easy for the technicians of the field to determine.

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents that may be included within the scope disclosed herein as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application shall prevail.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito: 1999, 1999, and Smith et al., "March's Advanced Organic Chemistry", John Wiley & Sons, New York: 2007, the entire contents of which are hereby incorporated by reference.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of example, "a component" means one or more components, and thus, possibly, more than one component is contemplated and may be employed or used in an implementation of the described embodiments.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, "patient" refers to a human (including adults and children) or other animal. In one embodiment, "patient" refers to a human.

The term "comprising" or "comprise" is an open expression, it means comprising the contents disclosed herein, but does not exclude other contents.

"Stereoisomers" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc.

"Chiral" refers to molecules which have the property of non-superimposability of the mirror image partner, while the term "achiral" refers to molecules which are superimposable on their mirror image partner.

"Enantiomers" refers to two stereoisomers of a compound which are non-superimposable mirror images of one another.

"Diastereomer" refers to a stereoisomer with two or more centers of chirality and whose molecules are not mirror images of one another. Diastereomers have different physical properties, e.g., melting points, boiling points, spectral properties and biological activities. Mixture of diastereomers may separate under high resolution analytical procedures such as electrophoresis and chromatography such as HPLC.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "*Stereochemistry of Organic Compounds*", John Wiley & Sons, Inc., New York, 1994.

Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur where there has been no stereoselection or stereospecificity in a chemical reaction or process.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any resulting mixtures of stereoisomers can be separated on the basis of the physicochemical differences of the constituents, into the pure or substantially pure geometric isomers, enantiomers, diastereomers, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., *Enantiomers. Racemates and Resolutions* (Wiley Interscience, New York, 1981); *Principles of Asymmetric Synthesis* (2nd Ed. Robert E. Gawley, Jeffrey Aubé, Elsevier, Oxford, U K, 2012); Eliel, E. L. *Stereochemistry of Carbon Compounds* (McGraw-Hill, N Y, 1962); Wilen, S. H. Tables of Resolving Agents and Optical Resolutions p. 268 (E. L. Eliel, Ed., Univ. of Notre Dame Press, Notre Dame, Ind. 1972); *Chiral Separation Techniques: A Practical Approach* (Subramanian, G. Ed., Wiley-VCH Verlag GmbH & Co. KGaA, Weinheim, Germany, 2007).

The term "tautomer" or "tautomeric form" refers to structural isomers of different energies which are interconvertible via a low energy barrier. Where tautomerization is possible (e.g., in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. The specific example of phenol-keto tautomerisms is pyridin-4-ol and pyridin-4(1H)-one tautomerism. Unless otherwise stated, all tautomeric forms of the compounds disclosed herein are within the scope of the invention.

At various places in the present specification, substituents of compounds disclosed herein are disclosed in groups or in ranges. It is specifically intended that the invention include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

As described herein, compounds disclosed herein may optionally be substituted with one or more substituents, such as are illustrated generally below, or as exemplified by particular classes, subclasses, and species of the invention. It will be appreciated that the phrase "optionally substituted" is used interchangeably with the phrase "substituted or unsubstituted". In general, the term "substituted" refers to the replacement of one or more hydrogen radicals in a given structure with the radical of a specified substituent; the term "optional" or "optionally" whenever before the term "substituted" or not, refers to one or more hydrogen radicals in a given structure substituted or unsubstituted with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position, wherein the substitutent may be, but are not limited to, hydrogen, oxo (=O), alkyl, F, Cl, Br, amino, hydrogen, carboxy, alkoxy, alkylamino, haloalkyl, formyl, cyano, heterocyclyl, H—C(H)$_2$—O—C(=O)—C(H)$_2$—, H$_2$N—C(H)$_2$—, H—C(H)$_2$—SO$_2$—C(H)$_2$—, HO—C(H)$_2$—, HO—(CH$_2$)—C(=O)—, NH$_2$—C(=O)—, CN—C(H)$_2$—C(=O)—, heteroaryl, cycloalkyl or nitro, and the like.

The term "alkyl" or "alkyl group" refers to a saturated linear or branched-chain monovalent hydrocarbon radical of 1 to 20 carbon atoms, wherein the alkyl radical may be independently and optionally substituted with one or more substituents described herein. In some embodiments, the alkyl group contains 1-10 carbon atoms. In other embodiments, the alkyl group contains 1-8 carbon atoms. In other embodiments, the alkyl group contains 1-6 carbon atoms. In still other embodiments, the alkyl group contains 1-4 carbon atoms. In yet other embodiments, the alkyl group contains 1-3 carbon atoms; and in still yet other embodiments, the alkyl group contains 2-6 carbon atoms. Further embodiments of the alkyl group include, but are not limited to, methyl, ethyl, n-propyl, isopropyl, n-butyl, 2-methylpropyl or isobutyl, 1-methylpropyl or sec-butyl, tert-butyl, n-pentyl, 2-pentyl, 3-pentyl, 2-methyl-2-butyl, 3-methyl-2-butyl, 3-methyl-1-butyl, 2-methyl-1-butyl, n-hexyl, 2,3-dimethyl-2-butyl, 3,3-dimethyl-2-butyl, n-heptyl, n-octyl, and the like. The term "alkyl" or the prefix "alk-" is inclusive of both straight chain and branched saturated carbon chain.

The term "alkenyl" refers to a straight or branched chain hydrocarbon which is non-aromatic containing two to ten carbon atoms and at least one carbon carbon double bond. The preferred example of alkenyl contains one carbon carbon double bond, and at most contains four carbon carbon double bonds which are not in aromatic skeleton. Thereby, "C$_{2-6}$ alkenyl" refers to an alkenyl that contains two to six carbon atoms. The alkenyl contains vinyl (ethenyl), allyl (propenyl), butenyl and hexenyl. In the above description relating to alkenyl groups, the linear or branched portion of the alkenyl group may contain a double bond and the alkenyl group may be substituted if it is indicated as substituted alkenyl.

"cycloalkenyl" refers to a 3- to 10-membered carbocyclic ring containing at least one carbon carbon double bond. Preferred example includes, cyclopropenyl, cyclobutenyl, cyclopentyl, cyclohexenyl, cycloheptenyl or cyclooctenyl.

The term "alkynyl" refers to a straight or branched chain hydrocarbon which contains two to ten carbon atoms and at least one carbon carbon triple bond, and at most three carbon carbon triple bonds. Thereby, "C$_{2-6}$ alkynyl" refers to an alkynyl that contains two to six carbon atoms. Examples of alkynyl include acetenyl, propynyl and butynyl. In the above description relating to alkynyl groups, the linear or branched portion of the hydrocarbon group may contain a triple bond and the hydrocarbon group may be substituted if indicated as a substituted hydrocarbon group.

The term "haloalkyl" refers to an alkyl group substituted with one or more identical or different halogen atoms. Wherein the alkyl group is as defined herein. Some non-limiting examples of the haloalkyl group include trifluoromethyl, 1-chloroethyl, difluoromethyl, dichloroethyl, 2,2-difluoroethyl, 3,3,3-trifluoropropyl, 2-fluoro-2-methylpropyl and the like.

The term "amino" refers to —NH$_2$.

The term "oxo" refers to =O.

The term "cycle" or "ring" embraces carbocyclic ring, heterocyclic ring, aromatic ring, heteroaromatic ring, spiro ring and fused ring, and the like, wherein the carbocyclic ring, heterocyclic ring, aromatic ring, heteroaromatic ring, spiro ring and fused ring are as defined herein. One or more hydrogen atoms on the ring are each independently and optionally substituted with one or more substituents described herein.

The term "alkamino" or "alkylamino" refers to "N-alkylamino" and "N,N-dialkylamino", wherein the amino groups are independently substituted with one or two alkyl groups, respectively, and wherein the alkyl group is as defined herein. Some non-limiting examples of alkylamino include, methylamino, ethylamino, dimethylamino and diethylamino, and the like.

The term "aminoalkyl" refers to an alkyl substituted with one or more amino groups. Wherein the alkyl group is as defined herein. In some embodiments, the aminoalkyl is an amino-C$_{1-6}$-alkyl group. In other embodiments, the aminoalkyl is an amino-C$_{1-3}$-alkyl group. Some non-limiting examples of the aminoalkyl group include aminomethyl, aminoethyl and aminopropyl, and the like.

The term "alkoxy" refers to an alkyl group, as defined herein, attached to the principal carbon chain through an oxygen atom. Some non-limiting examples of the alkoxy group include methoxy, ethoxy, propoxy, and the like.

The term "aryl" refers to monocyclic, bicyclic and tricyclic carbocyclic ring systems, wherein at least one ring in the system is aromatic, and wherein each ring in the system contains 3 to 7 ring members. The term "aryl" may be used interchangeably with the term "aryl ring" or "aromatic ring". Some non-limiting examples of the aryl group include phenyl, naphthyl and anthracene. Depending on the structure, the aryl group can be a divalent group such as an arylene group.

The term "heteroaryl" or "heteroaromatic ring" used interchangeably herein refers to a stable monocyclic, bicyclic, or tricyclic ring system having at most 10 ring members in each ring of the system, wherein at least one ring in the system is aromatic and contains one to four heteroatoms selected from O, N and S. Non-limiting examples of heteroaryl within definition include, benzimidazolyl, benzofuryl, benzofurazanyl, benzopyrazolyl, benzotriazolyl, benzothienyl, benzoxazolyl, carbazolyl, carbolinyl, cinnolinyl, furanyl, indolinyl, indolyl, indolizinyl, indazolyl, isobenzofuryl, isoindolyl, isoquinolinyl, isothiazolyl, isoxazolyl, naphthyridinyl, oxadiazolyl, oxazolyl, oxazoline, isoxazoline, pyranyl, pyrazinyl, pyrazolyl, pyridazinyl, pyridopyridyl, pyridyl, pyrimidinyl, pyrrolyl, quinazolinyl, quinolinyl, quinoxalinyl, tetrazolyl, tetrazolopyridyl, thiadiazolyl, thiazolyl, thienyl, triazolyl, dihydrobenzimidazolyl, dihydrobenzofuranyl, dihydrobenzothienyl, dihydrobenzoxazolyl, indolinyl, dihydroquinolinyl, 2-indolinyl, 1,3-benzodioxole, benzothiazolyl, benzothienyl, quinolyl, isoquinolyl, pteridinyl, purine, oxazolyl, triazolopyridyl, 1,4-benzodioxanyl and tetrahydroquinoline. When a substitutent of the heteroaryl is a bicyclolic ring system, and one ring of it is nonaromatic or does not contain heteroatom, it should be clearly noted that the substituent attaches to the heteroaryl via aromatic ring or ring containing heteroatom(s). In some embodiments, it should be clear that the definition of carbon, nitrogen or sulfur atom of the nonaromatic ring also include oxides of them, examples include, but are not limited to,

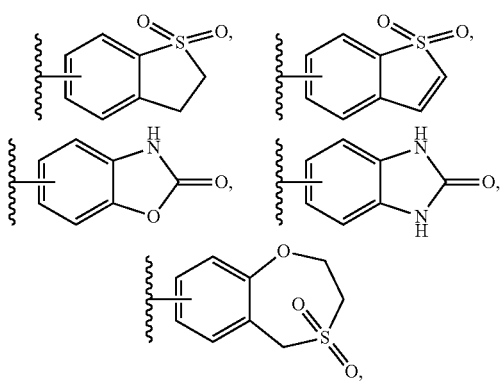

and the like.

The term "cycloalkyl" or "carbocyclic ring" refers to a monovalent or multivalent, non-aromatic, saturated or partially unsaturated ring that doesn't contain heteroatoms and includes 3-12 carbon atoms as a monocyclic ring or 7-12 carbon atoms as a bicyclic ring or tricyclic ring, aromatic ring does not exist in the cycloalkyl ring system, but a aromatic ring can be a substituent of the cycloalkyl group. Bicyclic carbocyclic ring having 7-12 ring atoms can be arranged, for example, as a bicyclo[4,5], [5,5], [5,6] or [6,6] system, and bicyclic carbocyclic ring having 9 or 10 ring atoms can be arranged as a bicyclo[5,6] or [6,6] system. Some non-limiting examples of the cycloalkyl group include cycloalkyl, cycloalkenyl and cycloalkynyl. Further examples of the cycloalkyl group include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, adamantly, and the like.

The term "heterocyclyl", "heterocycle", "heterocycloaliphatic" or "heterocyclic" as used interchangeably herein refers to a monocyclic, bicyclic, tricyclic or tetracyclic ring system in which one or more ring members are an independently selected heteroatom and that is completely saturated or that contains one or more units of unsaturation, but an aromatic ring can not exist in the heterocyclyl ring (but an aromatic ring can be a substituent of the heterocyclyl group). The heterocyclyl system may be attached to the main structure at any heteroatom or carbon atom which results in the creation of a stable compound. In some embodiments, the heterocyclyl, heterocyclic ring, heterocycloaliphatic or heterocyclic group is a monocyclic ring having 3-7 ring members (e.g., 1 to 6 carbon atoms and 1 to 3 heteroatoms selected from N, O, P and S, wherein the N, S or P is optionally substituted with one or more oxygen atoms to provide the group NO, $NO_2$, SO or $SO_2$, PO or $PO_2$, and the —$CH_2$— can also be optionally replaced by the group —C=O—) or a bicyclic ring having 7-10 ring members (e.g., 4 to 9 carbon atoms and 1 to 3 heteroatoms selected from N, O, P and S, wherein the N, S or P is optionally substituted with one or more oxygen atoms to provide the group NO, $NO_2$, SO or $SO_2$, PO or $PO_2$, and the —$CH_2$— can also be optionally replaced by the group —C=O—). Depending on the structure, the heterocyclyl may be a divalent group, i.e., a heterocyclylene.

The heterocyclyl may be a carbon radical or heteroatom radical. The heterocyclyl group also includes a group in which the heterocyclyl group is fused with a saturated or partially unsaturated ring or a heterocyclic ring. Some non-limiting examples of the heterocyclyl group include 1,2,3,6-tetrahydropyridyl, piperidyl, piperidinonyl, piperazinyl, pyrrolidinyl, pyrrolidin-2-onyl, imidazolidonyl, tetrahydrofuranyl, dihydrofuranyl, tetrahydrothienyl, tetrahydropyranyl, dihydropyranyl, tetrahydrothiopyranyl, 1,2,4-oxadiazol-5(4H)-onyl, oxazol-2-onyl, isothiazolin-onyl, isothiazolinyl-1,1-dioxide azetidinyl, oxetanyl, 1H-1,2,4-triazol-5(4H)-onyl, thietanyl, homopiperidinyl, epoxypropyl, azepanyl, oxepanyl, thiepanyl, N-morpholinyl, 2-morpholinyl, 3-morpholinyl, thiomorpholinyl, homopiperazinyl, thietanyl-1,1-dioxide, morpholin-3-onyl, oxazepinyl, diazepinyl, thiazepinyl, 1-pyrrolinyl, 2-pyrrolinyl, 3-pyrrolinyl, 2H-pyranyl, 4H-pyranyl, dioxanyl, 1,3-dioxolanyl, dithianyl, dithiolanyl, 1,2,6-thidiazine-1,1-dioxo-2-yl, hexahydro-2H-[1,4]dioxin[2,3-c]pyrrolyl, 1,1-dioxothiomorpholinyl, tetrahydro-2H-thiopyranyl-1,1-dioxide, dihydrothiophenyl, N-pyridyl urea, dioxolanyl, dihydropyrazinyl, dihydropyridyl, dihydropyrazolyl, dihydropyrimidinyl, dihydropyrrolyl, 1,4-dithianyl, morpholinyl, decahydroindolyl, decahydroisoindolyl and tetrahydro-2H-thiopyranyl-1-oxide.

As described herein, a bond drawn from a substituent R to the center of one ring within a ring system represents substitution of the substituent R at any substitutable position on the ring. For example, Formula a represents substitution of the substituent R any substitutable position on the ring A or B, such as Formula b, Formula c, Formula d, Formula e, Formula f, Formula g and Formula h,

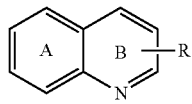

Formula a

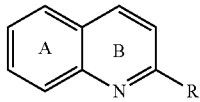

Formula b

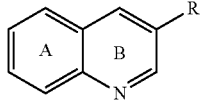

Formula c

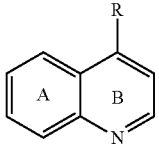

Formula d

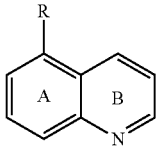

Formula e

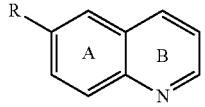

Formula f

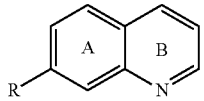

Formula g

-continued

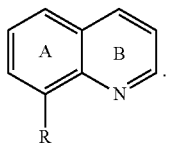
Formula h

As described herein, the attachment point can attach to the rest of the molecule at any attachable position on the rings. For example, Formula n represents any attachable position on ring A or ring B which can be attached can be the attachment point.

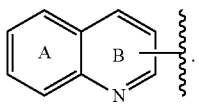
Formula n

Furthermore, unless otherwise stated, the phrase "each . . . is independently" is used interchangeably with the phrase "each (of) . . . and . . . is independently". It should be understood broadly that the specific options expressed by the same symbol are independently of each other in different radicals; or the specific options expressed by the same symbol are independently of each other in same radicals.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

A "hydrate" refers to a compound disclosed herein or a salt thereof, which further includes a stoichiometric or non-stoichiometeric amount of water bounded by non-covalent intermolecular forces, and also refers to the complex where the solvent molecule is water.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid and ethanolamine.

An "ester" refers to an in vivo hydrolysable ester of a compound of the Formula (I)-(IV) containing hydroxy group, for example, a pharmaceutically acceptable ester which is hydrolysed in the human or animal body to produce the parent alcohol. Some non-limiting examples of in vivo hydrolysable ester forming groups for hydroxy include phosphate, acetoxymethoxy, 2,2-dimethylpropionyloxymethoxy, alkanoyl, benzoyl, phenylacetyl, alkoxycarbonyl, dialkylcarbamoyl, N-(dialkylaminoethyl)-N-alkylcarbamoyl, and the like.

An "N-oxide" refers to one or more than one nitrogen atoms oxidised to form N-oxides, where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g., a peroxycarboxylic acid) (See, *Advanced Organic Chemistry*, by Jerry March, 4th Edition, Wiley Interscience, pages). More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Additionally, unless otherwise stated, structures depicted herein are also meant to include compounds that differ only in the presence of one or more isotopically enriched atoms. The present invention includes isotopically-labeled compounds, which are identical to those recited in Formula (I)-(IV), but that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine, and chlorine, such as $^2H$, $^3H$, $^{13}C$, $^{11}C$, $^{14}C$, $^{15}N$, $^{18}O$, $^{17}O$, $^{31}P$, $^{32}P$, $^{35}S$, $^{18}F$ and $^3Cl$, respectively. Compounds of the present invention, prodrugs thereof, and pharmaceutically acceptable salts of said compounds or said prodrugs which contain the aforementioned isotopes and/or other isotopes of other atoms are within the scope of this invention. Certain isotopically-labeled compounds of the present invention, for example those into which radioactive isotopes such as $^3H$ or $^{14}C$ are incorporated, are useful in drug and/or substrate tissue distribution assays. tritium ($^3H$) and carbon-14($^{14}C$) are the preferred isotopes, because they are easy to prepare and detect. Further, substitution with heavier isotopes, particularly deuterium (i.e., 2H or D) may afford certain therapeutic advantages resulting from greater metabolic stability, for example increased in vivo half-life or reduced dosage requirements, and may be preferred in some case. Isotopically labeled compounds of Formula (I)-(IV) of this invention and prodrugs thereof can generally be prepared by carrying out the procedures disclosed in the Schemes and/or in the Examples below, by replacement of a non-isotopically labeled reagent to a readily available isotopically labeled reagent.

A "metabolite" is a product produced through metabolism in the body of a specified compound or salt thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

The compounds disclosed herein are useful in various pharmaceutically acceptable salt forms. The term "pharmaceutically acceptable salt" refers to those salt forms which would be apparent to the pharmaceutical chemist, i.e., those which are substantially nontoxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients in combination with pharmaceutically acceptable carriers.

A "pharmaceutically acceptable salts" refers to organic or inorganic salts of a compound disclosed herein. Pharmaceutically acceptable salts are well known in the art. For example, S. M. Berge et al., describe pharmaceutically acceptable salts in detail in *J. Pharmacol Sci,* 1977, 66:1-19, which is incorporated herein by reference. Examples of pharmaceutically acceptable, nontoxic salts include, but are not limited to, salts of an amino group formed with inorganic acids such as hydrochloric acid, hydrobromic acid, phosphoric acid, sulfuric acid, perchloric acid and nitric acid or with organic acids such as acetic acid, propionic acid, glycollic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid or salts obtained by using other methods used in the art such as ion exchange.

Other pharmaceutically acceptable salts include adipate, malate, 2-hydroxy propionate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate, and the like. Salts derived from appropriate bases include alkali metal, alkaline earth metal, ammonium and $N^+(C_{1-4}\ \text{alkyl})_4$ salts.

This invention also envisions the quaternization of any basic nitrogen-containing groups of the compounds disclosed herein. Water or oil soluble or dispersable products may be obtained by such quaternization. Representative alkali or alkaline earth metal salts include sodium, lithium, potassium, calcium, magnesium, ferric salt, zinc salt, copper salt, manganese salt, aluminium salt, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate. Amine salts include, but are not limited to, N,N'-dibenzylethylenediamine, chloroprocaine, choline, ammonia, diethanolamine and other hydroxyalkylamine, ethylenediamine, N-methylglucamine, procaine, N-benzylphenethylamine, 1-para-chlorobenzyl-2-pyrrolidin-1'-ylmethylbenzimidazole, diethylamine and other alkylamine, piperazine and tris(hydroxymethyl)aminomethane. Alkali earth metal salts include, but are not limited to, barium, calcium and magnesium. Transition metal salts include, but are not limited to, zinc.

The term "protecting group" or "Pg" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl)ethyl, 2-(trimethylsilyl)ethoxy-methyl, 2-(p-toluenesulfonyl)ethyl, 2-(p-nitrophenylsulfenyl)-ethyl, 2-(diphenylphosphino) ethyl, nitroethyl and the like. For a general description of protecting groups and their use, see T. W. Greene, Protective Groups in Organic Synthesis, John Wiley & Sons, New York, 1991; and P. J. Kocienski, Protecting Groups, Thieme, Stuttgart, 2005.

In the present invention, if the chemical name of the compound doesn't match the corresponding structure, the compound is characterized by the corresponding structure.

As used herein, the abbreviations for any protective groups, amino acids and other compounds are, unless otherwise indicated, in accord with their common usage, recognized abbreviations, or the IUPAC-IUB Commission on Biochemical Nomenclature (See, Biochem. 1972, 11: 942-944).

DESCRIPTION OF COMPOUNDS OF THE INVENTION

The invention provides a class of high selective cathepsin K inhibitors having Formula (I) or a stereoisomer, a tautomer, a geometric isomer, an N-oxide, a prodrug or a pharmaceutically acceptable salt thereof,

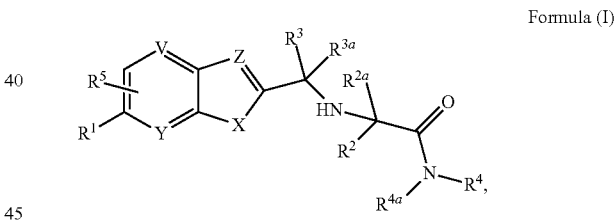

Formula (I)

wherein V, X, Z, Y, $R^{4a}$, $R^4$, $R^{2a}$, $R^2$, $R^{3a}$, $R^3$, $R^1$ and $R^5$ are as defined herein.

In some embodiments, $R^{4a}$ is H, $C_{1-6}$ alkyl or $C_{2-6}$ alkenyl, wherein each of the $C_{1-6}$ alkyl and $C_{2-6}$ alkenyl is independently and optionally substituted with 1, 2, 3, 4, 5 or 6 substituents selected from halogen, $C_{3-6}$ cycloalkyl, cyano, $C_{6-10}$ aryl, $C_{1-9}$ heteroaryl or $C_{2-9}$ heterocyclyl;

$R^4$ is $C_{1-6}$ alkyl, —C($R^7$)($R^{7a}$)—$R^8$, $C_{3-9}$ heterocyclyl or $C_{2-6}$ alkenyl, wherein each of the $C_{1-6}$ alkyl and $C_{2-6}$ alkenyl is independently and optionally substituted with 1, 2, 3, 4, 5 or 6 substituents selected from halogen, $C_{3-6}$ cycloalkyl, cyano, $C_{6-10}$ aryl, $C_{1-9}$ heteroaryl and $C_{3-9}$ heterocyclyl;

or, $R^4$ and $R^{4a}$, together with the nitrogen atom to which they are attached, form a $C_{3-9}$ heterocyclyl group containing nitrogen, wherein the $C_{3-9}$ heterocyclyl is optionally substituted with 1, 2, 3, 4 or 5 substituents selected from $C_{1-6}$ alkyl, $C_{1-6}$ hydroxyalkyl, cyano, —C($R^{10}$)($R^{10a}$)—C (=O)—N($R^{12}$)($R^{12a}$), —C(=O)—O$R^{8a}$, oxo (=O), $C_{1-6}$ haloalkyl and halogen;

wherein $R^{7a}$, $R^7$, $R^8$, $R^{10}$, $R^{10a}$, $R^{12}$, $R^{12a}$ and $R^{8a}$ are as defined herein.

In some embodiments, each of $R^7$ and $R^{7a}$ is independently H, $C_{1-6}$ alkyl, —C($R^{10}$)($R^{10a}$)—C(=O)—N($R^{12}$)($R^{12a}$), —C(=O)—OR$^{8a}$, $C_{2-6}$ heterocyclyl or $C_{2-6}$ alkenyl;

or, $R^1$ and $R^{7a}$, together with the carbon atom to which they are attached, form a $C_{3-6}$ carbocyclic ring or $C_{2-6}$ heterocyclic ring, wherein each of the $C_{3-6}$ carbocyclic ring and $C_{2-6}$ heterocyclic ring is independently and optionally substituted with 1, 2, 3, 4, 5 or 6 substituents selected from $C_{1-6}$ alkyl, $C_{1-6}$ hydroxyalkyl, $C_{1-6}$ haloalkyl, oxo (=O), cyano, —C(=O)—OR$^{8a}$ and halogen; wherein $R^{10}$, $R^{10a}$, $R^{12}$, $R^{12a}$ and $R^{8a}$ are as defined herein.

In some embodiments, $R^8$ is H, $C_{1-6}$ alkyl, cyano, —N($R^{12}$)($R^{12a}$), —C(=O)—C(=O)—N($R^{12}$)($R^{12a}$), —C(=O)—N($R^{12}$)($R^{12a}$), —C(=O)—OR$^{8a}$, $C_{3-6}$ heterocyclyl or $C_{2-6}$ alkenyl;

wherein $R^{12}$, $R^{12a}$ and $R^{8a}$ are as defined herein.

In some embodiments, each $R^{12}$ and $R^{12a}$ is independently H or $C_{1-6}$ alkyl, wherein the $C_{1-6}$ alkyl is optionally substituted with 1, 2, 3, 4, 5 or 6 substituents selected from halogen, hydroxy, amino, carboxy, cyano, $C_{3-6}$ cycloalkyl, $C_{6-10}$ aryl, $C_{1-9}$ heteroaryl and $C_{2-9}$ heterocyclyl.

In some embodiments, each $R^{10}$ and $R^{10a}$ is independently H or $C_{1-6}$ alkyl, wherein the $C_{1-6}$ alkyl is optionally substituted with 1, 2, 3, 4, 5 or 6 substituents selected from halogen, hydroxy, amino, carboxy, cyano, $C_{3-6}$ cycloalkyl, $C_{6-10}$ aryl, $C_{1-9}$ heteroaryl and $C_{2-9}$ heterocyclyl.

In some embodiments, $R^{8a}$ is H or $C_{1-6}$ alkyl, wherein the $C_{1-6}$ alkyl is optionally substituted with 1, 2, 3, 4, 5 or 6 substituents selected from halogen, hydroxy, amino, carboxy, cyano, $C_{3-6}$ cycloalkyl, $C_{6-10}$ aryl, $C_{1-9}$ heteroaryl and $C_{2-9}$ heterocyclyl.

In some embodiments, $R^{6a}$ is H or $C_{1-6}$ alkyl, wherein the $C_{1-6}$ alkyl is optionally substituted with 1, 2, 3, 4, 5 or 6 substituents selected from halogen, hydroxy, amino, carboxy, cyano, $C_{3-6}$ cycloalkyl, $C_{6-10}$ aryl, $C_{1-9}$ heteroaryl and $C_{2-9}$ heterocyclyl.

In some embodiments, $R^6$ is H or $C_{1-6}$ alkyl, wherein the $C_{1-6}$ alkyl is optionally substituted with 1, 2, 3, 4, 5 or 6 substituents selected from halogen, hydroxy, amino, carboxy, cyano, $C_{3-6}$ cycloalkyl, $C_{6-10}$ aryl, $C_{1-9}$ heteroaryl and $C_{2-9}$ heterocyclyl.

In some embodiments, each $R^2$ and $R^{2a}$ is independently H or $C_{1-6}$ alkyl, wherein the $C_{1-6}$ alkyl is optionally substituted with 1, 2, 3, 4, 5 or 6 substituents selected from halogen, hydroxy, amino, carboxy, cyano, $C_{3-6}$ cycloalkyl, $C_{6-10}$ aryl, $C_{1-9}$ heteroaryl and $C_{2-9}$ heterocyclyl;

or, $R^2$ and $R^{28}$, together with the carbon atom to which they are attached, form a $C_{3-9}$ carbocyclic ring or $C_{2-9}$ heterocyclic ring, wherein each of the $C_{3-9}$ carbocyclic ring and $C_{2-9}$ heterocyclic ring is independently and optionally substituted with 1, 2, 3, 4, 5 or 6 substituents selected from $C_{1-6}$ alkyl, $C_{2-6}$ alkenyl, $C_{1-6}$ hydroxyalkyl, $C_{1-6}$ haloalkyl, hydroxy, amino, carboxy, cyano and halogen;

In some embodiments, each $R^3$ and $R^{3a}$ is independently H or $C_{1-6}$ alkyl, wherein the $C_{1-6}$ alkyl is optionally substituted with 1, 2, 3, 4, 5 or 6 substituents selected from halogen, hydroxy, amino, carboxy, cyano, $C_{3-6}$ cycloalkyl, $C_{6-10}$ aryl, $C_{1-9}$ heteroaryl and $C_{2-9}$ heterocyclyl;

or, $R^3$ and $R^{3a}$, together with the carbon atom to which they are attached, form a >C(=O), $C_{3-9}$ carbocyclic ring or $C_{2-9}$ heterocyclic ring, wherein each of the $C_{3-9}$ carbocyclic ring and $C_{2-9}$ heterocyclic ring is independently and optionally substituted with 1, 2, 3, 4, 5 or 6 substituents selected from $C_{1-6}$ alkyl, $C_{2-6}$ alkenyl, $C_{1-6}$ hydroxyalkyl, $C_{1-6}$ haloalkyl, hydroxy, amino, carboxy, cyano and halogen.

In some embodiments, X is —O—, —S— or —NH—.

In some embodiments, V is C($R^9$) or N, wherein $R^9$ is as defined herein.

In some embodiments, each of Z and Y is independently C($R^9$) or N, wherein $R^9$ is as defined herein.

In some embodiments, each $R^9$ is independently H, halogen, cyano, hydroxy, $C_{1-4}$ alkoxy, —N($R^6$)($R^{6a}$), $C_{1-4}$ haloalkyl or $C_{1-4}$ alkyl, wherein each of the $C_{1-4}$ alkyl is optionally substituted with 1, 2, 3, 4, 5 or 6 substituents selected from halogen, $C_{3-6}$ cycloalkyl, $C_{6-10}$ aryl, $C_{1-9}$ heteroaryl and $C_{2-9}$ heterocyclyl; wherein $R^6$ and $R^{6a}$ are as defined herein.

In some embodiments, $R^5$ is H, $C_{1-4}$ alkyl, $C_{2-6}$ alkenyl, $C_{2-6}$ alkynyl, $C_{1-6}$ alkoxy, F, Cl, Br, nitro, cyano, —N($R^6$)($R^3$), or $C_{1-4}$ haloalkyl, wherein $R^6$ and $R^{6a}$ are as defined herein.

In some embodiments, $R^5$ is H, methyl, ethyl, F, Cl, Br or trichloromethyl.

In some embodiments, $R^1$ is aryl, heteroaryl, cycloalkyl or heterocyclyl, wherein each of the aryl, heteroaryl, cycloalkyl and heterocyclyl is independently and optionally substituted with 1, 2, 3, 4 or 5 $R^{1a}$ which are the same or different; wherein $R^{1a}$ is as defined herein.

In some embodiments, each $R^{1a}$ is independently H, alkyl, haloalkyl, halo, cyano, oxo (=O), alkoxy, aryl, heteroaryl, cycloalkyl, heterocyclyl, —SR$^{14}$, —OR$^{14}$, —SO$_2$—N($R^{13}$)($R^{13a}$), —N($R^{13a}$)—SO$_2$—R$^{14}$, —N($R^{13}$)($R^{13a}$), —C(=O)—C(=O)—N($R^{13}$)($R^{13a}$), —C(=O)—N($R^{13}$)($R^{13a}$), —C(=N—OH)($R^{14a}$), —N($R^{13}$)—C(=O)R$^{14a}$, —C(=O)—OR$^{14}$, —C(=O)—R$^{14a}$ and —SO$_2$R$^{14}$, wherein each of the aryl, heteroaryl, cycloalkyl, heterocyclyl, alkyl, haloalkyl, alkoxy, —SR$^{14}$, —OR$^{14}$, —SO$_2$—N($R^{13}$)($R^{13a}$), —N($R^{13a}$)—SO$_2$—R$^{14}$, —N($R^{13}$)($R^{13a}$), —C(=O)—C(=O)—N($R^{13}$)($R^{13a}$), —C(=O)—N($R^{13}$)($R^{13a}$), —C(=N—OH)($R^{14a}$), —N($R^{13}$)—C(=O)R$^{14a}$, —C(=O)—OR$^{14}$, —C(=O)—R$^{14a}$ and —SO$_2$R$^{14}$ in $R^{1a}$ is independently and optionally substituted with 1, 2, 3, 4 or 5 $R^{1b}$ which are the same or different; wherein $R^{1b}$, $R^{13}$, $R^{13a}$, $R^{14}$ and $R^{14a}$ are as defined herein.

In some embodiments, each $R^{1b}$ is independently H, alkyl, haloalkyl, alkenyl, alkynyl, alkoxy, halogen, nitro, cyano, hydroxy, oxo (=O), —OR$^{15}$, —SO$_2$R$^{15}$, —N($R^{16}$)($R^{16a}$), —C(=O)—N($R^{16}$)($R^{16a}$), aryl, heteroaryl, cycloalkyl or heterocyclyl, wherein each of the $R^{1b}$ is independently and optionally substituted with 1, 2, 3, 4 or 5 substituents selected from hydroxy, nitro, cyano, alkyl, haloalkyl, halogen, oxo (=O), alkoxy, aryl, heteroaryl, cycloalkyl, heterocyclyl and amino; wherein $R^{15}$, $R^{16}$ and $R^{16a}$ is as defined herein.

In some embodiments, each $R^{16}$ and $R^{16a}$ is independently H, $C_{1-4}$ alkyl, $C_{2-6}$ alkenyl, $C_{2-6}$ alkynyl, $C_{6-10}$ aryl, $C_{1-9}$ heteroaryl, $C_{3-6}$ cycloalkyl, —SO$_2$R$^{17}$, —N($R^{18}$)($R^{18a}$), $C_{1-4}$ haloalkyl or $C_{2-9}$ heterocyclyl; wherein $R^{17}$, $R^{18}$ and $R^{18a}$ are as defined herein.

In some embodiments, $R^{15}$ is H, $C_{1-4}$ alkyl, $C_{1-4}$ haloalkyl, $C_{2-6}$ alkenyl, $C_{2-6}$ alkynyl, $C_{6-10}$ aryl, $C_{1-9}$ heteroaryl, $C_{3-6}$ cycloalkyl or $C_{2-9}$ membered heterocyclyl, wherein each of the $C_{6-10}$ aryl, $C_{1-9}$ heteroaryl, $C_{3-6}$ cycloalkyl and $C_{2-9}$ membered heterocyclyl is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, each $R^{13}$ and $R^{13a}$ is independently H, $C_{1-4}$ alkyl, $C_{1-4}$ haloalkyl, $C_{2-6}$ alkenyl, $C_{2-6}$ alkynyl, $C_{6-10}$ aryl, $C_{1-9}$ heteroaryl, $C_{3-6}$ cycloalkyl or $C_{2-9}$ heterocyclyl, wherein each of the $C_{6-10}$ aryl, $C_{1-9}$ heteroaryl, $C_{3-6}$ cycloalkyl and $C_{1-9}$ heterocyclyl is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, each $R^{18}$ and $R^{18a}$ is independently H, $C_{1-4}$ alkyl, $C_{1-4}$ haloalkyl, $C_{2-6}$ alkenyl, $C_{2-6}$ alkynyl, $C_{6-10}$ aryl, $C_{1-9}$ heteroaryl, $C_{3-6}$ cycloalkyl or $C_{2-9}$ heterocyclyl, wherein each of the $C_{6-10}$ aryl, $C_{1-9}$ heteroaryl, $C_{3-6}$ cycloalkyl and $C_{2-9}$ heterocyclyl is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, each $R^{14}$ and $R^{14a}$ is independently H, $C_{1-4}$ alkyl, $C_{1-4}$ haloalkyl, $C_{2-6}$ alkenyl, $C_{2-6}$ alkynyl, $C_{6-10}$ aryl, $C_{1-9}$ heteroaryl, $C_{3-6}$ cycloalkyl or $C_{2-6}$ heterocyclyl, wherein each of the $C_{6-10}$ aryl, $C_{1-9}$ heteroaryl, $C_{3-6}$ cycloalkyl and $C_{2-9}$ heterocyclyl is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, $R^{17}$ is independently H, $C_{1-4}$ alkyl, $C_{1-4}$ haloalkyl, $C_{2-6}$ alkenyl, $C_{2-6}$ alkynyl, $C_{6-10}$ aryl, $C_{1-9}$ heteroaryl, $C_{3-6}$ cycloalkyl or $C_{2-9}$ heterocyclyl, wherein each of the $C_{6-10}$ aryl, $C_{1-9}$ heteroaryl, $C_{3-6}$ cycloalkyl and $C_{2-9}$ heterocyclyl is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, $R^{4a}$ is H, methyl, ethyl, n-propyl, or isopropyl;

$R^4$ is methyl, ethyl, n-propyl, isopropyl, —C($R^7$)($R^{7a}$)—$R^8$, 5- to 6-membered heterocyclyl or vinyl, wherein each of the methyl, ethyl, n-propyl, isopropyl, —C($R^7$)($R^{7a}$)—$R^8$, 5- to 6-membered heterocyclyl and vinyl is independently and optionally substituted with 1, 2, 3, 4 or 5 substituents selected from halogen, $C_{3-6}$ cycloalkyl and cyano;

or, $R^4$ and $R^{4a}$, together with the nitrogen atom to which they are attached, form one of the following sub-formulae:

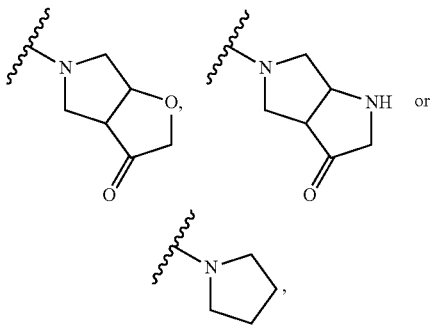

wherein each sub-formula is independently and optionally substituted with 1, 2, 3, 4 or 5 substituents selected from $C_{1-4}$ alkyl, $C_{1-4}$ hydroxyalkyl, oxo (=O), cyano, —C($R^{10}$)($R^{10a}$)—C(=O)—N($R^{12}$)($R^{12a}$), —C(=O)—OR$^{8a}$, $C_{1-4}$ haloalkyl and halogen;

wherein $R^{7a}$, $R^7$, $R^8$, $R^{10}$, $R^{10a}$, $R^{12}$, $R^{12a}$ and $R^{8a}$ are as defined herein.

In some embodiments, each of $R^7$ and $R^{7a}$ is independently H, $C_{1-4}$ alkyl, —C($R^{10}$)($R^{10a}$)—C(=O)—N($R^{12}$)($R^{12a}$), —C(=O)—OR$^{8a}$, $C_{1-6}$ heterocyclyl or $C_{2-6}$ alkenyl;

or, $R^7$ and $R^{7a}$, together with the carbon atom to which they are attached, form a cyclopropyl, cyclopentyl, cyclobutyl, cyclohexyl, morpholinyl, piperidyl or pyrrolyl group, wherein each of the cyclopropyl, cyclopentyl, cyclobutyl, cyclohexyl, morpholinyl, piperidyl and pyrrolyl is independently and optionally substituted with 1, 2, 3, 4 or 5 substituents selected from $C_{1-4}$ alkyl, $C_{1-4}$ hydroxyalkyl, $C_{1-4}$ haloalkyl, oxo (=O), cyano, —C(=O)—OR$^{8a}$ and halogen;

wherein $R^{10}$, $R^{10a}$, $R^{12}$, $R^{12a}$ and $R^{8a}$ are as defined herein.

In some embodiments, $R^8$ is H, $C_{1-4}$ alkyl, cyano, —N($R^{12}$)($R^{12a}$), —C(=O)—C(=O)—N($R^{12}$)($R^{12a}$), —C(=O)—N($R^{12}$)($R^{12a}$), —C(=O)—OR$^{8a}$, $C_{3-6}$ heterocyclyl or $C_{2-6}$ alkenyl;

wherein $R^{12}$, $R^{12a}$ and $R^{8a}$ are as defined herein.

In some embodiments, $R^{8a}$ is H or $C_{1-4}$ alkyl, wherein $C_{1-4}$ alkyl is optionally substituted with 1, 2, 3, 4 or 5 substituents selected from halogen, hydroxy, amino, carboxy, cyano, $C_{3-6}$ cycloalkyl, $C_{6-10}$ aryl, $C_{1-9}$ heteroaryl and $C_{2-9}$ heterocyclyl.

In some embodiments, each $R^{10}$ and $R^{10a}$ is independently H or $C_{1-4}$ alkyl, wherein $C_{1-4}$ alkyl is optionally substituted with 1, 2, 3, 4 or 5 substituents selected from halogen, hydroxy, amino, carboxy, cyano, $C_{3-6}$ cycloalkyl, $C_{6-10}$ aryl, $C_{1-9}$ heteroaryl and $C_{2-9}$ heterocyclyl.

In some embodiments, each $R^{12}$ and $R^{12a}$ is independently H or $C_{1-4}$ alkyl, wherein $C_{1-4}$ alkyl is optionally substituted with 1, 2, 3, 4 or 5 substituents selected from halogen, hydroxy, amino, carboxy, cyano, $C_{3-6}$ cycloalkyl, $C_{6-10}$ aryl, $C_{1-9}$ heteroaryl and $C_{2-9}$ heterocyclyl.

In some embodiments, $R^6$ is H, methyl, ethyl, n-propyl, isopropyl, 1-methylpropyl, 2-methylpropyl or tert-butyl, wherein each of the methyl, ethyl, n-propyl, isopropyl, 1-methylpropyl, 2-methylpropyl and tert-butyl is independently and optionally substituted with 1, 2, 3, 4, 5 or 6 substituents selected from F, Cl, Br, hydroxy, amino, carboxy, cyano, cyclohexyl, cyclopentyl, cyclobutyl, cyclopropyl, phenyl, pyridyl, thiazolyl, diazolyl, triazolyl, piperidyl, furyl, tetrahydrofuryl, azetanyl, oxetanyl and morpholinyl.

In some embodiments, $R^{6a}$ is H, methyl, ethyl, n-propyl, isopropyl, 1-methylpropyl, 2-methylpropyl or tert-butyl, wherein each of the methyl, ethyl, n-propyl, isopropyl, 1-methylpropyl, 2-methylpropyl and tert-butyl is independently and optionally substituted with 1, 2, 3, 4, 5 or 6 substituents selected from F, Cl, Br, hydroxy, amino, carboxy, cyano, cyclohexyl, cyclopentyl, cyclobutyl, cyclopropyl, phenyl, pyridyl, thiazolyl, diazolyl, triazolyl, piperidyl, furyl, tetrahydrofuryl, azetanyl, oxetanyl and morpholinyl:

In some embodiments, each $R^{12}$ and $R^{12a}$ is independently H, methyl, ethyl, n-propyl, isopropyl, 1-methylpropyl, 2-methylpropyl or tert-butyl, wherein each of the methyl, ethyl, n-propyl, isopropyl, 1-methylpropyl, 2-methylpropyl and tert-butyl is independently and optionally substituted with 1, 2, 3, 4, 5 or 6 substituents selected from F, Cl, Br, hydroxy, amino, carboxy, cyano, cyclohexyl, cyclopentyl, cyclobutyl, cyclopropyl, phenyl, pyridyl, thiazolyl, diazolyl, triazolyl, piperidyl, furyl, tetrahydrofuryl, azetanyl, oxetanyl and morpholinyl.

In some embodiments, each $R^{10}$ and $R^{10a}$ is independently H, methyl, ethyl, n-propyl, isopropyl, 1-methylpropyl, 2-methylpropyl or tert-butyl, wherein each of the methyl, ethyl, n-propyl, isopropyl, 1-methylpropyl, 2-methylpropyl and tert-butyl is independently and optionally substituted with 1, 2, 3, 4, 5 or 6 substituents selected from F, Cl, Br, hydroxy, amino, carboxy, cyano, cyclohexyl, cyclopentyl, cyclobutyl, cyclopropyl, phenyl, pyridyl, thiazolyl, diazolyl, triazolyl, piperidyl, furyl, tetrahydrofuryl, azetanyl, oxetanyl and morpholinyl.

In some embodiments, $R^{8a}$ is H, methyl, ethyl, n-propyl, isopropyl, 1-methylpropyl, 2-methylpropyl or tert-butyl, wherein each of the methyl, ethyl, n-propyl, isopropyl, 1-methylpropyl, 2-methylpropyl and tert-butyl is independently and optionally substituted with 1, 2, 3, 4, 5 or 6 substituents selected from F, Cl, Br, hydroxy, amino, carboxy, cyano, cyclohexyl, cyclopentyl, cyclobutyl, cyclopropyl, phenyl, pyridyl, thiazolyl, diazolyl, triazolyl, piperidyl, furyl, tetrahydrofuryl, azetanyl, oxetanyl and morpholinyl.

In some embodiments, each $R^2$ and $R^{2a}$ is independently H, methyl, ethyl, n-propyl, isopropyl, 1-methylpropyl, 2-methylpropyl or tert-butyl, wherein each of the methyl, ethyl, n-propyl, isopropyl, 1-methylpropyl, 2-methylpropyl and tert-butyl is independently and optionally substituted with 1, 2, 3, 4, 5 or 6 substituents selected from F, Cl, Br, hydroxy, amino, carboxy, cyano, cyclohexyl, cyclopentyl, cyclobutyl, cyclopropyl, phenyl, pyridyl, thiazolyl, diazolyl, triazolyl, piperidyl, furyl, tetrahydrofuryl, azetanyl, oxetanyl and morpholinyl;

or, $R^2$ and $R^{2a}$, together with the carbon atom to which they are attached, form a cyclohexyl, cyclopentyl, cyclobutyl, cyclopropyl, cycloheptyl, piperidyl, pyrrolidyl, piperazinyl, tetrahydropyranyl, morpholinyl or tetrahydrofuryl group, wherein each of the cyclohexyl, cyclopentyl, cyclobutyl, cyclopropyl, cycloheptyl, piperidyl, pyrrolidyl, piperazinyl, tetrahydropyranyl, morpholinyl and tetrahydrofuryl is independently and optionally substituted with 1, 2, 3, 4 or 5 substituents selected from $C_{1-4}$ alkyl, $C_{2-4}$ alkenyl, $C_{1-4}$ hydroxyalkyl, $C_{1-4}$ haloalkyl, hydroxy, amino, carboxy, cyano, F, Cl and Br.

In some embodiments, each $R^3$ and $R^{3a}$ is independently H, methyl, ethyl, n-propyl, isopropyl, 1-methylpropyl, 2-methylpropyl or tert-butyl, wherein each of the methyl, ethyl, n-propyl, isopropyl, 1-methylpropyl, 2-methylpropyl and tert-butyl is independently and optionally substituted with 1, 2, 3, 4, 5 or 6 substituents selected from F, Cl, Br, hydroxy, amino, carboxy, cyano, cyclohexyl, cyclopentyl, cyclobutyl, cyclopropyl, phenyl, pyridyl, thiazolyl, diazolyl, triazolyl, piperidyl, furyl, tetrahydrofuryl, azetanyl, oxetanyl and morpholinyl;

or, $R^3$ and $R^{3a}$, together with the carbon atom to which they are attached, form a >C(=O), cyclohexyl, cyclopentyl, cyclobutyl, cyclopropyl, cycloheptyl, piperidyl, pyrrolidyl, piperazinyl, tetrahydropyranyl, morpholinyl or tetrahydrofuryl group, wherein each of the cyclohexyl, cyclopentyl, cyclobutyl, cyclopropyl, cycloheptyl, piperidyl, pyrrolidyl, piperazinyl, tetrahydropyranyl, morpholinyl and tetrahydrofuryl is independently and optionally substituted with 1, 2, 3, 4 or 5 substituents selected from $C_{1-4}$ alkyl, $C_{1-4}$ hydroxyalkyl, $C_{1-4}$ haloalkyl, hydroxy, amino, carboxy, cyano and halogen.

In some embodiments, $R^1$ is $C_{6-10}$ aryl, $C_{1-9}$ heteroaryl, $C_{3-12}$ cycloalkyl or $C_{2-12}$ heterocyclyl, wherein each $R^1$ is independently and optionally substituted with 1, 2, 3 or 5 $R^{1a}$ which are the same or different; wherein $R^{1a}$ is as defined herein.

In some embodiments, each $R^{1a}$ is independently H, $C_{1-6}$ alkyl, $C_{1-6}$ haloalkyl, halogen, cyano, oxo (=O), $C_{1-6}$ alkoxy, $C_{6-10}$ aryl, $C_{1-9}$ heteroaryl, $C_{3-12}$ cycloalkyl, $C_{2-12}$ heterocyclyl, —$SR^{14}$, —$OR^{14}$, —$SO_2$—$N(R^{13})(R^{13a})$, —$N(R^{13a})$—$SO_2$—$R^{14}$, —$N(R^{13})(R^{13a})$, —C(=O)—C(=O)—$N(R^{13})(R^{13a})$, —C(=O)—$N(R^{13})(R^{13a})$, —C(=N—OH)($R^{14a}$), —$N(R^{13})$—C(=O)$R^{14a}$, —C(=O)—$OR^{14}$, —C(=O)—$R^{14a}$ or —$SO_2R^{14}$, wherein each $R^{1a}$ is independently and optionally substituted with 1, 2, 3, 4 or 5 $R^{1b}$ which are the same or different; wherein $R^{1b}$ is as defined herein;

$R^{1b}$, $R^{13}$, $R^{13a}$, $R^{14}$ and $R^{14a}$ are as defined herein.

In some embodiments, each $R^{1b}$ is independently H, $C_{1-6}$ alkyl, $C_{1-6}$ haloalkyl, $C_{2-6}$ alkenyl, $C_{2-6}$ alkynyl, $C_{1-6}$ alkoxy, halogen, nitro, cyano, hydroxy, oxo (=O), —$OR^{15}$, —$SO_2R^{15}$, —$N(R^{16})(R^{16a})$, —C(=O)—$N(R^{16})(R^{16a})$, $C_{6-10}$ aryl, $C_{1-9}$ heteroaryl, $C_{3-12}$ cycloalkyl or $C_{2-12}$ heterocyclyl, wherein each $R^{1b}$ is independently and optionally substituted with 1, 2, 3, 4 or 5 substituents selected from hydroxy, nitro, cyano, $C_{1-6}$ alkyl, $C_{1-6}$ haloalkyl, halogen, oxo (=O), $C_{1-6}$ alkoxy, $C_{6-10}$ aryl, $C_{1-9}$ heteroaryl, $C_{3-12}$ cycloalkyl, $C_{2-12}$ heterocyclyl and amino;

$R^{15}$, $R^{16}$ and $R^{16a}$ are as defined herein.

In some embodiments, each $R^{16}$ and $R^{16a}$ is independently H, $C_{1-4}$ alkyl, $C_{2-6}$ alkenyl, $C_{2-6}$ alkynyl, $C_{6-10}$ aryl, $C_{1-9}$ heteroaryl, $C_{3-6}$ cycloalkyl, —$SO_2R^{17}$, —$N(R^{18})(R^{18a})$, $C_{1-4}$ haloalkyl or $C_{2-9}$ heterocyclyl;

$R^{17}$, $R^{18}$ and $R^{18a}$ are as defined herein.

In some embodiments, $R^{15}$ is independently H, $C_{1-4}$ alkyl, $C_{1-4}$ haloalkyl, $C_{2-6}$ alkenyl, $C_{2-6}$ alkynyl, phenyl, 5- to 6-membered heteroaryl, $C_{3-6}$ cycloalkyl or 4- to 7-membered heterocyclyl, wherein each of the phenyl, 5- to 6-membered heteroaryl, $C_{3-6}$ cycloalkyl and 4- to 7-membered heterocyclyl is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, each $R^{13}$ and $R^{13a}$ is independently H, $C_{1-4}$ alkyl, $C_{1-4}$ haloalkyl, $C_{2-6}$ alkenyl, $C_{2-6}$ alkynyl, phenyl, 5- to 6-membered heteroaryl, $C_{3-6}$ cycloalkyl or 4- to 7-membered heterocyclyl, wherein each of the phenyl, 5- to 6-membered heteroaryl, $C_{3-6}$ cycloalkyl and 4-7 membered heterocyclyl is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, each $R^{14}$ and $R^{14a}$ is independently H, $C_{1-4}$ alkyl, $C_{1-4}$ haloalkyl, $C_{2-6}$ alkenyl, $C_{2-6}$ alkynyl, phenyl, 5- to 6-membered heteroaryl, $C_{3-6}$ cycloalkyl or 4- to 7-membered heterocyclyl, wherein each of the phenyl, 5- to 6-membered heteroaryl, $C_{3-6}$ cycloalkyl and 4- to 7-membered heterocyclyl is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, $R^{17}$ is independently H, $C_{1-4}$ alkyl, $C_{1-4}$ haloalkyl, $C_{2-6}$ alkenyl, $C_{2-6}$ alkynyl, phenyl, 5- to 6-membered heteroaryl, $C_{3-6}$ cycloalkyl or 4- to 7-membered heterocyclyl, wherein each of the phenyl, 5- to 6-membered heteroaryl, $C_{3-6}$ cycloalkyl and 4-7 membered heterocyclyl is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, each $R^{18}$ and $R^{18a}$ is independently H, $C_{1-4}$ alkyl, $C_{1-4}$ haloalkyl, $C_{2-6}$ alkenyl, $C_{2-6}$ alkynyl, phenyl, 5- to 6-membered heteroaryl, $C_{3-6}$ cycloalkyl or 4- to 7-membered heterocyclyl, wherein each of the phenyl, 5- to 6-membered heteroaryl, $C_{3-6}$ cycloalkyl and 4- to 7-membered heterocyclyl is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, $R^1$ is one of the following sub-formulae:

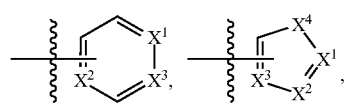

-continued

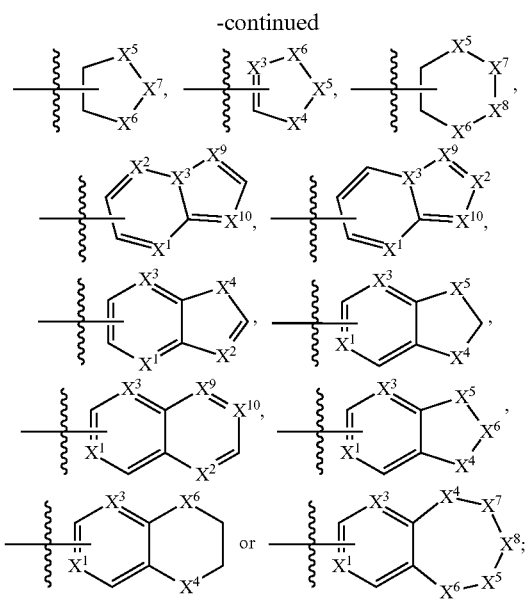

wherein, each $X^1$, $X^2$, $X^3$, $X^9$ and $X^{10}$ is independently CH or N;

each $X^4$, $X^5$, $X^6$, $X^7$ and $X^8$ is independently —CH$_2$—, —C(=O)—, —O—, —S—, —S(=O)—, —S(=O)$_2$— or —NH—;

$R^1$ is independently and optionally substituted with 1, 2, 3, 4 or 5 $R^{1a}$ which are the same or different; wherein $R^{1a}$ is as defined herein.

In some embodiments, each $R^{1a}$ is independently H, $C_{1-4}$ alkyl, $C_{1-4}$ haloalkyl, halogen, cyano, oxo (=O), $C_{1-4}$ alkoxy, —SR$^{14}$, —OR$^{14}$, —SO$_2$—N(R$^{13}$)(R$^{13a}$), —N(R$^{13a}$)—SO$_2$—R$^{14}$, —N(R$^{13}$)(R$^{13a}$), —C(=O)—C(=O)—N(R$^{13}$)(R$^{13a}$), —C(=O)—N(R$^{13}$)(R$^{13a}$), —C(=N—OH)(R$^{14a}$), —N(R$^{13}$)—C(=O)R$^{14a}$, —C(=O)—OR$^{14}$, —C(=O)—R$^{14a}$ or —SO$_2$R$^{14}$, or one of the following sub-formulae:

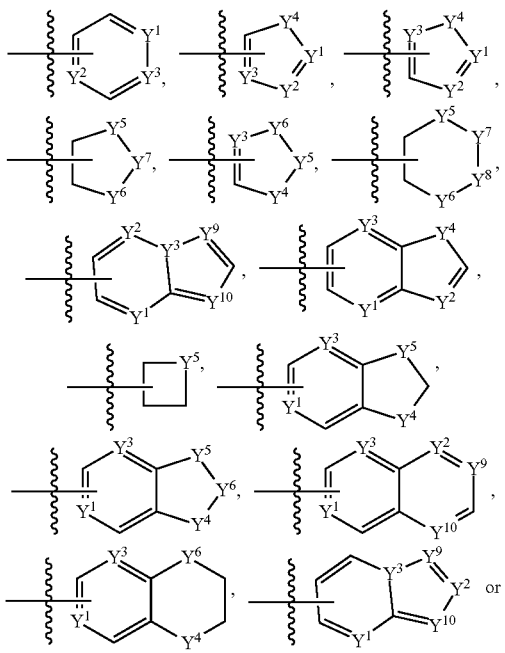

-continued

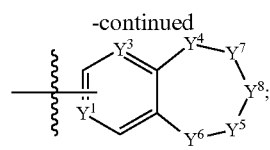

wherein, each $Y^1$, $Y^2$, $Y^3$, $Y^9$ and $Y^{10}$ is independently CH or N;

each $Y^4$, $Y^5$, $Y^6$, $Y^7$ and $Y^8$ is independently —CH$_2$—, —C(=O)—, —O—, —S—, —S(=O)—, —S(=O)$_2$— or —NH—;

each $R^{1a}$ in independently and optionally substituted with 1, 2, 3, 4 or 5 $R^{1b}$ which are the same or different;

$R^{1b}$, $R^{13}$, $R^{13a}$, $R^{14}$ and $R^{14a}$ are as defined herein.

In some embodiments, each $R^{1b}$ is independently H, $C_{1-4}$ alkyl, $C_{1-4}$ haloalkyl, $C_{2-6}$ alkenyl, $C_{2-6}$ alkynyl, $C_{1-4}$ alkoxy, halogen, nitro, cyano, hydroxy, oxo (=O), —OR$^{15}$, —SO$_2$R$^{15}$, —N(R$^{16}$)(R$^{16a}$), —C(=O)—N(R$^{16}$)(R$^{16a}$), or one of the following sub-formulae:

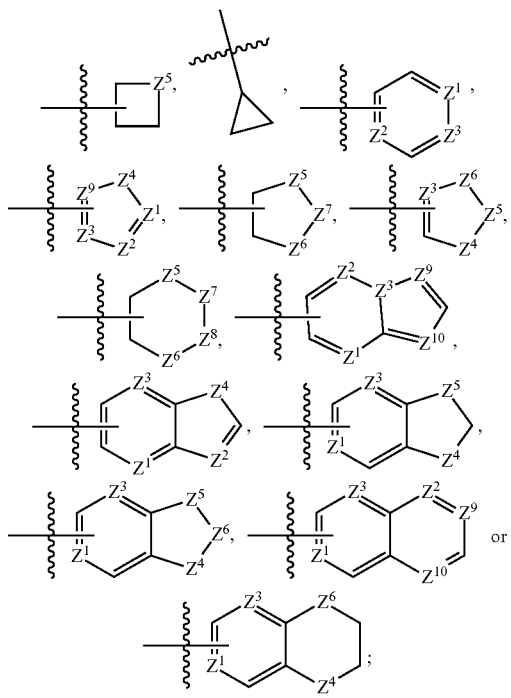

wherein, each $Z^1$, $Z^2$, $Z^3$, $Z^9$ and $Z^{10}$ is independently CH or N;

each $Z^1$, $Z^5$, $Z^6$, $Z^7$ and $Z^8$ is independently —CH$_2$—, —C(=O)—, —O—, —S—, —S(=O)—, —S(=O)$_2$— or —NH—;

each $R^{1b}$ is independently and optionally substituted with 1, 2, 3, 4 or 5 substituents selected from hydroxy, nitro, cyano, $C_{1-4}$ alkyl, $C_{1-4}$ haloalkyl, halogen, oxo (=O), $C_{1-4}$ alkoxy, phenyl, 5- to 6-membered heteroaryl, 4- to 7-membered cycloalkyl, 4- to 7-membered heterocyclyl and amino; wherein $R^{15}$, $R^{16}$ and $R^{16a}$ are as defined herein.

In some embodiments, each $R^{16}$ and $R^{16a}$ is independently H, $C_{1-4}$ alkyl, $C_{2-6}$ alkenyl, $C_{2-6}$ alkynyl, $C_{6-10}$ aryl, $C_{1-9}$ heteroaryl, $C_{3-6}$ cycloalkyl, —SO$_2$R$^{17}$, —N(R$^{18}$)(R$^{18a}$), $C_{1-4}$ haloalkyl or $C_{2-6}$ heterocyclyl; $R^{17}$, $R^{18}$ and $R^{18a}$ are as defined herein.

In some embodiments, $R^{15}$ is H, $C_{1-4}$ alkyl, $C_{1-4}$ haloalkyl, $C_{2-6}$ alkenyl, $C_{2-6}$ alkynyl, phenyl, 5- to 6-membered heteroaryl, $C_{3-6}$ cycloalkyl or 4 to 6-membered heterocyclyl, wherein each of the phenyl, 5- to 6-membered heteroaryl, $C_{3-6}$ cycloalkyl and 4- to 6-membered heterocyclyl is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, each $R^{13}$ and $R^{13a}$ is independently H, $C_{1-4}$ alkyl, $C_{1-4}$ haloalkyl, $C_{2-6}$ alkenyl, $C_{2-6}$ alkynyl, phenyl, 5- to 6-membered heteroaryl, $C_{3-6}$ cycloalkyl or 4- to 6-membered heterocyclyl, wherein each of the phenyl, 5- to 6-membered heteroaryl, $C_{3-6}$ cycloalkyl and 4- to 6-membered heterocyclyl is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, each $R^{14}$ and $R^{14a}$ is independently H, $C_{1-4}$ alkyl, $C_{1-4}$ haloalkyl, $C_{2-6}$ alkenyl, $C_{2-6}$ alkynyl, phenyl, 5- to 6-membered heteroaryl, $C_{3-6}$ cycloalkyl or 4- to 6-membered heterocyclyl, wherein each of the phenyl, 5- to 6-membered heteroaryl, $C_{3-6}$ cycloalkyl and 4- to 6-membered heterocyclyl is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, $R^{17}$ is independently H, $C_{1-4}$ alkyl, $C_{1-4}$ haloalkyl, $C_{2-6}$ alkenyl, $C_{2-6}$ alkynyl, phenyl, 5- to 6-membered heteroaryl, $C_{3-6}$ cycloalkyl or 4- to 6-membered heterocyclyl, wherein each of the phenyl, 5- to 6-membered heteroaryl, $C_{3-6}$ cycloalkyl and 4- to 6-membered heterocyclyl is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, each $R^{18}$ and $R^{18a}$ is independently H, $C_{1-4}$ alkyl, $C_{1-4}$ haloalkyl, $C_{2-6}$ alkenyl, $C_{2-6}$ alkynyl, phenyl, 5- to 6-membered heteroaryl, $C_{3-6}$ cycloalkyl or 4- to 6-membered heterocyclyl, wherein each of the phenyl, 5- to 6-membered heteroaryl, $C_{3-6}$ cycloalkyl and 4- to 6-membered heterocyclyl is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, $R^1$ is one of the following sub-formulae:

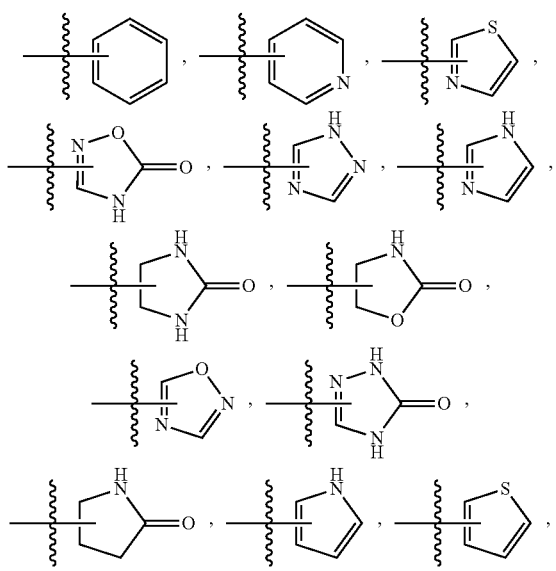

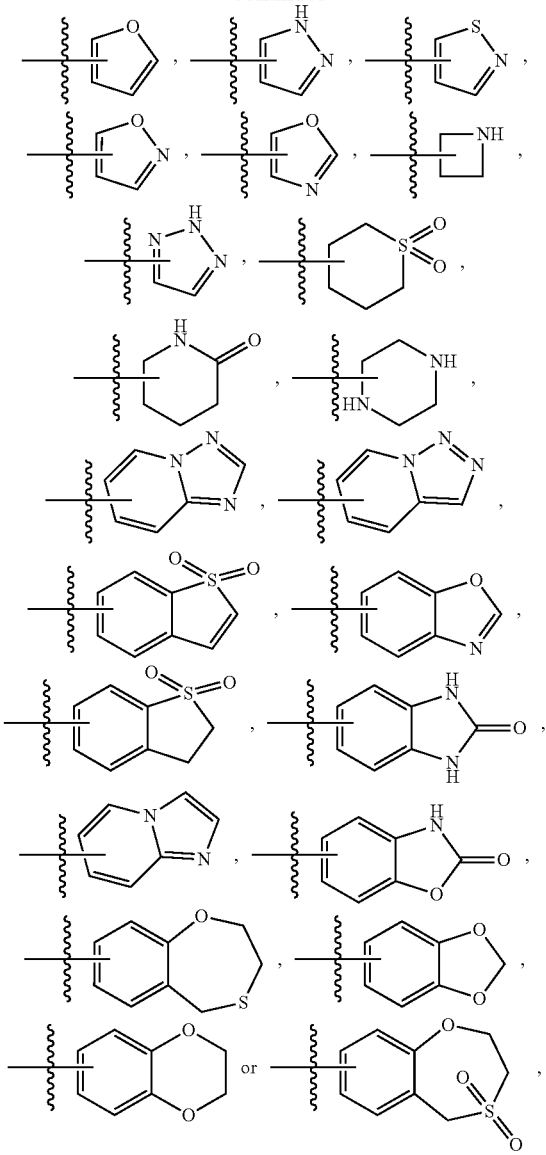

wherein each $R^1$ is independently and optionally substituted with 1, 2, 3, 4 or 5 $R^{1a}$ which are the same or different;

$R^{1a}$ is as defined herein.

In some embodiments, each $R^{1a}$ is independently H, ethyl, methyl, n-propyl, i-propyl, n-butyl, t-butyl, cyano, trifluoromethyl, 2,2-difluoroethyl, 3,3,3-trifluoropropyl, F, Cl, Br, oxo (=O), methoxy, n-propoxy, ethoxy, t-butoxy, 2-methylpropoxy, i-propoxy, —$SR^{14}$, —$OR^{14}$, —$SO_2$—$N(R^{13})(R^{13a})$, —$N(R^{13a})$—$SO_2$—$R^{14}$, —$N(R^{13})(R^{13a})$, —C(=O)—C(=O)—$N(R^{13})(R^{13a})$, —C(=O)—$N(R^{13})(R^{13a})$, —C(=N—OH)($R^{14a}$), —$N(R^{13})$—C(=O)$R^{14a}$, —C(=O)—$OR^{14}$, —C(=O)—$R^{14a}$, —$SO_2R^{14}$, or one of the following sub-formulae:

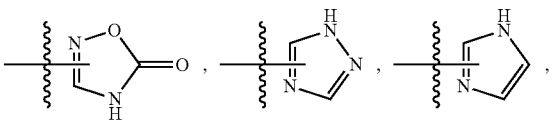

-continued

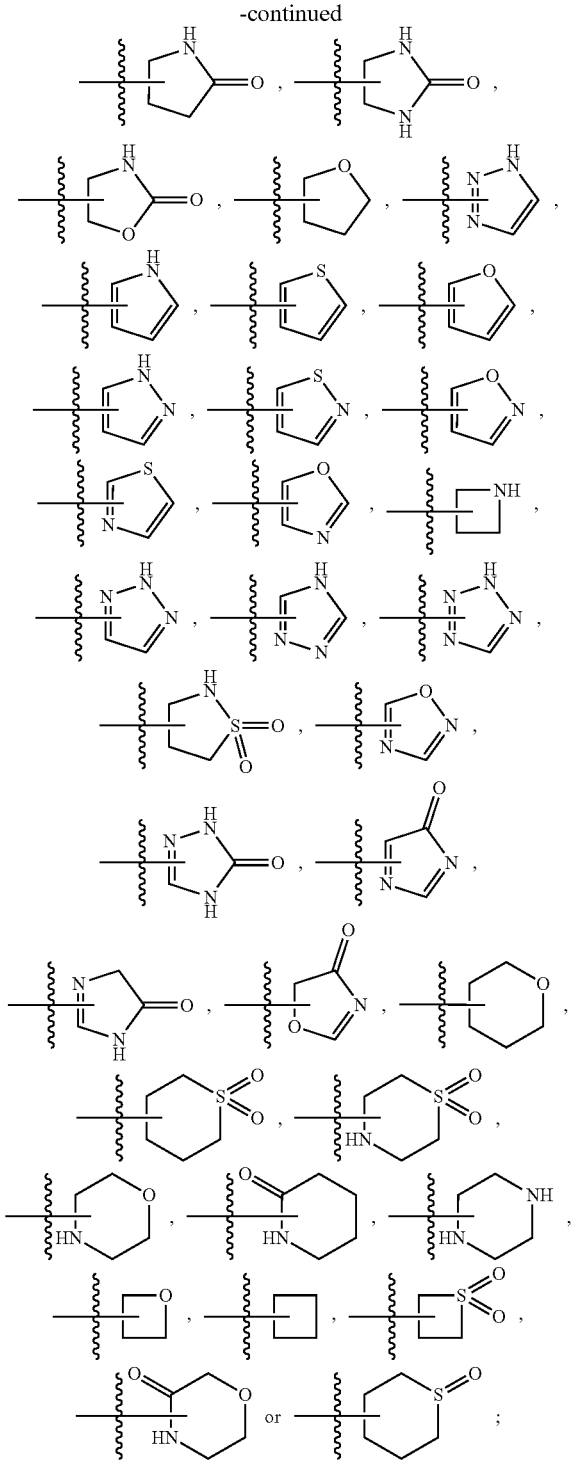

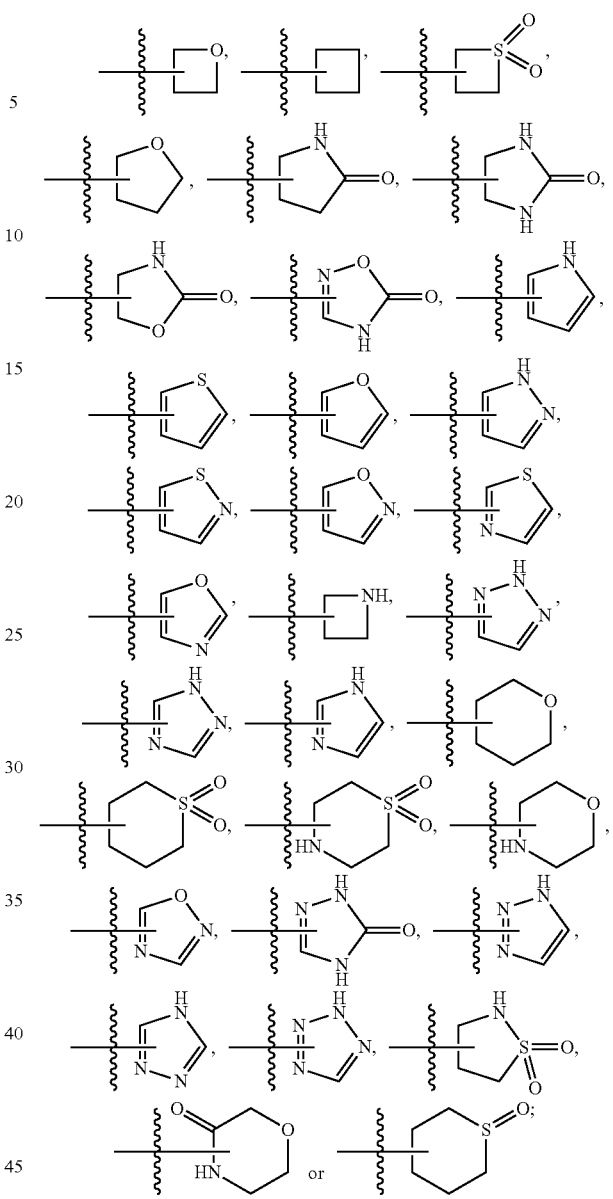

wherein each $R^{1a}$ is independently and optionally substituted with 1, 2, 3, 4 or 5 $R^{1b}$ which are the same or different;

$R^{1b}$, $R^{13}$, $R^{13a}$, $R^{14}$ and $R^{14a}$ are as defined herein.

In some embodiments, each $R^{1b}$ is independently H, methyl, ethyl, n-propyl, i-propyl, n-butyl, t-butyl, cyclopropyl, cyclohexyl, cyclopentyl, $C_{1-4}$ haloalkyl, $C_{2-6}$ alkenyl, $C_{2-6}$ alkynyl, methoxy, F, Cl, Br, nitro, cyano, hydroxy, oxo (=O), —$OR^{15}$, —$SO_2R^{15}$, —$N(R^{16})(R^{16a})$, —C(=O)—N$(R^{16})(R^{16a})$, or one of the following sub-formulae:

wherein each $R^{1b}$ is independently and optionally substituted with 1, 2, 3, 4 or 5 substituents selected from hydroxy, nitro, cyano, methyl, ethyl, n-propyl, i-propyl, n-butyl, t-butyl, $C_{1-4}$ haloalkyl, F, Cl, Br, oxo (=O), $C_{1-4}$ alkoxy, phenyl, pyridyl, thiazolyl, thienyl, diazolyl, triazolyl, tetrazolyl, epoxypropyl, tetrahydrofuryl, tetrahydropyranyl, morpholinyl, piperdyl, cyclobutyl, cyclopentyl, dioxanyl, cyclohexyl and amino;

$R^{15}$, $R^{16}$ and $R^{16a}$ are as defined herein.

In some embodiments, each $R^{16}$ and $R^{16a}$ is independently H, $C_{1-4}$ alkyl, $C_{2-6}$ alkenyl, $C_{2-6}$ alkynyl, phenyl, —$SO_2R^{17}$, —$N(R^{18})(R^{18a})$, $C_{1-4}$ haloalkyl, cyclopropyl, cyclohexyl,

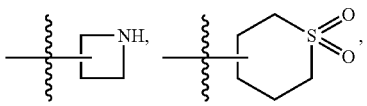

-continued

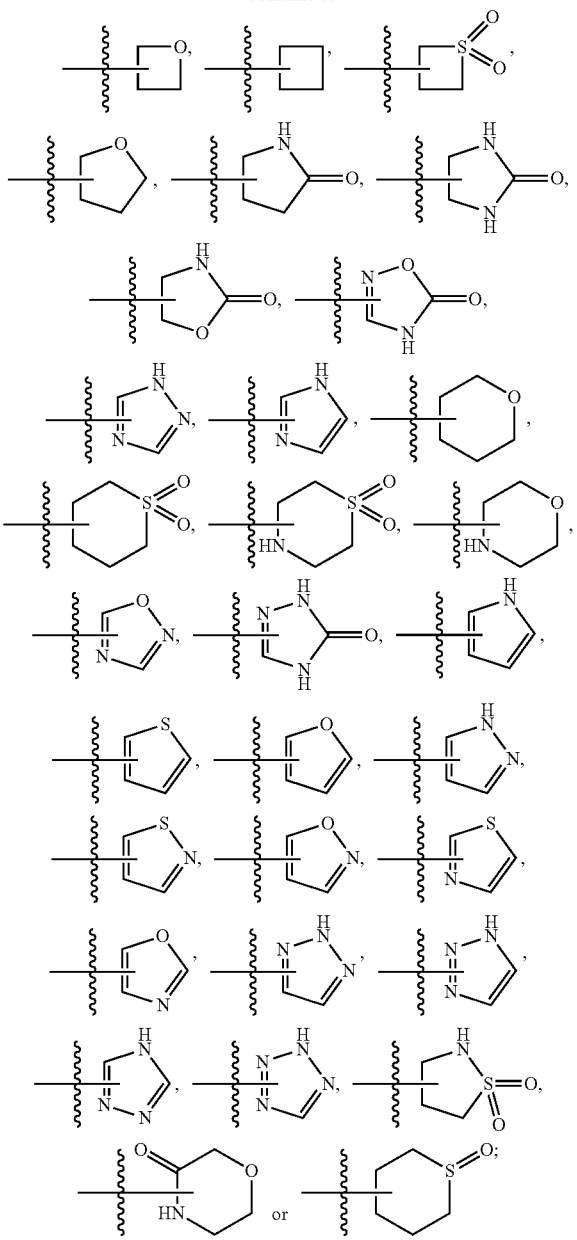

$R^{17}$, $R^{18}$ and $R^{18a}$ are as defined herein.

In some embodiments, $R^{15}$ is H, methyl, ethyl, n-propyl, i-propyl, n-butyl, 2-methylpropyl, t-butyl, trifluoromethyl, difluoromethyl, 2,2-difluoroethyl, 3,3,3-trifluoropropyl, phenyl, cyclopropyl, cyclohexyl,

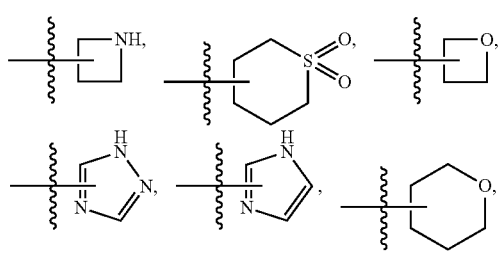

-continued

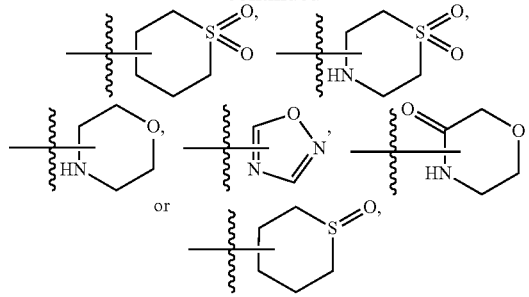

wherein each sub-formula is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, each $R^{13}$ and $R^{13a}$ is independently H, methyl, ethyl, n-propyl, i-propyl, n-butyl, 2-methylpropyl, t-butyl, trifluoromethyl, difluoromethyl, 2,2-difluoroethyl, 3,3,3-trifluoropropyl, phenyl, cyclopropyl, cyclohexyl,

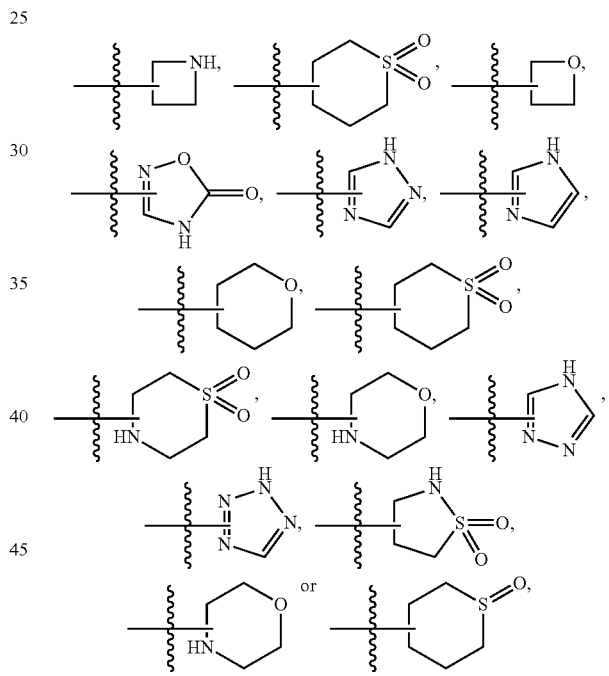

wherein each sub-formula is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, each $R^{14}$ and $R^{14a}$ is independently H, methyl, ethyl, n-propyl, i-propyl, n-butyl, 2-methylpropyl, t-butyl, trifluoromethyl, difluoromethyl, 2,2-difluoroethyl, 3,3,3-trifluoropropyl, phenyl, cyclopropyl, cyclohexyl,

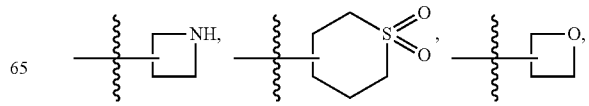

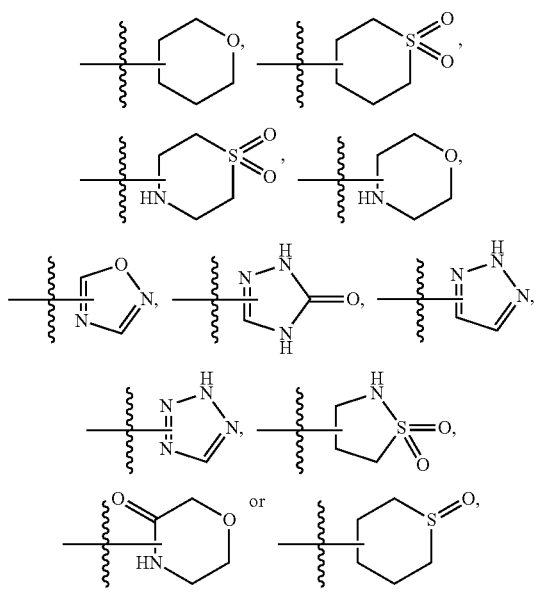

wherein each sub-formula is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, $R^{17}$ is H, methyl, ethyl, n-propyl, i-propyl, n-butyl, 2-methylpropyl, t-butyl, trifluoromethyl, difluoromethyl, 2,2-difluoroethyl, 3,3,3-trifluoropropyl, phenyl, cyclopropyl, cyclohexyl,

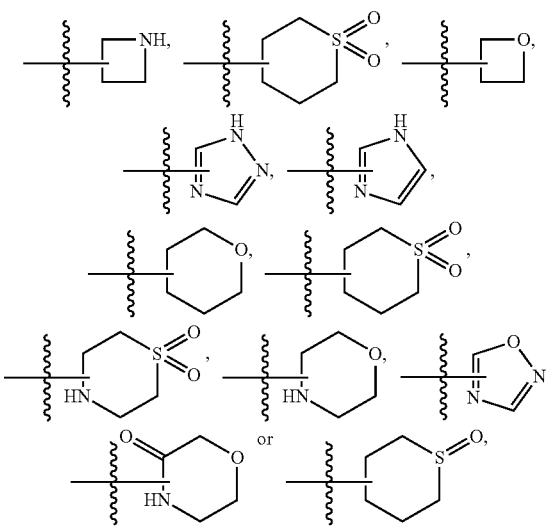

wherein each sub-formula is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, each $R^{18}$ and $R^{18a}$ is independently H, methyl, ethyl, n-propyl, i-propyl, n-butyl, 2-methylpropyl, t-butyl, trifluoromethyl, difluoromethyl, 2,2-difluoroethyl, 3,3,3-trifluoropropyl, phenyl, cyclopropyl, cyclohexyl,

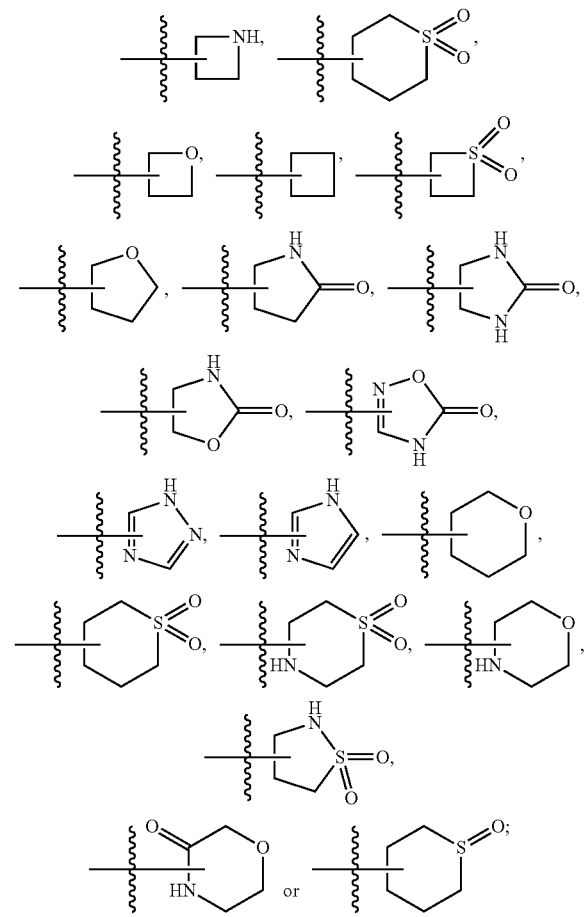

wherein each sub-formula is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

In some embodiments, the compound of the invention has Formula (II) or a stereoisomer, a tautomer, a geometric isomer, an N-oxide or a pharmaceutically acceptable salt thereof, Formula (II)

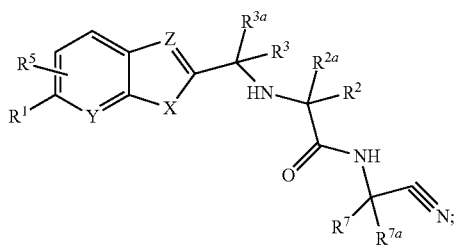

wherein X, Z, Y, $R^{7a}$, $R^7$, $R^{2a}$, $R^2$, $R^{3a}$, $R^3$, $R^1$ and $R^5$ are as defined herein.

In some embodiments, the compound of the invention has Formula (III) or a stereoisomer, a tautomer, a geometric isomer, an N-oxide or a pharmaceutically acceptable salt thereof, Formula (III)

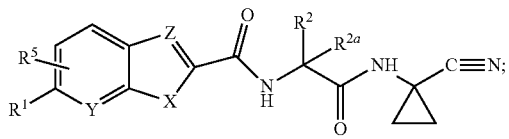

wherein X, Z, Y, $R^{2a}$, $R^2$, $R^1$ and $R^5$ are as defined herein.

In some embodiments, the compound of the invention has Formula (IV) or a stereoisomer, a tautomer, a geometric isomer, an N-oxide or a pharmaceutically acceptable salt thereof, Formula (IV)

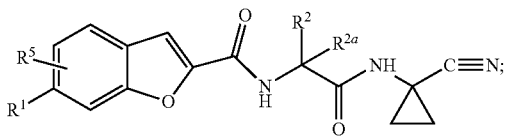

wherein $R^{2a}$, $R^2$, $R^1$ and $R^5$ are as defined herein.

In some embodiments, the invention provides a compound having one of the following structures or a stereoisomer, a geometric isomer, a tautomer, an N-oxide, a hydrate, a solvate, a metabolite, a salt or a pharmaceutically acceptable prodrug thereof, (1)

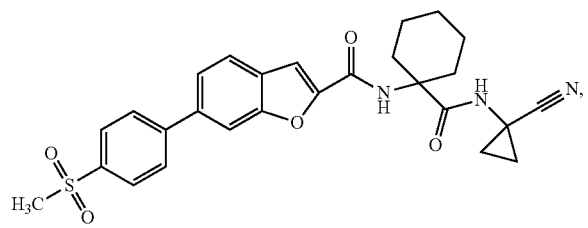

(2)

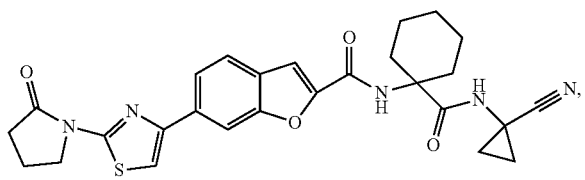

(3)

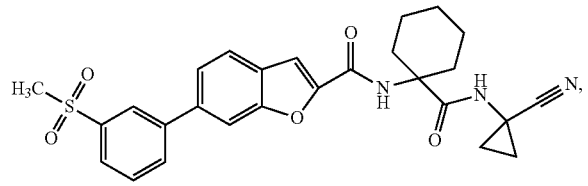

(4)

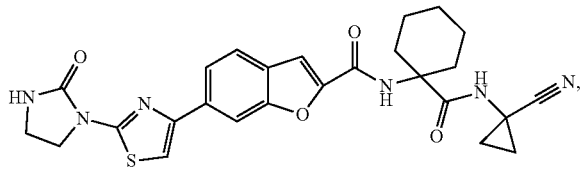

(5)

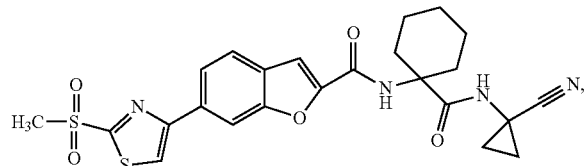

(6)

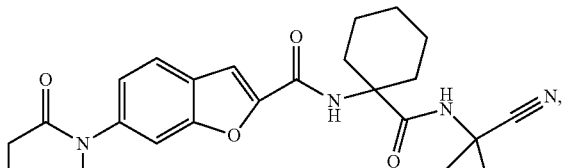

(7)

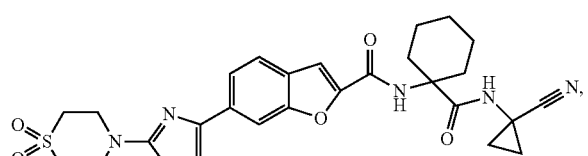

(8)

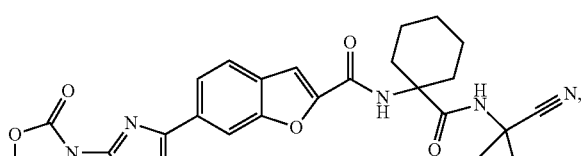

(9)

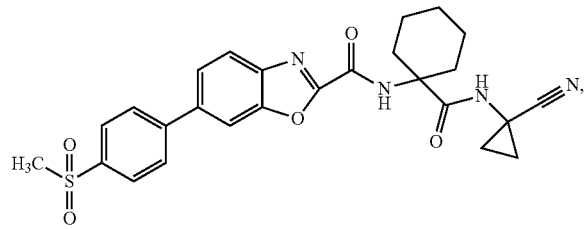

(10)

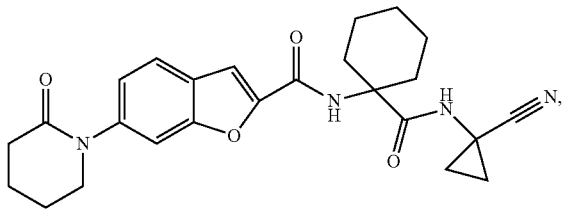

-continued
(11)
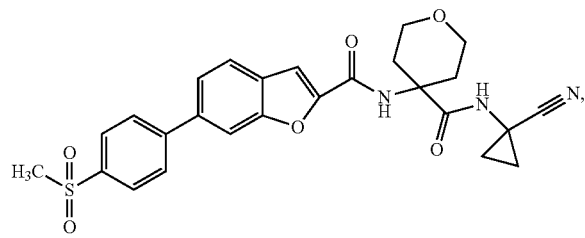
(12)
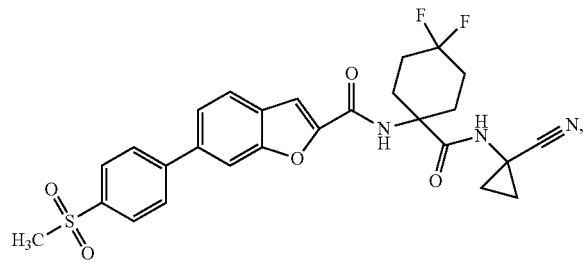
(13)
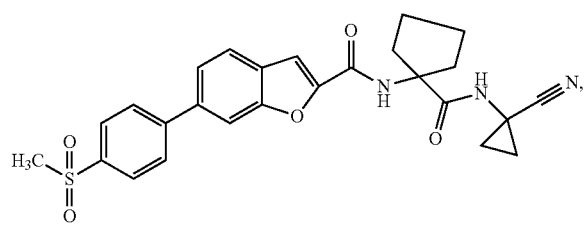
(14)
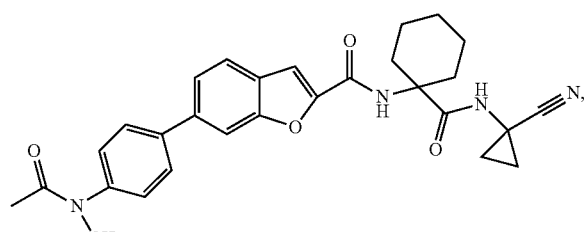
(15)
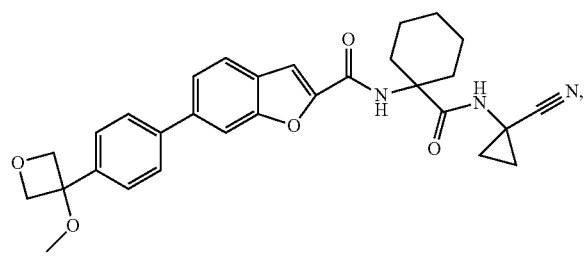
(16)
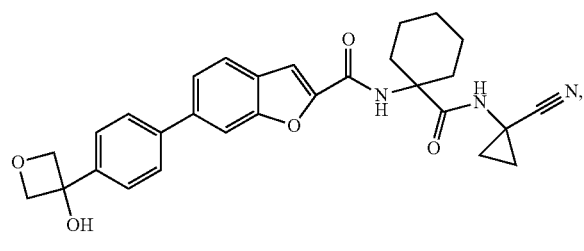
(17)
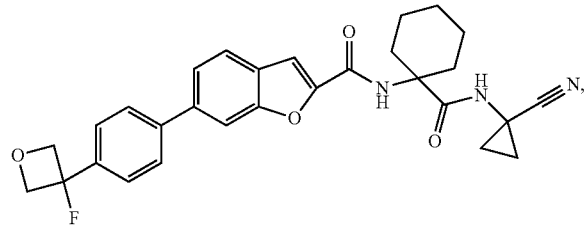
(18)
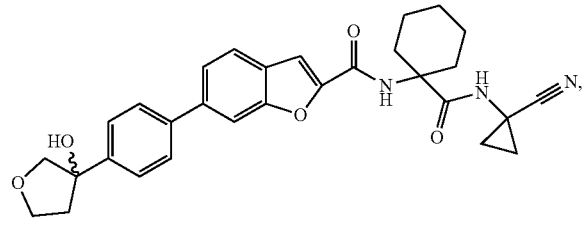
(19)
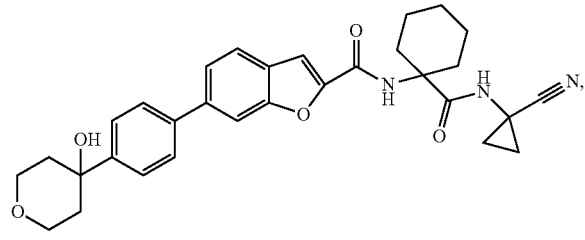
(20)
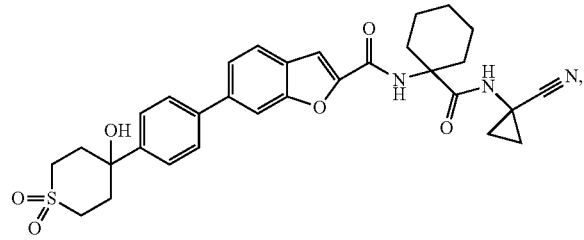
(21)
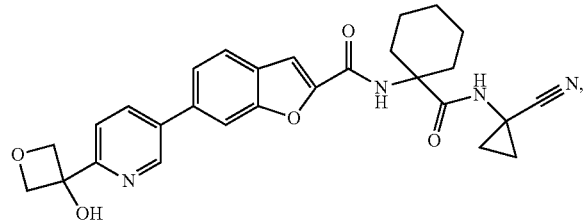
(22)
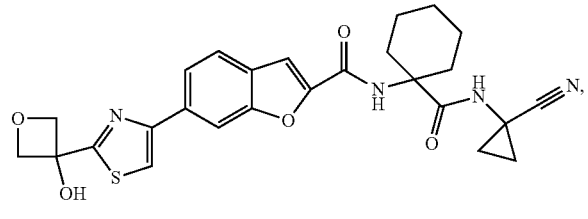

-continued
(23)
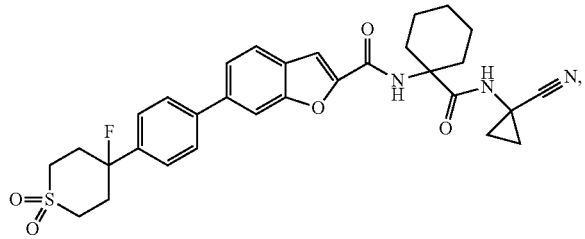
(24)
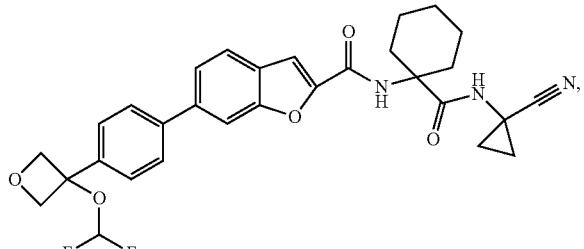
(25)
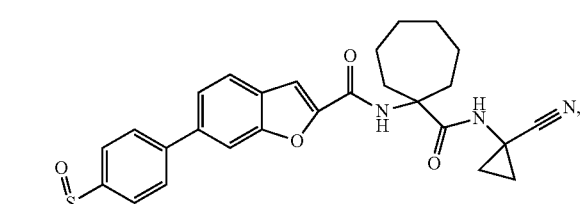
(26)
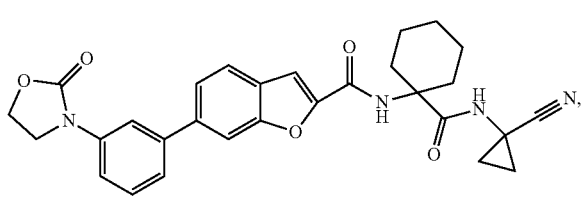
(27)
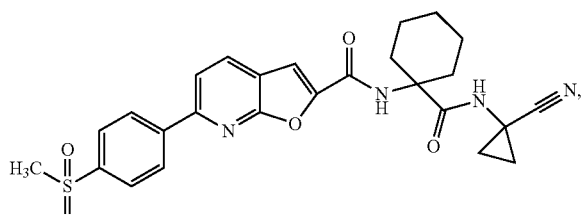
(28)
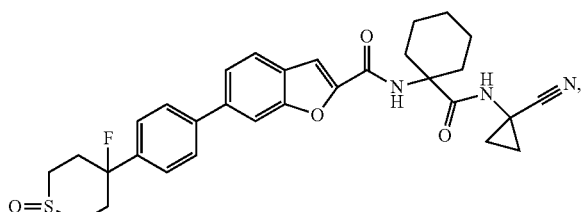
(29)
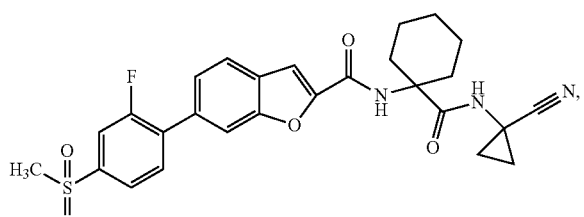
(30)
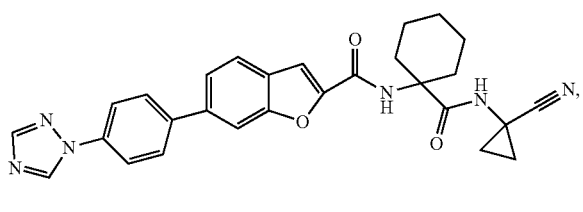
(31)
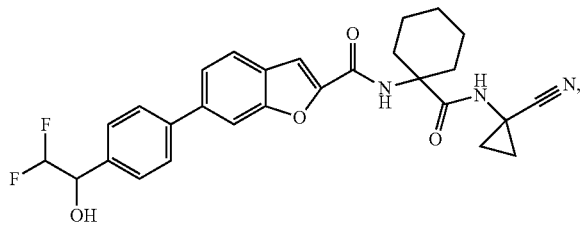
(32)
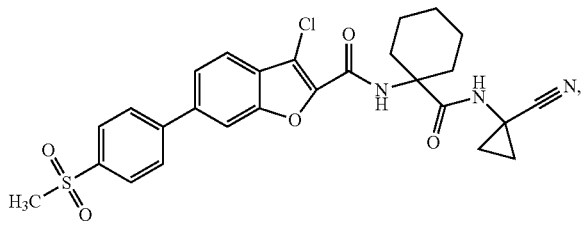
(33)
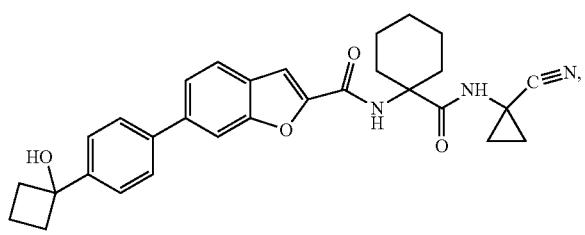
(34)
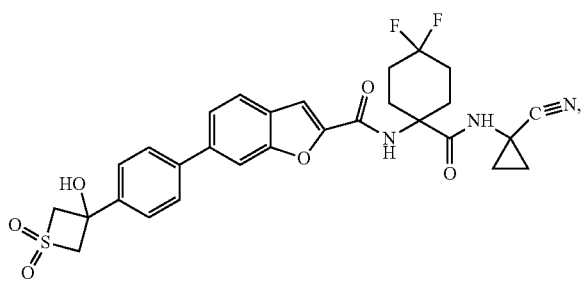

-continued
(35)
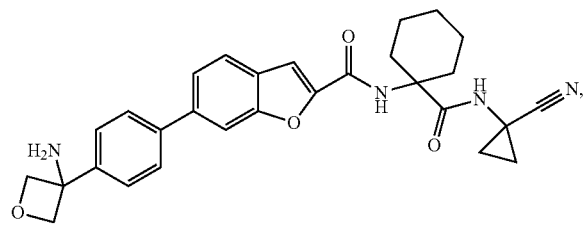
(36)
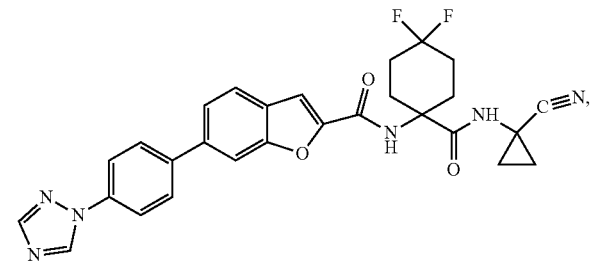
(37)
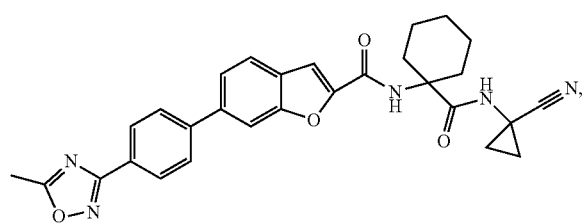
(38)
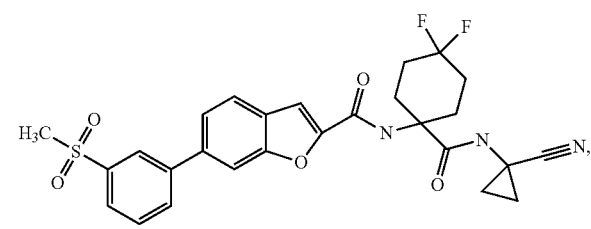
(39)
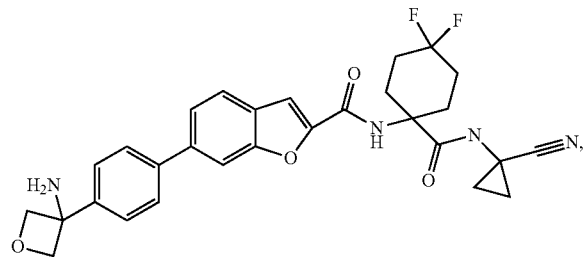
(40)
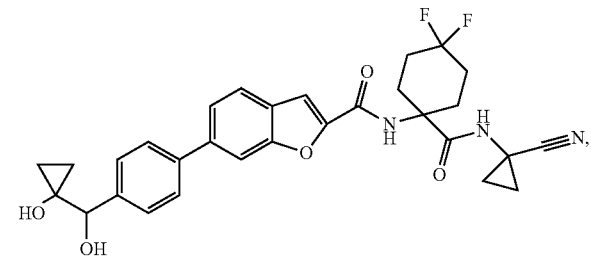
(41)
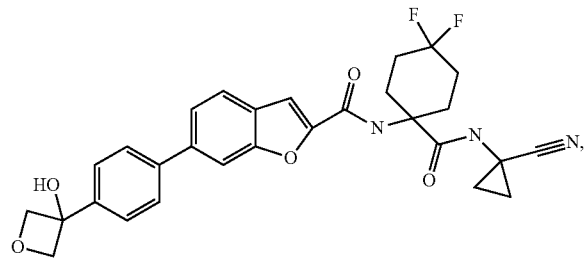
(42)
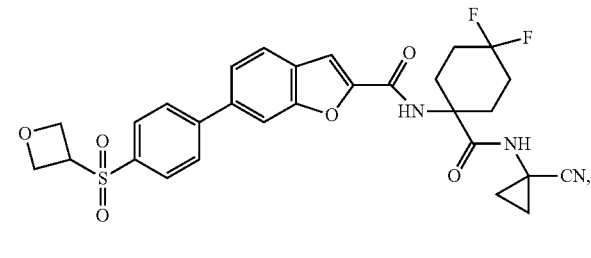
(43)
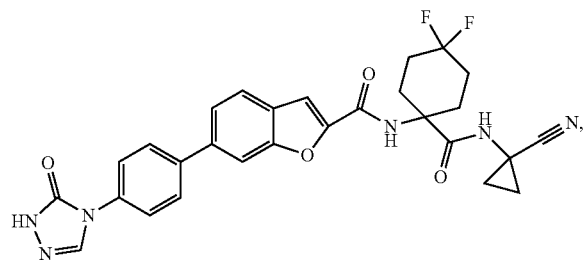
(44)
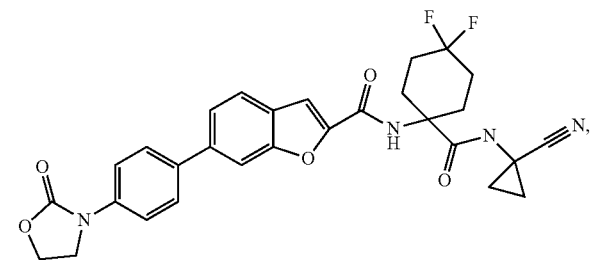

-continued
(45)
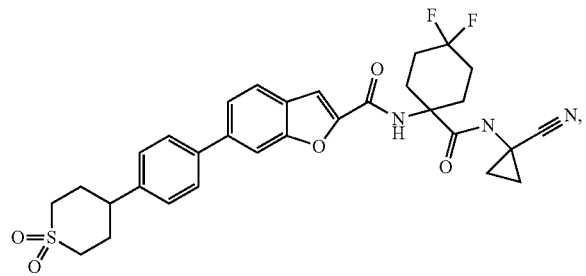
(46)
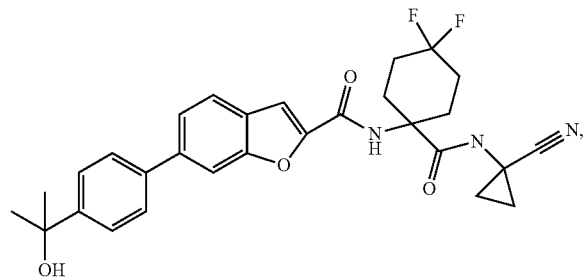
(47)
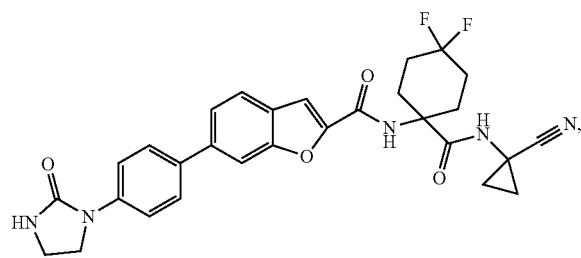
(48)
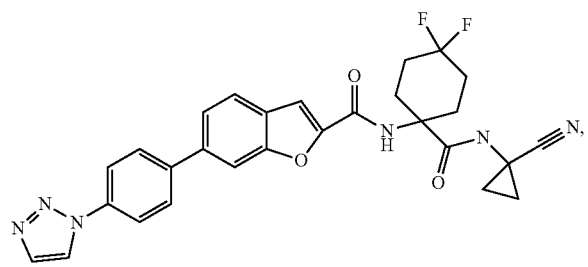
(49)
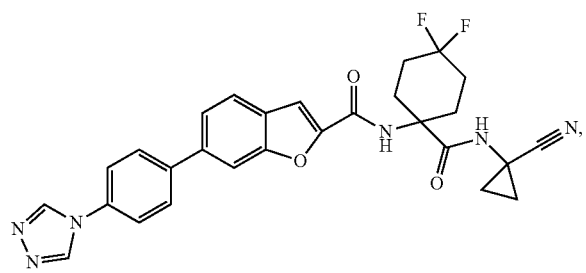
(50)
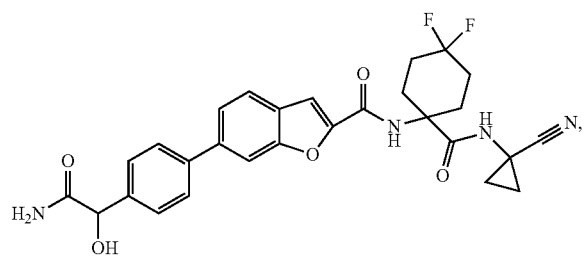
(51)
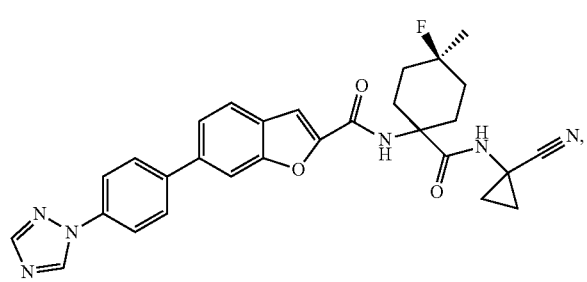
(52)
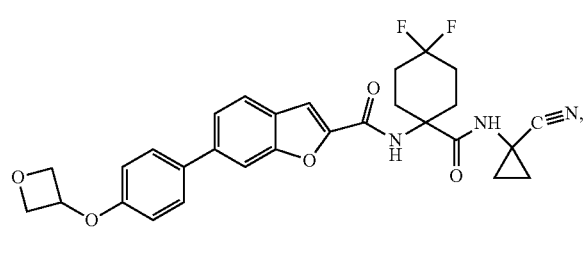
(53)
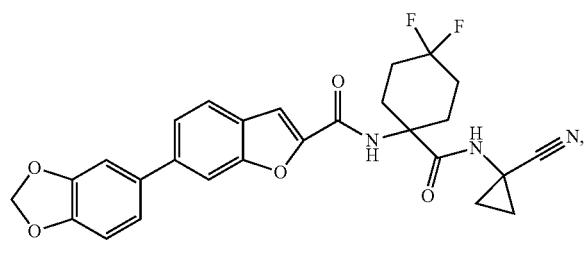
(54)
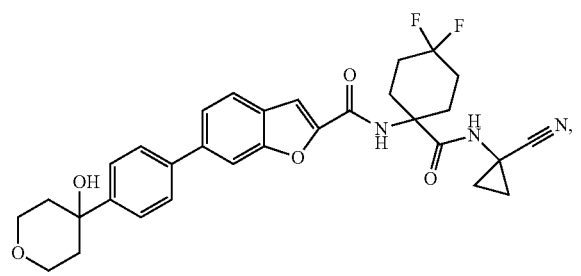

-continued
(55)
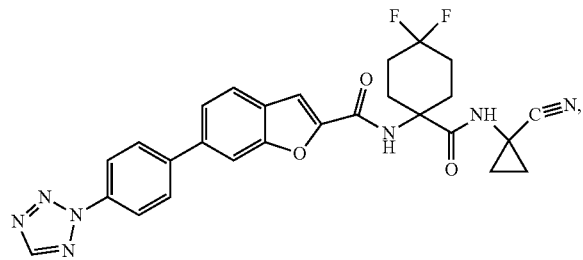
(56)
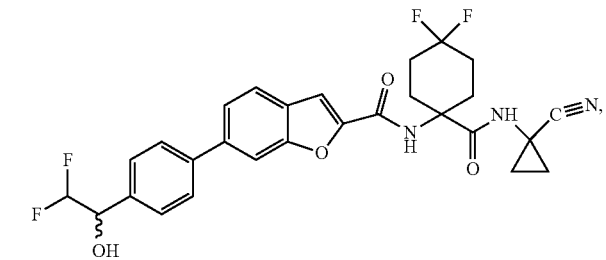
(57)
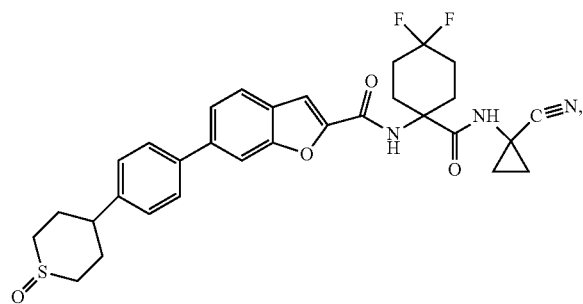
(58)
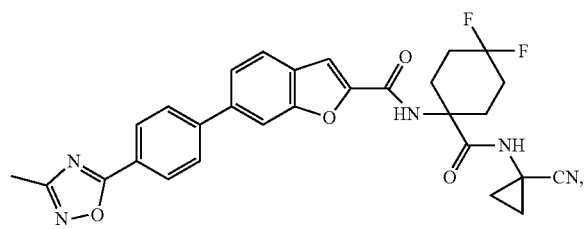
(59)
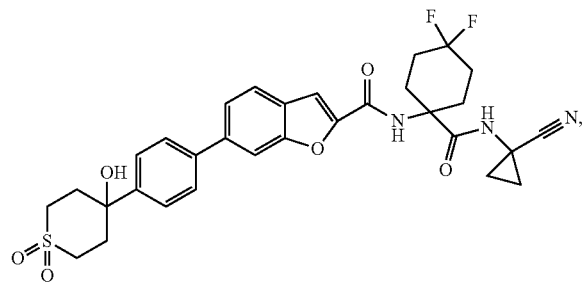
(60)
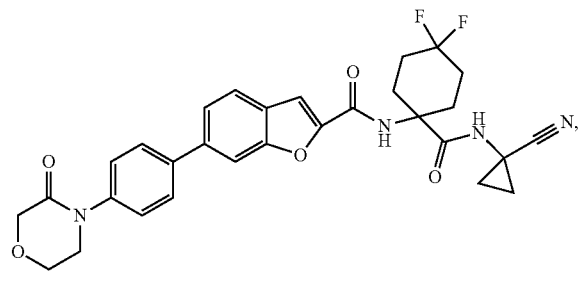
(61)
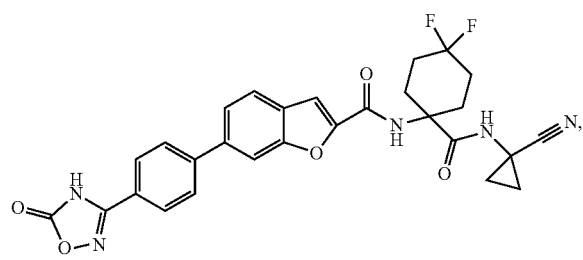
(62)
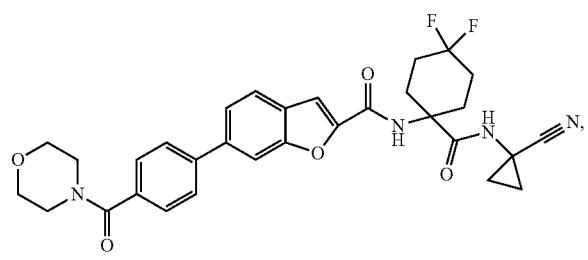
(63)
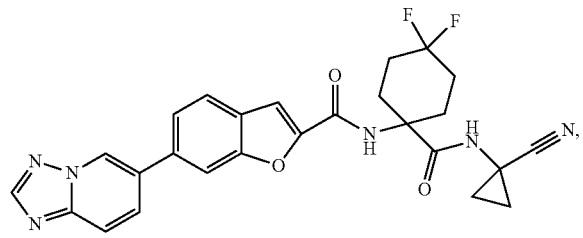
(64)
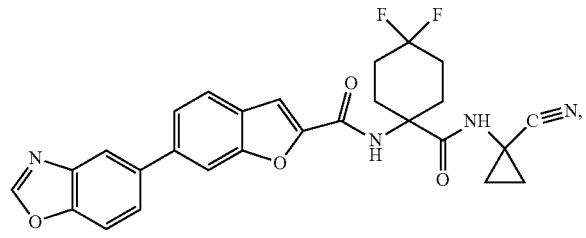

-continued
(65)
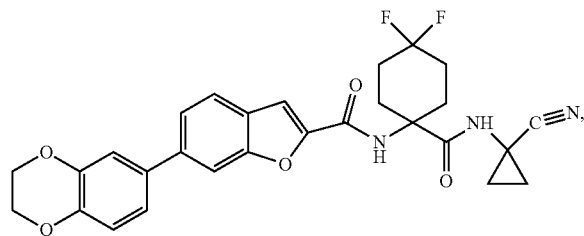
(66)
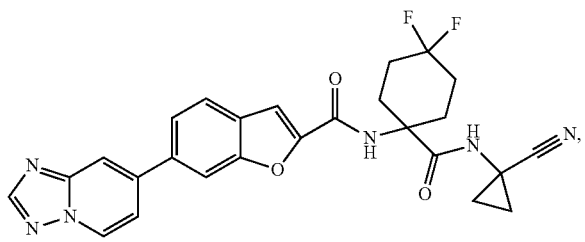
(67)
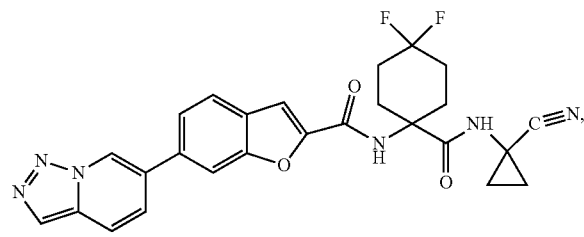
(68)
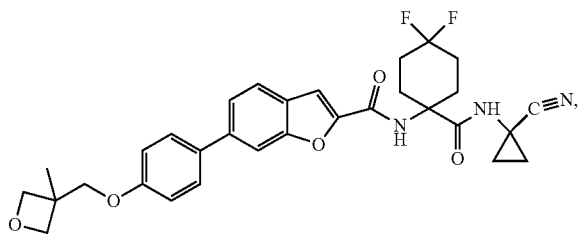
(69)
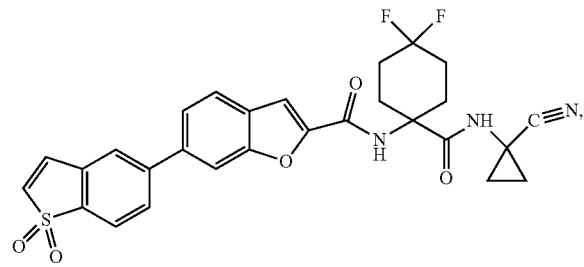
(70)
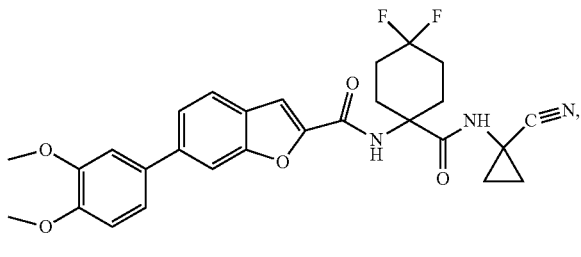
(71)
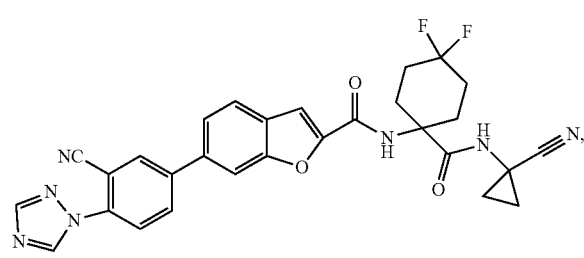
(72)
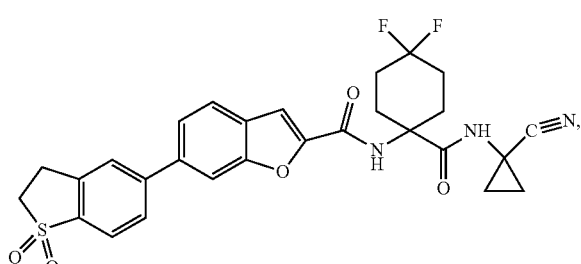
(73)
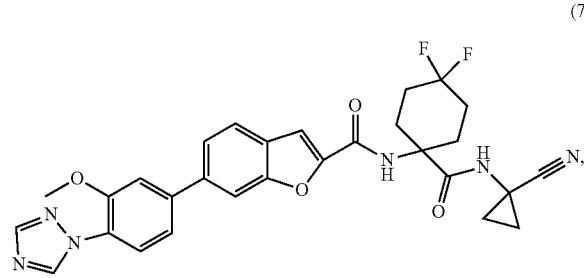
(74)
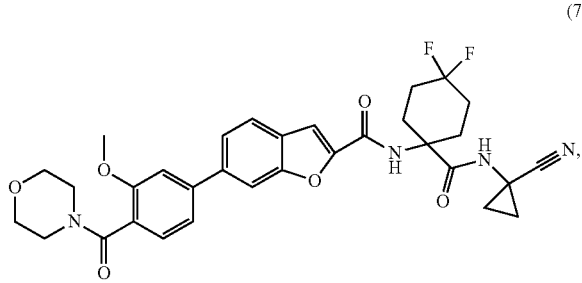
(75)
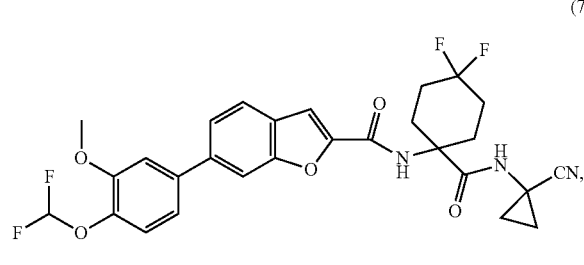
(76)
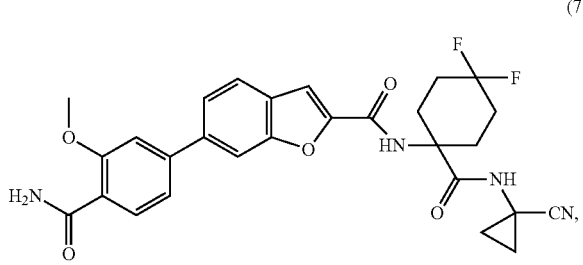

-continued
(77)
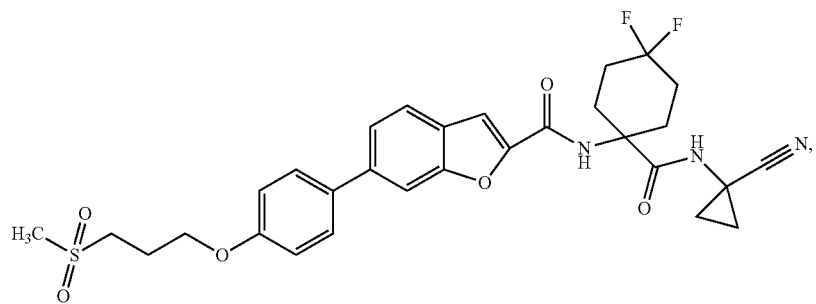
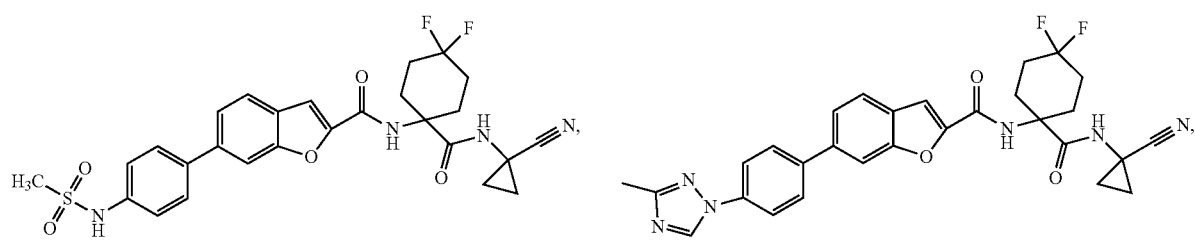
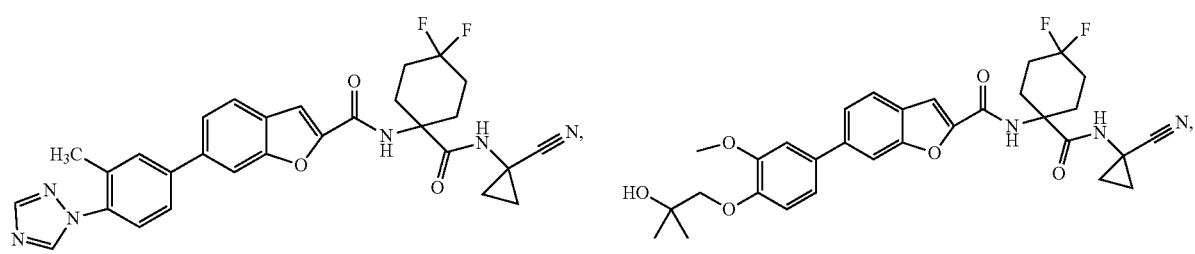
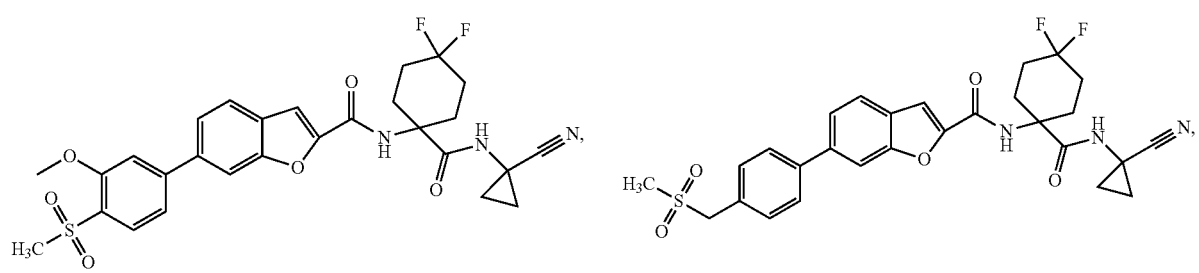
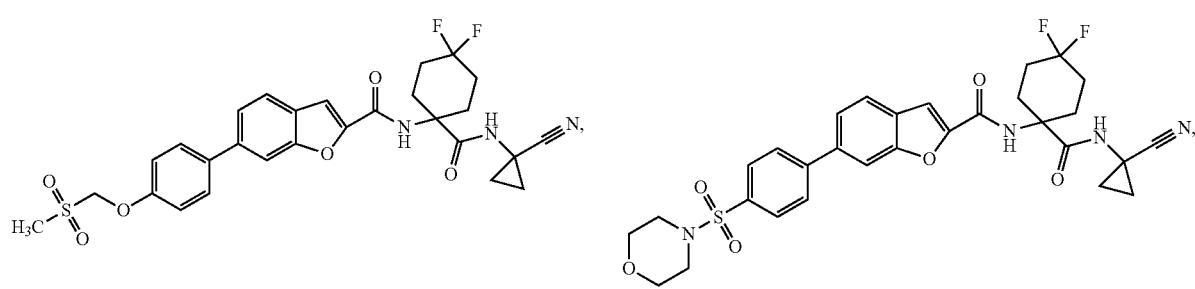

-continued
(86) 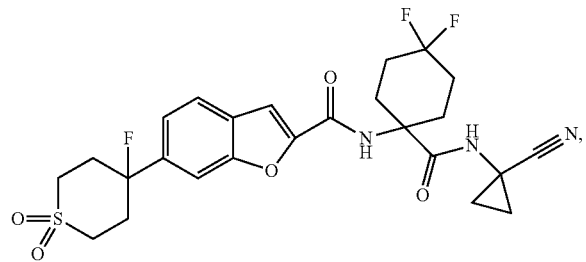
(87) 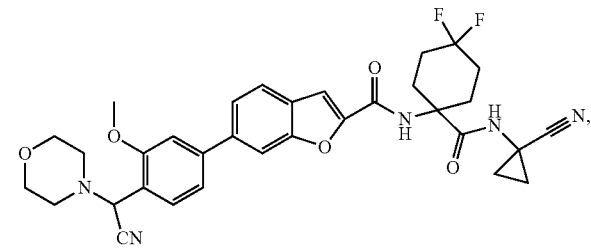
(88) 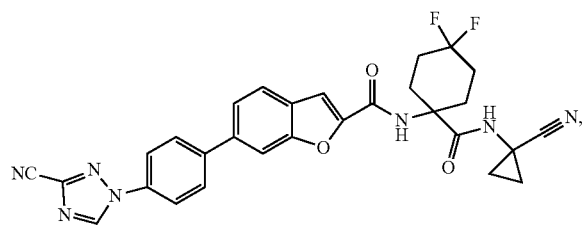
(89) 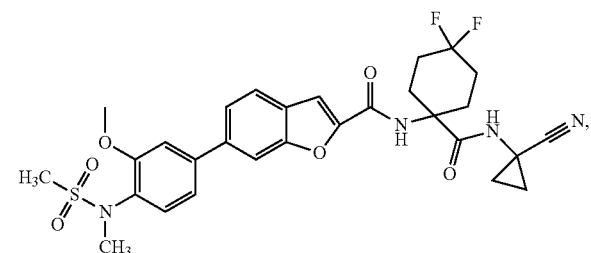
(90) 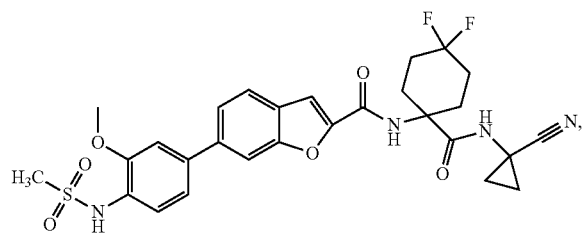
(91) 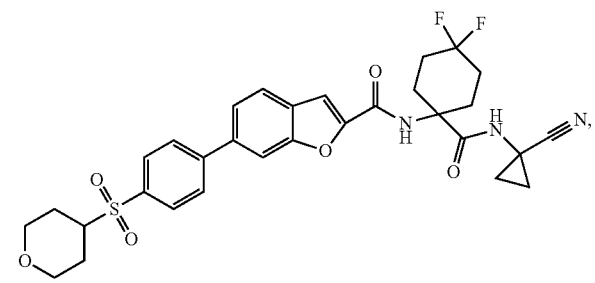
(92) 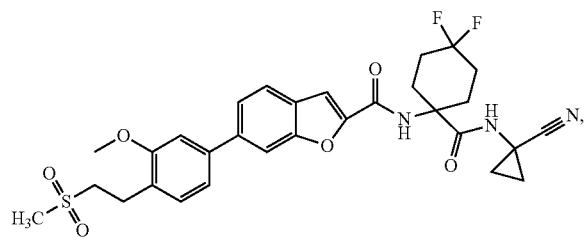
(93) 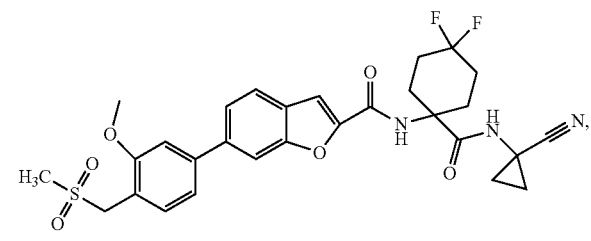
(94) 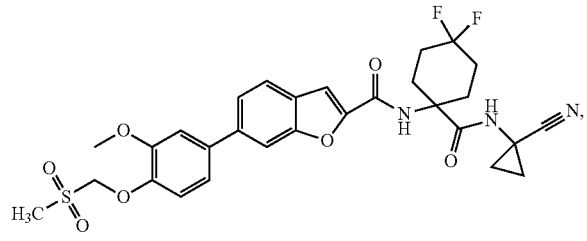
(95) 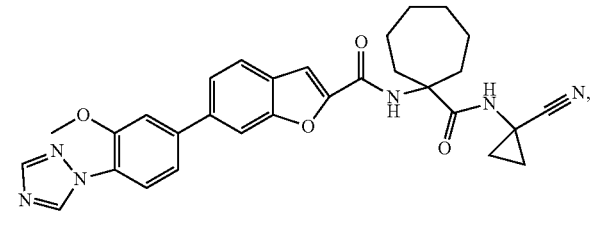

(96)
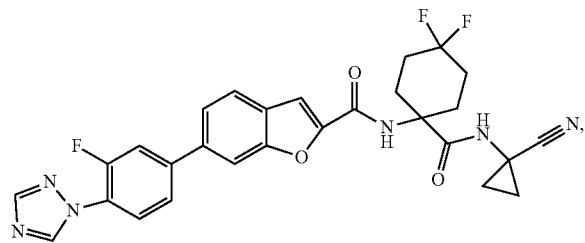
(97)
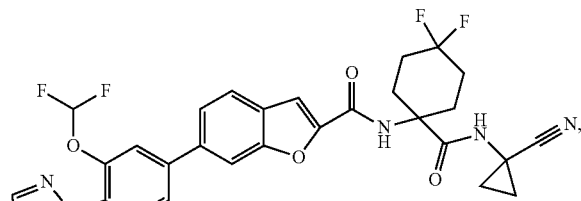
(98)
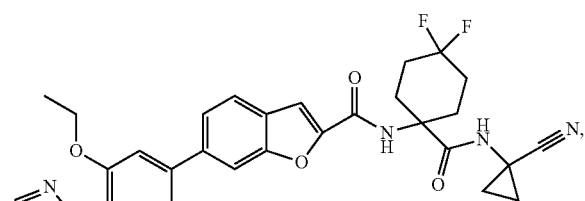
(99)
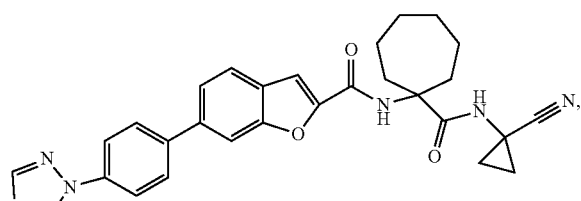
(100)
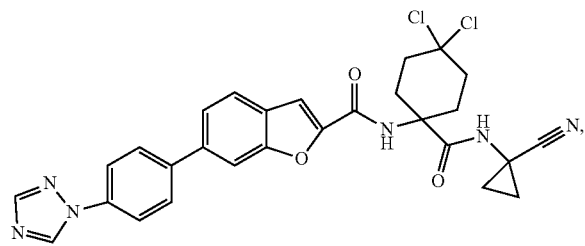
(101)
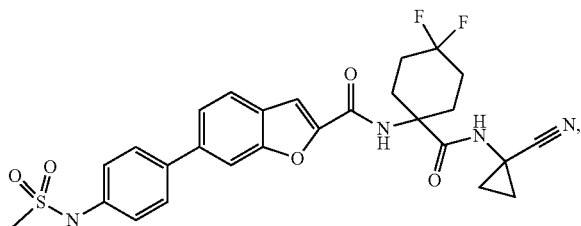
(102)
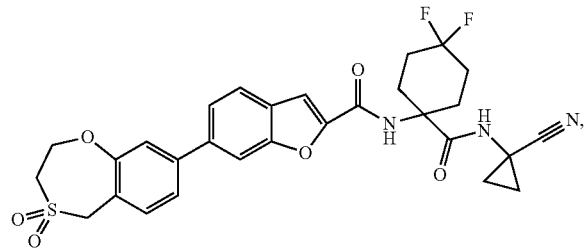
(103)
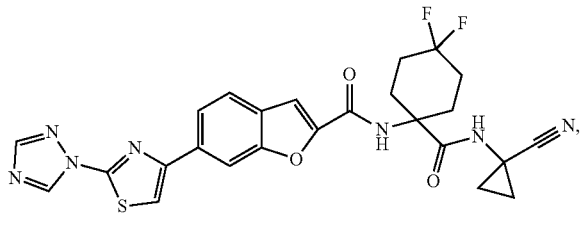
(104)
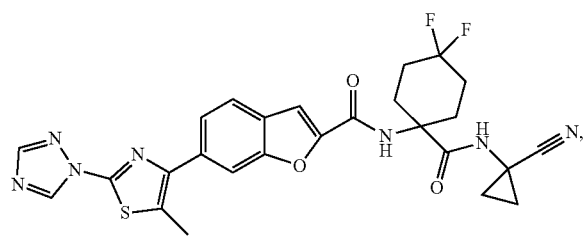
(105)
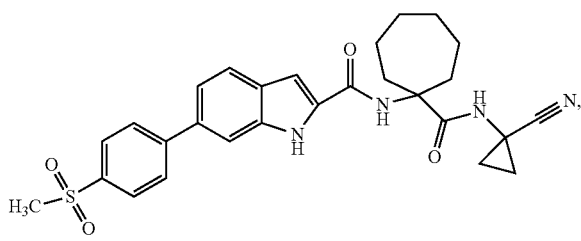
(106)
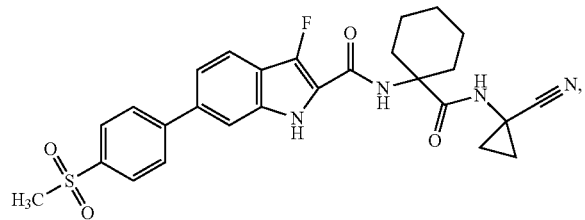
(107)
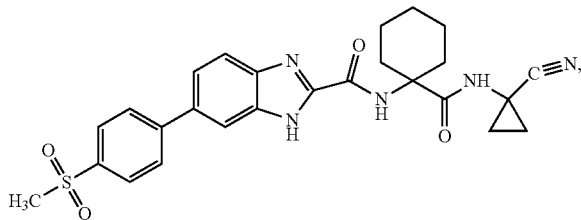

-continued
(108)
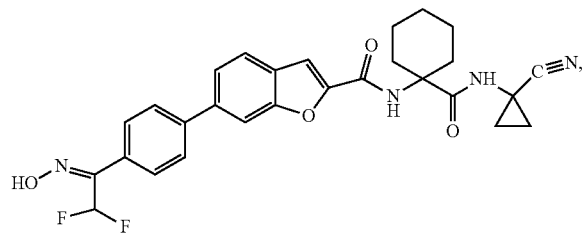
(109)
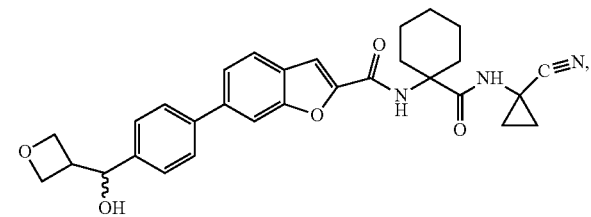
(110)
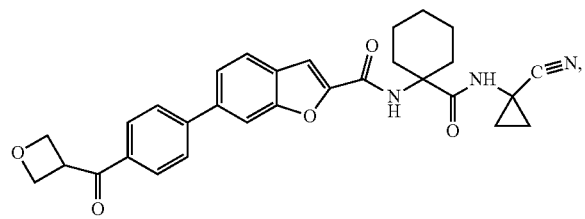
(111)
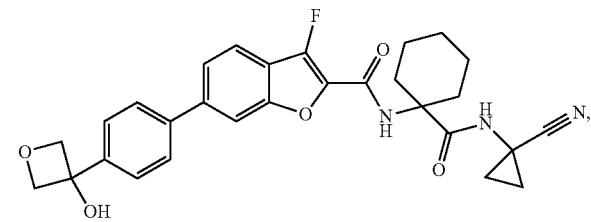
(112)
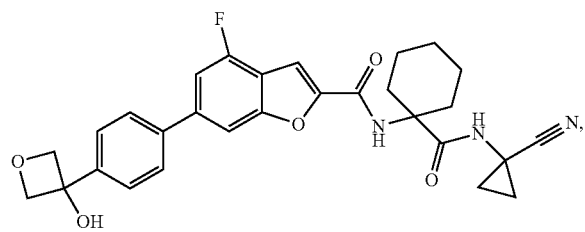
(113)
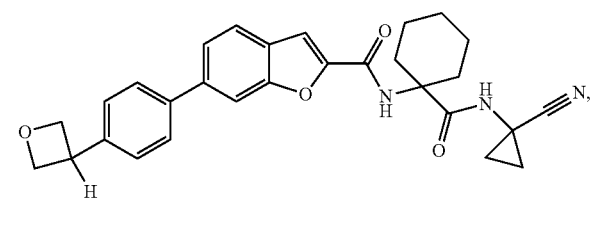
(114)
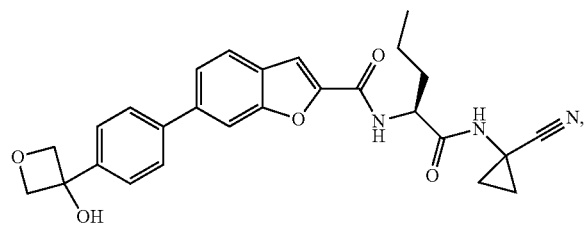
(115)
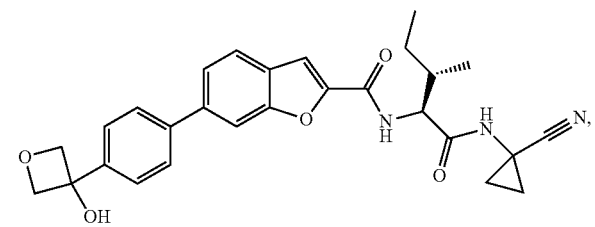
(116)
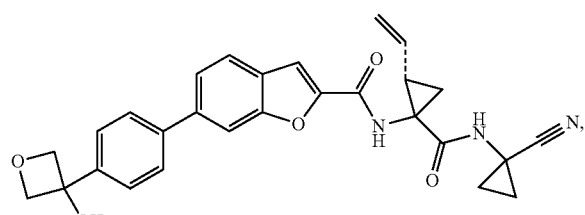
(117)
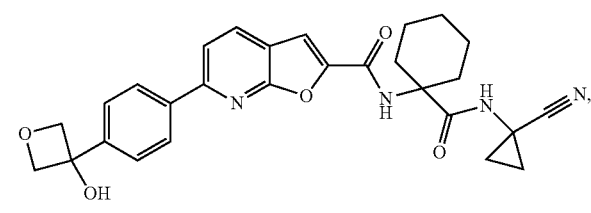
(118)
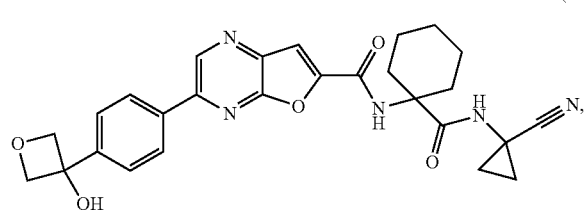
(119)
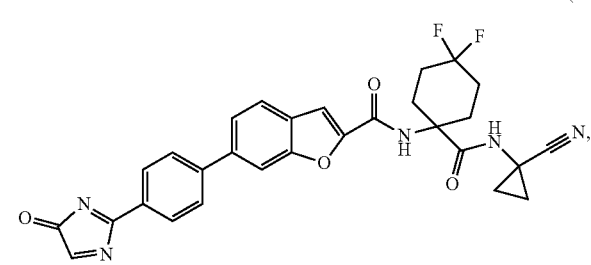

-continued
(120)
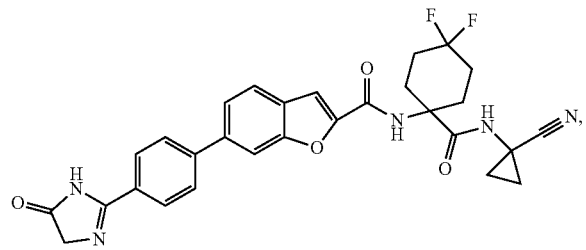
(121)
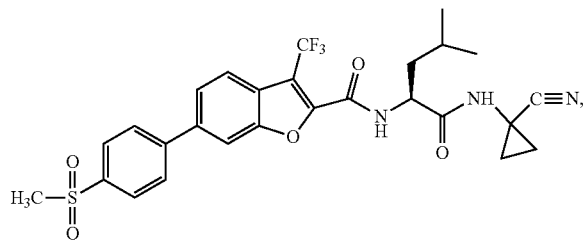
(122)
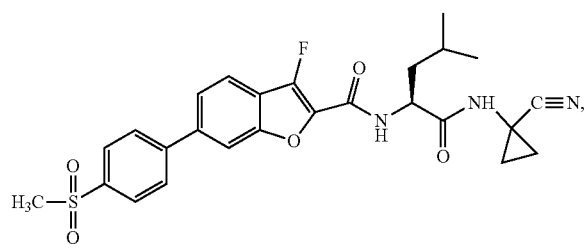
(123)
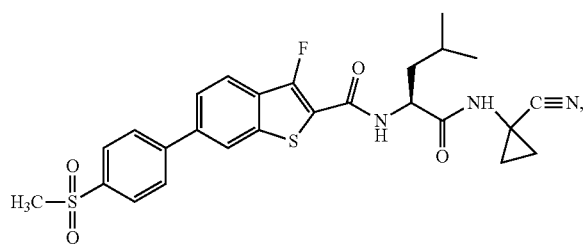
(124)
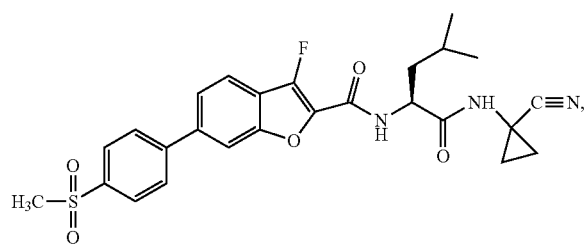
(125)
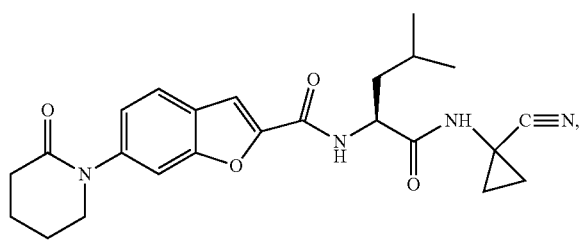
(126)
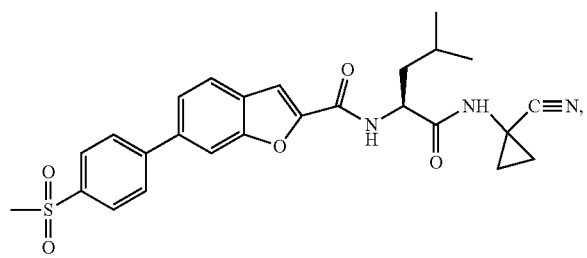
(127)
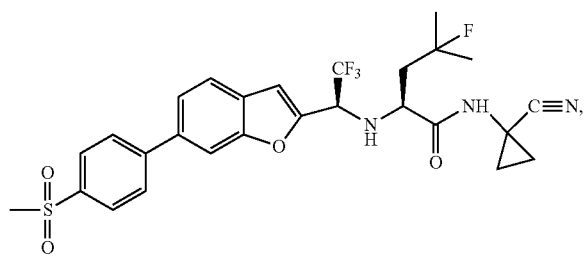
(128)
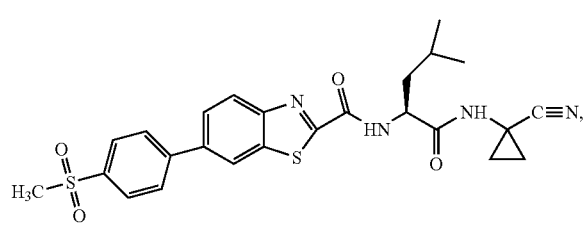
(129)
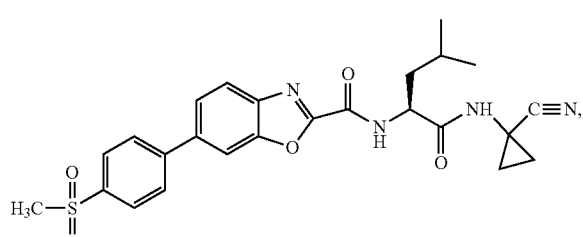
(130)
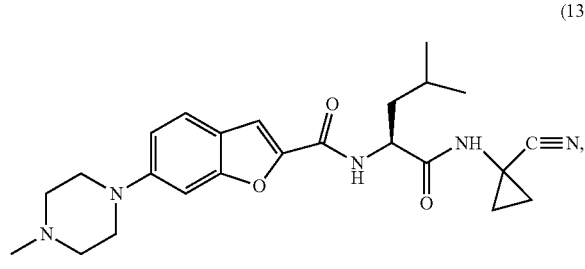
(131)
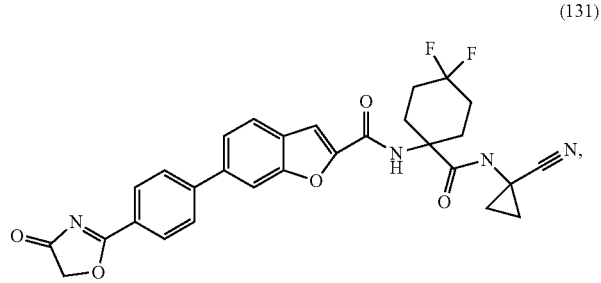

(132)
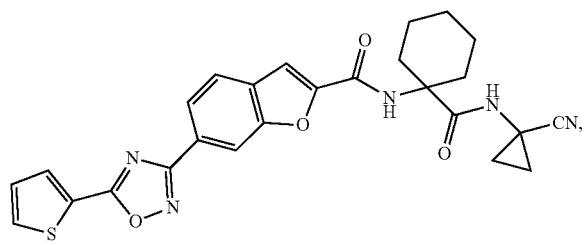
(133)
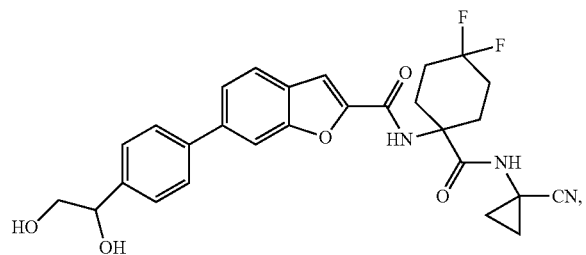
(134)
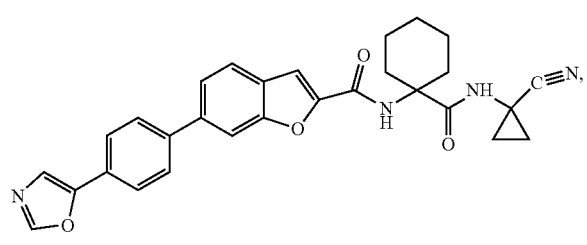
(135)
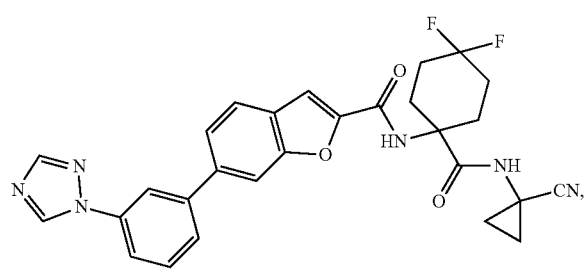
(136)
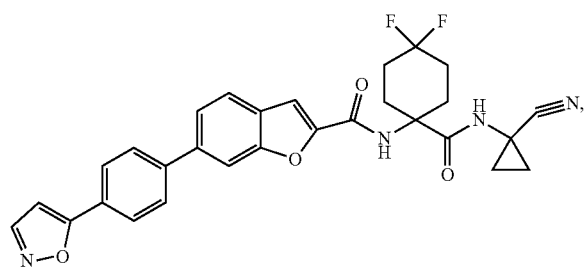
(137)
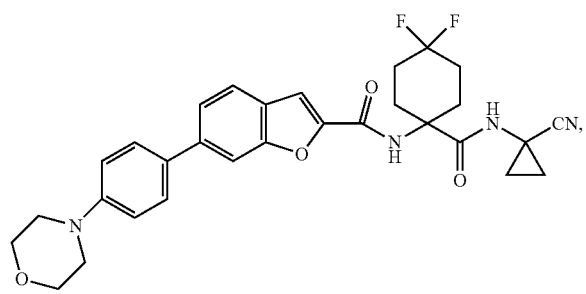
(138)
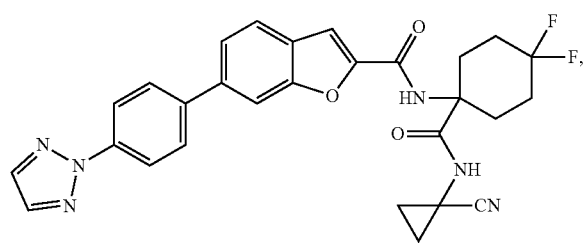
(139)
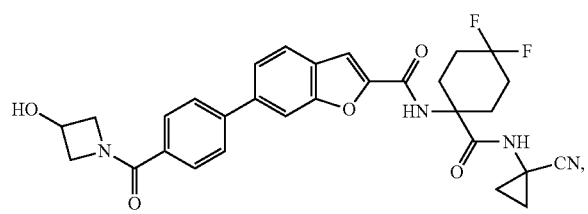
(140)
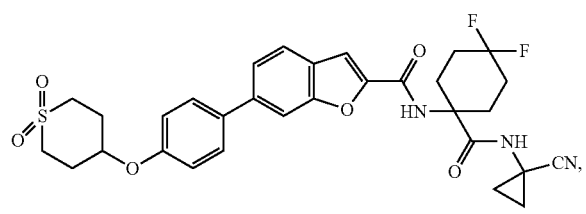
(141)
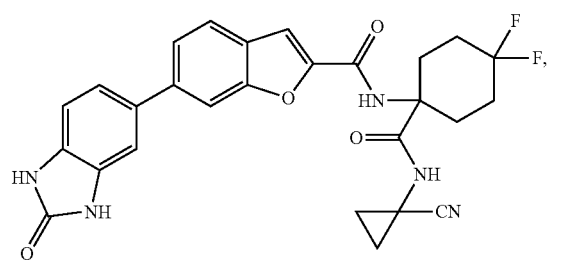

-continued (142)
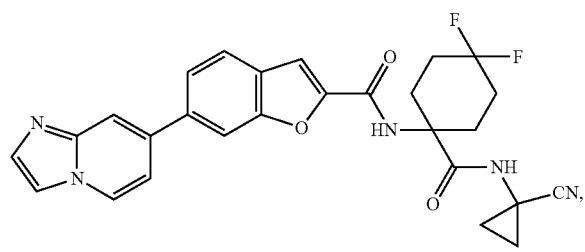

(143)
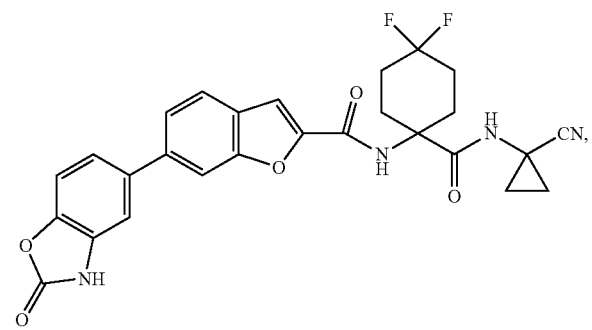

(144)
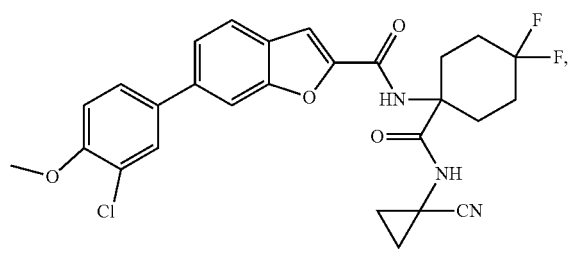

(145)
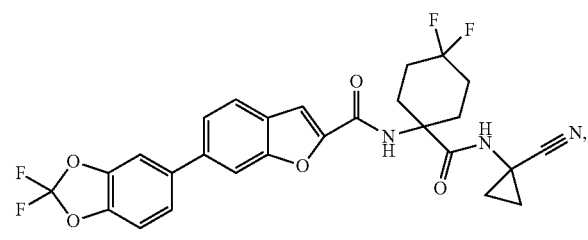

(146)
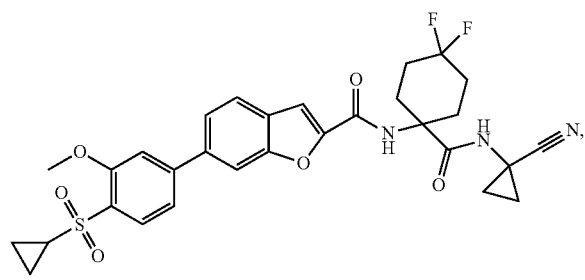

(147)
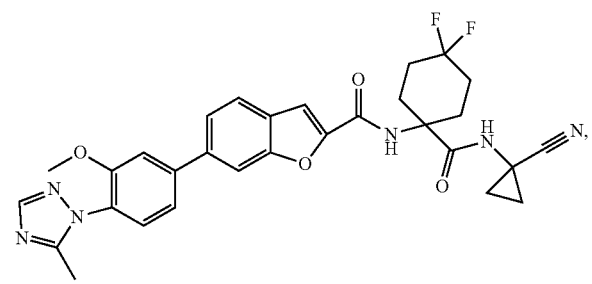

(148)
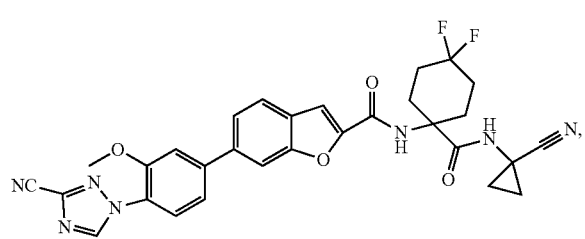

(149)
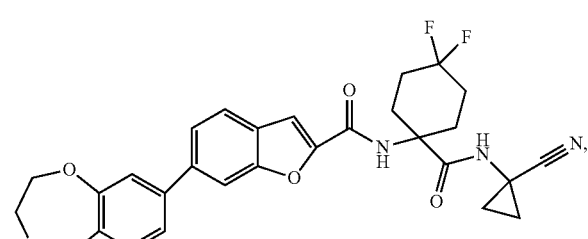

(150)
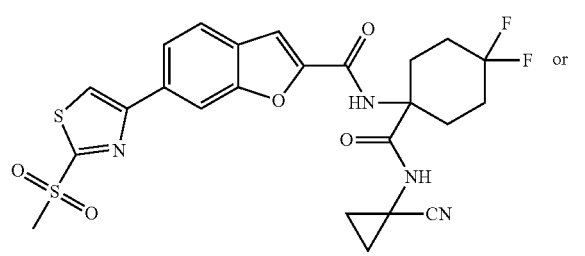 or (151)
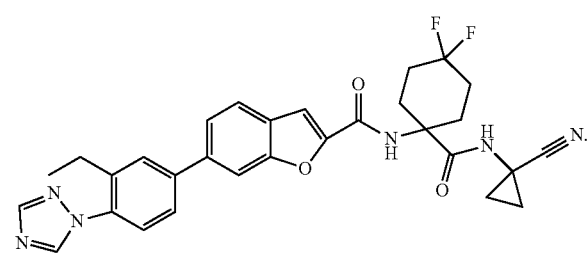

Unless otherwise stated, all stereoisomers, geometric isomers, tautomers, N-oxides, hydrates, solvates, metabolites, salts and pharmaceutically acceptable prodrugs of the compounds disclosed herein are within the scope of the invention. In certain embodiments, the salt is a pharmaceutically acceptable salt. The phrase "pharmaceutically acceptable" refers to that the substance or composition must be compatible chemically and/or toxicologically, with the other ingredients comprising a formulation, and/or the mammal being treated therewith. The compounds disclosed herein also include salts of the compounds which are not necessarily pharmaceutically acceptable salts, and which may be useful as intermediates for preparing and/or purifying compounds of Formula (I)-Formula (IV), and/or for separating enantiomers of compounds of Formula (I)-Formula (IV).

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, malic acid, 2-hydroxypropionic acid, citric acid, oxalic acid, glycolic acid and salicylic acid; a pyranosidyl acid, such as glucuronic acid and galacturonic acid; an alpha-hydroxy acid, such as citric acid and tartaric acid; an amino acid, such as aspartic acid and glutamic acid; an aromatic acid, such as benzoic acid and cinnamic acid; a sulfonic acid, such as p-toluenesulfonic acid, benzenesulfonic acid, methanesulfonic acid, ethanesulfonic acid, trifluoromethanesulfonic acid, and the like; or a combination thereof.

If the compound disclosed herein is an acid, the desired salt may be prepared by any suitable method, for example, treatment of the free acid with an inorganic or organic base, such as an amine (primary, secondary or tertiary), an alkali metal hydroxide, ammonium, $N^+(R^{14})_4$ salt or alkaline earth metal hydroxide, and the like. Some non-limiting examples of suitable salts include organic salts derived from amino acids, such as glycine and arginine; ammonia, such as primary, secondary and tertiary amine, $N^+(R^4)_4$ salt, wherein $R^{14}$ is H, $C_{1-4}$ alkyl, $C_{6-10}$ aryl, $C_{6-10}$ aryl-$C_{1-4}$ alkyl, and the like; and cyclic amines, such as piperidine, morpholine and piperazine, and inorganic salts derived from sodium, calcium, potassium, magnesium, manganese, iron, copper, zinc, aluminum, lithium, and the like, and further include, when appropriate, nontoxic ammonium, quaternary ammonium and amine cations formed using counterions such as halide, hydroxide, carboxylate, sulfate, phosphate, nitrate, $C_{1-8}$ sulfonate or aryl sulfonate.

Compounds, Compositions and Uses Thereof of the Invention

The compound of the invention may be used alone or preferably together with pharmaceutically acceptable carriers or diluents, and optionally known adjuvants such as alum in pharmaceutical composition which is used in standard pharmaceutical practice to be administered to mammals, preferably humans. Compounds may be administered orally or parenterally, including intravenous, intramuscular, intraperitoneal, subcutaneous, rectal and topical routes of administration.

In the case of tablets for oral use, carriers which are commonly used include lactose and corn starch, and lubricating agents, such as magnesium stearate, are commonly added. For oral administration in capsule form, useful diluents include lactose and dried corn starch. For instance, for oral administration in the form of a tablet or capsule, the active pharmaceutical ingredient can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the active pharmaceutical ingredient can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. When aqueous suspensions are required for oral use, the active ingredient is combined with lubricant and suspending agents. If desired, certain sweetening or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the present invention can also be administered in the form of liposome delivery systems, such as small umilamellar vesicles, large unilamellar vesicles and mutilamerilar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxy propylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The instant compounds are also useful in combination with known agents useful for treating or preventing osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy, and multiple myeloma. Combinations of the presently disclosed compounds with other agents useful in treating or preventing osteoporosis or other bone disorders are within the scope of the invention. A person of ordinary skill in the art would be able to discern which combinations of agents would be useful based on the particular characteristics of the drugs and the disease involved. Such agents include the following: an organic bisphosphonic acid compound; an estrogen receptor modulator; an androgen receptor modulator; an inhibitor of osteoclast protonATPase; an inhibitor of HMG-CoA reductase; an integrin receptor antagonist; an ostoblast anabolic agent, such as PTH; and the pharmaceutically acceptable salts and mixtures thereof. A preferred combination is a compound of the present invention and an organic bisphosphonic acid compound. Another preferred combination is a compound of the present invention and an estrogen receptor modulator. Another prepared combination is a compound of the present invention and an estrogen receptor modulator. Another prepared combination is a compound of the present invention and an androgen receptor modulator. Another prepared combination is a compound of the present invention and an osteoblast anabolic agent.

"Organic bisphosphonic acid compound" includes, but is not limited to, compounds of the chemical formula

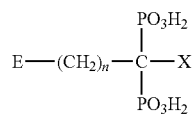

wherein n is an integer from 0 to 7 and wherein E and X are independently selected from the group consisting of H, OH, halogen, $NH_2$, SH, phenyl, $C_1$-$C_{30}$ alkyl, $C_3$-$C_{30}$ branched or cycloalkyl, bicyclic structure containing two or three N, $C_1$-$C_{30}$ substituted alkyl, $C_1$-$C_{10}$ alkyl substituted $NH_2$, $C_3$-$C_{10}$ branched or cycloalkyl substituted $NH_2$, $C_1$-$C_{10}$ diallyl substituted $NH_2$, $C_1$-$C_{10}$ alkoxy, $C_1$-$C_{10}$ alkyl substituted mercapto, thiophenyl, halophenylthio, $C_1$-$C_{10}$ alkyl substituted phenyl, pyridyl, furanyl, pyrrolidinyl, imidazolyl, imidazopyridinyl, and benzyl, such that both E and X are not selected from H or OH when n is 0; or E and X are taken together with the carbon atom or atoms to which they are attached to form a $C_3$-$C_{10}$ ring.

In the foregoing chemical formula, the alkyl groups may be straight, branched, or cyclic, provided sufficient atoms are selected for the chemical formula. The $C_1$-$C_{30}$ substituted alkyl can include a wide variety of substituents, non-limiting examples include those selected from the group consisting of phenyl, pyridyl, furanyl, pyrrolidinyl, imidazonyl, $NH_2$, $C_1$-$C_{10}$ alkyl or dialkyl substituted $NH_2$, OH, SH, and $C_1$-$C_{10}$ alkoxy.

The foregoing chemical formula is also intended to encompass complex carbocyclic, aromatic and hetero atom structures for the E and/or X substituents, non-limiting examples of which include naphthyl, quinolyl, isoquinolyl, adamantyl, and chlorophenylthio.

Pharmaceutically acceptable salts and derivatives of the bisphosphonic acid compound are also useful herein. Non-limiting examples of salts include those selected from the group consisting alkali metal, alkaline metal, ammonium, and mono-, di-, tri-, or tetra-$C_1$-$C_{30}$-alkyl-substituted ammonium. Preferred salts are those selected from the group consisting of sodium, potassium, calcium, magnesium, and ammonium salts. More preferred are sodium salts. Non-limiting examples of derivatives include those selected from the group consisting of esters, hydrates, and amides.

It should be noted that the terms "bisphosphonic acid compound" and "bisphosphonic acid derivative", as used herein in referring to the therapeutic agents of the present invention are meant to also encompass diphosphonic compounds, biphosphonic acid compounds, and biphosphonic acid derivatives, as well as salts and derivatives of these materials. The use of a specific nomenclature in referring to the bisphosphonic acid compound or bisphosphonic acid derivative is not meant to limit the scope of the present invention, unless specifically indicated. Because of the mixed nomenclature currently in use by those of ordinary skill in the art, reference to a specific weight or percentage of a bisphosphonic acid compound in the present invention is on an acid active weight basis, unless indicated otherwise herein. For example, the phrase "about 5 mg of a bone resorption inhibiting bisphosphonic acid compound selected from the group consisting of alendronate, pharmaceutically acceptable salts thereof, and mixtures thereof, on an alendronic acid active weight basis" means that the amount of the bisphosphonic acid compound selected is calculated based on 5 mg of alendronic acid.

Non-limiting examples of bisphosphonic acid compound useful herein include the following compounds; alendronic acid, 4-amino-1-hydroxybutylidene-1,1-bisphosphonic acid. Non-limiting examples of bisphosphonic acid compound include alendronate, cimadronate, clodronate, etidronate, ibandronate, incadronate, minodronate, neridronate, olpadronate, pamidronate, piridronate, risedronate, tiludronate, and zolendronate, and pharmaceutically acceptable salts and esters thereof. A particularly preferred bisphosphonic acid compound is alendronate, especially a sodium, potassium, calcium, magnesium or ammonium salt of alendronic acid. Exemplifying the preferred bisphosphonic acid compound is a sodium salt of alendronic acid, especially a hydrated sodium salt of alendronic acid. The salt can be hydrated with a whole number of moles of water or non whole numbers of moles of water. Further exemplifying the preferred bisphosphonic compound is a hydrated sodium salt of alendronic acid, especially when the hydrated salt is alendronate monosodium trihydrate.

The precise dosage of the organic bisphosphonic acid compound ill vary with the dosing schedule, the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. Generally, an appropriate amount of bisphosphpnic acid compound is chosen to obtain a bone resorption inhibiting effect, i.e. a bone resorption inhibiting amount of the bisphosphonic acid compound is administered. For humans, an effective oral dose of bisposphonic acid compound is typically from about 1.5 to about 6000 µg/kg body weight and preferably about 10 to 2000 µg/kg body weight. For alendronate monosodium trihydrate, common human doses which are administered are generally in the range of about 2 mg/day to about 40 mg/day, preferably about 5 mg/day to about 40 mg/day. In the U.S. Presently approved dosages for alendronate monosodim trihydrate are 5 mg/day for preventing osteoporosis, 10 mg/day for treating osteoporosis, and 40 mg/day for treating Paget's disease.

In alternative dosing regimens, the bisphosphonic acid compound can be administered at intervals other than daily, for example once-weekly dosing, twice-weekly dosing, biweekly dosing, and once-monthly dosing. In a once weekly dosing regimen, alendronate monosodium trihydrate would be administered at dosages of 35 mg/week or 70 mg/week.

"Selective estrogen receptor modulators" refers to compounds which interfere or inhibit the binding of estrogen to the receptor, regardless of mechanism. Examples of estrogen receptor modulators include, but are not limited to, estrogen, progestogen, estradiol, droloxifene, raloxifene, lasofoxifene, TSE424, tamoxifen, idoxifene. LY353381, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone.

An "estrogen receptor beta modulator" is a compound that selectively agonizes or antagonizes estrogen receptor beta (ERβ). Agonizing ERβ increases transcription of the tryptophan hydroxy lase gene (TPH, the key enzyme in serotonin synthesis) via an ERβ mediated event.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"An inhibitor of osteoclast proton ATPase" refers to an inhibitor of the proton ATPase, which is found on the apical membrane of the osteoclast, and has been reported to play a significant role in the bone resorption process. This proton pump represents an attractive target for the design of inhibitors of bone resorption which are potentially useful for the treatment and prevention of osteoporosis and related metabolic diseases.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. Examples of HMG-CoA reductase inhibitors that may be used include but are not limited to lovastatin, simvastatin, pravastatin, fluvastatin, atorvastatin and cerivastatin. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, omithine, choline, N,N'-dibenzylethylenediamine, chloroprocaine, diethanolamine, procaine. N-benzylphenethylamine, 1-p-chlorobenzyl-2-pyrrolidine-1'-yl-methylbenzimidazole, diethylamine, piperazine, and tris(hydroxymethyl)aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexlresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, toslate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

As used above, "integrin receptor antagonists" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

"An osteoblst anabolic agent" refers to agents that build bone, such as PTH. The intermittent administration of parathyroid hormone (PTH) or its amino-terminal fragments and analogues have been shown to prevent arrest, partially reverse bone loss and stimulate bone formation in animals and humans.

"Nonsteroidal anti-inflammatory drugs" or NSAIDs, inhibit the metabolism of arachidonic acid to proinflammatory prostaglandins via cyclooxygenase (COX)-1 and COX-2. Non-limiting examples of NSAIDs include: aspirin, ibuprofen, naproxen, diclofenac, etodolac, fenoporfen, flubiprofen, indomethacin, ketoprofen, ketorolac, meloxicam, nabumetone, oxaprozin, piroxican, sulindac, tolmetin, diflunisal, meclofenamate and phenylbutazone.

"A selective cyclooxygenase-2 inhibitor," or COX-2 inhibitor, refers to a type of nonsteroidal anti-inflammatory drug (NSAID), that inhibit the with the COX-2 coenzyme, which contributes to pain and inflammation in the body. Non-limiting examples of COX-2 inhibitors include: celecoxib, etoricoxib, parecoxib, rofecoxib valdecoxib and lumiracoxib.

An "inhibitor of interleukin-1 beta" or IL-1β refers to in inhibitors of IL-1, which is a soluble factor produced by monocytes, macrophages, and other cells which activates T-lymphocytes and potentiates their response to mitogens or antigens. Non-limiting examples of IL-1B inhibitors include diacerein and rhein.

A "LOX/COX inhibitor" refers to an inhibitor or all three of the major enzymes involved in arachidonic acid pathway-namely, 5-LOX, COX-1 and COX-2. A non-limiting example of a LOX/COX inhibitor is licofelone.

"Vitamin D" includes, but is not limited to, vitamin D3 (cholecalciferol) and vitamin D2 (ergocalciferol), which are naturally occurring, biologically inactive precursors of the hydroxylated biologically active metabolites of vitamin D: 1α-hydroxy vitamin D; 25-hydroxy vitamin D, and 1α,25-dihydroxy vitamin D. Vitamin D2 and vitamin D3 have the same biological efficacy in humans. When either vitamin D2 or D3 enters the circulation, it is hydroxylated by cytochrome P450-vitamin D-25-hydroxylase to give 25-hydroxy vitamin D. The 25-hydroxy vitamin D metabolite is biologically inert and is further hydroxylated in the kidney by cytochrome P450-monooxygenase, 25 (OH) D-1α-hydroxylase to give 1,25-dihydroxy vitamin D. When serum calcium decreases, there is an increase in the production of parathyroid hormone (PTH), which regulates calcium homeostasis and increases plasma calcium levels by increasing the conversion of 25-hydroxy vitamin D to 1,25-dihydroxy vitamin D.

In embodiments of the present invention, an appropriate amount of the vitamin D compound is chosen to provide adequate vitamin D nutrition during the dosing interval without interfering with the cathepsin K inhibitor's ability to obtain a bone resorption inhibiting effect. For oral compositions of the present invention comprising a cathepsin K inhibitor, and a vitamin D compound, an amount of the vitamin D compound comprises from about 100 IU to about 60,000 TU. Non-limiting examples of an oral amount of the vitamin D compound in embodiments of the present invention include, but are not limited to, dosages of 2,800 IU, 5,600 IU, 7,000 IU, 8,400 IU, 11,200 IU, 14,000 IU, 16,800 IU or 19,600 IU. Non-limiting examples of an oral amount of vitamin D for weekly dosing are 2.800 IU, 5,600 IU, 7,000 IU, 8,400 IU and 11,200 IU. Non-limiting examples of an oral amount of vitamin D for monthly dosing are 11,200 IU, 14,000 IU, 15,400 IU, 16,800 IU and 19,600 IU.

"Synthetic vitamin D analogues" includes non-naturally occurring compounds that act like vitamin D.

"Calcium" includes, but is not limited to, calcium carbonate, calcium citrate or any other compound containing elemental calcium. Calcium is essential to human health and is required for the structural integrity of the skeleton. The ionized fraction of blood calcium is physiologically important and is tightly maintained by both parathyroid hormone (PTH) and 1,25-dihydrox Vitamin D. As such, decreases in blood calcium (or the mere insufficiency of dietary calcium) can readily affect PTH and 1,25-dihydroxy Vitamin D levels in such as way as to adversely affect skeletal health. Provision of supplemental calcium consequently tends to lower PTH levels, to diminish the removal of calcium from skeletal stores and, in so doing, to benefit skeletal health. Non-limiting examples of an oral amount of the calcium in embodiments of the present invention include, but are not limited to, dosages of 1200-1500 mgs of elemental calcium per day in divided doses.

A "RANKL inhibitor" refers to an inhibitor of receptor activator NF-kB ligand (RANKL), which has previously been called osteoclast differentiation factor (ODF), osteoprotegerin ligand (OPGL) and TNF-related activation induced cytokine (TRANCE). RANKL is a key stimulator of osteoclast formation and maturation. A non-limiting example or a RANKL inhibitor is AMG-162.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents. The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, *Elsevier,* 1985, which is incorporated by reference herein in its entirety. Metabolites of these compounds include active apecies produced upon introduction of compounds of this invention into the biological milieu.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The terms "treating" or "treatment" of a disease as used herein includes: preventing the disease, i.e., causing the clinical symptoms of the disease not to develop in a mammal that may be exposed to or predisposed to the disease but does not yet experience or display symptoms of the disease; inhibiting the disease, i.e., arresting or reducing the development of the disease or its clinical symptoms; or relieving the disease, i.e., causing regression of the disease or its clinical symptoms.

The term "bone resorption." as used herein, refers to the process by which osteoclasts degrade bone.

The present invention also encompasses a pharmaceutical composition useful in the treatment of osteoporosis or other bone disorders, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for a cathepsin dependent condition. Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg 1 minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The compounds of the invention can be used in combination with other agents useful for treating cathepsin-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating cathepsin-mediated conditions includes in principle any combination with any pharmaceutical composition useful for treating disorders related to estrogen functioning.

The scope of the invention therefore encompasses the use of the instantly claimed compounds in combination with a second agent selected from: an organic bisphosphonate; an estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; and the pharmaceutically acceptable salts and mixtures thereof.

The pharmaceutically acceptable salts of the compounds of this invention include the conventional non-toxic salts of the compounds of this invention as formed with inorganic or organic acids. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic and the like. The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt forming inorganic or organic acid in a suitable solvent or various combinations of solvents. Similarly, the salts of the acidic compounds are formed by reactions with the appropriate inorganic or organic base.

General Synthetic Procedures

Generally, the compounds disclosed herein may be prepared by methods described herein, wherein the substituents are as defined for Formula (I), except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with CaH2. EtOAc, PE, hexane, N,N-dimethylacetamide and N,N-dimethylformamide were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1H$ NMR spectra were recorded by a Bruker Avance 400 MHz spectrometer or Bruker Avance III HD 600 spectrometer, using $CDCl_3$, DMSO-da, $CD_3OD$ or acetone-$d_6$ (reported in ppm) as solvent, and using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), dt (doublet of triplets), ddd (doublet of doublet of doublets), ddt (doublet of doublet of triplets), dddd (doublet of doublet of doublet of doublets). Coupling constants, when given, were reported in Hertz (Hz).

Low-resolution mass spectral (MS) data were determined on an Agilent 6120 Quadrupole HPLC-MS spectrometer equipped with an Agilent Zorbax SB-C18 (2.1×30 mm, 3.5 µm). The flow rate was 0.6 mL/min; the mobile phases consisted of a combination of A (0.1% formic acid in $CH_3CN$) and B (0.1% formic acid in $H_2O$) in gradient mode (5% to 95%), and an ESI source was used, the peak of HPLC was recorded with UV-Vis detection at 210/254 nm.

Purification of compound by preparative chromatography was implemented on Agilent 1260 Series high performance liquid chromatography (Pre-HPLC) or Calesep Pump 250 Series high performance liquid chromatography (Pre-HPLC) (NOVASEP, 50/80 mm. DAC) with UV detection at 210/254 nm.

The following abbreviations are used throughout the specification:

EDC 1-(3-dimethylaminopropyl)-3-ethylcarbodiimide hydrochloride

HATU 2-(7-aza-1H-benzotriazole-1-yl)-1,1,3,3-tetramethyluronium hexafluorophosphate KOH potassium hydroxide $Pd(Ph_3P)_4$ tetrakis(triphenylphosphine)platinum(0)

$Pd(dppf)Cl_2.CH_2Cl_2$ 1,1'-Bis(diphenylphosphino)ferrocene-palladium(II)dichloride dichloromethane complex DMF N,N-dimethylformamide NaOH sodium hydroxide $CDCl_3$ chloroform-d $H_2O_2$ hydrogen peroxide n-BuLi n-butyllithium DMSO dimethylsulfoxide DMSO-$d_6$ deuterated dimethyl sulfoxide Pd/C Palladium on activated carbon t-BuOK potassium tert-butoxide $Pd(OH)_2$ palladium hydroxide

Scheme 1

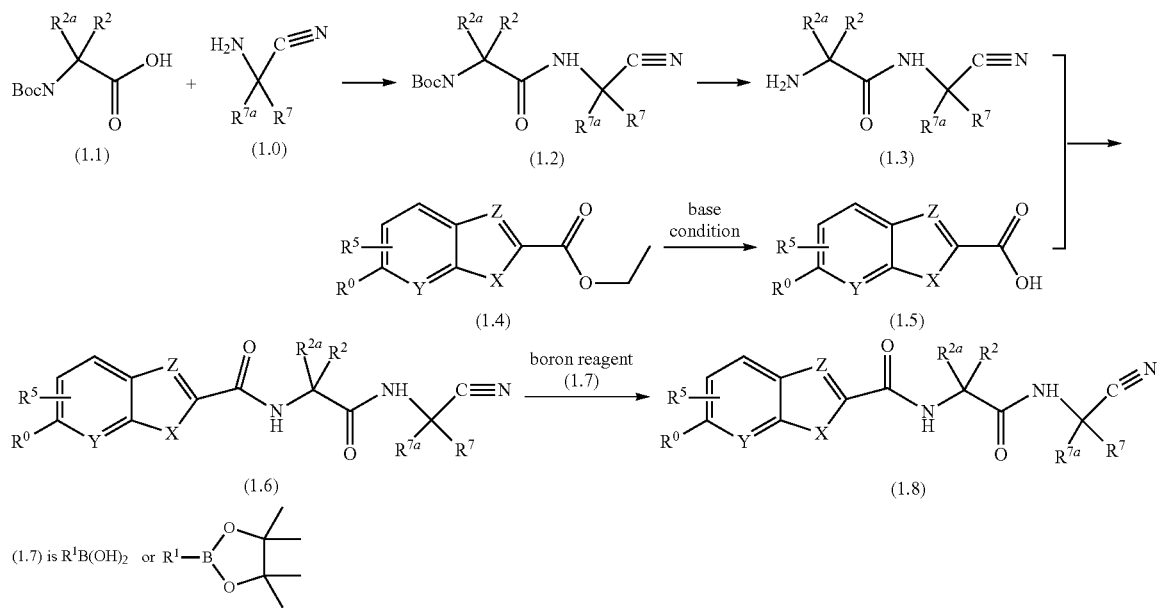

Compound disclosed herein can be prepared by the process illustrated in scheme 1.

Condensation reaction between Compound (1.1) and amine (1.0) in the presence of a base (such as triethyl, diisopropylethylamine, and the like) can give compound (1.2), and the condensating agent used in the reaction includes, but is not limited to, HATU, EDC, and the like.

Compound (1.2) can undergo deprotection reaction to give compound (1.3);

Compound (1.4) can undergo saponification in the presence of a base to give the corresponding acid (1.5), and the base used can be inorganic base, including but not limited to, sodium hydroxide, potassium hydroxide, etc.;

Condensation reaction between compound (1.3) and compound (1.4) can give compound (1.6);

Suzuki cross-coupling reaction between compound (1.6) and boron reagent (1.7) can give the objective compound (1.8), and the suzuki reaction can be carried out in the presence of a catalyst, wherein the catalyst includes, but is not limited to, $Pd(Ph_3P)_4$, $Pd(dppf)Cl_2$—$CH_2Cl_2$, etc.;

wherein the $R^0$ is an easy-leaving group, such as halogen, trifluoromethylsulfonyl, etc.; Z, X, Y, $R^{2a}$, $R^2$, $R^7$, $R^{7a}$, $R^5$ and $R^1$ are as defined herein.

Scheme 2

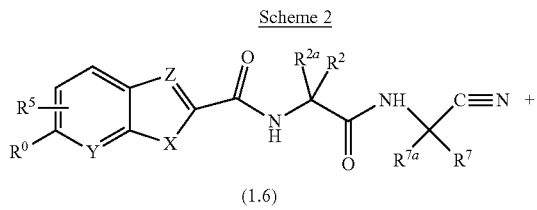

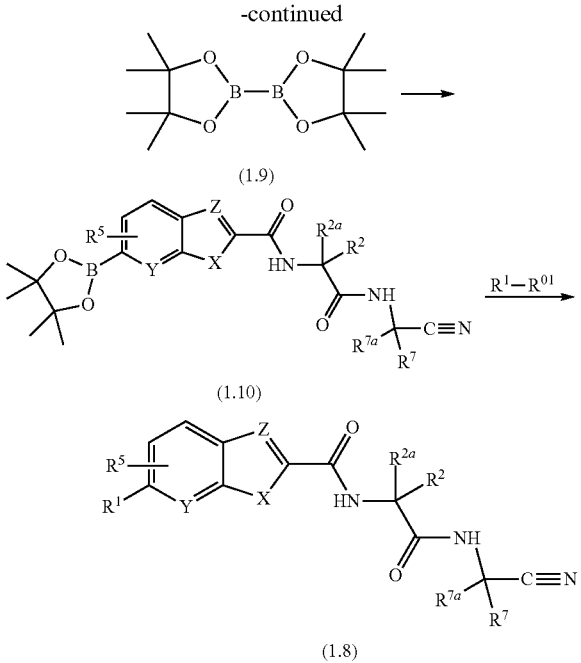

Compound disclosed herein can be prepared by the process illustrated in scheme 2.

Suzuki cross-coupling reaction between Compound (1.6) and compound (1.9) can give compound (1.10);

Suzuki cross-coupling reaction between compound (1.10) and $R^1$—$R^{01}$ in the presence of a catalyst can give the objective compound (1.8), wherein the catalyst includes, but is not limited to, $Pd(Ph_3P)_4$, $Pd(dppf)Cl_2CH_2Cl_2$, etc.;

wherein $R^{01}$ is Br, I, trifluoromethylsulfonyl, etc.; Z, X, Y, $R^{2a}$, $R^2$, $R^7$, $R^{7a}$, $R^5$ and $R^1$ are as defined herein.

Example 1 of Intermediate N-(1-((1-cyanocyclopropyl)carbamoyl)cyclohexyl)-6-(4,4,5,5-tetramethyl-1,3,2-dioxaborolan-2-yl)benzofuran-2-carboxamide

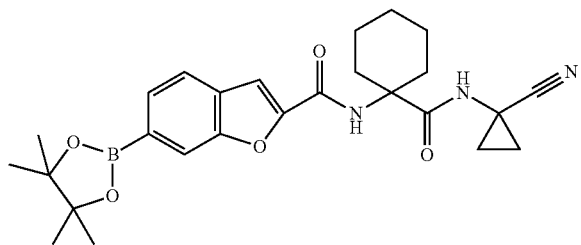 [SMILES: CC1(C)OB(c2ccc3cc(C(=O)NC4(C(=O)NC5(C#N)CC5)CCCCC4)oc3c2)OC1(C)C]

Step 1: ethyl 6-bromobenzofuran-2-carboxylate

To a 250 mL two-neck flask were added 4-bromo-2-hydroxybenzaldehyde (15 g, 74.63 mmol), ethyl bromoacetate (18.7 g, 111.9 mmol), potassium carbonate (31 g, 223.9 mmol) and anhydrous DMF (80 mL). The mixture was heated to 130° C. and stirred for 5 hours. The reaction mixture was cooled to rt, filtered. The filtrate was concentrated in vacuo, and the residue was dissolved in ethyl acetate (100 mL). The mixture was washed with saturated brine (50 mL×3), dried over anhydrous sodium sulfate and filtered. The filtrate was concentrated in vacuo, and the residue was purified by silica-gel column chromatography (EtOAc:PE=1:20, V/V) to give a light yellow solid (16.6 g, 83%).

MS (ESI, pos. ion) m/z: 269.9 (M+2);

Step 2: 6-bromobenzofuran-2-carboxylic acid

To a 100 mL two-neck flask were added ethyl 6-bromobenzofuran-2-carboxylate (4 g, 14.86 mmol) and methanol (50 mL), then sodium hydroxide solution (22.3 mL, 44.6 mmol, 2 mol/L) was added. The mixture was stirred at rt overnight. The reaction mixture was concentrated in vacuo to remove most of the solvent, and to the residue was added water (20 mL). The mixture was adjusted with diluted hydrochloric acid (2 mol/L) to pH 3-4, and the resulting mixture was filtered by suction. The filter cake was dried in vacuo to give a white solid (3.30 g, 92%).

MS (ESI, pos. ion) m/z: 241.9 (M+2);

Step 3: tert-butyl (1-((1-cyanocyclopropyl)carbamoyl)cyclohexyl)carbamate

To a 100 mL two-neck flask were added 1-((tert-butylcarbonyl)amino)cyclohexanecarboxylic acid (2.43 g, 10 mmol), 1-amino-1-cyclopropanecarbonitrile hydrochloride (1.42 g, 12 mmol) and DMF (15 mL). To the mixture were added HATU (5.32 g, 14 mmol) and ethyldiisopropylamine (8.8 mL, 50 mmol) at 0° C. under nitrogen protection. The mixture was stirred for 1.0 h at 0° C. under nitrogen protection. To the reaction mixture was added saturated aqueous sodium chloride (30 mL), and the resulting mixture was extracted with ethyl acetate (30 mL×3). The combined organic layer was washed with saturated brine (30 mL×3), dried over anhydrous sodium sulfate and filtered. The filtrate was concentrated in vacuo to give light yellow oil (2.82 g, 91%). This crude product was used in next step without further purification.

Step 4: 1-amino-N-(1-cyanocyclopropyl)cyclohexanecarboxamide hydrochloride

To a 100 mL two-neck flask were added tert-butyl (1-((1-cyanocyclopropyl)carbamoyl)cyclohexyl)carbamate (2.82 g, 9.1 mmol) and ethyl acetate (50 mL). To the mixture were added a solution of hydrogen chloride in ethyl acetate (20 mL, 3.5 mol/L) at 0° C. under nitrogen protection. The mixture was stirred for 1.0 h at rt under nitrogen protection. The reaction mixture was concentrated to remove most of the solvent, and the residue was washed with petroleum ether (20 mL) to give a white solid (2.2 g, 98%).

MS (ESI, pos. ion) m/z: 208.1 (M+1);

Step 5: 6-bromo-N-(1-((1-cyanocyclopropyl)carbamoyl)cyclohexyl)benzofuran-2-carboxamide To a solution of 1-amino-N-(1-cyanocyclopropyl)cyclohexanecarboxamide hydrochloride (1.46 g, 6.0 mmol) in anhydrous DMF (18 mL) was added 6-bromobenzofuran-2-carboxylic acid (1.11 g, 4.62 mmol) in an 50 mL round-bottom flask. The mixture was cooled to 0° C., then HATU (1.75 g, 4.62 mmol) and triethylamine (2.5 mL, 13.85 mmol) were added. The resulting mixture was stirred at 1 hour under 0° C. After the reaction was completed, to the reaction mixture was added saturated brine (100 mL). The resulting mixture was extracted with EtOAc (30 mL×3), then the combined organic layers were dried over anhydrous sodium sulfate, and filtered. The filtrate was concentrated in vacuo, and the residue was purified by silica-gel column chromatography (DCM:EtOAc=50:1, V/V) to give a white solid (430 mg, 21.6%).

MS (ESI, pos. ion) m/z: 430.3 (M+1);

Step 6: N-(1-((1-cyanocyclopropyl)carbamoyl)cyclohexyl)-6-(4,4,5,5-tetramethyl-1,3,2-dioxaborolan-2-yl)benzofuran-2-carboxamide To a solution of 6-bromo-N-(1-((1-cyanocyclopropyl)carbamoyl) cyclohexyl)benzofuran-2-carboxamide (427 mg, 1.0 mmol) in anhydrous DMF (10 mL) was added Bis(pinacolato)diboron (330 mg, 1.3 mmol) and Pd(dppf)Cl$_2$·CH$_2$Cl$_2$ (82 mg, 0.1 mmol), then potassium acetate (344 mg, 3.5 mmol) was added quickly. The resulting mixture was stirred at 90° C. for 3.5 h under nitrogen protection. The reaction mixture was cooled to rt and to the mixture was added saturated brine (100 mL). The resulting mixture was extracted with EtOAc (30 mL×3). The combined organic layers were washed with saturated brine (50 mL×2), dried over anhydrous Na$_2$SO$_4$, and filtered. The filtrate was concentrated in vacuo, and the residue was purified by silica-gel column chromatography (DCM:EtOAc=40:1, V/V) to give a white solid (330 mg, 69.2%).

MS (ESI, pos. ion) m/z: 478.1 (M+1);

Example 2 of Intermediate N-(1-((1-cyanocyclopropyl)carbamoyl)-4,4-difluorocyclohexyl)-6-(4,4,55-tetramethyl-1,3,2-dioxaborolan-2-yl)benzofuran-2-carboxamide

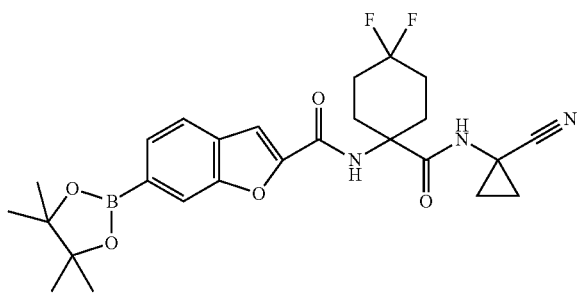 [SMILES: CC1(C)OB(c2ccc3cc(C(=O)NC4(C(=O)NC5(C#N)CC5)CCC(F)(F)CC4)oc3c2)OC1(C)C]

Step 1: 4,4-difluorocyclohexanecarbonyl chloride

To a 100 mL two-neck flask were added 4,4-difluorocyclohexanecarboxylic acid (3.28 g, 20 mmol) and thionyl chloride (1.77 mL, 24.5 mmol). After the addition, the mixture was stirred at 85° C. for 3 h. The reaction mixture was cooled to rt to give colourless liquid (3.58 g, 98%).

Step 2: methyl 1-bromo-4,4-difluorocyclohexanecarboxylate

To a 100 mL two-neck flask was added 4,4-difluorocyclohexanecarbonyl chloride (3.58 g, 19.6 mmol), then liquid bromine (1.24 mL, 24.2 mmol) was added slowly at 90° C. After the addition, the mixture was stirred at 100° C. for 1.5 h. Then the reaction mixture was cooled to rt, and to the reaction was added anhydrous methanol (4.2 mL). After the addition, the resulting mixture was refluxed for 1 h. The reaction mixture was cooled to rt, and ice-water (40 mL) was added. The resulting mixture was extracted with diethyl ether (40 mL×3). The combined organic layers were washed with sodium thiosulfate (40 mL), saturated aqueous sodium bicarbonate (40 mL) and saturated brine (40 mL) in turn, dried over anhydrous sodium sulfate, filtered. The filtrate was concentrated in vacuo, and the residue was purified by silica-gel column chromatography (DCM:PE=1:2, V/V) to give light yellow oil (330 mg, 69.2%).

$^1$H NMR (600 MHz, CDCl$_3$) δ 3.86 (s, 3H), 2.52-2.34 (m, 2H), 2.35-2.14 (m, 4H), 2.06 (d, J=5.8 Hz, 2H).

Step 3: methyl 1-azido-4,4-difluorocyclohexanecarboxylate

To a 100 mL single-neck flask were added methyl 1-bromo-4,4-difluorocyclohexanecarboxylate (3.11 g, 12.1 mmol) and dimethyl sulfoxide (10 mL). Then, sodium azide (1.57 g, 24.2 mmol) was added. After the addition, the mixture was stirred at 45° C. for 12 h. The reaction mixture was cooled to rt, then to the mixture was added saturated brine (80 mL) and ethyl acetate (80 mL). The resulting mixture was partitioned. The c organic layer was washed with saturated brine (40 mL), dried over anhydrous Na$_2$SO$_4$, and filtered. The filtrate was concentrated in vacuo to remove the solvent and give the product (2.17 g, 82%).

Step 4: methyl 1-amino-4,4-difluorocyclohexanecarboxylate

To a 100 mL single-neck flask were added methyl 1-azido-4,4-difluorocyclohexanecarboxylate (2.17 g, 9.9 mmol) and anhydrous methanol (30 mL), then Pd/C (0.5 g, 10%) was added. After the addition, the mixture was stirred at rt overnight under hydrogen atomosphere. The filtrate was concentrated in vacuo to remove the methanol, and the residue was purified by silica-gel column chromatography (EtOAc:PE=1:3, V/V) to give light yellow oil (0.29 g, 15%).

MS (ESI, pos. ion) m/z: 194.1 (M+1);

Step 5: methyl 1-(6-bromobenzofuran-2-carboxamido)-4,4-difluorocyclohexanecarboxylate To a 50 mL two-neck flask were added 6-bromobenzofuran-2-carboxylic acid (290 mg, 1.2 mmol), methyl 1-amino-4,4-difluorocyclohexanecarboxylate (280 mg, 1.4 mmol) and DMF (6 mL). To the mixture were added HATU (479 mg, 1.26 mmol) and triethylamine (0.44 mL, 2.4 mmol) at 0° C. under nitrogen protection. The mixture was stirred for 2.0 h at 0° C. under nitrogen protection. To the reaction mixture was added saturated aqueous sodium bicarbonate (30 mL), and the resulting mixture was extracted with ethyl acetate (30 mL×3). The combined organic layer was washed with saturated brine (30 mL×2), dried over anhydrous sodium sulfate and filtered. The filtrate was concentrated in vacuo, and the residue was purified by silica-gel column chromatography (EtOAc:PE=1:5, V/V) to give a white solid (410 mg, 82%).

MS (ESI, pos. ion) m/z: 418.0 (M+1);

Step 6: 1-(6-bromobenzofuran-2-carboxamido)-4,4-difluorocyclohexanecarboxylic acid To a 100 mL single-neck flask were added methyl 1-(6-bromobenzofuran-2-carboxamido)-4,4-difluorocyclohexanecarboxylate (3.0 g, 7.2 mmol), methanol (10 mL), tetrahydrofuran (10 mL) and water (10 mL), then to the mixture was added lithium hydroxide (0.52 g, 22 mmol). After the addition, the mixture was stirred at rt for 1 h. The reaction mixture was concentrated in vacuo to remove most of the solvent, and to the residue was added water (60 mL). The resulting mixture was extracted with ethyl ether (60 mL), and the aqueous layer was acidified with diluted hydrochloric acid (2 mol/L) to pH 1, then a solid was precipitated out. The mixture was filtered, and the filter cake was dried to give a white solid (2.75 g, 95%).

Step 7: 6-bromo-N-(1-((1-cyanocyclopropyl)carbamoyl)-4,4-difluorocyclohexyl)benzofuran-2-carboxamide To a 50 mL two-neck flask were added 1-(6-bromobenzofuran-2-carboxamido)-4,4-difluorocyclohexanecarboxylic acid (402 mg, 1.0 mmol), 1-amino-1-cyclopropanecarbonitrile hydrochloride (154 mg, 1.3 mmol) and DMF (5 mL). To the mixture were added HATU (399 mg, 1.05 mmol) and triethylamine (0.5 mL, 3.0 mmol). The mixture was stirred for 24 h at rt. To the reaction mixture was added saturated aqueous sodium bicarbonate (30 mL), and the resulting mixture was extracted with ethyl acetate (30 mL×3). The combined organic layers were washed with saturated brine (30 mL×2), dried over anhydrous sodium sulfate and filtered. The filtrate was concentrated in vacuo, and the residue was purified by silica-gel column chromatography (DCM) to give a white solid (298 mg, 64%).

MS (ESI, pos. ion) m/z: 466.1 (M+1);

Step 8: N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide To a two-neck flask were added 6-bromo-N-(1-((1-cyanocyclopropyl)carbamoyl)-4,4-difluorocyclohexyl)benzofuran-2-carboxamide (1.5 g, 3.22 mmol), bis(pinacolato) diboron (1.23 g, 4.82 mmol), potassium acetate (0.98 g, 10 mmol) and Pd(dppf)Cl$_2$·CH$_2$Cl$_2$ (100 mg, 0.12 mmol), then DMF (20 mL) was added under nitrogen protection. The resulting mixture was stirred at 85° C. for 3 h under nitrogen protection. The reaction mixture was cooled to rt and to the mixture was added water (80 mL) to quench the reaction. The resulting mixture was extracted with EtOAc (50 mL×2). The combined organic layers were washed with water (80 mL×2) and saturated brine (80 mL×2), dried over anhydrous Na$_2$SO$_4$, and concentrated, and the residue was purified by silica-gel column chromatography (DCM:EtOAc=20:1, V/V) to give a yellow solid (1.43 g, 87%).

MS (ESI, pos. ion) m/z: 514.20 (M+1).

Example 1: 6-(4-(3-aminooxetan-3-yl)phenyl)-N-(1-((1-cyanocyclopropyl)carbamoyl) cyclohexyl)benzofuran-2-carboxamide

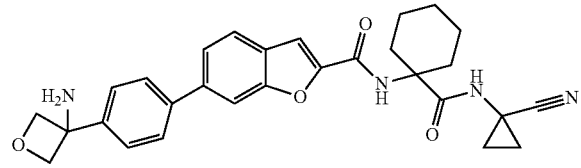 [SMILES: N#CC1(NC(=O)C2(NC(=O)c3cc4ccc(-c5ccc(C6(N)COC6)cc5)cc4o3)CCCCC2)CC1]

Step 1:
2-methyl-N-(oxetan-3-ylidene)propane-2-sulfinamide

To a 100 mL round-bottom flask were added oxetan-3-one (1.62 mL, 27.9 mmol), 2-methylpropane-2-sulfinamide (4.0 g, 33 mmol) and anhydrous DCM (30 mL), then to the mixture was added titanium iso-propylate (16.6 mL) over 40 min via constant pressure funnel at rt under nitrogen protection. After the addition, the mixture was refluxed overnight. After the reaction was completed, the reaction mixture was cooled to rt, and saturated aqueous sodium bicarbonate (100 mL) was added. The resulting mixture was stirred for 20 min, then diatomite was added to filter the mixture by suction. After the mixture was filtered, the filter cake was washed with dichoromethane (20 mL). The combined filtrates were extracted with DCM (30 mL×2), and the combined organic layers were dried over anhydrous sodium sulfate, and filtered. The filtrate was concentrated in vacuo, and the residue was purified by silica-gel column chromatography (n-hexane:EtOAc=1:1, V/V) to give colourless oil (2.35 g, 48.1%).

MS (ESI, pos. ion) m/z: 176.1 (M+1);

Step 2: N-(3-(4-bromophenyl)oxetan-3-yl)-2-methylpropane-2-sulfinamide

To a dried 50 mL two-neck flask were added 1-bromo-4-iodobenzene (2.10 g, 7.4 mmol) and anhydrous tetrahydrofuran (10 mL). To the mixture was added dropwise n-BuLi (3.45 mL, 2.4 mol/L) at −78° C. under nitrogen protection. After the addition, the mixture was stirred for 1 h, then a solution of 2-methyl-N-(oxetan-3-ylidene)propane-2-sulfinamide (1.0 g, 5.7 mmol) in anhydrous tetrahydrofuran (8 mL) was added dropwise at −78° C. After the addition, the mixture was stirred for 0.5 h, then warmed slowly to rt and stirred overnight. After the reaction was completed, saturated aqueous ammonium chloride (3 mL) was added to quench the reaction. Then water (20 mL) and ethyl acetate (40 mL) was added to the mixture. The resulting mixture was partitioned, then the organic layer was dried over anhydrous sodium sulfate, and filtered. The filtrate was concentrated in vacuo, and the residue was purified by silica-gel column chromatography (n-hexane:EtOAc=1:1, V/V) to give light yellow oil (763 mg, 40.2%).

MS (ESI, pos. ion) m/z: 332.1 (M+1);

Step 3: 3-(4-bromophenyl)oxetan-3-amine

To a dried 50 mL two-neck round-bottom flask were added N-(3-(4-bromophenyl)oxetan-3-yl)-2-methylpropane-2-sulfinamide (313 mg, 0.94 mmol), anhydrous methanol (4 mL) and ethyl acetate (4 mL). The mixture was cooled under ice-bath condition, then a solution of hydrogen chloride in ethyl acetate (5 mL, 3.5 mol/L) were added. The resulting mixture was stirred for 30 min, then concentrated in vacuo to remove the solvent. The residue was dissolved in ethyl acetate (50 mL), then the mixture was washed with saturated aqueous sodium bicarbonate (20 mL) and saturated aqueous sodium chloride (20 mL) in turn, dried over anhydrous sodium sulfate, and filtered. The filtrate was concentrated in vacuo to give a light yellow solid (200 mg, 93%).

MS (ESI, pos. ion) m/z: 229.0 (M+2);

Step 4: 6-(4-(3-aminooxetan-3-yl)phenyl)-N-(1-((1-cyanocyclopropyl)carbamoyl)cyclohexyl) benzofuran-2-carboxamide To a 50 mL two-neck flask were added N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (110 mg, 0.21 mmol), toluene (6 mL), ethanol (2 mL) and 3-(4-bromophenyl)oxetan-3-amine (50 mg, 0.22 mmol), then tetrakis(triphenylphosphine)palladium(0 (25 mg, 0.02 mmol) was added under nitrogen protection, and aqueous potassium carbonate (2 mol/L, 0.4 mL) was added into the reaction mixture. The resulting mixture was stirred at 90° C. for 1 h. The reaction mixture was cooled to rt and to the mixture was added saturated brine (20 mL). The resulting mixture was extracted with EtOAc (20 mL×3). The combined organic layers were dried over anhydrous Na$_2$SO$_4$, and filtered. The filtrate was concentrated in vacuo, and the residue was purified by silica-gel column chromatography (DCM:MeOH=10:1, V/V) to give white powder (60 mg, 52.6%).

MS (ESI, pos. ion) m/z: 499.2 (M+1);

$^1$H NMR (600 MHz, DMSO-d6) δ 9.10 (br, 2H), 8.61 (s, 1H), 8.05 (s, 1H), 7.98 (s, 1H), 7.91 (dd, J=18.4, 8.2 Hz, 3H), 7.77-7.70 (m, 2H), 7.66 (dd, J=8.3, 2.6 Hz, 2H), 4.98 (s, 4H), 2.05 (d, J=13.3 Hz, 2H), 1.83-1.71 (m, 2H), 1.61-1.41 (m, 6H), 1.30 (d, J=9.1 Hz, 2H), 1.06 (dd, J=7.9, 5.6 Hz, 2H).

Example 2: N-(1-((1-cyanocyclopropyl)carbamoyl)-4,4-difluorocyclohexyl)-6-(4-(methylsulfonyl)phenyl)benzofuran-2-carboxamide

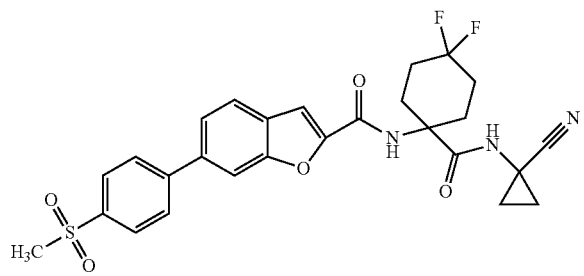 [SMILES: CS(=O)(=O)c1ccc(-c2ccc3cc(C(=O)NC4(C(=O)NC5(C#N)CC5)CCC(F)(F)CC4)oc3c2)cc1]

6-Bromo-N-(1-((1-cyanocyclopropyl)carbamoyl)-4,4-difluorocyclohexyl)benzofuran-2-carboxamide (50 mg, 0.107 mmol) was dissolved in a mixture of ethanol (2 mL) and toluene (6 mL) in a 50 mL two-neck round-bottom flask. Then 4-methylfulfonylphenylboronic acid (26 mg, 0.129 mmol) was added, and Pd(Ph$_3$P)$_4$ (25 mg, 0.02 mmol) was added under nitrogen protection, and aqueous potassium carbonate (0.14 mL, 0.28 mmol, 2 mol/L) was added into the reaction mixture. The resulting mixture was stirred at 95° C. for 1 h. After the reaction mixture was completed, to the mixture was added saturated brine (20 mL). The resulting mixture was extracted with EtOAc (20 mL×3). The combined organic layers were washed with saturated brine (20 mL×2), dried over anhydrous Na$_2$SO$_4$, and filtered. The filtrate was concentrated in vacuo, and the residue was purified by silica-gel column chromatography (DCM:EtOAc=3:1, V/V) to give white powder (50 mg, 86%).

MS (ESI, pos. ion) m/z: 542.2 [M+1]+; and $^1$H NMR (600 MHz, CDCl$_3$) δ 8.10-7.99 (m, 2H), 7.81 (d, J=8.0 Hz, 2H), 7.77 (s, 1H), 7.66 (d, J=8.2 Hz, 1H), 6.64 (s, 1H), 3.11 (s, 3H), 2.52-2.31 (m, 4H), 2.26-2.12 (m, 2H), 2.08-1.94 (m, 2H), 1.30-1.23 (m, 4H).

Example 3: N-(1-((1-cyanocyclopropyl)carbamoyl)cyclohexyl)-6-(5-(thiophen-2-yl)-1,2,4-oxadiazol-3-yl)benzofuran-2-carboxamide

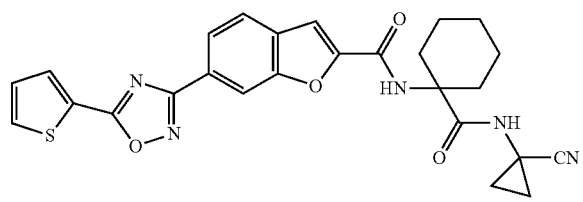 [SMILES: N#CC1(NC(=O)C2(NC(=O)c3cc4ccc(-c5noc(-c6cccs6)n5)cc4o3)CCCCC2)CC1]

Step 1: 6-cyanobenzofuran-2-carboxylic acid

To a 50 mL round-bottom flask were added 6-bromobenzofuran-2-carboxylic acid (4.82 g, 20 mmol) and anhydrous N-methylimidazole (16 mL), then to the mixture were added potassium ferricyanide (1.32 g, 4.0 mmol) and cuprous iodide (380 mg, 2.00 mmol). The resulting mixture was heated to 160° C. and stirred overnight. The reaction mixture was cooled to rt and to the mixture was added saturated aqueous sodium bicarbonate (100 mL). The resulting mixture was extracted with EtOAc (40 mL×3). The combined organic layers were washed with water (80 mL×2) and saturated brine (100 mL×1), dried over anhydrous Na$_2$SO$_4$, and filtered. The filtrate was concentrated in vacuo to give a light yellow solid (3.2 g, 47.9%).

MS (ESI, pos. ion) m/z: 188.1 (M+1);

Step 2: ethyl 6-cyanobenzofuran-2-carboxylate

To a 100 mL two-neck round-bottom flask were added 6-cyanobenzofuran-2-carboxylic acid (3.20 g, 17.1 mmol) and ethanol (50 mL), then thionyl chloride (2.2 mL, 30.0 mmol) was added under nitrogen protection. The mixture was refluxed for 4 h. After the reaction was completed, the reaction mixture was concentrated in vacuo to remove ethanol and to the mixture was added saturated brine (50 mL). The resulting mixture was extracted with EtOAc (30 mL×3). The combined organic layers were washed with saturated brine (40 mL×2), dried over anhydrous Na$_2$SO$_4$, and filtered. The filtrate was concentrated in vacuo, and the residue was purified by silica-gel column chromatography (PE:EtOAc=20:1, V/V) to give a white solid (700 mg, 25.2%).

MS (ESI, pos. ion) m/z: 216.1 (M+1);

Step 3: ethyl 6-(N-((thiophene-2-carbonyl)oxy)carbamimidoyl)benzofuran-2-carboxylate To a 50 mL round-bottom flask were added ethyl 6-cyanobenzofuran-2-carboxylate (350 mg, 1.63 mmol) and anhydrous ethanol (12 mL), then to the mixture were added hydroxylamine hydrochloride (226 mg, 3.26 mmol) and triethylamine (0.45 mL, 3.26 mmol) in turn under nitrogen protection. The resulting mixture was stirred at 90° C. for 3 h. The reaction mixture was cooled to rt and concentrated in vacuo to remove ethanol. To the residue was added saturated brine (40 mL). The resulting mixture was extracted with EtOAc (20 mL×3). The combined organic layers were washed with saturated brine (40 mL×2), dried over anhydrous Na$_2$SO$_4$, and filtered. The filtrate was concentrated in vacuo to remove the solvent, and the crude product was used in the next step.

The crude product was dissolved in anhydrous acetonitrile (12 mL), then triethylamine (0.45 mL, 3.26 mmol) and thiophene-2-carbonyl chloride (0.35 mL, 3.26 mmol) were added into the mixture. The resulting mixture was stirred at rt overnight. To the mixture was added saturated brine (50 mL). The resulting mixture was extracted with EtOAc (30 mL×3). The combined organic layers were washed with saturated brine (40 mL×2), dried over anhydrous Na$_2$SO$_4$, and filtered. The filtrate was concentrated in vacuo, and the residue was purified by silica-gel column chromatography (DCM:EtOAc=40:1, V/V) to give a white solid (220 mg, 37.7%).

MS (ESI, pos. ion) m/z: 359.1 (M+1);

Step 4: ethyl 6-(5-(thiophen-2-yl)-1,2,4-oxadiazol-3-yl)benzofuran-2-carboxylate To a 50 mL two-neck flask were added ethyl 6-(N-((thiophene-2-carbonyl)oxy)carbamimidoyl)benzofuran-2- carboxylate (220 mg, 0.64 mmol) and acetic acid (12 mL) in turn. The resulting mixture was stirred at 80° C. overnight under nitrogen protection. After the reaction was completed, to the mixture was added saturated brine (80 mL). The resulting mixture was extracted with EtOAc (30 mL×3). The combined organic layers were washed with saturated brine (50 mL×2), dried over anhydrous $Na_2SO_4$, and filtered. The filtrate was concentrated in vacuo, and the residue was purified by silica-gel column chromatography (PE: EtOAc=20:1, V/V) to give a white solid (180 mg, 82.6%).

MS (ESI, pos. ion) m/z: 341.1 (M+1);

Step 5: 6-(5-(thiophen-2-yl)-1,2,4-oxadiazol-3-yl) benzofuran-2-carboxylic acid To a 50 mL two-neck flask were added ethyl 6-(5-(thiophen-2-yl)-1,2,4-oxadiazol-3-yl)benzofuran-2-carboxylate (180 mg, 0.53 mmol) and methanol (10 mL), then sodium hydroxide (0.8 mL, 1.60 mmol, 2 mol/L) was added under nitrogen protection. The resulting mixture was stirred at rt for 80 min. After the reaction was completed, the reaction mixture was diluted with water (20 mL), and the resulting mixture was concentrated in vacuo to remove the methanol. The aqueous layer was extracted with ethyl ether (40 mL×2), then the aqueous layer was acidified with hydrochloric acid (1 mol/L) to adjust pH 5-6, and the resulting mixture was extracted with EtOAc (30 mL×3). The combined organic layers were washed with saturated brine (50 mL×2), dried over anhydrous $Na_2SO_4$, and filtered. The filtrate was concentrated in vacuo to give a white solid (160 mg, 97.0%).

MS (ESI, pos. ion) m/z: 313.1 [M+1]+;

Step 6: N-(1-((1-cyanocyclopropyl)carbamoyl)cyclohexyl)-6-(5-(thiophen-2-yl)-1,2,4-oxadiazol-3-yl) benzofuran-2-carboxamide To a solution of 1-amino-N-(1-cyanocyclopropyl)cyclohexanecarboxamide hydrochloride (250 mg, 1.0 mmol) in anhydrous DMF (10 mL) was added 6-(5-(thiophen-2-yl)-1,2,4-oxadiazol-3-yl)benzofuran-2-carboxylic acid (160 mg, 0.52 mmol) in a 50 mL round-bottom flask. The mixture was cooled to 0° C., then HATU (210 mg, 0.52 mmol) and triethylamine (0.4 mL, 2.10 mmol) were added. The resulting mixture was stirred at 0° C. for 1 hour. After the reaction was completed, to the reaction mixture was added saturated brine (80 mL). The resulting mixture was extracted with EtOAc (30 mL×3), then the combined organic layers were washed with saturated brine (50 mL×2), dried over anhydrous sodium sulfate, and filtered. The filtrate was concentrated in vacuo, and the residue was purified by silica-gel column chromatography (DCM:EtOAc=20:1, V/V) to give a white solid (80 mg, 26.7%).

MS (ESI, pos. ion) m/z: 502.3 (M+1);

$^1$H NMR (600 MHz, $CDCl_3$) δ 8.40 (s, 1H), 8.17 (d, J=8.2 Hz, 1H), 8.08 (s, 1H), 8.01 (d, J=3.7 Hz, 1H), 7.84 (d, J=8.2 Hz, 1H), 7.72 (d, J=4.9 Hz, 1H), 7.64 (s, 1H), 7.56 (s, 1H), 7.27 (d, J=4.8 Hz, 1H), 6.65 (s, 1H), 4.68 (s, 2H), 3.74 (q, J=7.0 Hz, 2H), 2.28 (d, J=13.8 Hz, 2H), 2.04 (dd, J=19.2, 8.2 Hz, 2H), 1.94 (d, J=7.1 Hz, 2H), 1.88 (t, J=11.1 Hz, 2H), 1.80-1.73 (m, 2H), 1.58-1.53 (m, 2H), 1.20 (dd, J=8.2, 5.7 Hz, 2H).

Example 4: N-(1-((1-cyanocyclopropyl)carbamoyl)-4,4-difluorocyclohexyl)-6-(3,4-dimethoxyphenyl) benzofuran-2-carboxamide

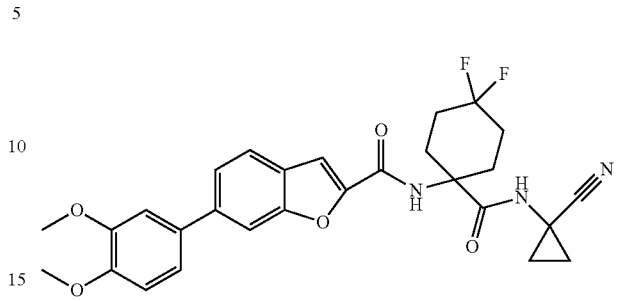

The title compound was prepared according to the step 4 of example 1, using N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (80 mg, 0.16 mmol), ethanol (2 mL), toluene (6 mL), 4-bromo-1,2-dimethoxybenzene (55 mg, 0.25 mmol), tetrakis(triphenylphosphine)palladium(0) (20 mg, 0.017 mmol) and aqueous potassium carbonate (2 mol/L, 0.23 mL), to give a white solid (50 mg, 1.3%).

MS (ESI, pos. ion) m/z: 524.2 (M+1);

$^1$H NMR (400 MHz, $CDCl_3$) δ 8.26 (s, 1H), 7.80-7.67 (m, 2H), 7.62-7.53 (m, 2H), 7.25-7.20 (m, 1H), 7.17 (s, 1H), 7.01 (d, J=8.2 Hz, 1H), 6.60 (s, 1H), 3.99 (d, J=11.3 Hz, 6H), 2.52-2.31 (m, 4H), 2.26-2.12 (m, 2H), 2.08-1.94 (m, 2H), 1.30-1.23 (m, 4H).

Example 5: N-(1-((1-cyanocyclopropyl)carbamoyl) cyclohexyl)-6-(2-fluoro-4-(methylsulfonyl)phenyl) benzofuran-2-carboxamide

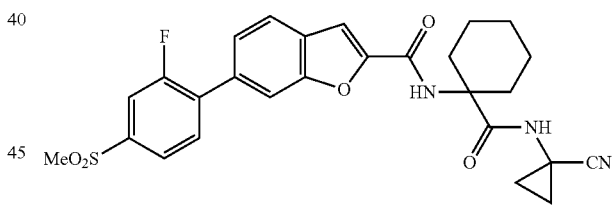

Step 1: ethyl 6-bromobenzofuran-2-carboxylate

To a 250 mL two-neck flask were added 4-bromosalicylaldehyde (16.08 g, 80 mmol) and anhydrous N,N-dimethylformamide (50 mL), then to the mixture were added potassium carbonate (33.12 g, 240 mmol) and ethyl bromoacetate (13.3 mL, 120 mmol) under nitrogen protection. The mixture was heated to 130° C. and stirred for 3 hours. The reaction mixture was cooled to rt, and saturated brine (300 mL) was added into the mixture. The mixture was extracted with ethyl acetate (80 mL×3), then the combined organic layers were washed with water (150 mL×2) and saturated brine (100 mL×2), dried over anhydrous sodium sulfate and filtered. The filtrate was concentrated in vacuo, and the residue was purified by silica-gel column chromatography (PE:EtOAc=20:1, V/V) to give a white solid (10.3 g, 47.9%).

MS (ESI, pos. ion) m/z: 269.9 (M+2);

Step 2: 6-bromobenzofuran-2-carboxylic acid

To a 250 mL two-neck flask were added ethyl 6-bromobenzofuran-2-carboxylate (10.3 g, 38.3 mmol) and methanol (100 mL), then sodium hydroxide solution (57 mL, 114 mmol, 2 mol/L) was added under nitrogen protection. The mixture was stirred at rt for 4 hours. After the reaction was completed, the mixture was diluted with water (100 mL), and then concentrated in vacuo to remove the methanol. The aqueous layer was extracted with ethyl ether (40 mL×2), then the aqueous layer was adjusted with hydrochloric acid (3 mol/L) to pH about 3 to 4, and there was a solid precipitated out. The mixture was filtered to give a white solid (7.8 g, 84.5%).

MS (ESI, pos. ion) m/z: 242 (M+1);

Step 3: 6-bromo-N-(1-((1-cyanocyclopropyl)carbamoyl)cyclohexyl)benzofuran-2-carboxamide 1-Amino-N-(1-cyanocyclopropyl)cyclohexanecarboxamide hydrochloride (1.46 g, 6.0 mmol) was dissolved in anhydrous N,N-dimethylformamide (18 mL) in a 50 mL round-bottom flask, then 6-bromobenzofuran-2-carboxylic acid (1.11 g, 4.62 mmol) was added. To the resulting mixture was added HATU (1.75 g, 4.62 mmol) at 0° C., then triethylamine (2.5 mL, 13.85 mmol) was added dropwise into the mixture, and then the mixture was stirred at 0° C. for 1 hour. After the reaction was completed, to the reaction mixture was added saturated brine (100 mL). The resulting mixture was extracted with EtOAc (30 mL×3), then the combined organic layers were washed with saturated brine (50 mL×2), dried over anhydrous sodium sulfate, and filtered. The filtrate was concentrated in vacuo, and the residue was purified by silica-gel column chromatography (DCM:EtOAc=50:1, V/V) to give a white solid (430 mg, 21.6%).

MS (ESI, pos. ion) m/z: 430.3 (M+1);

Step 4: N-(1-((1-cyanocyclopropyl)carbamoyl)cyclohexyl)-6-(4,4,5,5-tetramethyl-1,3,2-dioxaborolan-2-yl)benzofuran-2-carboxamide 6-Bromo-N-(1-((1-cyanocyclopropyl)carbamoyl)cyclohexyl)benzofuran-2-carboxamide (427 mg, 1.0 mmol) was dissolved in anhydrous N,N-dimethylformamide (10 mL) in a 50 mL two-neck round-bottom flask, and to the resulting mixture were added bis(pinacolato)diboron (330 mg, 1.3 mmol) and 1,1'-bis(diphenylphosphino)ferrocene-palladium (II)dichloride dichloromethane complex (82 mg, 0.1 mmol). Then potassium acetate (344 mg, 3.5 mmol) was added quickly into the mixture. The resulting mixture was stirred for 3.5 hours at 90° C. under nitrogen protection. The mixture was cooled to rt, and to the mixture was added saturated brine (100 mL). The mixture was extracted with ethyl acetate (30 mL×3), and the combined organic layers were washed with saturated brine (50 mL×2), dried over anhydrous sodium sulfate and filtered. The filtrate was concentrated in vacuo, and the residue was purified by silica-gel column chromatography (DCM:EtOAc=40:1, V/V) to give a white solid (330 mg, 69.2%).

MS (ESI, pos. ion) m/z: 478.1 (M+1);

Step 5: N-(1-((1-cyanocyclopropyl)carbamoyl)cyclohexyl)-6-(2-fluoro-4-(methylsulfonyl)phenyl)benzofuran-2-carboxamide N-(1-((1-cyanocyclopropyl)carbamoyl)cyclohexyl)-6-(4,4,5,5-tetramethyl-1,3,2-dioxaborolan-2-yl)benzofuran-2-carboxamide (80 mg, 0.168 mmol) was dissolved in a mixture of ethanol (2 mL) and toluene (6 mL) in a 50 mL two-neck round-bottom flask. Then 1-bromo-2-fluoro-4-(methylsulfonyl)benzene (51 mg, 0.20 mmol) was added, and Pd(Ph$_3$P)$_4$ (15.5 mg, 0.013 mmol) was added under nitrogen protection, and then aqueous potassium carbonate (0.17 mL, 0.34 mmol, 2 mol/L) was added into the reaction mixture. The resulting mixture was stirred at 90° C. for 1 h. After the reaction was completed, to the mixture was added saturated brine (60 mL). The resulting mixture was extracted with EtOAc (20 mL×3). The combined organic layers were washed with saturated brine (30 mL×2), dried over anhydrous Na$_2$SO$_4$, and filtered. The filtrate was concentrated in vacuo, and the residue was purified by silica-gel column chromatography (DCM:EtOAc=8:1, V/V) to give a white solid (30 mg, 34.4%).

MS (ESI, pos. ion) m/z: 523.9 (M+1);
$^1$H NMR (600 MHz, CDCl$_3$) δ 8.10 (s, 1H), 7.86 (d, J=7.7 Hz, 1H), 7.82 (t, J=7.4 Hz, 1H), 7.79 (s, 2H), 7.73 (t, J=7.3 Hz, 1H), 7.71-7.63 (m, 1H), 7.59-7.51 (m, 2H), 7.49 (d, J=5.9 Hz, 1H), 6.64 (s, 1H), 3.15 (s, 3H), 2.27 (d, J=12.9 Hz, 2H), 2.03 (t, J=11.0 Hz, 2H), 1.75 (d, J=9.3 Hz, 2H), 1.58-1.46 (m, 4H), 1.26 (d, J=12.3 Hz, 4H).

Example 6: N-(1-((1-cyanocyclopropyl)carbamoyl)-4,4-difluorocyclohexyl)-6-(4-(1,2-dihydroxyethyl)phenyl)benzofuran-2-carboxamide

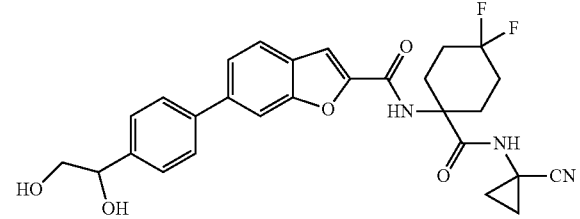 [SMILES: N#CC1(NC(=O)C2(NC(=O)c3cc4ccc(-c5ccc(C(O)CO)cc5)cc4o3)CCC(F)(F)CC2)CC1]

Step 1: 1-(4-bromophenyl)ethane-1,2-diol

To a 50 mL round-bottom flask were added ethyl 4-bromobenzoylformate (0.30 g, 1.2 mmol) and methanol (10 mL), then sodium borohydride (0.13 g, 0.41 mmol) was added in portions at 0° C. The resulting mixture was stirred at rt for 10 min. The reaction mixture was acidified with hydrochloric acid (5.0 mol/L) to pH 6, then the resulting mixture was concentrated in vacuo to remove the methanol. The residue was dissolved in water (50 mL), and the resulting mixture was extracted with ethyl acetate (30 mL×3). The combined organic layers were dried over anhydrous sodium sulfate, concentrated in vacuo, and the residue was purified by silica-gel column chromatography (DCM:MeOH=30:1, V/V) to give a white solid (0.12 g, 47%).

MS (ESI, pos. ion) m/z: 217.9 (M+2);

Step 2: N-(1-((1-cyanocyclopropyl)carbamoyl)-4,4-difluorocyclohexyl)-6-(4-(1,2-dihydroxy ethyl)phenyl)benzofuran-2-carboxamide To a 50 mL two-neck flask were added N-(1-((1-cyanocyclopropyl)carbamoyl)cyclohexyl)-6-(4,4,5,5-tetramethyl-1,3,2-dioxaborolan-2-yl)benzofuran-2-carboxamide (62 mg, 0.12 mmol), Pd(dppf)Cl$_2$.CH$_2$Cl$_2$ (8 mg, 0.01 mmol) and DMF (8 mL), then potassium carbonate solution (0.10 mL, 0.20 mmol, 2 mol/L) was added under nitrogen protection. The resulting mixture was stirred at 85° C. for 2 h. The reaction mixture was cooled to rt and the mixture was quenched with water (100 mL). The resulting mixture was extracted with EtOAc (30 mL×2). The combined organic layers were washed with saturated brine (20 mL), dried over anhydrous $Na_2SO_4$, and filtered. The filtrate was concentrated in vacuo, and the residue was purified by silica-gel column chromatography (DCM:MeOH=30:1, V/V) to give a white solid (42 mg, 79%).

MS (ESI, pos. ion) m/z: 524.2 (M+1);

$^1$H NMR (400 MHz, DMSO-$d_6$) δ: 8.76 (s, 1H), 8.47 (s, 1H), 7.94 (s, 1H), 7.86 (d, J=8.2 Hz, 1H), 7.69 (dd, J=15.3, 7.8 Hz, 4H), 7.46 (d, J=7.6 Hz, 2H), 5.28 (d, J=4.2 Hz, 1H), 4.74 (t, J=5.7 Hz, 1H), 4.60 (d, J=4.9 Hz, 1H), 3.48 (t, J=5.7 Hz, 3H), 2.22 (s, 2H), 2.07 (d, J=14.8 Hz, 5H), 1.46 (s, 2H), 1.09 (d, J=5.6 Hz, 2H), 0.86 (s, 2H).

$^{19}$F NMR (376 MHz, DMSO-$d_6$) δ: −92.53 (s), −93.16 (s), −97.79 (s), −98.41 (s).

Example 7: N-(1-((1-cyanocyclopropyl)carbamoyl) cyclohexyl)-6-(4-(2,2-difluoro-1-hydroxyethyl)phenyl)benzofuran-2-carboxamide

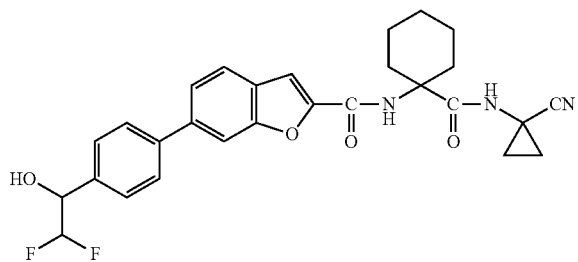 [SMILES: N#CC1(NC(=O)C2(NC(=O)c3cc4ccc(-c5ccc(C(O)C(F)F)cc5)cc4o3)CCCCC2)CC1]

Step 1: N-(1-bromophenyl)ethylidenebutan-1-amine

To a 50 mL two-neck round-bottom flask were added (4-bromophenyl)ethanone (1.99 g, 10 mmol) and cyclohexane (20 mL). To the mixture were added n-butylamine (1.19 mL, 12 mmol) and a catalytic amount of trifluoroacetic acid at 0° C. under nitrogen protection. The reaction mixture was equipped with a water-separator and stirred at 130° C. for 24 h. The reaction mixture was cooled to rt and concentrated in vacuo to remove the solvent to give a yellow crude product, which was used directly in the next step.

Step 2: 1-(4-bromophenyl)-2,2-difluoroethanone

To a 100 mL two-neck flask were added N-(1-bromophenyl)ethylidenebutan-1-amine (2.54 g, 10 mmol), anhydrous sodium sulfate (1.0 g) and 1-chloromethyl-4-fluoro-1,4-diazoniabicyclo[2.2.2]octane bis(tetrafluoroborate) (7.1 g, 2.0 mmol). To the mixture was added acetonitrile (50 mL) under nitrogen protection. The reaction mixture was stirred at 90° C. for 5 h. The reaction mixture was cooled to rt and concentrated hydrochloric acid (5 mL, 37%) was added, then the resulting mixture was stirred at rt for 10 min. The mixture was concentrated in vacuo to remove the acetonitrile, and to the residue was added diethyl ether (40 mL). The mixture was washed with saturated aqueous sodium bicarbonate (50 mL) and saturated brine (40 mL), dried over anhydrous $Na_2SO_4$, filtered. The filtrate was concentrated in vacuo, and the residue was purified by silica-gel column chromatography (PE:EtOAc=1:50, V/V) to give yellow oil (2.06 g, 88%).

MS (ESI, pos. ion) m/z: 235.1 (M+1);

Step 3: 1-(4-bromophenyl)-2,2-difluoroethanol

To a 50 mL two-neck flask were added 1-(4-bromophenyl)-2,2-difluoroethanone (2.06 g, 8.8 mmol) and anhydrous ethanol (15 mL). To the mixture was added sodium borohydride (0.499 g, 13.2 mmol) under nitrogen protection. The reaction mixture was stirred at rt for 2 h. The mixture was concentrated in vacuo to remove the ethanol, and to the residue was added ethyl acetate (80 mL). The mixture was washed with saturated brine (40 mL), dried over anhydrous $Na_2SO_4$, and filtered. The filtrate was concentrated in vacuo, and the residue was purified by silica-gel column chromatography (PE:EtOAc=1:15, V/V) to give colourless oil (1.2 g, 57%).

$^1$H NMR (400 MHz, CDCl$_3$) δ: 7.54 (d, J=8.2 Hz, 2H), 7.31 (d, J=8.2 Hz, 2H), 5.72 (td, J=55.9, 4.7 Hz, 1H), 4.93-4.69 (m, 1H), 2.47 (s, 1H).

Step 4: N-(1-((1-cyanocyclopropyl)carbamoyl)cyclohexyl)-6-(4-(2,2-difluoro-1-hydroxyethyl) phenyl)benzofuran-2-carboxamide To a 50 mL two-neck flask were added 1-(4-bromophenyl)-2,2-difluoroethanol (41 mg, 0.17 mmol), N-(1-((1-cyanocyclopropyl)carbamoyl)cyclohexyl)-6-(4,4,5,5-tetramethyl-1,3,2-dioxaborolan-2-yl)benzofuran-2-carboxamide (82.5 mg, 0.17 mmol), Pd(dppf)Cl$_2$.CH$_2$Cl$_2$ (20 mg) and DMF (5 mL). To the mixture was added aqueous potassium carbonate (0.26 mL, 2 mol/L) under nitrogen protection. The resulting mixture was stirred at 90° C. for 3 h. The reaction mixture was cooled to rt, and to the reaction mixture was added saturated aqueous sodium chloride (50 mL), and the resulting mixture was extracted with ethyl acetate (50 mL×2). The combined organic layers were washed with saturated brine (40 mL×2), dried over anhydrous sodium sulfate and filtered. The filtrate was concentrated in vacuo, and the residue was purified by silica-gel column chromatography (DCM:EtOAc=30:1, V/V) to give a white solid (22 mg, 25%).

MS (ESI, pos. ion) m/z: 508.20 (M+1);

$^1$H NMR (600 MHz, CDCl$_3$) δ 8.05 (s, 1H), 7.80 (d, J=8.0 Hz, 2H), 7.62 (dd, J=13.1, 8.2 Hz, 4H), 7.36 (d, J=8.1 Hz, 2H), 6.28 (s, 1H), 3.69 (d, J=5.4 Hz, 2H), 2.59 (t, J=5.8 Hz, 2H), 2.39-2.21 (m, 2H), 2.13 (dd, J=14.4, 8.0 Hz, 2H), 1.98 (s, 4H), 1.78-1.42 (m, 12H), 1.24 (dd, J=23.2, 6.4 Hz, 4H).

Example 8: 3-chloro-N-(1-((1-cyanocyclopropyl) carbamoyl)cyclohexyl)-6-(4-(methylsulfonyl)phenyl)benzofuran-2-carboxamide

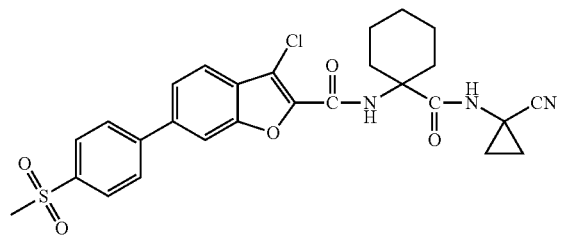 [SMILES: CS(=O)(=O)c1ccc(-c2ccc3c(Cl)c(C(=O)NC4(C(=O)NC5(C#N)CC5)CCCCC4)oc3c2)cc1]

Step 1: 2-chloro-1-(2-hydroxy-4-iodophenyl)ethanone

To a 100 mL round-bottom flask was added a solution of boron trichloride in dichloromethane (12 mL, 12 mmol, 1 mol/L). Then to the flask were added dropwise 3-iodophenol (2.2 g, 10 mmol), chloroacetonitrile (0.76 mL, 12 mmol) and aluminum chloride (668 mg) at 0° C. The resulting mixture was stirred at rt for 48 h. Then to the mixture were added ice-water (50 mL) and diluted hydrochloric acid (2 mol/L, 8 mL, 16 mmol). The resulting mixture was stirred at rt for 0.5 h. To the reaction mixture was added water (60 mL), and the resulting mixture was extracted with DCM (80 mL). The combined organic layers were washed with saturated brine (40 mL×2), dried over anhydrous sodium sulfate and filtered. The filtrate was concentrated in vacuo, and the residue was purified by silica-gel column chromatography (PE:EtOAc-40:1, V/V) to give a yellow solid (2.7 g, 91%).

MS (ESI, pos. ion) m/z: 297.1 (M+1);

Step 2: 6-iodobenzofuran-3(2H)-one

To a 50 mL two-neck flask were added 2-chloro-1-(2-hydroxy-4-iodophenyl)ethanone (2.4 g, 8.1 mmol), triethylamine (5.7 mL, 40.5 mmol) and acetonitrile (20 mL), then the resulting mixture was stirred at rt for 40 min. To the reaction mixture was added saturated aqueous sodium chloride (60 mL), and the resulting mixture was extracted with ethyl acetate (40 mL×2). The combined organic layers were washed with saturated brine (50 mL×2), dried over anhydrous sodium sulfate and filtered. The filtrate was concentrated in vacuo, and the residue was purified by silica-gel column chromatography (PE:EtOAc=40:1, V/V) to give a yellow solid (1.53 g, 73%).

MS (ESI, pos. ion) m/z: 260.9 (M+1);

Step 3: 3-chloro-6-iodobenzofuran-2-carbaldehyde

To a 50 mL two-neck flask were added phosphorus oxychloride (15 mL), then DMF (347 mg, 4.73 mmol) was added at rt, and the resulting mixture was stirred for 30 min. To the reaction mixture was added 6-iodobenzofuran-3(2H)-one (1.23 g, 4.73 mmol), and the resulting mixture was stirred at rt for 30 min. The reaction mixture was stirred at 90° C. for 4 h. The reaction mixture was cooled to rt and to the mixture was added ice-water (100 mL). The resulting mixture was extracted with EtOAc (60 mL×2). The combined organic layers were washed with saturated brine (60 mL×2), dried over anhydrous Na$_2$SO$_4$, and filtered. The filtrate was concentrated in vacuo, and the residue was purified by silica-gel column chromatography (PE) to give a yellow solid (780 mg, 54%).

MS (ESI, pos. ion) m/z: 306.9 (M+1);

Step 4: 3-chloro-6-iodobenzofuran-2-carboxylic acid

To a 500 mL three-neck flask were added 3-chloro-6-iodobenzofuran-2-carbaldehyde (567 mg, 1.85 mmol), hydrogen peroxide (1.26 g, 11.1 mmol, 30%), sodium dihydrogen phosphate (1.33 g, 11.1 mmol), acetone (200 mL) and water (60 mL). Then to the reaction mixture was added sodium chlorite (50 mL, 1.25 g, 11.1 mmol) while keeping the temperature at about 10° C. to about 15° C. over 2 h. The resulting mixture was stirred at rt overnight. The reaction mixture was concentrated to remove acetone, and to the residue was added water (20 mL), and the resulting mixture was extracted with ethyl acetate (60 mL×2). The combined organic layers were washed with saturated brine (50 mL×2), dried over anhydrous sodium sulfate and filtered. The filtrate was concentrated in vacuo to give a white solid (537 mg, 90%).

MS (ESI, pos. ion) m/z: 320.9 (M-1);

Step 5: 3-chloro-N-(1-((1-cyanocyclopropyl)carbamoyl)cyclohexyl)-6-iodobenzofuran-2-carboxamide To a 50 mL two-neck flask were added 3-chloro-6-iodobenzofuran-2-carboxylic acid (355 mg, 1.1 mmol), 1-amino-N-(1-cyanocyclopropyl)cyclohexanecarboxamide hydrochloride (349 mg, 1.43 mmol) and DMF (6 mL). To the mixture were added 2-HATU (411 mg, 1.16 mmol) and triethylamine (0.6 mL, 3.3 mmol) at 0° C. under nitrogen protection. The mixture was stirred for 3.0 h at 0° C. To the reaction mixture was added saturated aqueous sodium bicarbonate (30 mL), and the resulting mixture was extracted with ethyl acetate (30 mL×3). The combined organic layers were washed with saturated brine (50 mL), hydrochloric acid (10 mL, 1 mol/L) and saturated brine (30 mL×2), dried over anhydrous sodium sulfate and filtered. The filtrate was concentrated in vacuo, and the residue was purified by silica-gel column chromatography (DCM:EtOAc=50:1, V/V) to give a white solid (119 mg, 21%).

MS (ESI, pos. ion) m/z: 512.0 (M+1);

Step 6: 3-chloro-N-(1-((1-cyanocyclopropyl)carbamoyl)cyclohexyl)-6-(4-(methylsulfonyl) phenyl)benzofuran-2-carboxamide To a 50 mL two-neck flask were added 3-chloro-N-(1-((1-cyanocyclopropyl)carbamoyl)cyclohexyl)-6-iodobenzofuran-2-carboxamide (119 mg, 0.23 mmol), 4-mesylphenylboronic acid (42 mg, 0.21 mmol), Pd(Ph$_3$P)$_4$ (17 mg, 0.021 mmol) and DMF (5 mL). To the mixture was added aqueous potassium carbonate (0.2 mL, 2 mol/L) under nitrogen protection. The resulting mixture was stirred at 90° C. for 2 h. The reaction mixture was cooled to rt, then to the reaction mixture was added saturated brine (50 mL), and the resulting mixture was extracted with ethyl acetate (50 mL×2). The combined organic layers were washed with saturated brine (40 mL×2), dried over anhydrous sodium sulfate and filtered. The filtrate was concentrated in vacuo, and the residue was purified by silica-gel column chromatography (DCM:EtOAc=15:1, V/V) to give a white solid (85 mg, 75%).

MS (ESI, pos. ion) m/z: 540.2 (M+1);
$^1$H NMR (600 MHz, CDCl$_3$) δ: 8.10-7.99 (m, 2H), 7.81 (d, J=8.0 Hz, 2H), 7.77 (s, 1H), 7.66 (d, J=8.2 Hz, 1H), 6.64 (s, 1H), 3.11 (s, 3H), 2.26 (d, J=13.8 Hz, 2H), 2.01 (t, J=11.4 Hz, 2H), 1.82-1.62 (m, 2H), 1.62-1.43 (m, 4H), 1.44-1.16 (n, 4H).

Example 9: N-(1-((1-cyanocyclopropyl)carbamoyl)cyclohexyl)-6-(4-(1-hydroxycyclobutyl) phenyl)benzofuran-2-carboxamide

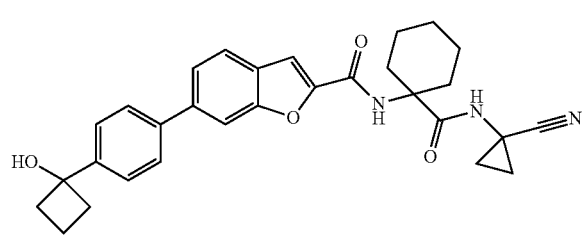 [SMILES: N#CC1(NC(=O)C2(NC(=O)c3cc4ccc(-c5ccc(C6(O)CCC6)cc5)cc4o3)CCCCC2)CC1]

Step 1: 1-(4-bromophenyl)cyclobutanol

To a 250 mL round-bottom flask were added 1-bromo-4-idiobenzene (2.0 g, 7.07 mmol) and anhydrous tetrahydrofuran (10 mL). Then to the mixture were added isopropylmagnesium chloride solution (3.9 mL, 7.78 mmol) and cyclobutanone (643 mg, 9.19 mmol) under nitrogen protection. The resulting mixture was stirred at 0° C. for 3 h. The reaction mixture was cooled to rt and to the mixture was added saturated brine (30 mL). The resulting mixture was extracted with EtOAc (80 mL×3). The combined organic layers were washed with water (150 mL×2) and saturated brine (100 mL×2), dried over anhydrous Na$_2$SO$_4$, and filtered. The filtrate was concentrated in vacuo, and the residue was purified by silica-gel column chromatography (PE:EtOAc=20:1, V/V) to give a white solid (600 mg, 47.9%).

MS (ESI, pos. ion) m/z: 228.0 (M+2);

Step 2: N-(1-((1-cyanocyclopropyl)carbamoyl)cyclohexyl)-6-(4-(1-hydroxycyclobutyl)phenyl) benzofuran-2-carboxamide To a 50 mL two-neck flask were added 1-(4-bromophenyl)cyclobutanol (80 mg, 0.35 mmol), N-(1-((1-cyanocyclopropyl)carbamoyl)cyclohexyl)-6-(4,4,5,5-tetramethyl-1,3,2-dioxaborolan-2-yl)benzofuran-2-carboxamide (168.0 mg, 0.35 mmol), Pd(dppf)Cl$_2$.CH$_2$Cl$_2$ (40 mg) and DMF (15 mL). To the mixture was added aqueous potassium carbonate (0.45 mL, 2 mol/L) under nitrogen protection. The resulting mixture was stirred at 90° C. for 3 h. To the reaction mixture was added saturated brine (50 mL), and the resulting mixture was extracted with ethyl acetate (50 mL×2). The combined organic layers were washed with saturated brine (40 mL×2), dried over anhydrous sodium sulfate and filtered. The filtrate was concentrated in vacuo, and the residue was purified by silica-gel column chromatography (DCM:EtOAc=4:1, V/V) to give a white solid (80 mg, 50%).

MS (ESI, pos. ion) m/z: 498.2 (M+1);

$^1$H NMR (600 MHz, CDCl$_3$) δ 8.16 (s, 1H), 7.77 (d, J=10.6 Hz, 2H), 7.67 (dd, J=20.5, 8.3 Hz, 4H), 7.61 (d, J=8.2 Hz, 1H), 7.54 (s, 1H), 6.61 (s, 1H), 2.69-2.61 (m, 2H), 2.45 (dt, J=12.5, 9.5 Hz, 2H), 2.28 (d, J=13.8 Hz, 2H), 2.15-1.98 (m, 5H), 1.82-1.72 (m, 4H), 1.55 (dt, J=24.7, 9.6 Hz, 4H), 1.26-1.23 (m, 2H).

Example 10: N-(1-((1-cyanocyclopropyl)carbamoyl)-4,4-difluorocyclohexyl)-6-(4-(3-hydroxy-1,1-dioxidothietan-3-yl)phenyl)benzofuran-2-carboxamide

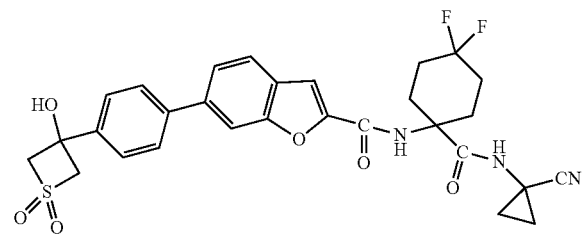 [SMILES: N#CC1(NC(=O)C2(NC(=O)c3cc4ccc(-c5ccc(C6(O)CS(=O)(=O)C6)cc5)cc4o3)CCC(F)(F)CC2)CC1]

Step 1: 3-(4-bromophenyl)thietan-3-ol

To a 50 mL two-neck flask were added 4-bromoiodobenzene (0.59 g, 2.1 mmol) and anhydrous tertrahydrofuran (6 mL). Then isopropylmagnesium chloride (1.26 mL, 2.5 mmol) was added dropwise into the mixture at −40° C. under nitrogen protection. The resulting mixture was stirred at −40° C. for 2 h. Then a solution of thietanone (270 mg, 3.1 mmol) in tetrahydrofuran (4 mL) was added to the reaction mixture at −40° C., and the resulting mixture was warmed to rt slowly and stirred overnight. To the reaction mixture was added saturated aqueous ammonium chloride (30 mL), and the resulting mixture was extracted with ethyl acetate (30 mL×2). The combined organic layers were washed with saturated brine (20 mL×2), dried over anhydrous sodium sulfate and filtered. The filtrate was concentrated in vacuo, and the residue was purified by silica-gel column chromatography (PE:DCM=1:1, V/V) to give a white solid (216 mg, 49%).

MS (ESI, pos. ion) m/z: 245.95 (M+2);

Step 2: 3-(4-bromophenyl)-3-hydroxythietane 1,1-dioxide

To a 50 mL single-neck flask were added 3-(4-bromophenyl)thietan-3-ol (0.22 g, 0.88 mmol) and glacial acetic acid (3 mL). Then aqueous hydrogen peroxide solution (0.55 mL, 4.4 mmol, 30%) was added to the mixture at 0° C. The resulting mixture was stirred at 0° C. for 0.5 h, then stirred at 70° C. for 7 h. The reaction mixture was cooled to rt and concentrated in vacuo to remove glacial acetic acid. To the residue were added saturated aqueous sodium bicarbonate (40 mL) and ethyl acetate (50 mL), and the resulting mixture was partitioned. The organic layer was washed with saturated brine, dried over anhydrous sodium sulfate, and filtered. The filtrate was concentrated in vacuo, and the residue was purified by silica-gel column chromatography (DCM:EtOAc=20:1, V/V) to give a white solid (176 mg, 72%).

MS (ESI, pos. ion) m/z: 277.9 (M+2);

Step 3: N-(1-((1-cyanocyclopropyl)carbamoyl)-4,4-difluorocyclohexyl)-6-(4-(3-hydroxy-1,1-dioxidothietan-3-yl)phenyl)benzofuran-2-carboxamide To a 50 mL two-neck flask were added N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (95 mg, 0.18 mmol), 3-(4-bromophenyl)-3-hydroxythietane 1,1-dioxide (53 mg, 0.19 mmol), Pd(dppf)Cl$_2$.CH$_2$Cl$_2$ (15 mg, 0.018 mmol) and DMF (5 mL). To the mixture was added aqeuous potassium carbonate (0.25 mL, 2 mol/L) under nitrogen protection. The resulting mixture was stirred at 90° C. for 1.5 h. The reaction mixture was cooled to rt and to the reaction mixture was added saturated aqueous sodium chloride (50 mL), and the resulting mixture was extracted with ethyl acetate (50 mL×2). The combined organic layers were washed with saturated brine (40 mL×2), dried over anhydrous sodium sulfate and filtered. The filtrate was concentrated in vacuo, and the residue was purified by silica-gel column chromatography (DCM:EtOAc=1:8, V/V) to give a white solid (65 mg, 62%).

MS (ESI, pos. ion) m/z: 584.1 (M+1);

$^1$H NMR (400 MHz, DMSO-d$_6$) δ: 8.78 (s, 1H), 8.53 (s, 1H), 8.17 (d, J=8.3 Hz, 2H), 8.12 (s, 1H), 8.00 (d, J=8.3 Hz, 2H), 7.94 (d, J=8.2 Hz, 1H), 7.80 (d, J=8.2 Hz, 1H), 7.76 (s, 1H), 5.17 (s, 2H), 3.19 (s, 2H), 2.09 (dd, J=53.3, 38.6 Hz, 8H), 1.46 (s, 2H), 1.24 (s, 2H), 1.08 (s, 2H), 0.85 (d, J=7.1 Hz, 2H).

Example 11: N-(1-((1-cyanocyclopropyl)carbamoyl)cyclohexyl)-4-(oxazol-5-yl)phenyl) benzofuran-2-carboxamide

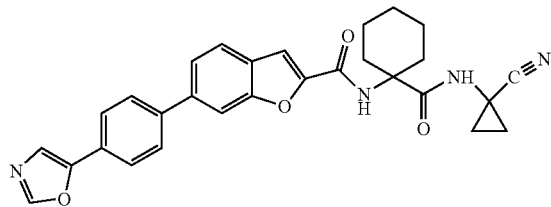 [SMILES: N#CC1(NC(=O)C2(NC(=O)c3cc4ccc(-c5ccc(-c6cnco6)cc5)cc4o3)CCCCC2)CC1]

5-(4-Bromophenyl)oxazole (45 mg, 0.201 mmol) was dissolved in a mixture of ethanol (2 mL) and toluene (6 mL). Then N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (80 mg, 0.168 mmol) was added, and Pd(Ph$_3$P)$_4$ (16 mg, 0.013 mmol) was added under nitrogen protection, and aqueous potassium carbonate (0.18 mL, 0.36 mmol) was added into the reaction mixture. The resulting mixture was stirred at 90° C. for 1 h. The title product was afforded according to step 4 of example 1 as a white solid (50 mg, 60%).

MS (ESI, pos. ion) m/z: 495.2 (M+1);

$^1$H NMR (600 MHz, DMSO-d$_6$) δ 8.61 (s, 1H), 8.48 (s, 1H), 8.06 (s, 1H), 7.97 (s, 1H), 7.91 (d, J=8.3 Hz, 2H), 7.87 (dd, J=12.7, 8.3 Hz, 3H), 7.78 (s, 1H), 7.74 (d, J=8.2 Hz, 1H), 7.69 (s, 1H), 2.04 (d, J=13.5 Hz, 2H), 1.79 (t, J=10.9 Hz, 2H), 1.53 (dt, J=22.1, 10.6 Hz, 6H), 1.44 (dd, J=7.8, 5.4 Hz, 2H), 1.06 (dd, J=7.8, 5.5 Hz, 2H).

Example 12: 6-(4-(1H-1,2,4-triazol-1-yl)phenyl)-N-(1-((1-cyanocyclopropyl)carbamoyl)-4,4-difluorocyclohexyl)benzofuran-2-carboxamide

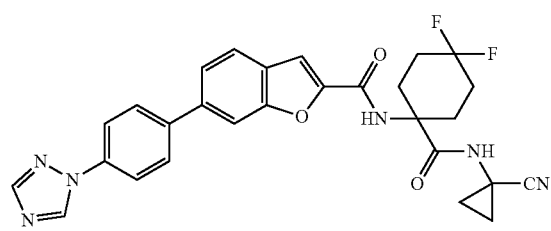 [SMILES: N#CC1(NC(=O)C2(NC(=O)c3cc4ccc(-c5ccc(-n6cncn6)cc5)cc4o3)CCC(F)(F)CC2)CC1]

Step 1: 1-(4-bromophenyl)-1H-1,2,4-triazole

To a 20 mL sealed tube were added 1H-1,2,4-triazole (245 mg, 3.55 mmol) and anhydrous N,N-dimethylformamide (15 mL), then 1-bromo-4-idiobenzene (2.00 g, 7.10 mmol), cuprous iodide (68 mg, 0.35 mmol) and tripotassium phosphate (2.26 g, 9.97 mmol) were added under nitrogen protection, and N,N'-dimethylethylenediamine (64 mg, 0.719 mmol) was added at last. The mixture was stirred at 110° C. overnight in the sealed tube. The reaction mixture was cooled to rt and to the mixture was added saturated brine (60 mL). The resulting mixture was extracted with EtOAc (30 mL×3). The combined organic layers were washed with water (50 mL×2) and saturated brine (50 mL×1), dried over anhydrous Na$_2$SO$_4$, and filtered. The filtrate was concentrated in vacuo, and the residue was purified by silica-gel column chromatography (n-hexane:EtOAc=5:1, V/V) to give a white solid (360 mg, 45%).

MS (ESI, pos. ion) m/z: 224.1 (M+1);

Step 2: 6-(4-(1H-1,2,4-triazol-1-yl)phenyl)-N-(1-((1-cyanocyclopropyl)carbamoyl)-4,4-difluorocyclohexyl)benzofuran-2-carboxamide N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (80 mg, 0.156 mmol) was dissolved in a mixture of ethanol (2 mL) and toluene (6 mL) in a 50 mL two-neck flask. Then 1-(4-bromophenyl)-1H-1,2,4-triazole (42 mg, 0.19 mmol) was added, and Pd(Ph$_3$P)$_4$ (14.4 mg, 0.012 mmol) was added under nitrogen protection, and aqueous potassium carbonate (0.16 mL, 0.32 mmol, 2 mol/L) was added into the reaction mixture. The resulting mixture was stirred at 90° C. for 1 h. After the reaction was completed, to the mixture was added saturated brine (60 mL). The resulting mixture was extracted with EtOAc (20 mL×3). The combined organic layers were washed with saturated brine (30 mL×2), dried over anhydrous Na$_2$SO$_4$, and filtered. The filtrate was concentrated in vacuo, and the residue was purified by silica-gel column chromatography (DCM:EtOAc=4:1, V/V) to give a white solid (50 mg, 60.4%).

MS (ESI, pos. ion) m/z: 531.2 (M+1);

$^1$H NMR (600 MHz, DMSO-d$_6$) δ 9.24 (s, 1H), 8.79 (s, 1H), 8.61 (s, 1H), 8.52 (s, 1H), 8.05 (s, 1H), 7.95 (s, 3H), 7.90 (d, J=8.2 Hz, 1H), 7.79-7.71 (m, 2H), 2.22 (s, 2H), 2.14-2.01 (m, 6H), 1.47 (dd, J=8.1, 5.4 Hz, 2H), 1.08 (dd, J=8.2, 5.5 Hz, 2H).

Example 13: 6-(3-(1H-1,2,4-triazol-1-yl)phenyl)-N-(1-((1-cyanocyclopropyl)carbamoyl)-4,4-difluorocyclohexyl)benzofuran-2-carboxamide

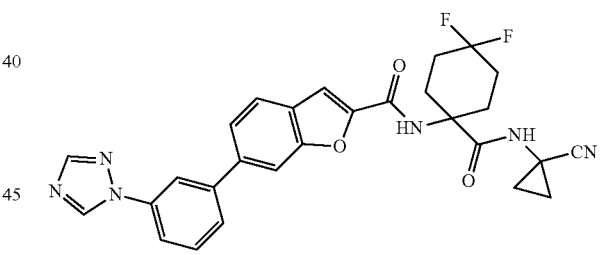

Step 1: 1-(3-bromophenyl)-1H-1,2,4-triazole

The title compound was prepared according to the synthetic procedure described in step 1 of example 12 using 1H-1,2,4-triazole (230 mg, 3.33 mmol), anhydrous dimethyl sulfoxide (6 mL), 1-bromo-3-iodiobenzene (1.13 g, 4.01 mmol), cuprous iodide (68 mg, 0.357 mmol), tripotassium phosphate (2.16 g, 9.97 mmol) and N,N'-dimethylethylenediamine (64 mg, 0.719 mmol) to give a white solid (350 mg, 47.1%).

MS (ESI, pos. ion) m/z: 224.1 (M+1);

Step 2: 6-(3-(1H-1,2,4-triazol-1-yl)phenyl)-N-(1-((1-cyanocyclopropyl)carbamoyl)-4,4-difluorocyclohexyl)benzofuran-2-carboxamide The title compound was prepared according to the step 2 of example 12 using N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (80 mg, 0.156 mmol), ethanol (2 mL), toluene (6 mL), 1-(3-bromophenyl)-1H-1,2,4-triazole (42 mg, 0.186 mmol), Pd(Ph$_3$P)$_4$ (14.4 mg, 0.012 mmol) and aqueous potassium carbonate (0.16 mL, 0.32 mmol) to give a white solid (27 mg, 32.7%).

MS (ESI, pos. ion) m/z: 531.2 (M+1);

$^1$H NMR (600 MHz, CDCl$_3$) δ 8.66 (s, 1H), 8.22 (s, 1H), 8.17 (s, 1H), 8.02 (s, 1H), 7.86-7.76 (m, 2H), 7.69-7.65 (m, 3H), 7.59 (s, 1H), 6.62 (s, 1H), 2.45 (d, J=10.5 Hz, 2H), 2.38 (d, J=13.8 Hz, 2H), 2.26-2.13 (m, 2H), 2.04 (dd, J=18.2, 12.3 Hz, 2H), 1.26 (d, J=2.4 Hz, 2H), 1.00-0.80 (m, 2H).

Example 14: 6-(4-(3-aminooxetan-3-yl)phenyl)-N-(1-((1-cyanocyclopropyl)carbamoyl)-4,4-difluorocyclohexyl)benzofuran-2-carboxamide

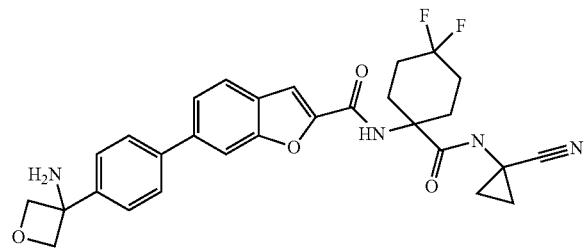 [SMILES: N#CC1(NC(=O)C2(NC(=O)c3cc4ccc(-c5ccc(C6(N)COC6)cc5)cc4o3)CCC(F)(F)CC2)CC1]

The title compound was prepared according to the step 4 of example 1 using N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (110 mg, 0.21 mmol), toluene (2 mL), ethanol (6 mL), 3-(4-bromophenyl)oxetan-3-amine (50 mg, 0.22 mmol), Pd(Ph$_3$P)$_4$ (25 mg, 0.02 mmol) and aqueous potassium carbonate (2 mol/L, 0.4 mL) to give a white solid (58 mg, 50.6%).

MS (ESI, pos. ion) m/z: 535.2 (M+1);

$^1$H NMR (400 MHz, DMSO-d$_6$) δ 8.78 (s, 1H), 8.48 (s, 1H), 7.97 (s, 1H), 7.87 (d, J=8.2 Hz, 1H), 7.79 (d, J=8.4 Hz, 2H), 7.73-7.66 (m, 4H), 4.73 (dd, J=21.7, 6.1 Hz, 4H), 2.21 (d, J=6.0 Hz, 2H), 2.12-1.99 (m, 6H), 1.45 (dd, J=8.1, 5.4 Hz, 2H), 1.08 (dd, J=8.3, 5.6 Hz, 2H).

Example 15: N-(1-((1-cyanocyclopropyl)carbamoyl)-4,4-difluorocyclohexyl)-6-(4-(hydroxy(1-hydroxycyclopropyl)methyl)phenyl)benzofuran-2-carboxamide

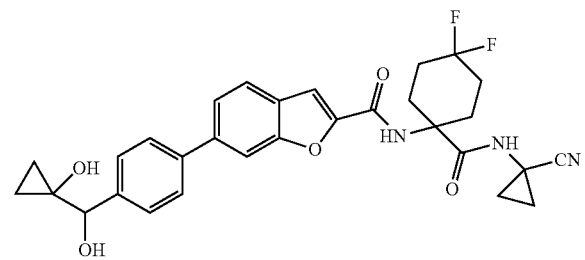 [SMILES: N#CC1(NC(=O)C2(NC(=O)c3cc4ccc(-c5ccc(C(O)C6(O)CC6)cc5)cc4o3)CCC(F)(F)CC2)CC1]

Step 1: 5-bromobenzo[d]oxazol-2(3H)-one

To a mixture of cyclopropyltriphenylphosphonium bromide (2.69 g, 7.02 mmol) and tetrahydrofuran (15 mL) in a two-neck flask were added sodium hydride (0.28 g, 7.02 mmol), 4-bromobenzaldehyde (1.00 g, 5.40 mmol) and tris(2-(2-methoxyethoxy)ethyl)amine (0.17 mL, 7.02 mmol) in turn. The mixture was stirred at 62° C. overnight. The reaction mixture was cooled to rt, and water (20 mL) was added to quench the reaction. The resulting mixture was extracted with EtOAc (80 mL×3). The combined organic layers were dried over anhydrous Na$_2$SO$_4$, and filtered. The filtrate was concentrated in vacuo, and the residue was purified by silica-gel column chromatography (PE) to give colourless oil (0.42 g, 37%).

MS (ESI, pos. ion) m/z: 210.01 (M+2);

Step 2: 1-((4-bromophenyl)(hydroxy)methyl)cyclopropane

To a 50 mL round-bottom flask were added 5-bromobenzo[d]oxazol-2(3H)-one (0.30 g, 1.4 mmol), acetone (6 mL) and water (1 mL), then 4-methyl-morpholine 4-oxide (0.84 g, 7.0 mmol) and osmium tetroxide (5 mg, 0.02 mmol) were added. The resulting mixture was stirred at rt for 36 h, then sodium thiosulfate (50 mL, 1 mol/L) was added. The mixture was extracted with EtOAc (40 mL×2). The combined organic layers were dried over anhydrous Na$_2$SO$_4$, and concentrated to remove the solvent. The residue was purified by silica-gel column chromatography (DCM:MeOH=20:1, V/V) to give a white solid (67 mg, 19%).

MS (ESI, pos. ion) m/z: 247.01 (M+2);

Step 3: N-(1-((1-cyanocyclopropyl)carbamoyl)-4,4-difluorocyclohexyl)-6-(4-(hydroxy(1-hydroxycyclopropyl)methyl)phenyl)benzofuran-2-carboxamide To a 50 mL round-bottom flask were added 1-((4-bromophenyl)(hydroxy)methyl)cyclopropane (0.025 g, 0.10 mmol), N-(1-((1-cyanocyclopropyl)carbamoyl)cyclohexyl)-6-(4,4,5,5-tetramethyl-1,3,2-dioxaborolan-2-yl)benzofuran-2-carboxamide (0.052 g, 0.10 mmol), Pd(dppf)Cl$_2$.CH$_2$Cl$_2$ (8 mg, 0.01 mmol) and DMF (8 mL), then aqueous potassium sulfate solution (0.10 mL, 0.20 mmol, 2 mol/L) was added under nitrogen protection. The resulting mixture was stirred at 85° C. for 2 h. The reaction mixture was cooled to rt and the mixture was quenched with water (60 mL). The resulting mixture was extracted with EtOAc (50 mL×2). The combined organic layers were washed with water (80 mL×2) and saturated brine (80 mL), dried over anhydrous Na$_2$SO$_4$, and filtered. The filtrate was concentrated to remove the solvent, and the residue was purified by silica-gel column chromatography (DCM:MeOH=50:1, V/V) to give a white solid (16 mg, 28%).

MS (ESI, pos. ion) m/z: 550.25 (M+1);

$^1$H NMR (400 MHz, DMSO-d$_6$) δ: 8.76 (s, 1H), 8.48 (s, 1H), 7.94 (s, 1H), 7.87 (d, J=8.3 Hz, 1H), 7.69 (dt, J=7.8, 3.9 Hz, 4H), 7.52 (d, J=7.8 Hz, 2H), 5.28 (d, J=4.5 Hz, 1H), 5.16 (s, 1H), 4.41 (d, J=4.4 Hz, 1H), 2.22 (s, 2H), 2.07 (d, J=15.0 Hz, 5H), 1.46 (s, 2H), 1.08 (s, 2H), 0.86 (s, 1H), 0.75 (d, J=5.8 Hz, 1H), 0.65 (d, J=5.9 Hz, 1H), 0.53 (s, 2H).

$^{19}$F NMR (376 MHz, DMSO-d$_6$) δ: −92.86 (d, J=232.3 Hz), −97.83 (s), −98.44 (s).

Example 16: N-(1-((1-cyanocyclopropyl)carbamoyl)-4,4-difluorocyclohexyl)-6-(4-(3-hydroxyoxetan-3-yl)phenyl)benzofuran-2-carboxamide

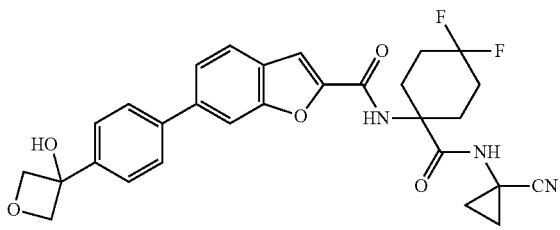 [SMILES: N#CC1(NC(=O)C2(NC(=O)c3cc4ccc(-c5ccc(C6(O)COC6)cc5)cc4o3)CCC(F)(F)CC2)CC1]

Step 1: 3-(4-bromophenyl)oxetan-3-ol

The title compound was prepared according to the procedure described in step 1 of example 10 using 1,4-dibromobenzene (1.00 g, 4.28 mmol), anhydrous tetrahydrofuran (10 mL), n-butyllithium solution (2.67 mL, 4.28 mmol) and 3-oxetanone (308 mg, 4.28 mmol) to give a white solid (420 mg, 43.0%).

MS (ESI, pos. ion) m/z: 230.01 (M+2);

Step 2: N-(1-((1-cyanocyclopropyl)carbamoyl)-4,4-difluorocyclohexyl)-6-(4-(3-hydroxyoxetan-3-yl)phenyl)benzofuran-2-carboxamide The title compound was prepared according to the step 3 of example 10 using N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (80 mg, 0.156 mmol), ethanol (2 mL), toluene (6 mL), 3-(4-bromophenyl)oxetan-3-ol (43 mg, 0.186 mmol), Pd(Ph$_3$P)$_4$ (14.4 mg, 0.012 mmol) and aqueous potassium carbonate (0.16 mL, 0.32 mmol) to give a white solid (20 mg, 24.0%).

MS (ESI, pos. ion) m/z: 536.2 (M+1);

$^1$H NMR (400 MHz, DMSO-d$_6$) δ: 8.77 (s, 1H), 8.48 (s, 1H), 7.98 (s, 1H), 7.88 (d, J=8.2 Hz, 1H), 7.81 (d, J=8.4 Hz, 2H), 7.72 (dd, J=6.6, 4.1 Hz, 3H), 6.42 (s, 1H), 4.82 (d, J=6.6 Hz, 2H), 4.73 (d, J=6.6 Hz, 2H), 2.22 (s, 2H), 2.07 (d, J=15.3 Hz, 6H), 1.46 (dd, J=8.1, 5.3 Hz, 2H), 1.08 (dd, J=8.2, 5.5 Hz, 2H).

Example 17: N-(1-((1-cyanocyclopropyl)carbamoyl)-4,4-difluorocyclohexyl)-6-(4-(oxetan-3-ylsulfonyl)phenyl)benzofuran-2-carboxamide

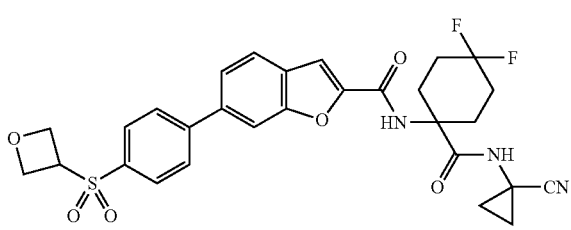 [SMILES: N#CC1(NC(=O)C2(NC(=O)c3cc4ccc(-c5ccc(S(=O)(=O)C6COC6)cc5)cc4o3)CCC(F)(F)CC2)CC1]

Step 1: oxetan-3-yl 4-methylbenzenesulfonate

To a 50 mL two-neck flask were added oxetan-3-ol (1.00 g, 13.0 mmol) and anhydrous pyridine (25 mL), then para-toluensulfonyl chloride (3.10 g, 16.0 mmol) was added to the mixture under nitrogen protection. The reaction mixture was stirred at rt overnight. The reaction was monitored by TLC until oxetan-3-ol consumed completely, then the mixture was concentrated in vacuo to remove pyridine. To the residue was added saturated brine (60 mL). The resulting mixture was extracted with EtOAc (20 mL×3). The combined organic layers were washed with saturated brine (30 mL×2), dried over anhydrous Na$_2$SO$_4$, and filtered. The filtrate was concentrated in vacuo, and the residue was purified by silica-gel column chromatography (PE:EtOAc=10:1, V/V) to give a white solid (2.40 g, 78.0%).

MS (ESI, pos. ion) m/z: 229.1 (M+1);

Step 2: 3-((4-bromophenyl)thio)oxetane

To a 50 mL two-neck flask were added 4-bromo thiophenol (380 mg, 2.00 mmol) and anhydrous N,N-dimethylacetamide (20 mL), and oxetan-3-yl 4-methylbenzenesulfonate (551 mg, 2.40 mmol) was added under nitrogen protection. Then sodium iodide (304 mg, 2.00 mmol) and potassium carbonate (310 mg, 2.20 mmol) were added in turn. The resulting mixture was stirred at 130° C. for 2 h. The reaction mixture was cooled to rt and to the mixture was added saturated brine (60 mL). The resulting mixture was extracted with EtOAc (20 mL×3). The combined organic layers were washed with saturated brine (30 mL×2), dried over anhydrous Na$_2$SO$_4$, and filtered. The filtrate was concentrated in vacuo, and the residue was purified by silica-gel column chromatography (PE:EtOAc=10:1, V/V) to give light yellow oil (0.41 g, 83.0%).

MS (ESI, pos. ion) m/z: 245.1 (M+1);

Step 3: 3-((4-bromophenyl)sulfonyl)oxetane

To a 50 mL two-neck flask were added 3-((4-bromophenyl)thio)oxetane (610 mg, 2.49 mmol), anhydrous DCM (10 mL) and anhydrous toluene (10 mL). Then sodium tungstate monohydrate (37.5 mg, 0.11 mmol) and tetrabutylammonium hydrogen sulfate (150 mg, 0.44 mmol) were added slowly in turn, and hydrogen peroxide (1.5 mL, 30%) were added at last. The mixture was stirred at rt for 6 h. To the mixture was added saturated sodium bicarbonate solution (20 mL). The resulting mixture was extracted with EtOAc (30 mL×3). The combined organic layers were washed with saturated aqueous NaCl solution (40 mL×2), dried over anhydrous Na$_2$SO$_4$, and filtered. The filtrate was concentrated in vacuo, and the residue was purified by silica-gel column chromatography (DCM:EtOAc=20:1, V/V) to give a white solid (600 mg, 87.0%).

MS (ESI, pos. ion) m/z: 277.0 (M+1);

Step 4: N-(1-((1-cyanocyclopropyl)carbamoyl)-4,4-difluorocyclohexyl)-6-(4-(oxetan-3-yl sulfonyl)phenyl)benzofuran-2-carboxamide N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (80 mg, 0.16 mmol) was dissolved in a mixture of ethanol (2 mL) and toluene (6 mL) in a 50 mL two-neck flask. Then 3-((4-bromophenyl)sulfonyl)oxetane (52 mg, 0.19 mmol) was added, and Pd(Ph$_3$P)$_4$ (14.4 mg, 0.012 mmol) was added under nitrogen protection, and aqueous potassium carbonate (0.16 mL, 0.32 mmol, 2 mol/L) was added into the reaction mixture. The resulting mixture was stirred at 90° C. for 1 h. After the reaction was completed, to the mixture was added saturated brine (20 mL). The resulting mixture was extracted with EtOAc (20 mL×3). The combined organic layers were washed with saturated brine (30 mL×2), dried over anhydrous Na₂SO₄, and filtered. The filtrate was concentrated in vacuo, and the residue was purified by silica-gel column chromatography (DCM:EtOAc=1:1, V/V) to give a white solid (70 mg, 77.0%).

MS (ESI, pos. ion) m/z: 584.1 (M+1);

$^1$H NMR (400 MHz, DMSO-d₆) δ: 8.77 (s, 1H), 8.54 (s, 1H), 8.11 (s, 1H), 8.08 (d, J=8.6 Hz, 2H), 8.02 (d, J=8.6 Hz, 2H), 7.95 (d, J=8.2 Hz, 1H), 7.77 (dd, J=8.3, 1.2 Hz, 2H), 4.96 (dd, J=14.0, 7.6 Hz, 1H), 4.88-4.67 (m, 4H), 2.22 (s, 2H), 2.11-1.99 (m, 6H), 1.46 (dd, J=8.1, 5.4 Hz, 2H), 1.08 (dd, J=8.4, 5.4 Hz, 2H).

Example 18: 6-(4-(1H-1,2,3-triazol-1-yl)phenyl)-N-(1-((1-cyanocyclopropyl)carbamoyl)-4,4-difluorocyclohexyl)benzofuran-2-carboxamide

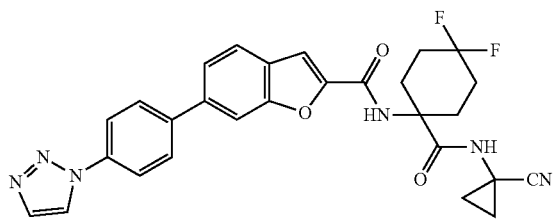 [SMILES: N#CC1(NC(=O)C2(NC(=O)c3cc4ccc(-c5ccc(-n6ccnn6)cc5)cc4o3)CCC(F)(F)CC2)CC1]

Step 1: 1-(4-bromophenyl)-1H-1,2,3-triazole

The title compound was prepared according to the synthetic procedure described in step 1 of example 12 using 1H-1,2,3-triazole (245 mg, 3.55 mmol), anhydrous DMF (15 mL), 1-bromo-4-iodobenzene (2.00 g, 7.10 mmol), cuprous iodide (68 mg, 0.357 mmol), tripotassium phosphate (2.26 g, 9.97 mmol) and N,N'-dimethylethylenediamine (64 mg, 0.72 mmol) to give a white solid (230 mg, 28.9%).

MS (ESI, pos. ion) m/z: 225.1 (M+2); calculated exact mass of C8H6BrN3: 222.97.

Step 2: 6-(4-(1H-1,2,3-triazol-1-yl)phenyl)-N-(1-((1-cyanocyclopropyl)carbamoyl)-4,4-difluorocyclohexyl)benzofuran-2-carboxamide The title compound was prepared according to the step 2 of example 12 using N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (80 mg, 0.16 mmol), ethanol (2 mL), toluene (6 mL), 1-(4-bromophenyl)-1H-1,2,3-triazole (42 mg, 0.19 mmol), Pd(Ph₃P)₄ ((14.4 mg, 0.012 mmol) and aqueous potassium carbonate (0.16 mL, 0.32 mmol) to give a white solid (56 mg, 67.7%).

MS (ESI, pos. ion) m/z: 531.2 (M+1);

$^1$H NMR (600 MHz, DMSO-d₆) δ 8.79 (s, 1H), 8.61 (s, 1H), 8.52 (s, 1H), 8.05 (d, J=8.2 Hz, 2H), 7.95 (s, 3H), 7.90 (d, J=8.2 Hz, 1H), 7.79-7.71 (m, 2H), 2.22 (s, 2H), 2.14-2.01 (m, 6H), 1.47 (dd, J=8.1, 5.4 Hz, 2H), 1.08 (dd, J=8.2, 5.5 Hz, 2H).

Example 19: N-(1-((1-cyanocyclopropyl)carbamoyl)-4,4-difluorocyclohexyl)-6-(4-(oxetan-3-yloxy)phenyl)benzofuran-2-carboxamide

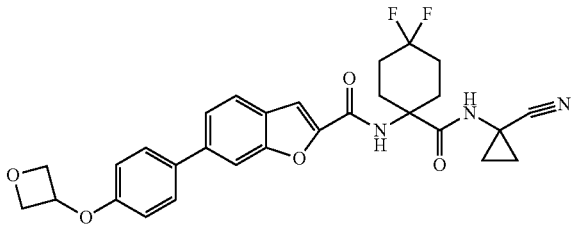 [SMILES: N#CC1(NC(=O)C2(NC(=O)c3cc4ccc(-c5ccc(OC6COC6)cc5)cc4o3)CCC(F)(F)CC2)CC1]

Step 1: 3-(4-bromophenoxy)oxetane

To a 20 mL sealed tube were added 4-bromophenol (590 mg, 3.41 mmol), potassium carbonate (1.28 g, 9.28 mmol), oxetan-3-yl 4-methylbenzenesulfonate (700 mg, 3.06 mmol) and DMF (6 mL), and the sealed tube was plugged with a polytetrafluoroethylene plug. The mixture was stirred at 100° C. for 16 h in sealed tube. After the reaction was completed, the reaction mixture was cooled to rt and to the mixture was added saturated brine (20 mL). The resulting mixture was extracted with EtOAc (20 mL×3). The combined organic layers were dried over anhydrous Na₂SO₄, and filtered. The filtrate was concentrated in vacuo, and the residue was purified by silica-gel column chromatography (DCM:EtOAc=2:1, V/V) to give a white solid (700 mg, 69.7%).

MS (ESI, pos. ion) m/z: 229.01 (M+1);

Step 2: N-(1-((1-cyanocyclopropyl)carbamoyl)-4,4-difluorocyclohexyl)-6-(4-(oxetan-3-yloxy) phenyl)benzofuran-2-carboxamide N-(1-((1-cyanocyclopropyl)carbamoyl)-4,4-difluorocyclohexyl)-6-(4,4,5,5-tetramethyl-1,3,2-dioxaborolan-2-yl) benzofuran-2-carboxamide (70 mg, 0.14 mmol), toluene (6 mL) and ethanol (2 mL) were added into a 50 mL two-neck flask. Then 3-(4-bromophenoxy)oxetane (37 mg, 0.16 mmol) was added, and Pd(Ph₃P)₄ (18 mg, 0.016 mmol) was added under nitrogen protection, and aqueous potassium carbonate (0.21 mL, 2 mol/L) was added into the reaction mixture. The resulting mixture was stirred at 90° C. for 1 h. After the reaction mixture was completed, to the mixture was added saturated brine (20 mL). The resulting mixture was extracted with EtOAc (20 mL×3). The combined organic layers were dried over anhydrous Na₂SO₄, and filtered. The filtrate was concentrated in vacuo, and the residue was purified by silica-gel column chromatography (DCM:EtOAc=6:1, V/V) to give a white solid (50 mg, 68.5%).

MS (ESI, pos. ion) m/z: 536.2 (M+1);

$^1$H NMR (400 MHz, CDCl₃) δ 7.70-7.61 (m, 2H), 7.50 (dd, J=16.2, 6.7 Hz, 4H), 7.29 (d, J=1.1 Hz, 2H), 6.80-6.73 (m, 2H), 5.23 (dd, J=10.9, 5.2 Hz, 1H), 4.99 (t, J=6.4 Hz, 2H), 4.79-4.71 (m, 2H), 2.35-2.21 (m, 4H), 2.16-2.07 (m, 2H), 2.00-1.90 (m, 2H), 1.51-1.42 (m, 2H), 0.81 (dd, J=18.8, 8.2 Hz, 2H).

Example 20: N-(1-((1-cyanocyclopropyl)carbamoyl)-4,4-difluorocyclohexyl)-6-(4-(isoxazol-5-yl)phenyl)benzofuran-2-carboxamide

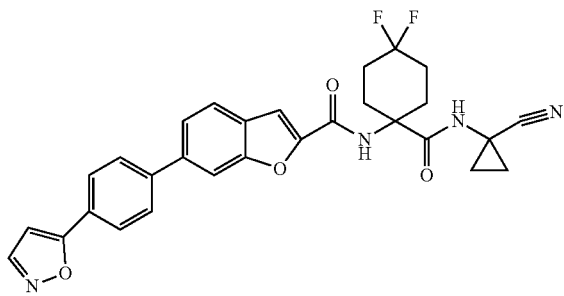 [SMILES: N#CC1(NC(=O)C2(NC(=O)c3cc4ccc(-c5ccc(-c6ccno6)cc5)cc4o3)CCC(F)(F)CC2)CC1]

The title compound was prepared according to the step 4 of example 1 using N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (80 mg, 0.16 mmol), toluene (6 mL), ethanol (2 mL), 5-(4-bromophenyl)isoxazole (42 mg, 0.19 mmol), Pd(Ph$_3$P)$_4$ (18 mg, 0.016 mmol) and aqueous potassium carbonate (2 mol/L, 0.23 mL) to give a white solid (40 mg, 48.3%).

MS (ESI, pos. ion) m/z: 531.2 (M+1);
$^1$H NMR (400 MHz, DMSO-d$_6$) δ 8.77 (s, 1H), 8.69 (d, J=1.9 Hz, 1H), 8.51 (s, 1H), 8.08 (s, 1H), 7.99 (dd, J=20.6, 8.5 Hz, 4H), 7.92 (d, J=8.3 Hz, 1H), 7.76 (dt, J=9.7, 2.8 Hz, 2H), 7.12 (d, J=1.8 Hz, 1H), 2.26-2.17 (m, 2H), 2.06 (t, J=16.1 Hz, 6H), 1.47 (dd, J=8.1, 5.3 Hz, 2H), 1.09 (dd, J=8.2, 5.4 Hz, 2H).

Example 21: N-(1-((1-cyanocyclopropyl)carbamoyl)-4,4-difluorocyclohexyl)-6-(4-morpholinophenyl)benzofuran-2-carboxamide

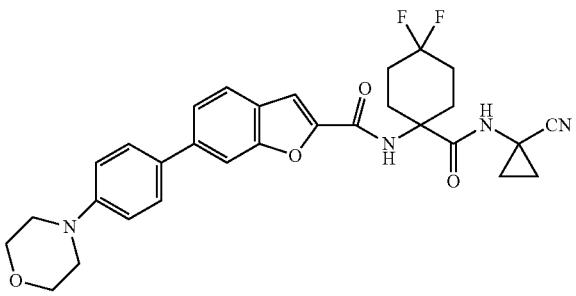 [SMILES: N#CC1(NC(=O)C2(NC(=O)c3cc4ccc(-c5ccc(N6CCOCC6)cc5)cc4o3)CCC(F)(F)CC2)CC1]

Step 1: 4-(4-bromophenyl)morpholine

To a 50 mL sealed tube were added R-(+)-2,2'-bis(diphenylphosphino)-1,1'-binaphthyl (0.20 g, 0.31 mmol), tris(dibenzylideneacetone)dipalladium (0.095 g, 0.10 mmol), sodium tert-butoxide (0.49 g, 5.0 mmol), p-dibromobenzene (1.00 g, 4.15 mmol) and morpholine (0.37 mL, 4.2 mmol), then anhydrous toluene (8 mL) was added under nitrogen protection. The resulting mixture was stirred for 16 h at an oil bath temperature of 80° C. The reaction mixture was cooled to rt and to the mixture was added EtOAc (20 mL). The mixture was filtered and the filtrate was concentrated in vacuo. The residue was purified by silica-gel column chromatography (PE:EtOAc=15:1, V/V) to give a white solid (0.56 g, 56%).

MS (ESI, pos. ion) m/z: 242.00 (M+1)

Step 2: N-(1-((1-cyanocyclopropyl)carbamoyl)-4,4-difluorocyclohexyl)-6-(4-morpholino phenyl)benzofuran-2-carboxamide To a 50 mL round-bottom flask were added 4-(4-bromophenyl)morpholine (0.024 g, 0.099 mmol), N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (0.061 g, 0.12 mmol), Pd(dppf)Cl$_2$.CH$_2$Cl$_2$ (8 mg, 0.01 mmol) and DMF (5 mL), then aqueous potassium sulfate solution (0.10 mL, 0.20 mmol, 2 mol/L) was added under nitrogen protection. The resulting mixture was stirred at 85° C. for 2 h. The reaction mixture was cooled to rt and the mixture was quenched with water (60 mL). The resulting mixture was extracted with EtOAc (60 mL×2). The combined organic layers were washed with water (80 mL×2) and saturated aqueous NaCl solution (80 mL), dried over anhydrous Na$_2$SO$_4$, and filtered. The filtrate was concentrated in vacuo, and the residue was purified by silica-gel column chromatography (DCM:MeOH=100:1, V/V) to give a white solid (21 mg, 38%).

MS (ESI, pos. ion) m/z: 549.20 (M+1);
$^1$H NMR (400 MHz, DMSO-d$_6$) δ 8.77 (s, 1H), 8.44 (s, 1H), 7.88 (s, 1H), 7.81 (d, J=8.2 Hz, 1H), 7.66 (dd, J=17.7, 8.9 Hz, 4H), 7.06 (d, J=8.6 Hz, 2H), 3.81-3.72 (m, 4H), 3.18 (s, 4H), 2.21 (s, 2H), 2.07 (d, J=14.5 Hz, 6H), 1.46 (dd, J=7.9, 5.6 Hz, 2H), 1.08 (d, J=2.3 Hz, 2H).
$^{19}$F NMR (376 MHz, DMSO-d$_6$) δ: −92.47 (s), −98.46 (s).

Example 22: N-(1-((1-cyanocyclopropyl)carbamoyl)-4,4-difluorocyclohexyl)-6-(4-(4-hydroxytetrahydro-2H-pyran-4-yl)phenyl)benzofuran-2-carboxamide

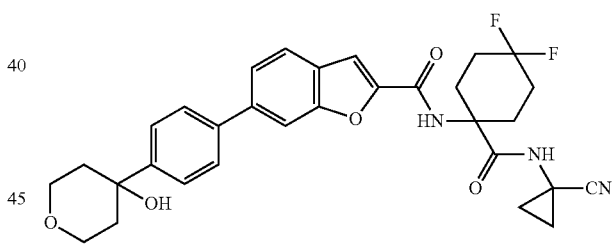

Step 1: 4-(4-bromophenyl)tetrahydro-2H-pyran-4-ol

The title compound was prepared according to the procedure described in step 1 of example 10 using 1,4-dibromobenzene (1.00 g, 4.28 mmol), anhydrous tetrahydrofuran (10 mL), n-butyllithium solution (2.67 mL, 4.28 mmol), dihydro-2H-pyran-4-one (430 mg, 4.28 mmol) and anhydrous tetrahydrofuran (2 mL) to give a white solid (620 mg, 56.6%).

MS (ESI, pos. ion) m/z: 258.01 (M+2);

Step 2: N-(1-((1-cyanocyclopropyl)carbamoyl)-4,4-difluorocyclohexyl)-6-(4-(4-hydroxytetrahydro-2H-pyran-4-yl)phenyl)benzofuran-2-carboxamide The title compound was prepared according to the procedure described in step 3 of example 10 using N-(1-((1-cyanocyclopropyl)carbamoyl)-4,4-difluorocyclohexyl)-6-

(4,4,5,5-tetramethyl-1,3,2-dioxaborolan-2-yl)benzofuran-2-carboxamide (80 mg, 0.16 mmol), ethanol (2 mL), toluene (6 mL), 4-(4-bromophenyl)tetrahydro-2H-pyran-4-ol (48 mg, 0.19 mmol), Pd(Ph$_3$P)$_4$ (14.4 mg, 0.012 mmol) and aqueous potassium carbonate (0.16 mL, 0.32 mmol) to give a white solid (35 mg, 39.8%).

MS (ESI, pos. ion) m/z: 564.2 (M+1);

$^1$H NMR (400 MHz, DMSO-d$_6$) δ: 8.77 (s, 1H), 8.49 (s, 1H), 7.95 (s, 1H), 7.87 (d, J=8.2 Hz, 1H), 7.77-7.70 (m, 3H), 7.68 (d, J=8.2 Hz, 1H), 7.61 (d, J=8.4 Hz, 2H), 3.87-3.69 (m, 4H), 2.21 (s, 2H), 2.13-1.96 (m, 8H), 1.58 (d, J=12.5 Hz, 2H), 1.50-1.43 (m, 2H), 1.08 (d, J=2.7 Hz, 2H).

Example 23: 6-(4-(1H-tetrazol-1-yl)phenyl)-N-(1-((1-cyanocyclopropyl)carbamoyl)-4,4-difluorocyclohexyl)benzofuran-2-carboxamide

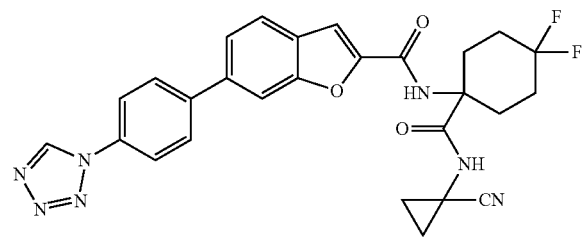 [SMILES: N#CC1(NC(=O)C2(NC(=O)c3cc4ccc(-c5ccc(-n6cnnn6)cc5)cc4o3)CCC(F)(F)CC2)CC1]

Step 1: 1-(4-nitrophenyl)-1H-tetrazole

To a 150 mL ampoule bottle were added tetrazole (1.80 g, 25.7 mmol), p-fluoronitrobenzene (3.0 g, 21.26 mmol) and DMF (40 mL), then potassium carbonate (8.97 g, 64.3 mmol) was added. The ampoule bottle was sealed and the mixture in the ampoule bottle was stirred at 110° C. overnight. After the reaction was completed, the pressure was discharged slowly. The reaction mixture was concentrated in vacuo to remove the solvent, and to the residue was added water (20 mL). The mixture was extracted with ethyl acetate (60 mL×4). The combined organic layers were dried over anhydrous sodium sulfate, filtered and concentrated. The residue was purified by silica-gel column chromatography (EtOAc:PE=1:10, V/V) to give a light yellow solid (1.0 g, 24.70%).

$^1$H NMR (400 MHz, CDCl$_3$) δ: 8.76 (s, 1H), 8.55-8.46 (m, 2H), 8.45-8.36 (m, 2H).

Step 2: 1-(4-aminophenyl)-1H-tetrazole

To a suspension of 1-(4-nitrophenyl)-1H-tetrazole (95 mg, 0.5 mmol) in a mixture of ethanol (2 mL) and ethyl acetate (2 mL) was added Pd/C (114 mg) under nitrogen protection, then the nitrogen in the reaction system was replaced with hydrogen. The reaction mixture was stirred for 2 h in hydrogen atomosphere. The reaction mixture was filtered, and the filtrate was concentrated to give a light yellow solid (60 mg, 74.91%).

MS (ESI, pos. ion) m/z: 162.1 (M+1);

Step 3: 1-(4-hydroxyphenyl)-1H-tetrazole

A suspension of 1-(4-aminophenyl)-1H-tetrazole (60 mg, 0.37 mmol) in a mixture of water (4 mL) and concentrated sulfuric acid (0.2 mL) was cooled to 0° C. To the suspension was added dropwise a solution of sodium nitrite (26 mg, 0.57 mmol) in water (4 mL), then the resulting mixture was stirred at 0° C. for 30 min. To the mixture were added water (1 mL) and concentrated sulfuric acid (0.37 mL), and the mixture was stirred at 120° C. for 1 h. After the reaction was complete, the reaction mixture was extracted with ethyl acetate (60 mL×3). The combined organic layers were dried over anhydrous sodium sulfate, filtered and the filtrate was concentrated. The residue was purified by silica-gel column chromatography (EtOAc:n-hexane=1:30, V/V) to give a yellow solid (38 mg, 63%).

MS (ESI, pos. ion) m/z: 163.1 (M+1);

Step 4: 1-(4-trifluoromethyl sulfonyloxyphenyl)-1H-tetrazole

To a solution of 1-(4-hydroxyphenyl)-1H-tetrazole (200 mg, 1.23 mmol) in anhydrous dichloromethane (20 mL) was added pyridine (0.2 mL, 2 mmol), then trifluoromethanesulfonic anhydride (0.31 mL, 1.8 mmol) was added dropwise at 0° C., and the mixture was stirred for 0.5 h. After the reaction monitored by TLC was completed, the mixture was poured into water (20 mL), and the resulting mixture was stirred. The mixture was extracted with DCM (100 mL×3). The combined organic layers were dried over anhydrous sodium sulfate, filtered and concentrated. The residue was purified by silica-gel column chromatography (EtOAc:PE=3:1, V/V) to give a yellow solid (310 mg, 85%).

MS (ESI, pos. ion) m/z: 295.01 (M+1);

Step 5: 6-(4-(1H-tetrazol-1-yl)phenyl)-N-(1-((1-cyanocyclopropyl)carbamoyl)-4,4-difluorocyclohexyl)benzofuran-2-carboxamide To a 50 mL two-neck round-bottom flask were added 1-(4-trifluoromethyl sulfonyloxyphenyl)-1H-tetrazole (44 mg, 0.15 mmol), N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (70 mg, 0.14 mmol), Pd(Ph$_3$P)$_4$ (20 mg), toluene (6 mL) and ethanol (2 mL). Aqueous potassium carbonate solution (0.16 mL, 0.31 mmol, 2 mol/L) was added into flask under nitrogen protection. The mixture was stirred at 90° C. for 3 h. After the reaction was completed, the reaction mixture was cooled to rt and concentrated in vacuo to remove the solvent. To the residue was added water (100 mL), and the mixture was extracted with ethyl acetate (100 mL×3). The combined organic layers were dried over anhydrous sodium sulfate, filtered and concentrated. The residue was purified by silica-gel column chromatography (EtOAc:DCM=1:4, V/V) to give a white solid (59 mg, 81.3%).

MS (ESI, pos. ion) m/z: 532.2 (M+1);

$^1$H NMR (400 MHz, DMSO-d$_6$) δ 9.30 (s, 1H), 8.78 (s, 1H), 8.53 (s, 1H), 8.24 (d, J=8.8 Hz, 2H), 8.09 (d, J=8.8 Hz, 3H), 7.94 (d, J=8.2 Hz, 1H), 7.82-7.72 (m, 2H), 2.26-1.93 (m, 8H), 1.47 (d, J=2.8 Hz, 2H), 1.32 (dd, J=26.1, 11.2 Hz, 2H), 1.24 (s, 4H), 1.09 (dd, J=8.3, 5.6 Hz, 2H).

Example 24: N-(1-((1-cyanocyclopropyl)carbamoyl)-4,4-difluorocyclohexyl)-6-(4-(2,2-difluoro-1-hydroxyethyl)phenyl)benzofuran-2-carboxamide

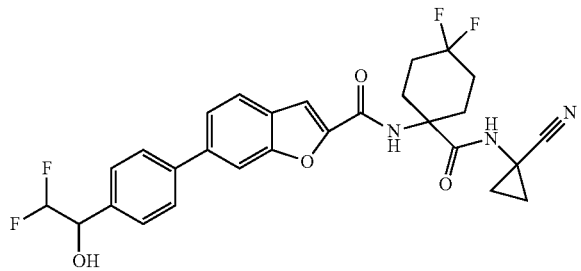 [SMILES: N#CC1(NC(=O)C2(NC(=O)c3cc4ccc(-c5ccc(C(O)C(F)F)cc5)cc4o3)CCC(F)(F)CC2)CC1]

The title compound was prepared according to the step 4 of example 1 using 1-(4-bromophenyl)-2,2-difluoroethanol (40 mg, 0.17 mmol), N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (70 mg, 0.14 mmol), [1,1'-bis(diphenylphosphino) ferrocene]dichloropalladium(II) (18 mg, 0.016 mmol), DMF (6 mL) and aqueous potassium carbonate (0.21 mL, 2 mol/L) to give a white solid (30 mg, 40.48%).

MS (ESI, pos. ion) m/z: 544.2 (M+1);
¹H NMR (600 MHz, CDCl₃) δ 8.05 (s, 1H), 7.80 (d, J=8.0 Hz, 2H), 7.62 (dd, J=13.1, 8.2 Hz, 4H), 7.36 (d, J=8.1 Hz, 2H), 6.28 (s, 1H), 3.69 (d, J=5.4 Hz, 2H), 2.59 (t, J=5.8 Hz, 2H), 2.39-2.21 (m, 2H), 2.13 (dd, J=14.4, 8.0 Hz, 2H), 1.98 (s, 4H), 1.78-1.42 (m, 12H), 1.24 (dd, J=23.2, 6.4 Hz, 4H).
¹⁹F NMR (376 MHz, CD₃OD) δ −96.22 (d, J=238.1 Hz), −101.43 (d, J=238.5 Hz).

Example 25: 6-(4-(2H-1,2,3-triazol-2-yl)phenyl)-N-(1-((1-cyanocyclopropyl)carbamoyl)-4,4-difluorocyclohexyl)benzofuran-2-carboxamide

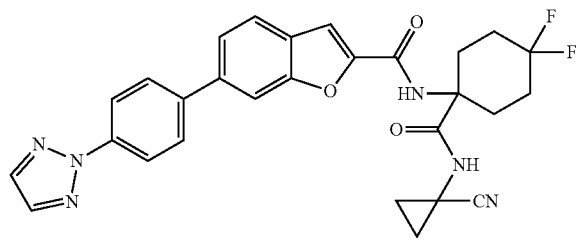 [SMILES: N#CC1(NC(=O)C2(NC(=O)c3cc4ccc(-c5ccc(-n6nccn6)cc5)cc4o3)CCC(F)(F)CC2)CC1]

Step 1: (1E,2E)-1,2-trans(2-(4-bromophenyl)hydrazono)ethane

To a 100 mL two-neck flask were added a solution of 4-bromophenylhydrazine hydrochloride (2.23 g, 10 mmol) in ethyl acetate (50 mL) and aqueous sodium hydroxide (25 mL, 3 mol/L) in turn. The mixture was stirred until the solid in the mixture dissolved completely, then partitioned. The organic layer was dried over anhydrous sodium sulfate, and concentrated in vacuo to give a yellow solid (1.85 g).

The yellow solid (1.85 g, 10 mmol) product described above was mixed with anhydrous toluene (30 mL) in a 100 mL two-neck flask, then glyoxal water solution (0.57 mL, 5 mmol, 40%) was added dropwise. The mixture was stirred at rt overnight. After the reaction, the mixture was filtered by suction. The filter cake was collected, washed with toluene (25 mL) and n-hexane (50 mL), dried in vacuo to give a yellow solid (2.97 g, 75%).

MS (ESI, pos. ion) m/z: 395.9 (M+2);

Step 2: 2-(4-bromophenyl)-2H-1,2,3-triazole

To a 50 mL round-bottom flask were added (1E,2E)-1,2-trans(2-(4-bromophenyl)hydrazono)ethane (1.91 g, 11.5 mmol), copper(II) trifluoromethanesulfonate (32 mg, 0.087 mmol) and toluene (10 mL), then the mixture was stirred at 110° C. for 5 h. After the reaction was completed, the mixture was concentrated in vacuo to remove the solvent. The residue was poured into water (50 mL), and the resulting mixture was extracted with EtOAc (15 mL×3). The combined organic layers were dried over anhydrous sodium sulfate and concentrated in vacuo. The residue was purified by silica-gel column chromatography (n-hexane:EtOAc=30:1, V/V) to give a red solid (145 mg, 25.63%).

¹H NMR (400 MHz, CDCl₃) δ 8.00 (d, J=8.9 Hz, 2H), 7.84 (s, 2H), 7.64 (d, J=9.0 Hz, 2H).

Step 3: 6-(4-(2H-1,2,3-triazol-2-yl)phenyl)-N-(1-((1-cyanocyclopropyl)carbamoyl)-4,4-difluorocyclohexyl)benzofuran-2-carboxamide To a 50 mL two-neck flask were added 2-(4-bromophenyl)-2H-1,2,3-triazole (42 mg, 0.18 mmol), N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (80 mg, 0.15 mmol), toluene (6 mL) and ethanol (2 mL). Then Pd(Ph₃P)₄ (156 mg, 0.14 mmol) and potassium carbonate (43.5 mg, 0.31 mmol) were added. The resulting mixture was stirred at 90° C. for 3 h. After the reaction was completed, the mixture was cooled to rt, and poured into water (20 mL). The mixture was stirred vigorously, then extracted with ethyl acetate (20 mL×3). The combined organic layers were dried over anhydrous sodium sulfate, filtered and concentrated in vacuo. The residue was purified by silica-gel column chromatography (EtOAc:DCM=1:20, V/V) to give a white solid (45 mg, 54.43%).

MS (ESI, pos. ion) m/z: 531.4 (M+1);
¹H NMR (400 MHz, DMSO-d₆) δ 8.78 (s, 1H), 8.52 (s, 1H), 8.20-8.12 (m, 3H), 8.06 (s, 1H), 8.00 (d, J=8.6 Hz, 2H), 7.92 (d, J=8.2 Hz, 1H), 7.76 (d, J=7.8 Hz, 2H), 2.22 (s, 3H), 2.02 (d, J=25.0 Hz, 6H), 1.08 (s, 3H), 0.86 (s, 2H).

Example 26: N-(1-((1-cyanocyclopropyl)carbamoyl)-4,4-difluorocyclohexyl)-6-(4-(3-methyl-1,2,4-oxadiazol-5-yl)phenyl)benzofuran-2-carboxamide

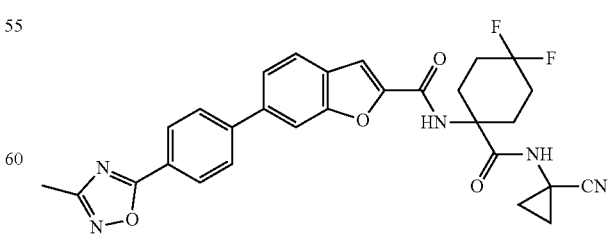

The title compound was prepared according to the step 4 of example 1 using N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (80 mg, 0.16 mmol), ethanol (2 mL), toluene (6 mL), 5-(4-bromophenyl)-3-methyl-1,2,4-oxadiazole (45 mg, 0.19 mmol), Pd(Ph$_3$P)$_4$ (14.4 mg, 0.012 mmol) and aqueous potassium carbonate (0.16 mL, 0.32 mmol) to give a white solid (40 mg, 47.1%).

MS (ESI, pos. ion) m/z: 546.2 (M+1);

$^1$H NMR (400 MHz, DMSO-d$_6$) δ 8.78 (s, 1H), 8.53 (s, 1H), 8.21 (d, J=8.4 Hz, 2H), 8.11 (s, 1H), 8.05 (d, J=8.4 Hz, 2H), 7.94 (d, J=8.2 Hz, 1H), 7.82-7.74 (m, 2H), 2.45 (s, 3H), 2.22 (s, 2H), 2.08 (d, J=14.9 Hz, 6H), 1.47 (dd, J=8.1, 5.4 Hz, 2H), 1.08 (dd, J=8.2, 5.5 Hz, 2H).

Example 27: N-(1-((1-cyanocyclopropyl)carbamoyl)-4,4-difluorocyclohexyl)-6-(4-(4-hydroxy-1,1-dioxidotetrahydro-2H-thiopyran-4-yl)phenyl)benzofuran-2-carboxamide

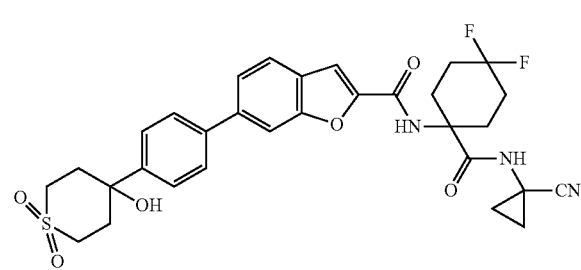 [SMILES: N#CC1(NC(=O)C2(NC(=O)c3cc4ccc(-c5ccc(C6(O)CCS(=O)(=O)CC6)cc5)cc4o3)CCC(F)(F)CC2)CC1]

Step 1: 3-(4-bromophenyl)oxetan-3-ol

The title compound was prepared according to the procedure described in step 1 of example 10 using 1,4-dibromobenzene (1.00 g, 4.28 mmol), anhydrous tetrahydrofuran (12 mL), n-butyllithium solution (2.67 mL, 4.28 mmol) and dihydro-2H-thiopyran-4-one (500 mg, 4.28 mmol) to give a white solid (540 mg, 41.5%).

MS (ESI, pos. ion) m/z: 273.1 (M+1);

Step 2: 4-(4-bromophenyl)-4-hydroxytetrahydro-2H-thiopyran 1,1-dioxide

To a 50 mL two-neck flask were added 3-(4-bromophenyl)oxetan-3-ol (300 mg, 1.10 mmol) and acetic acid (6.0 mL), then aqueous hydrogen peroxide solution (622 mg, 5.48 mmol, 30%). The mixture was stirred at 70° C. for 6 h. The reaction mixture was cooled to rt, and added dropwise into ice-water (100 mL), then there was a white solid precipitated out. The mixture was filtered to give a white solid (260 mg, 77.6%).

MS (ESI, pos. ion) m/z: 305.1 (M+1);

Step 3: N-(1-((1-cyanocyclopropyl)carbamoyl)-4,4-difluorocyclohexyl)-6-(4-(4-hydroxy-1,1-dioxidotetrahydro-2H-thiopyran-4-yl)phenyl)benzofuran-2-carboxamide The title compound was prepared according to the procedure described in step 3 of example 10 using N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (80 mg, 0.156 mmol), ethanol (2 mL), toluene (6 mL), 4-(4-bromophenyl)-4-hydroxytetrahydro-2H-thiopyran 1,1-dioxide (57 mg, 0.19 mmol), Pd(Ph$_3$P)$_4$ (14.4 mg, 0.012 mmol) and aqueous potassium carbonate (0.16 mL, 0.32 mmol) to give a white solid (31 mg, 32.5%).

MS (ESI, pos. ion) m/z: 612.2 (M+1);

$^1$H NMR (400 MHz, DMSO-d$_6$) δ 8.77 (s, 1H), 8.49 (s, 1H), 7.96 (s, 2H), 7.87 (d, J=8.2 Hz, 1H), 7.77 (d, J=8.4 Hz, 1H), 7.72 (s, 1H), 7.68 (dd, J=8.2, 1.3 Hz, 1H), 7.65 (s, 1H), 7.58 (d, J=3.1 Hz, 2H), 5.71 (s, 1H), 3.51-3.37 (m, 2H), 3.06 (d, J=12.4 Hz, 2H), 2.44 (d, J=12.5 Hz, 2H), 2.22 (s, 2H), 2.06 (d, J=9.4 Hz, 8H), 1.46 (dd, J=8.1, 5.4 Hz, 2H), 1.08 (dd, J=8.2, 5.6 Hz, 2H).

Example 28: N-(1-((1-cyanocyclopropyl)carbamoyl)-4,4-difluorocyclohexyl)-6-(4-(3-oxomorpholino)phenyl)benzofuran-2-carboxamide

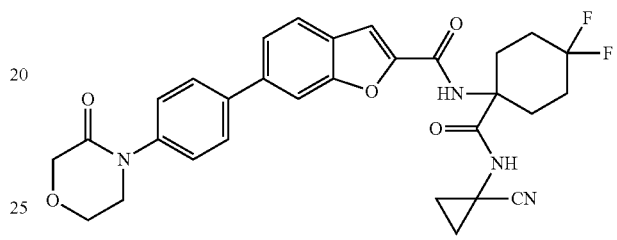

Step 1: 4-(4-bromophenyl)morpholin-3-one

A mixture of 4-bromoiodobenzene (1.10 g, 3.77 mmol), morpholin-3-one (0.58 g, 5.74 mmol), potassium carbonate (1.05 g, 7.52 mmol), cuprous iodide (72 mg, 0.38 mmol), N$^1$,N$^2$-dimethylethane-1,2-diamine (68 mg, 0.76 mmol) and anhydrous toluene (20 mL) in a 50 mL two-neck flask was refluxed for 6 h. The reaction mixture was cooled to rt, and added dropwise into ice-water. The mixture was stirred, and extracted with ethyl acetate (50 mL×3). The combined organic layers were dried over anhydrous sodium sulfate, filtered and concentrated in vacuo to remove the solvent. The residue was purified by silica-gel column chromatography (EtOAc:DCM=1:7, V/V) to give a white solid (0.58 g, 60%).

MS (ESI, pos. ion) m/z: 257.01 (M+2);

Step 2: N-(1-((1-cyanocyclopropyl)carbamoyl)-4,4-difluorocyclohexyl)-6-(4-(3-oxomorpholino) phenyl)benzofuran-2-carboxamide To a 50 mL two-neck round-bottom flask were added 4-(4-bromophenyl)morpholin-3-one (0.04 g, 0.2 mmol), N-(1-((1-cyanocyclopropyl) carbamoyl)-4,4-difluorocyclohexyl)-6-(4,4,5,5-tetramethyl-1,3,2-dioxaborolan-2-yl)benzofuran-2-carboxamide (81 mg, 0.16 mmol), Pd(Ph$_3$P)$_4$ (146 mg, 0.126 mmol), toluene (6 mL) and ethanol (2 mL). Aqueous potassium carbonate solution (0.16 mL, 0.32 mmol, 2 mol/L) was added into flask under nitrogen protection. The mixture was stirred at 90° C. for 2.5 h, then to the mixture was added water (20 mL), and the mixture was extracted with dichloromethane (50 mL×3). The combined organic layers were dried over anhydrous sodium sulfate, filtered and concentrated in vacuo. The residue was purified by silica-gel column chromatography (EtOAc:DCM=1:2, V/V) to give a white solid (55 mg, 60%).

MS (ESI, pos. ion) m/z: 563.2 (M+1);

$^1$H NMR (400 MHz, DMSO-d$_6$) δ 8.77 (s, 1H), 8.50 (s, 1H), 7.99 (s, 1H), 7.88 (d, J=8.3 Hz, 1H), 7.81 (d, J=8.6 Hz,

2H), 7.74-7.67 (m, 2H), 7.54 (d, J=8.6 Hz, 2H), 4.24 (s, 1H), 4.05-3.96 (m, 1H), 3.85-3.76 (m, 1H), 2.35-2.07 (m, 4H), 2.05 (s, 3H), 1.46 (d, J=2.8 Hz, 2H), 1.08 (d, J=2.7 Hz, 2H).

Example 29: N-(1-((1-cyanocyclopropyl)carbamoyl)-4,4-difluorocyclohexyl)-6-(4-(3-hydroxyazetidine-1-carbonyl)phenyl)benzofuran-2-carboxamide

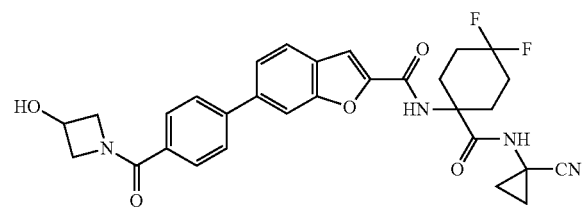 [SMILES: N#CC1(NC(=O)C2(NC(=O)c3cc4ccc(-c5ccc(C(=O)N6CC(O)C6)cc5)cc4o3)CCC(F)(F)CC2)CC1]

Step 1:
(4-bromophenyl)(3-hydroxyazetidin-1-yl)methanone

To a 10 mL sealed tube were added p-bromobenzoic acid (500 mg, 2.49 mmol) and anhydrous DMF (10 mL), then azetidin-3-ol hydrochloride (373 mg, 3.23 mmol) and HATU (1.35 g, 3.48 mmol) were added at 0° C., and diisopropylanmine (2.09 g, 16.0 mmol) was added dropwise at last. The mixture was stirred at 0° C. for 1 h. To the mixture was added saturated brine (60 mL). The resulting mixture was extracted with EtOAc (30 mL×3). The combined organic layers were washed with water (40 mL×2) and saturated brine (40 mL), dried over anhydrous Na$_2$SO$_4$, and filtered. The filtrate was concentrated in vacuo, and the residue was purified by silica-gel column chromatography (n-hexane:EtOAc-2:1, V/V) to give colourless oil (600 mg, 94.2%).
MS (ESI, pos. ion) m/z: 257.01 (M+2);

Step 2: N-(1-((1-cyanocyclopropyl)carbamoyl)-4,4-difluorocyclohexyl)-6-(4-(3-hydroxyazetidine-1-carbonyl)phenyl)benzofuran-2-carboxamide N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (80 mg, 0.16 mmol) was dissolved in a mixture of ethanol (2 mL) and toluene (6 mL) in a 50 mL two-neck flask. Then (4-bromophenyl)(3-hydroxyazetidin-1-yl)methanone (40 mg, 0.16 mmol) was added, and Pd(Ph$_3$P)$_4$ (14.4 mg, 0.012 mmol) was added under nitrogen protection, and aqueous potassium carbonate (0.16 mL, 0.32 mmol 2 mol/L) was added into the reaction mixture. The resulting mixture was stirred at 90° C. for 1 h. After the reaction was completed, to the mixture was added saturated brine (60 mL). The resulting mixture was extracted with EtOAc (20 mL×3). The combined organic layers were washed with saturated brine (30 mL×2), dried over anhydrous Na$_2$SO$_4$, and filtered. The filtrate was concentrated in vacuo, and the residue was purified by silica-gel column chromatography (DCM:EtOAc=20:1, V/V) to give a white solid (34 mg, 38.8%).
MS (ESI, pos. ion) m/z: 563.3 (M+1);
$^1$H NMR (400 MHz, DMSO-d$_6$) δ 8.77 (s, 1H), 8.51 (s, 1H), 8.03 (s, 1H), 7.91 (d, J=8.2 Hz, 1H), 7.86 (d, J=8.4 Hz, 2H), 7.78-7.67 (m, 4H), 4.52 (s, 2H), 4.28 (s, 1H), 4.09 (s, 1H), 3.83 (s, 1H), 2.22 (s, 2H), 2.07 (d, J=15.1 Hz, 6H), 1.46 (dd, J=8.2, 5.4 Hz, 2H), 1.08 (dd, J=8.3, 5.6 Hz, 2H).

Example 30: N-(1-((1-cyanocyclopropyl)carbamoyl)-4,4-difluorocyclohexyl)-6-(4-((1,1-dioxidotetrahydro-2H-thiopyran-4-yl)oxy)phenyl)benzofuran-2-carboxamide

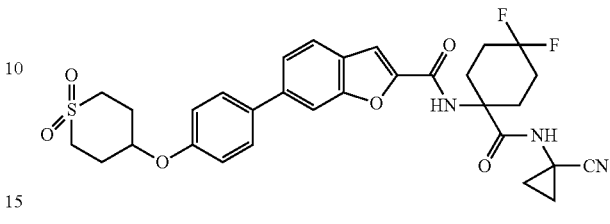

Step 1: tetrahydro-2H-thiopyran-4-ol

To a 50 mL two-neck flask were added tetrahydro-2H-thiopyran-4-one (1.00 g, 8.61 mmol) and anhydrous methanol (20 mL), then sodium borohydride (330 mg, 8.61 mmol) was added at 0° C. The mixture was warmed to rt and stirred at rt overnight. After the reaction monitored by TLC was completed, the reaction mixture was concentrated in vacuo to remove the solvent, and to the residue was added water (30 mL). The resulting mixture was acidified with hydrochloric acid (1 mol/L) to adjust pH 5-6, then extracted with EtOAc (30 mL×2). The combined organic layers were washed with saturated brine (30 mL×2), dried over anhydrous Na$_2$SO$_4$, and filtered. The filtrate was concentrated in vacuo to give colorless oil (0.91 g, 89%).

Step 2:
4-(4-bromophenoxy)tetrahydro-2H-thiopyran

To a 50 mL two-neck flask were added tetrahydro-2H-thiopyran-4-ol (568 mg, 4.80 mmol) and anhydrous tetrahydrofuran (15 mL). Then p-bromophenol (530 mg, 3.00 mmol) was added at 0° C., and Ph$_3$P (1.50 g, 5.66 mmol) and diethyl azodicarboxylate (1.00 g, 5.63 mmol) were added at last. The mixture was warmed to rt and stirred for 2 h. The reaction mixture was concentrated in vacuo to remove tetrahydrofuran, and to the residue was added saturated brine (50 mL). The resulting mixture was extracted with EtOAc (30 mL×2). The combined organic layers were washed with saturated brine (30 mL×2), dried over anhydrous Na$_2$SO$_4$, and filtered. The filtrate was concentrated in vacuo, and the residue was purified by silica-gel column chromatography (n-hexane:EtOAc=100:1, V/V) to give a white solid (440 mg, 53.6%).
$^1$H NMR (400 MHz, CDCl$_3$) δ 7.39 (d, J=8.9 Hz, 1H), 6.80 (d, J=8.9 Hz, 1H), 4.52-4.17 (m, 1H), 3.02-2.85 (m, 1H), 2.70-2.44 (m, 1H), 2.35-2.14 (m, 1H), 2.05-2.01 (m, 1H).

Step 3:
4-(4-bromophenoxy)tetrahydro-2H-thiopyran 1,1-dioxide

To a 50 mL two-neck flask were added 4-(4-bromophenoxy)tetrahydro-2H-thiopyran (430 mg, 1.57 mmol) and anhydrous ethyl acetate (10 mL), then metachloroperbenzoic acid (760 mg, 3.14 mmol) was added slowly. The mixture was stirred at rt for 2 h. After the reaction monitored by TLC was completed, to the mixture was added saturated brine (40 mL). The resulting mixture was extracted with EtOAc (30 mL×3). The combined organic layers were washed with saturated brine (40 mL×2), dried over anhydrous Na₂SO₄, and filtered. The filtrate was concentrated in vacuo, and the residue was purified by silica-gel column chromatography (n-hexane:EtOAc=5:1, V/V) to give a white solid (425 mg, 88.5%).

MS (ESI, pos. ion) m/z: 305.01 (M+2);

Step 4: N-(1-((1-cyanocyclopropyl)carbamoyl)-4,4-difluorocyclohexyl)-6-(4-((1,1-dioxidotetrahydro-2H-thiopyran-4-yl)oxy)phenyl)benzofuran-2-carboxamide N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (80 mg, 0.156 mmol) was dissolved in a mixture of ethanol (2 mL) and toluene (6 mL) in a 50 mL two-neck flask. Then 4-(4-bromophenoxy)tetrahydro-2H-thiopyran 1,1-dioxide (48 mg, 0.16 mmol) was added, and Pd(Ph₃P)₄ (14.4 mg, 0.012 mmol) was added under nitrogen protection, and aqueous potassium carbonate (0.16 mL, 0.32 mmol, 2 mol/L) was added into the reaction mixture. The resulting mixture was stirred at 90° C. for 1 h. After the reaction was completed, to the mixture was added saturated brine (60 mL). The resulting mixture was extracted with EtOAc (20 mL×3). The combined organic layers were washed with saturated brine (30 mL×2), dried over anhydrous Na₂SO₄, and filtered. The filtrate was concentrated in vacuo, and the residue was purified by silica-gel column chromatography (DCM:EtOAc=2:1, V/V) to give a white solid (52 mg, 54.5%).

MS (ESI, pos. ion) m/z: 612.2 (M+1);
¹H NMR (400 MHz, DMSO-d₆) δ 8.77 (s, 1H), 8.47 (s, 1H), 7.91 (s, 1H), 7.84 (d, J=8.2 Hz, 1H), 7.76-7.68 (m, 3H), 7.64 (d, J=7.7 Hz, 1H), 7.17 (d, J=8.6 Hz, 2H), 4.81 (s, 1H), 3.21 (s, 3H), 2.24 (s, 4H), 2.07 (d, J=14.3 Hz, 4H), 1.46 (d, J=2.3 Hz, 2H), 1.08 (d, J=2.3 Hz, 2H).

Example 31: N-(1-((1-cyanocyclopropyl)carbamoyl)-4,4-difluorocyclohexyl)-6-(2-oxo-2,3-dihydro-1H-benzo[d]imidazol-5-yl)benzofuran-2-carboxamide

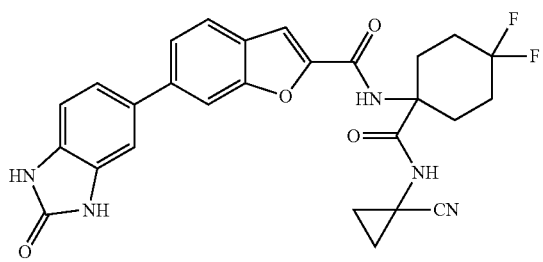 [SMILES: N#CC1(NC(=O)C2(NC(=O)c3cc4ccc(-c5ccc6[nH]c(=O)[nH]c6c5)cc4o3)CCC(F)(F)CC2)CC1]

The title compound was prepared according to the procedure described in step 4 of example 1 using 5-bromo-1H-benzo[d]imidazol-2(3H)-one (35 mg, 0.16 mmol), N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (93 mg, 0.18 mmol), toluene (6 mL), ethanol (2 mL), Pd(Ph₃P)₄ (20 mg, 0.017 mmol) and aqueous potassium carbonate (46 mg, 0.33 mmol) to give a white solid (36 mg, 42.81%).

MS (ESI, pos. ion) m/z: 520.15 (M+1);
¹H NMR (400 MHz, DMSO-d₆) δ 10.75 (d, J=13.8 Hz, 2H), 8.83 (s, 1H), 8.48 (s, 1H), 7.91-7.78 (m, 2H), 7.74 (s, 1H), 7.64-7.54 (m, 1H), 7.33 (dd, J=8.1, 1.6 Hz, 1H), 7.25 (s, 1H), 7.04 (d, J=8.0 Hz, 1H), 2.23 (s, 4H), 2.07 (d, J=15.2 Hz, 4H), 1.33-1.17 (m, 2H), 1.08 (dd, J=8.3, 5.6 Hz, 2H).

Example 32: 6-(benzo[d]oxazol-6-yl)-N-(1-((1-cyanocyclopropyl)carbamoyl)-4,4-difluorocyclohexyl)benzofuran-2-carboxamide

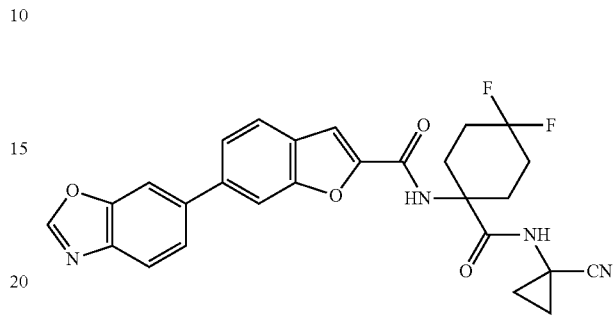

The title compound was prepared according to the procedure described in step 4 of example 1 using N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (80 mg, 0.16 mmol), ethanol (2 mL), toluene (6 mL), 6-bromobenzo[d]oxazole (34 mg, 0.171 mmol), Pd(Ph₃P)₄ (14.4 mg, 0.012 mmol) and aqueous potassium carbonate (0.16 mL, 0.32 mmol) to give a white solid (35 mg, 44.5%).

MS (ESI, pos. ion) m/z: 505.2 (M+1);
¹H NMR (400 MHz, DMSO-d₆) δ 8.81 (s, 2H), 8.53 (s, 1H), 8.20 (s, 1H), 8.07 (s, 1H), 7.90 (s, 2H), 7.84 (s, 1H), 7.76 (d, J=12.3 Hz, 1H), 2.22 (s, 2H), 2.06 (d, J=14.7 Hz, 6H), 1.46 (dd, J=8.1, 5.4 Hz, 2H), 1.08 (dd, J=7.6, 5.0 Hz, 2H).

Example 33: N-(1-((1-cyanocyclopropyl)carbamoyl)-4,4-difluorocyclohexyl)-6-(2,3-dihydrobenzo[b][1,4]dioxin-6-yl)benzofuran-2-carboxamide

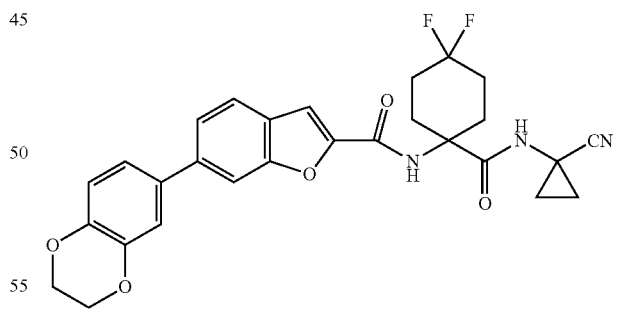

The title compound was prepared according to the procedure described in step 4 of example 1 using 6-bromo-2,3-dihydrobenzo[b][1,4]dioxine (35 mg, 0.16 mmol), N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (0.10 g, 0.19 mmol), Pd(dppf)Cl₂·CH₂Cl₂ (14 mg, 0.017 mmol), DMF (8 mL) and aqueous potassium carbonate (0.16 mL, 0.32 mmol, 2 mol/L) to give a white solid (45 mg, 53%).

MS (ESI, pos. ion) m/z: 522.20 (M+1);

$^1$H NMR (400 MHz, DMSO-d$_6$) δ 8.77 (s, 1H), 8.46 (s, 1H), 7.87 (s, 1H), 7.81 (d, J=8.1 Hz, 1H), 7.69 (s, 1H), 7.60 (d, J=8.3 Hz, 1H), 7.24 (d, J=11.0 Hz, 2H), 6.97 (d, J=8.2 Hz, 1H), 4.29 (s, 4H), 2.21 (s, 2H), 2.06 (d, J=14.7 Hz, 4H), 1.45 (s, 2H), 1.24 (s, 2H), 1.07 (s, 2H).

Example 34: N-(1-((1-cyanocyclopropyl)carbamoyl)-4,4-difluorocyclohexyl)-6-(imidazo[1,2-a]pyridin-7-yl)benzofuran-2-carboxamide

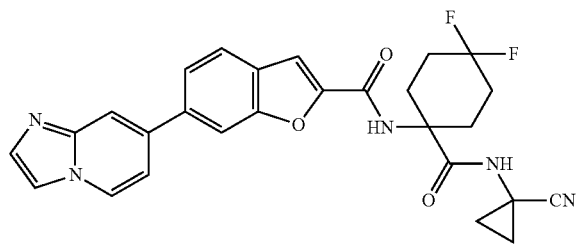 [SMILES: N#CC1(NC(=O)C2(NC(=O)c3cc4ccc(-c5ccn6ccnc6c5)cc4o3)CCC(F)(F)CC2)CC1]

The title compound was prepared according to the procedure described in step 4 of example 1 using N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (80 mg, 0.16 mmol), ethanol (2 mL), toluene (6 mL), 7-bromoimidazo[1,2-a]pyridine (35 mg, 0.18 mmol), Pd(Ph$_3$P)$_4$ (14.4 mg, 0.012 mmol) and aqueous potassium carbonate (0.16 mL, 0.32 mmol) to give a white solid (20 mg, 25.5%).

MS (ESI, pos. ion) m/z: 504.2 (M+1);
$^1$H NMR (400 MHz, DMSO-d$_6$) δ 8.79 (s, 2H), 8.57 (d, J=6.7 Hz, 1H), 8.23 (d, 1H), 8.10 (s, 2H), 7.92 (s, 1H), 7.72 (d, J=18.3 Hz, 3H), 7.57 (s, 1H), 2.22 (s, 2H), 2.06 (d, J=14.7 Hz, 6H), 1.46 (dd, J=8.1, 5.4 Hz, 2H), 1.08 (dd, J=7.6, 5.0 Hz, 2H).

Example 35: N-(1-((1-cyanocyclopropyl)carbamoyl)-4,4-difluorocyclohexyl)-6-(1,1-dioxidobenzo[b]thiophen-5-yl)benzofuran-2-carboxamide

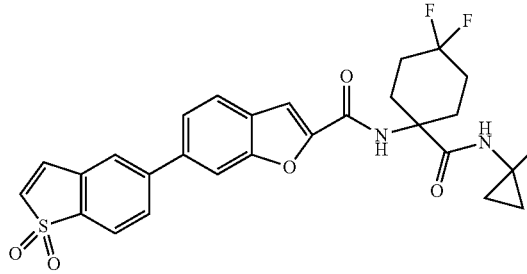

Step 1: 5-bromobenzo[b]thiophene 1,1-dioxide

To a 50 mL two-neck flask were added 5-bromobenzo[b]thiophene (231.1 mg, 1.08 mmol), dichloromethane (8 mL) and formic acid (0.25 mL), then H$_2$O$_2$ (0.15 mL, 30%) was added dropwise. The mixture was stirred at rt overnight. After the reaction was completed, to the mixture was added saturated brine (20 mL). The resulting mixture was extracted with DCM (20 mL×3). The combined organic layers were dried over anhydrous Na$_2$SO$_4$, and filtered. The filtrate was concentrated in vacuo, and the residue was purified by silica-gel column chromatography (PE:EtOAc=10:1, V/V) to give a white solid (240 mg, 90.9%).

MS (ESI, pos. ion) m/z: 244.9 (M+1);

Step 2: N-(1-((1-cyanocyclopropyl)carbamoyl)-4,4-difluorocyclohexyl)-6-(1,1-dioxidobenzo[b]thiophen-5-yl)benzofuran-2-carboxamide To 50 mL two-neck flask were added N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (80 mg, 0.16 mmol) and DMF (6 mL), then 5-bromobenzo[b]thiophene 1,1-dioxide (57 mg, 0.23 mmol) was added. To the mixture was added Pd(dppf)Cl$_2$.CH$_2$Cl$_2$ (20 mg, 0.025 mmol) under nitrogen protection, and aqueous potassium carbonate (0.23 mL, 2 mol/L) was added into the reaction mixture. The resulting mixture was stirred at 90° C. for 2 h. After the reaction was completed, to the mixture was added saturated brine (20 mL). The resulting mixture was extracted with EtOAc (20 mL×3). The combined organic layers were dried over anhydrous Na$_2$SO$_4$, and filtered. The filtrate was concentrated in vacuo, and the residue was purified by silica-gel column chromatography (DCM:EtOAc=2:1, V/V) to give a white solid (40 mg, 46.5%).

MS (ESI, pos. ion) m/z: 552.2 (M+1);
$^1$H NMR (400 MHz, DMSO-d$_6$) δ 7.70-7.61 (m, 4H), 7.55-7.48 (m, 3H), 7.29 (d, J=1.1 Hz, 2H), 6.80-6.73 (m, 2H), 2.35-2.21 (m, 4H), 2.16-2.07 (m, 2H), 2.00-1.90 (m, 2H), 1.51-1.42 (m, 2H), 0.81 (dd, J=18.8, 8.2 Hz, 2H).

Example 36: N-(1-((1-cyanocyclopropyl)carbamoyl)-4,4-difluorocyclohexyl)-6-(2-oxo-2,3-dihydrobenzo[d]oxazol-5-yl)benzofuran-2-carboxamide

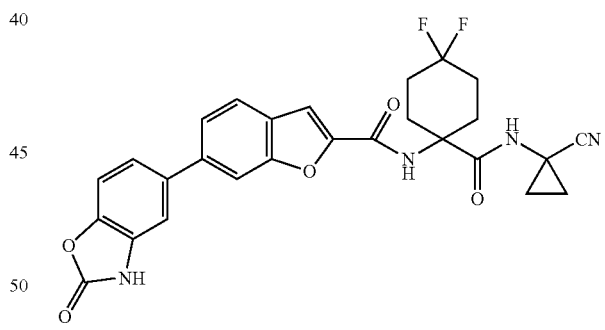

The title compound was prepared according to the procedure described in step 4 of example 1 using 5-bromobenzo[d]oxazol-2(3H)-one (25 mg, 0.12 mmol), N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (72 mg, 0.14 mmol), Pd(dppf)Cl$_2$.CH$_2$Cl$_2$ (10 mg, 0.012 mmol), DMF (8 mL) and aqueous potassium carbonate (0.12 mL, 0.24 mmol, 2 mol/L) to give a white solid (21 mg, 35%).

MS (ESI, pos. ion) m/z: 521.20 (M+1);
$^1$H NMR (400 MHz, DMSO-d$_6$) δ 11.80 (s, 1H), 8.77 (s, 1H), 8.48 (s, 1H), 7.94 (s, 1H), 7.87 (d, J=8.2 Hz, 1H), 7.73 (s, 1H), 7.65 (dd, J=8.2, 1.4 Hz, 1H), 7.47 (dd, J=8.5, 1.6 Hz, 1H), 7.41 (dd, J=5.0, 3.1 Hz, 2H), 2.21 (s, 2H), 2.07 (d, J=14.9 Hz, 4H), 1.46 (dd, J=8.2, 5.4 Hz, 2H), 1.28-1.20 (m, 2H), 1.08 (dd, J=8.3, 5.6 Hz, 2H).

Example 37: 6-(3-cyano-4-(1H-1,2,4-triazol-1-yl)phenyl)-N-(1-((1-cyanocyclopropyl) carbamoyl)-4,4-difluorocyclohexyl)benzofuran-2-carboxamide

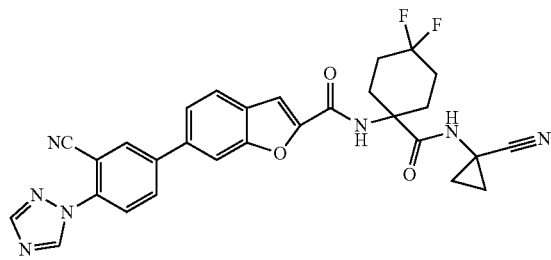 [SMILES: N#Cc1cc(-c2ccc3cc(C(=O)NC4(C(=O)NC5(C#N)CC5)CCC(F)(F)CC4)oc3c2)ccc1-n1cncn1]

Step 1: 5-bromo-2-(1H-1,2,4-triazol-1-yl)benzonitrile

To a 50 mL two-neck flask were added 1H-1,2,4-triazole (760 mg, 1.1 mmol) and anhydrous N,N-dimethylformamide (12 mL), then 5-bromo-2-fluorobenzonitrile (2.00 g, 10 mmol) and cesium carbonate (3.6 g, 11 mmol) were added. The mixture was stirred at 58° C. overnight. The reaction mixture was cooled to rt, and water (50 mL) was added, then there was a white solid precipitated out. The mixture was filtered, and the filter cake was dissolved in DCM (150 mL). The resulting mixture was concentrated in vacuo, and the residue was purified by silica-gel column chromatography (DCM) to give a white solid (360 mg, 47%).

MS (ESI, pos. ion) m/z: 249.6 (M+2);

Step 2: 6-(3-cyano-4-(1H-1,2,4-triazol-1-yl)phenyl)-N-(1-((1-cyanocyclopropyl)carbamoyl)-4,4-difluorocyclohexyl)benzofuran-2-carboxamide N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (80 mg, 0.156 mmol) was dissolved in a mixture of ethanol (2 mL) and toluene (6 mL) in a 50 mL two-neck flask. Then 5-bromo-2-(1H-1,2,4-triazol-1-yl)benzonitrile (40 mg, 0.16 mmol) was added, and $Pd(Ph_3P)_4$ (18 mg, 0.016 mmol) was added under nitrogen protection, and aqueous potassium carbonate (0.2 mL, 2 mol/L) was added into the reaction mixture. The resulting mixture was stirred at 85° C. for 80 min. After the reaction was completed, the reaction mixture was washed with saturated brine (60 mL). The resulting mixture was extracted with EtOAc (20 mL×3). The combined organic layers were washed with saturated brine (30 mL×2), dried over anhydrous $Na_2SO_4$, and filtered. The filtrate was concentrated in vacuo, and the residue was purified by silica-gel column chromatography (DCM:EtOAc=10:1, V/V) to give a white solid (52 mg, 70.6%).

MS (ESI, pos. ion) m/z: 556.2 (M+1);
$^1$H NMR (400 MHz, DMSO-$d_6$) δ 9.26 (s, 1H), 8.79 (s, 1H), 8.59-8.52 (m, 2H), 8.41 (s, 1H), 8.34 (dd, J=8.6, 2.1 Hz, 1H), 8.21 (s, 1H), 7.98 (dd, J=19.5, 8.4 Hz, 2H), 7.86 (dd, J=8.3, 1.4 Hz, 1H), 7.78 (s, 1H), 2.30-2.17 (m, 2H), 2.28-2.16 (m, 2H), 2.15-2.02 (m, 6H), 2.14-2.00 (m, 6H), 1.51-1.44 (m, 2H), 1.55-1.39 (m, 2H), 1.16-1.00 (m, 2H), 1.12-1.05 (m, 2H).

Example 38: N-(1-((1-cyanocyclopropyl)carbamoyl)-4,4-difluorocyclohexyl)-6-(1,1-dioxido-2,3-dihydrobenzo[b]thiophen-5-yl)benzofuran-2-carboxamide

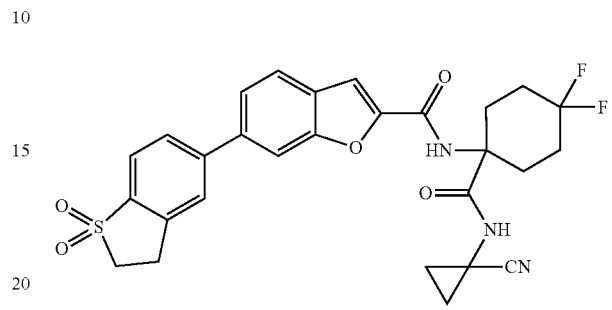

Step 1: 2,3-dihydrobenzo[b]thiophene

To a solution of benzothiophene (3.00 g, 22.35 mmol) in anhydrous ethanol (21 mL) was added sodium wire (1.4 g, 61 mmol) at 0° C. under nitrogen protection in a 50 mL two-neck flask. When the sodium wire disappeared, the mixture was warmed to rt and stirred for 24 h. After the reactant was consumed, 20 mL of the water was added to quench the reaction. The mixture was extracted with ethyl acetate (30 mL), and the organic layer was dried over anhydrous sodium sulfate and concentrated in vacuo, and the residue was purified by silica-gel column chromatography (PE) to give colourless oil (1.18 g, 38.80%%).

$^1$H NMR (400 MHz, CDCl$_3$) δ 7.30-7.19 (m, 2H), 7.16 (t, J=7.5 Hz, 1H), 7.06 (ddd, J=10.9, 8.2, 4.5 Hz, 1H), 3.42-3.35 (m, 2H), 3.35-3.26 (m, 2H).

Step 2: 5-bromo-2,3-dihydrobenzo[b]thiophene

Iron powder (41 mg, 0.73 mmol) was added into a solution of 3-dihydrobenzo[b]thiophene (200 mg, 1.47 mmol) in anhydrous DCM (10 mL) in a 50 mL round-bottom flask. Then a solution of bromine (235 mg, 1.47 mmol) in anhydrous DCM (0.5 mL) was added dropwise in an ice-bath. The mixture was stirred at 0° C. for 0.5 h. After the reaction was completed, to the mixture was added water (40 mL), and the resulting mixture was extracted with DCM (20 mL×3), and the organic layer was dried over anhydrous sodium sulfate, concentrated in vacuo. The residue was purified by silica-gel column chromatography (PE) to give a white crystalline compound (93 mg, 29%).

$^1$H NMR (400 MHz, CDCl$_3$) δ 8.01 (d, J=1.8 Hz, 1H), 7.73 (d, J=8.5 Hz, 1H), 7.61-7.45 (m, 1H), 5.32 (s, 1H), 3.52 (d, J=5.5 Hz, 1H).

Step 3: 5-bromo-2,3-dihydrobenzo[b]thiophene 1,1-dioxide

To a stirred solution of 5-bromo-2,3-dihydrobenzo[b]thiophene (90 mg, 0.42 mmol) in glacial acetic acid (7 mL) was added hydrogen peroxide solution (0.240 g, 2.12 mmol, 30%). The resulting mixture was stirred at 75° C. for 6.5 h. After the reaction was completed, the mixture was cooled to rt and concentrated in vacuo to remove the organic solvent.

The residue was washed with water (30 mL×3) to give a yellow solid (78 mg, 75.44%).

$^1$H NMR (400 MHz, CDCl$_3$) δ 7.63 (s, 2H), 7.58 (s, 1H), 3.57-3.48 (m, 2H), 3.45-3.33 (m, 2H).

Step 4: N-(1-((1-cyanocyclopropyl)carbamoyl)-4,4-difluorocyclohexyl)-6-(1,1-dioxido-2,3-dihydrobenzo[b]thiophen-5-yl)benzofuran-2-carboxamide To a 50 mL round-bottom flask were added 5-bromo-2,3-dihydrobenzo[b]thiophene 1,1-dioxide (37 mg, 0.15 mmol), N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (70 mg, 0.14 mmol), Pd(Ph$_3$P)$_4$ (16 mg, 0.014 mmol), toluene (6 mL) and ethanol (2 mL). Then potassium carbonate (38 mg, 0.27 mmol) was added into the flask under nitrogen protection. The mixture was stirred at 95° C. for 1 h. After the reaction was completed, the mixture was cooled to rt and concentrated in vacuo to remove the organic solvent. The residue was washed with water (50 mL×2), and extracted with ethyl acetate (20 mL×2). The combined organic layers were dried over anhydrous sodium sulfate, filtered and concentrated in vacuo to remove the solvent. The residue was purified by silica-gel column chromatography (DCM:EtOAc=10:1, V/V) to give a white solid (56 mg, 74.18%).

MS (ESI, pos. ion) m/z: 554.1 (M+1);

$^1$H NMR (400 MHz, DMSO-d$_6$) δ 8.78 (s, 1H), 8.53 (s, 1H), 8.06 (s, 1H), 7.93 (dd, J=9.4, 7.3 Hz, 3H), 7.85 (d, J=8.1 Hz, 1H), 7.78-7.70 (m, 2H), 3.66 (t, J=6.9 Hz, 2H), 3.45 (t, J=6.9 Hz, 2H), 2.28-1.96 (m, 8H), 1.53-1.41 (m, 2H), 1.08 (dd, J=8.2, 5.6 Hz, 2H).

Example 39: N-(1-((1-cyanocyclopropyl)carbamoyl)-4,4-difluorocyclohexyl)-6-(3-methoxy-4-(1H-1,2,4-triazol-1-yl)phenyl)benzofuran-2-carboxamide

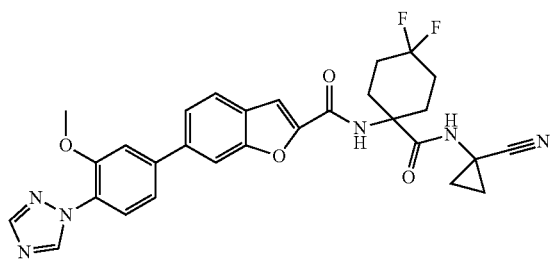 [SMILES: COc1cc(-c2ccc3cc(C(=O)NC4(C(=O)NC5(C#N)CC5)CCC(F)(F)CC4)oc3c2)ccc1-n1cncn1]

Step 1: 1-(2-methoxy-4-nitrophenyl)-1H-1,2,4-triazole

To a 100 mL dried sealed tube were added 1-fluoro-2-methoxy-4-nitrobenzene (0.6 g, 3.5 mmol), 1,2,4-triazole (0.36 g, 5.2 mmol) and potassium carbonate (0.9 g, 6.5 mmol), then DMSO (10 mL) was added. The sealed tube was sealed with teflon nut under nitrogen protection, then the mixture was heated to 75° C. and stirred for 2 h. The mixture was cooled to rt and to the residue was added water (60 mL). The mixture was stirred for 10 min and filtered. The filter cake was dried to give a light yellow solid (0.7 g, 90%).

MS (ESI, pos. ion) m/z: 221.1 (M+1);

Step 2: 3-methoxy-4-(1H-1,2,4-triazol-1-yl)aniline

To a solution of 1-(2-methoxy-4-nitrophenyl)-1H-1,2,4-triazole (0.7 g, 3.18 mmol) in ethyl acetate (20 mL) was added 10% Pd/C (100 mg). The mixture was stirred at rt for 6 h in a hydrogen atomosphere. After the reaction was completed, the mixture was filtered, and the filtrate was concentrated in vacuo to give a light yellow solid (0.58 g, 95%).

MS (ESI, pos. ion) m/z: 191.1 (M+1);

Step 3: 1-(4-bromo-2-methoxyphenyl)-1H-1,2,4-triazole

Cuprous bromide (1.22 g, 8.50 mmol) and anhydrous acetonitrile (15 mL) were placed in a dried flask, then tert-butyl nitrite (1.2 mL, 10 mmol) was added dropwise slowly at 50° C. After the addition, the mixture was stirred at 50° C. for 50 min, then a solution of 3-methoxy-4-(1H-1,2,4-triazol-1-yl)aniline (1.7 g, 8.98 mmol) in acetonitrile (15 mL) was added to the flask. The mixture was stirred at 80° C. for 6 h. The filtrate was concentrated in vacuo, and the residue was purified by silica-gel column chromatography (PE:EtOAc=4:1, V/V) to give a white solid (790 mg, 35%).

MS (ESI, pos. ion) m/z: 254.9 (M+2);

Step 4: N-(1-((1-cyanocyclopropyl)carbamoyl)-4,4-difluorocyclohexyl)-6-(3-methoxy-4-(1H-1,2,4-triazol-1-yl)phenyl)benzofuran-2-carboxamide To a 50 mL two-neck flask were added N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (60 mg, 0.12 mmol), DMF (6 mL) and 1-(4-bromo-2-methoxyphenyl)-1H-1,2,4-triazole (36 mg, 0.16 mmol), then Pd(dppf)Cl$_2$·CH$_2$Cl$_2$ (20 mg) and aqueous potassium carbonate (0.22 mL, 2 mol/L) were added to the mixture. The mixture was stirred at 90° C. for 1 h. After the reaction was completed, to the mixture was added saturated brine (20 mL). The resulting mixture was extracted with EtOAc (20 mL×3). The combined organic layers were dried over anhydrous Na$_2$SO$_4$, and filtered. The filtrate was concentrated in vacuo, and the residue was purified by silica-gel column chromatography (DCM:EtOAc=1:1, V/V) to give a white solid (45 mg, 68%).

MS (ESI, pos. ion) m/z: 561.2 (M+1);

$^1$H NMR (600 MHz, DMSO-d$_6$) δ 9.02 (s, 1H), 8.79 (s, 1H), 8.54 (s, 1H), 8.24 (s, 1H), 8.13 (s, 1H), 7.92 (d, J=8.2 Hz, 1H), 7.83-7.71 (m, 3H), 7.63 (s, 1H), 7.53 (d, J=8.3 Hz, 1H), 4.04 (s, 3H), 2.28-2.17 (m, 2H), 2.07 (q, J=15.4 Hz, 6H), 1.24 (s, 2H), 1.08 (t, J=6.5 Hz, 2H).

Example 40: N-(1-((1-cyanocyclopropyl)carbamoyl)-4,4-difluorocyclohexyl)-6-(3-methoxy-4-(morpholine-4-carbonyl)phenyl)benzofuran-2-carboxamide

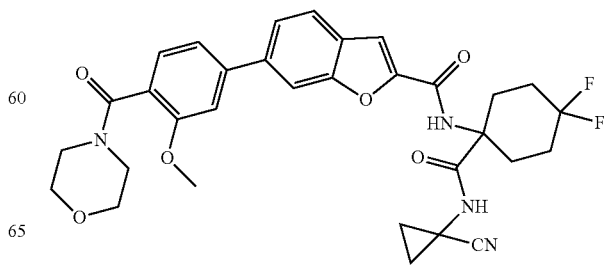

Step 1: (4-bromo-2-methoxyphenyl)(morpholino)methanone

To DMF (8 mL) were added 4-bromo-2-methoxybenzoic acid (250 mg, 1.08 mmol) and morpholine (0.124 g, 1.41 mmol) under an ice-bath condition. HATU (0.59 g, 1.5 mmol) was added under nitrogen protection, then N,N-diisopropylethylamine (1.1 mL, 6.6 mmol) was added dropwise at 0° C. After the addition, the mixture was stirred for 1 h under the ice-bath condition. After the reaction was completed, the mixture was poured into water (50 mL). The resulting mixture was extracted with EtOAc (25 mL×3). The combined organic layers were washed with saturated aqueous NaCl solution (20 mL×2), dried over anhydrous $Na_2SO_4$, and filtered. The filtrate was concentrated in vacuo, and the residue was purified by silica-gel column chromatography (DCM:EtOAc=10:1, V/V) to give a white solid (0.30 g, 92%).

MS (ESI, pos. ion) m/z: 301.0 (M+2);

Step 2: N-(1-((1-cyanocyclopropyl)carbamoyl)-4,4-difluorocyclohexyl)-6-(3-methoxy-4-(morpholine-4-carbonyl)phenyl)benzofuran-2-carboxamide (4-Bromo-2-methoxyphenyl)(morpholino)methanone (50 mg, 0.17 mmol), N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (100 mg, 0.19 mmol) and $Pd(Ph_3P)_4$ (20 mg, 0.017 mmol) were added to a mixture of toluene (6 mL) and ethanol (2 mL) in a 50 mL two-neck flask, then potassium carbonate was added (47 mg, 0.34 mmol). The mixture was stirred at 90° C. for 1.5 h in a nitrogen atmosphere. After the reaction was completed, the reaction mixture was cooled to rt and to the mixture was added EtOAc (50 mL). The mixture was washed with saturated brine (50 mL×2), dried over anhydrous $Na_2SO_4$, and filtered. The filtrate was concentrated in vacuo to remove the solvent, and the residue was purified by silica-gel column chromatography (MeOH:DCM=1:50, V/V) to give a white solid (50 mg, 49.48%).

MS (ESI, pos. ion) m/z: 607.3 (M+1);
$^1$H NMR (400 MHz, CDCl$_3$) δ 8.24 (s, 1H), 7.82-7.70 (m, 2H), 7.63-7.52 (m, 2H), 7.37 (t, J=12.0 Hz, 2H), 7.16 (s, 1H), 6.64 (s, 1H), 3.96 (s, 3H), 3.82 (s, 4H), 3.56 (dd, J=88.5, 32.6 Hz, 4H), 2.39 (s, 4H), 2.07 (s, 4H), 1.42 (d, J=22.4 Hz, 2H), 1.01-0.84 (m, 2H).

Example 41: 6-(chloro-4-methoxyphenyl)-N-(1-((1-cyanocyclopropyl)carbamoyl)-4,4-difluorocyclohexyl)benzofuran-2-carboxamide

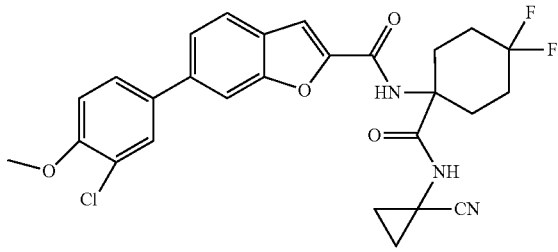 [SMILES: COc1ccc(-c2ccc3cc(C(=O)NC4(C(=O)NC5(C#N)CC5)CCC(F)(F)CC4)oc3c2)cc1Cl]

Step 1: 2-chloro-4-iodo-1-methoxybenzene

To a suspension of 2-chloro-4-iodo-1-methoxybenzene (1.0 g, 3.93 mmol) and potassium carbonate (1.10 g, 7.88 mmol) in acetonitrile (16 mL) which was placed in a 50 mL round bottom flask was added iodomethane (0.60 g, 4.23 mmol) under nitrogen protection. The mixture was stirred at rt overnight under nitrogen protection. After the reaction was completed, the reaction was quenched with aqueous ammonia (30 mL). The mixture was extracted with ethyl acetate (30 mL×2), and the combined organic layers were dried over anhydrous sodium sulfate, concentrated in vacuo to remove the solvent. The residue was purified by silica-gel column chromatography (PE:EtOAc=20:1, V/V) to give a white solid (785.8 mg, 74.4%).

$^1$H NMR (400 MHz, CDCl$_3$) δ 7.68 (d, J=2.1 Hz, 1H), 7.53 (dd, J=8.6, 2.1 Hz, 1H), 6.70 (d, J=8.7 Hz, 1H), 3.90 (s, 3H).

Step 2: 6-(3-chloro-4-methoxyphenyl)-N-(1-((1-cyanocyclopropyl)carbamoyl)-4,4-difluorocyclohexyl)benzofuran-2-carboxamide 2-Chloro-4-iodo-1-methoxybenzene (50 mg, 0.18 mmol), N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (80 mg, 0.15 mmol) and $Pd(Ph_3P)_4$ (20 mg, 0.017 mmol) were added to a mixture of toluene (6 mL) and ethanol (2 mL) in a 50 mL round-bottom flask, then potassium carbonate (44 mg, 0.32 mmol) was added. The mixture was stirred at 95° C. for 50 minutes in a nitrogen atmosphere. After the reaction was completed, the reaction mixture was diluted with EtOAc (100 mL), and then washed with water (50 mL×2), dried over anhydrous $Na_2SO_4$, filtered. The filtrate was concentrated in vacuo to remove the solvent, and the residue was purified by silica-gel column chromatography (DCM:EtOAc=25:1, V/V) to give a white solid (41 mg, 49.82%).

MS (ESI, pos. ion) m/z: 528.3 (M+1);
$^1$H NMR (400 MHz, DMSO-d$_6$) δ 8.78 (s, 1H), 8.49 (s, 1H), 7.97 (s, 1H), 7.85 (dd, J=5.1, 2.9 Hz, 2H), 7.81-7.55 (m, 3H), 7.27 (d, J=8.7 Hz, 1H), 3.92 (s, 3H), 2.28-1.89 (m, 8H), 1.46 (dd, J=8.0, 5.4 Hz, 2H), 1.26 (d, J=19.4 Hz, 2H).

Example 42: N-(1-((1-cyanocyclopropyl)carbamoyl)-4,4-difluorocyclohexyl)-6-(4-(3-methyl-1H-1,2,4-triazol-1-yl)phenyl)benzofuran-2-carboxamide

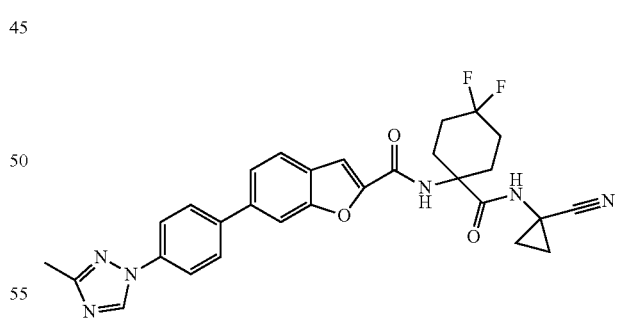

Step 1: 3-methyl-1-(4-nitrophenyl)-1H-1,2,4-triazole

To a 50 mL dried two-neck flask were added 3-methyl-1H-1,2,4-triazole (650 mg, 7.8 mmol), 1-fluoro-4-nitrobenzene (1.0 g, 7.1 mmol) and potassium carbonate (2.0 g, 14 mmol), then DMF (10 mL) was added. The mixture was stirred at 80° C. for 1 h under nitrogen protection. The mixture was cooled to rt and filtered. The filter cake was washed with DCM (20 mL), and the filtrate was concentrated in vacuo. To the residue was added water (20 mL). The mixture was stirred for 10 min and then a light yellow solid precipitated out. The mixture was filtered by suction, and the filter cake was dried to give a light yellow solid (0.7 g, 48%).

MS (ESI, pos. ion) m/z: 205.1 (M+1);

Step 2: 4-(3-methyl-1H-1,2,4-triazol-1-yl)aniline

To a solution of 3-methyl-1-(4-nitrophenyl)-1H-1,2,4-triazole (700 mg, 3.42 mmol) in a mixture of methanol (5 mL) and ethyl acetate (20 mL) was added 10% Pd/C (160 mg). The mixture was stirred at rt for 2 h in a hydrogen atmosphere. After the reaction was completed, the mixture was filtered, and the filtrate was concentrated in vacuo to give a light yellow solid (560 mg, 93.7%).

MS (ESI, pos. ion) m/z: 175.2 (M+1);

Step 3: 1-(4-bromophenyl)-3-methyl-1H-1,2,4-triazole

Cuprous bromide (618 mg, 4.30 mmol) and anhydrous acetonitrile (8 mL) were placed in a dried flask, then tert-butyl nitrite (0.62 mL, 5.2 mmol) was added dropwise slowly at 50° C. After the addition, the mixture was stirred at 50° C. for 50 min, then a solution of 4-(3-methyl-1H-1,2,4-triazol-1-yl)aniline (500 mg, 2.87 mmol) in acetonitrile (10 mL) was added to the flask. The mixture was stirred at 80° C. for 6 h. The filtrate was concentrated in vacuo, and the residue was purified by silica-gel column chromatography (DCM:EtOAc=1:1, V/V) to give a light yellow solid (350 mg, 51.2%).

MS (ESI, pos. ion) m/z: 239.1 (M+2);

Step 4: N-(1-((1-cyanocyclopropyl)carbamoyl)-4,4-difluorocyclohexyl)-6-(4-(3-methyl-1H-1,2,4-triazol-1-yl)phenyl)benzofuran-2-carboxamide To a 50 mL two-neck flask were added N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (70 mg, 0.13 mmol), DMF (6 mL) and 1-(4-bromophenyl)-3-methyl-1H-1,2,4-triazole (42 mg, 0.17 mmol), then Pd(dppf)Cl$_2$.CH$_2$Cl$_2$ (20 mg, 0.02 mmol) and aqueous potassium carbonate (0.2 mL, 2 mol/L) were added to the mixture. The mixture was stirred at 90° C. for 1 h. After the reaction was completed, to the mixture was added saturated brine (20 mL). The resulting mixture was extracted with EtOAc (20 mL×3). The combined organic layers were dried over anhydrous Na$_2$SO$_4$, and filtered. The filtrate was concentrated in vacuo, and the residue was purified by silica-gel column chromatography (DCM:EtOAc=1:1, V/V) to give a white solid (50 mg, 67.3%).

MS (ESI, pos. ion) m/z: 545.2 (M+1);

$^1$H NMR (600 MHz, DMSO-d$_6$) δ 9.24 (s, 1H), 8.79 (s, 1H), 8.52 (s, 1H), 8.05 (s, 1H), 7.95 (s, 3H), 7.90 (d, J=8.2 Hz, 1H), 7.79-7.71 (m, 2H), 2.39 (s, 3H), 2.22 (s, 2H), 2.14-2.01 (m, 6H), 1.47 (dd, J=8.1, 5.4 Hz, 2H), 1.08 (dd, J=8.2, 5.5 Hz, 2H).

$^{19}$F NMR (376 MHz, CDCl$_3$) δ −96.21 (d, J=228.7 Hz), −100.54 (d, J=247.7 Hz).

Example 43: N-(1-((1-cyanocyclopropyl)carbamoyl)-4,4-difluorocyclohexyl)-6-(3-methyl-4-(1H-1,2,4-triazol-1-yl)phenyl)benzofuran-2-carboxamide

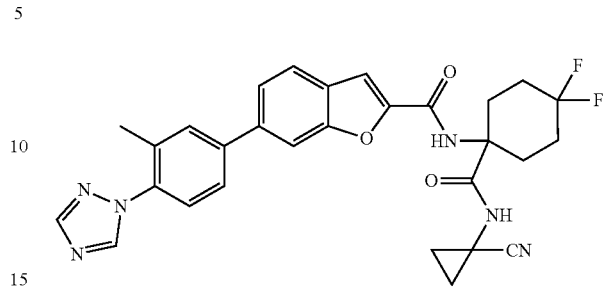

Step 1: 1-(2-methyl-4-nitrophenyl)-1H-1,2,4-triazole

The title compound was prepared according to the synthetic procedure described in step 1 of example 42 using 1H-1,2,4-triazole (0.35 g, 5.07 mmol), 1-fluoro-2-methyl-4-nitrobenzene (0.70 g, 4.5 mmol), potassium carbonate (0.50 g, 5.0 mmol) and DMF (10 mL) to give a white solid (660 mg, 71.64%).

MS (ESI, pos. ion) m/z: 205.2 (M+1)

Step 2:3-methyl-4-(1H-1,2,4-triazol-1-yl)aniline

The title compound was prepared according to the synthetic procedure described in step 2 of example 42 using 1-(2-methyl-4-nitrophenyl)-1H-1,2,4-triazole (660 mg, 3.23 mmol), ethyl acetate (10 mL) and 10% Pd/C (720 mg, 0.67 mmol) to give a pink solid (0.51 g, 91%).

MS (ESI, pos. ion) m/z: 175.2 (M+1);

Step 3:1-(4-bromo-2-methylphenyl)-1H-1,2,4-triazole

The title compound was prepared according to the synthetic procedure described in step 3 of example 42 using cuprous bromide (0.25 g, 1.7 mmol), anhydrous acetonitrile (10 mL), tert-butyl nitrite (0.22 g, 2.1 mmol) and a solution of 3-methyl-4-(1H-1,2,4-triazol-1-yl)aniline (200 mg, 1.15 mmol) in acetonitrile (10 mL) to give a luminous yellow solid (128 mg, 46.83%).

MS (ESI, pos. ion) m/z: 239.1 (M+2);

Step 4: N-(1-((1-cyanocyclopropyl)carbamoyl)-4,4-difluorocyclohexyl)-6-(3-methyl-4-(1H-1,2,4-triazol-1-yl)phenyl)benzofuran-2-carboxamide The title compound was prepared according to the step 4 of example 42 using 1-(4-bromo-2-methylphenyl)-1H-1,2,4-triazole (42 mg, 0.17 mmol), N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (70 mg, 0.14 mmol), Pd(Ph$_3$P)$_4$ (16 mg, 0.0138 mmol), toluene (6 mL), ethanol (2 mL) and aqueous potassium carbonate (0.14 mL, 0.27 mmol, 2 mol/L) to give a white solid (31 mg, 41.74%).

MS (ESI, pos. ion) m/z: 545.3 (M+1);

$^1$H NMR (600 MHz, DMSO-d$_6$) δ 8.94 (s, 1H), 8.81 (s, 1H), 8.54 (s, 1H), 8.27 (s, 1H), 8.07 (d, J=16.7 Hz, 1H), 7.92 (d, J=8.2 Hz, 1H), 7.87 (d, J=1.4 Hz, 1H), 7.81-7.73 (m, 3H), 7.55 (d, J=8.2 Hz, 1H), 2.30 (s, 3H), 2.26-2.00 (m, 9H), 1.28-1.14 (m, 3H), 1.13-0.98 (m, 3H).

Example 44: N-(1-((1-cyanocyclopropyl)carbamoyl)-4,4-difluorocyclohexyl)-6-(4-(2-hydroxy-2-methylpropoxy)-3-methoxyphenyl)benzofuran-2-carboxamide

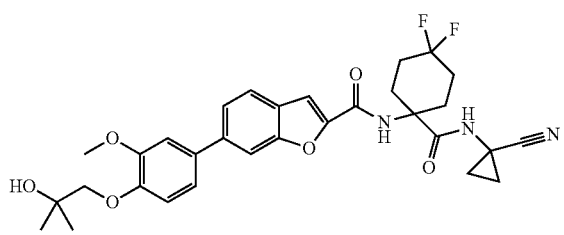 [SMILES: COc1cc(-c2ccc3cc(C(=O)NC4(C(=O)NC5(C#N)CC5)CCC(F)(F)CC4)oc3c2)ccc1OCC(C)(C)O]

Step 1: 1-(4-bromo-2-methoxyphenoxy)-2-methylpropan-2-ol

To a steel reaction vessel were added 4-bromo-2-methoxyphenol (1.0 g, 4.9 mmol), 2,2-dimethyloxirane (1.4 g, 19 mmol), potassium carbonate (0.61 g, 4.4 mmol) and sodium dihydrogen phosphate (0.53 g, 4.4 mmol), then a mixture of acetonitrile and water (20 mL, V/V=17/3) were added. The steel reaction vessel was sealed and placed in an oil-bath, and the mixture in the steel reaction vessel was stirred for 5 h at an oil-bath temperature of 150-160° C. The mixture was cooled to rt, then ethyl acetate (40 mL) and water (15 mL) were added. The mixture was partitioned, and the organic layer was dried over anhydrous sodium sulfate, concentrated in vacuo. The residue was purified by silica-gel column chromatography (PE:EtOAc=3:1, V/V) to give light yellow oil (0.5 g, 61.3%).

MS (ESI, pos. ion) m/z: 276.2 (M+2);

Step 2: N-(1-((1-cyanocyclopropyl)carbamoyl)-4,4-difluorocyclohexyl)-6-(4-(2-hydroxy-2-methylpropoxy)-3-methoxyphenyl)benzofuran-2-carboxamide To a 50 mL two-neck flask were added N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (80 mg, 0.15 mmol), DMF (6 mL) and 1-(4-bromo-2-methoxyphenoxy)-2-methylpropan-2-ol (52 mg, 0.19 mmol), then Pd(dppf)Cl$_2$.CH$_2$Cl$_2$ (20 mg) and aqueous potassium carbonate (0.2 mL, 2 mol/L) were added to the mixture under nitrogen protection. The mixture was stirred at 90° C. for 1.5 h. After the reaction was completed, to the mixture was added saturated brine (20 mL). The resulting mixture was extracted with EtOAc (20 mL×3). The combined organic layers were dried over anhydrous Na$_2$SO$_4$, and filtered. The filtrate was concentrated in vacuo, and the residue was purified by silica-gel column chromatography (DCM:EtOAc=2:1, V/V) to give a white solid (50 mg, 63%).

MS (ESI, pos. ion) m/z: 582.2 [M+1];

$^1$H NMR (400 MHz, DMSO-d$_6$) δ 8.78 (s, 1H), 8.47 (s, 1H), 7.95 (s, 1H), 7.83 (d, J=8.3 Hz, 1H), 7.71 (s, 1H), 7.67 (dd, J=8.3, 1.4 Hz, 1H), 7.35-7.25 (m, 2H), 7.07 (d, J=8.5 Hz, 1H), 4.62 (s, 1H), 3.89 (s, 3H), 3.75 (s, 2H), 2.21 (s, 2H), 2.04 (dd, J=20.5, 14.4 Hz, 6H), 1.47 (dd, J=8.2, 5.4 Hz, 2H), 1.08 (q, J=5.6 Hz, 2H).

$^{19}$F NMR (376 MHz, DMSO-d$_6$) δ -92.71 (d, J=238.0 Hz), -98.23 (d, J=229.7 Hz).

Example 45: N-(1-((1-cyanocyclopropyl)carbamoyl)-4,4-difluorocyclohexyl)-6-(2,2-difluorobenzo[d][1,3]dioxol-5-yl)benzofuran-2-carboxamide

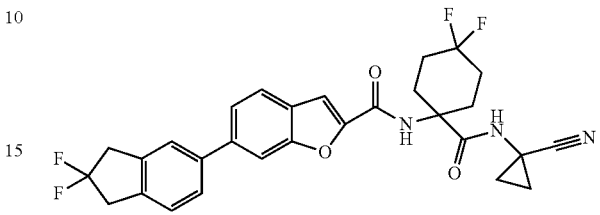

To a flask were added N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (80 mg, 0.15 mmol), DMF (6 mL) and 5-bromo-2,2-difluorobenzo[d][1,3]dioxole (45 mg, 0.19 mmol), then Pd(dppf)Cl$_2$.CH$_2$Cl$_2$ (20 mg, 0.02 mmol) and aqueous potassium carbonate (0.2 mL, 2 mol/L) were added to the mixture. The mixture was stirred at 90° C. for 1.5 h. After the reaction was completed, to the mixture was added saturated brine (20 mL). The resulting mixture was extracted with EtOAc (20 mL×3). The combined organic layers were dried over anhydrous Na$_2$SO$_4$, and filtered. The filtrate was concentrated in vacuo, and the residue was purified by silica-gel column chromatography (DCM:EtOAc=8:1, V/V) to give a white solid (32 mg, 45%).

MS (ESI, pos. ion) m/z: 544.1 (M+1);

$^1$H NMR (400 MHz, DMSO-d$_6$) δ 8.78 (s, 1H), 8.53 (s, 1H), 7.99 (s, 1H), 7.88 (d, J=8.7 Hz, 2H), 7.74 (s, 1H), 7.68 (d, J=8.1 Hz, 1H), 7.63 (dd, J=8.5, 1.7 Hz, 1H), 7.54 (d, J=8.4 Hz, 1H), 2.25-2.17 (m, 2H), 2.12-1.99 (m, 6H), 1.46 (dd, J=8.1, 5.4 Hz, 2H), 1.08 (dd, J=8.2, 5.7 Hz, 2H).

Example 46: N-(1-((1-cyanocyclopropyl)carbamoyl)-4,4-difluorocyclohexyl)-6-(4-((methylsulfonyl)methyl)phenyl)benzofuran-2-carboxamide

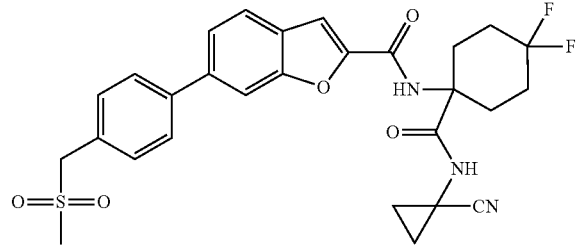 [SMILES: CS(=O)(=O)Cc1ccc(-c2ccc3cc(C(=O)NC4(C(=O)NC5(C#N)CC5)CCC(F)(F)CC4)oc3c2)cc1]

Step 1: (4-bromobenzyl)(methyl)sulfane

To anhydrous tetrahydrofuran (13 mL) were added sodium thiomethoxide (0.31 g, 4.2 mmol) and 1-bromo-4-(bromomethyl)benzene (800 mg, 3.13 mmol), and the mixture was stirred at 65° C. under nitrogen protection. Three hours later, sodium thiomethoxide (0.15 g, 2.0 mmol) was added, and the resulting mixture was stirred for 3 h. After the reaction was completed, the mixture was cooled to rt and concentrated in vacuo. The residue was washed with water (50 mL×2), and extracted with ethyl acetate (50 mL×2). The combined organic layers were concentrated in vacuo. The residue was purified by silica-gel column chromatography (PE) to give colourless oil (0.29 g, 43%).

$^1$H NMR (400 MHz, CDCl$_3$) δ 7.49-7.40 (m, 2H), 7.20 (d, J=8.3 Hz, 2H), 3.64 (s, 2H), 2.00 (s, 3H).

Step 2: 1-bromo-4-((methylsulfonyl)methyl)benzene (4-bromobenzyl)(methyl)sulfane (219 mg, 1.00 mmol) was dissolved in glacial acetic acid (10 mL) in a 50 mL two-neck round-bottom flask. To the stirred solution was added dropwise 30% aqueous hydrogen peroxide solution (0.52 mL, 5.1 mmol). After the addition, the mixture was stirred at 75° C. for 8 h. After the reaction was completed, the mixture was cooled to rt, and concentrated in vacuo to remove the solvent. The residue was washed with water (30 mL×2) to give a white solid (0.25 g, 98.7%).

$^1$H NMR (600 MHz, CDCl$_3$) δ 7.60-7.57 (m, 2H), 7.32 (d, J=8.4 Hz, 2H), 4.22 (s, 2H), 2.80 (s, 3H).

Step 3: N-(1-((1-cyanocyclopropyl)carbamoyl)-4,4-difluorocyclohexyl)-6-(4-((methylsulfonyl) methyl)phenyl)benzofuran-2-carboxamide N-(1-((1-Cyanocyclopropyl)carbamoyl)-4,4-difluorocyclohexyl)-6-(4,4,5,5-tetramethyl-1,3,2-dioxaborolan-2-yl)benzofuran-2-carboxamide (75 mg, 0.15 mmol) was dissolved in a mixture of ethanol (2 mL) and toluene (6 mL) in a 50 mL two-neck round-bottom flask. Then 1-bromo-4-((methylsulfonyl)methyl)benzene (44 mg, 0.18 mmol) was added, and Pd(Ph$_3$P)$_4$ (16.9 mg, 0.014 mmol) was added under nitrogen protection, and aqueous potassium carbonate (0.15 mL, 0.29 mmol, 2 mol/L) was added into the reaction mixture. The resulting mixture was stirred at 90° C. for 1 h under nitrogen protection. After the reaction was completed, the reaction mixture was washed with saturated brine (60 mL). The resulting mixture was extracted with EtOAc (20 mL×4). The combined organic layers were washed with saturated brine (30 mL×2), dried over anhydrous Na$_2$SO$_4$, and filtered. The filtrate was concentrated in vacuo, and the residue was purified by silica-gel column chromatography (DCM:EtOAc=1:5, V/V) to give a white solid (49 mg, 60.4%).

MS (ESI, pos. ion) m/z: 556.1 (M+1);

$^1$H NMR (400 MHz, DMSO-d$_6$) δ 8.78 (s, 1H), 8.52 (s, 1H), 8.00 (s, 1H), 7.89 (d, J=8.2 Hz, 1H), 7.82 (d, J=8.2 Hz, 2H), 7.71 (dd, J=10.2, 1.8 Hz, 2H), 7.54 (d, J=8.2 Hz, 2H), 4.56 (s, 2H), 2.96 (s, 3H), 2.30-1.84 (m, 9H), 1.46 (dd, J=8.1, 5.4 Hz, 2H), 1.08 (dd, J=8.2, 5.6 Hz, 2H).

Example 47: N-(1-((1-cyanocyclopropyl)carbamoyl)-4,4-difluorocyclohexyl)-6-(4-(morpholinosulfonyl)phenyl)benzofuran-2-carboxamide

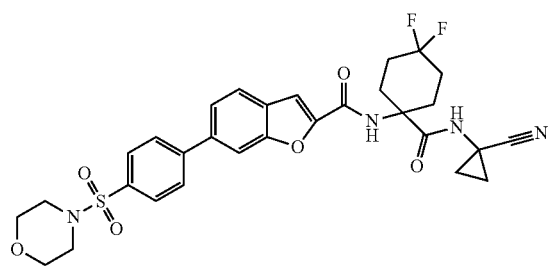 [SMILES: N#CC1(NC(=O)C2(NC(=O)c3cc4ccc(-c5ccc(S(=O)(=O)N6CCOCC6)cc5)cc4o3)CCC(F)(F)CC2)CC1]

Step 1: 4-((4-bromophenyl)sulfonyl)morpholine

To a solution of 4-bromobenzenesulfonyl chloride (0.6 g, 2 mmol) in dichloromethane (10 mL) were added morpholine (0.2 mL, 2 mmol) and triethylamine (0.4 mL, 3 mmol) at 0° C., then the mixture was stirred for 10 min. The mixture was warmed to rt and stirred for 2 h, then the reaction was stopped. The reaction mixture was extracted with DCM (20 mL×3). The combined organic layers were dried over anhydrous Na$_2$SO$_4$ and filtered. The filtrate was concentrated in vacuo, and the residue was purified by silica-gel column chromatography (DCM:EtOAc=2:1, V/V) to give a white solid (0.62 g, 90%).

MS (ESI, pos. ion) m/z: 306.9 (M+2);

Step 2: N-(1-((1-cyanocyclopropyl)carbamoyl)-4,4-difluorocyclohexyl)-6-(4-(morpholino sulfonyl)phenyl)benzofuran-2-carboxamide To a 50 mL two-neck round-bottom flask were added N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (70 mg, 0.13 mmol), DMF (6 mL) and 4-((4-bromophenyl)sulfonyl)morpholine (51 mg, 0.17 mmol), then Pd(dppf)Cl$_2$.CH$_2$Cl$_2$ (20 mg, 0.02 mmol) and aqueous potassium carbonate (0.2 mL, 2 mol/L) were added to the mixture. The mixture was stirred at 90° C. for 1 h. After the reaction was completed, the reaction mixture was washed with saturated brine (20 mL). The resulting mixture was extracted with EtOAc (20 mL×3). The combined organic layers were dried over anhydrous Na$_2$SO$_4$, and filtered. The filtrate was concentrated in vacuo, and the residue was purified by silica-gel column chromatography (DCM:EtOAc=1:1, V/V) to give a white solid (52 mg, 65%).

MS (ESI, pos. ion) m/z: 613.1 (M+1);

$^1$H NMR (400 MHz, DMSO-d$_6$) δ 8.79 (s, 1H), 8.55 (s, 1H), 8.14-8.04 (m, 3H), 7.94 (d, J=8.2 Hz, 1H), 7.85 (d, J=8.5 Hz, 2H), 7.80-7.74 (m, 2H), 3.70-3.63 (m, 4H), 2.96-2.90 (m, 4H), 2.21 (d, J=5.9 Hz, 2H), 2.07 (d, J=15.2 Hz, 6H), 1.46 (dd, J=8.2, 5.4 Hz, 2H), 1.10-1.05 (m, 2H).

$^{19}$F NMR (376 MHz, DMSO-d$_6$) δ -92.76 (d, J=236.2 Hz), -98.20 (d, J=231.0 Hz).

Example 48: N-(1-((1-cyanocyclopropyl)carbamoyl)-4,4-difluorocyclohexyl)-6-(4-(cyclopropylsulfonyl)-3-methoxyphenyl)benzofuran-2-carboxamide

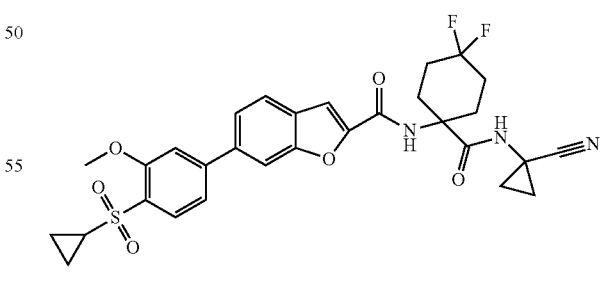

Step 1: (4-bromo-2-methoxyphenyl)(cyclopropyl)sulfane

To a 50 mL sealed tube were added potassium tert-butoxide (0.13 g, 1.1 mmol) and dimethyl sulfoxide (3 mL), then 4-bromo-2-methoxybenzenethiol (0.25 g, 1.1 mmol)

was added to the mixture. The mixture was stirred at rt for 15 min, then bromopropane (0.27 mL, 3.4 mmol) was added, and the resulting mixture was heated to 80° C. and stirred for 24 h. The reaction mixture was cooled to rt and to the mixture was added ethyl ether (30 mL). The mixture was washed with water (50 mL×2), dried over anhydrous sodium sulfate, and concentrated in vacuo. The residue was purified by silica-gel column chromatography (PE:EtOAc=30:1, V/V) to give oil (0.31 g, 67%).

MS (ESI, pos. ion) m/z: 259.7 (M+2);

Step 2: 4-bromo-1-(cyclopropylsulfonyl)-2-methoxybenzene

To a mixture of glacial acetic acid (2 mL, 34.9 mmol) and hydrogen peroxide (1 mL, 30%) was added (4-bromo-2-methoxyphenyl)cyclopropyl)sulfane (0.19 g, 0.73 mmol), and the mixture was stirred at 70° C. for 1 h. The mixture was cooled to rt, and neutralized with saturated aqueous sodium carbonate (10 mL). The resulting mixture was extracted with ethyl acetate (30 mL×2), and the combined organic layers were washed with saturated brine (10 mL×2), dried over anhydrous $Na_2SO_4$, and concentrated in vacuo. The residue was purified by silica-gel column chromatography (PE:EtOAc=5:1, V/V) to give a white solid (0.14 g, 66%).

MS (ESI, pos. ion) m/z: 291.05 (M+1);

Step 3: N-(1-(((1-cyanocyclopropyl)carbamoyl)-4,4-difluorocyclohexyl)-6-(4-(cyclopropyl sulfonyl)-3-methoxyphenyl)benzofuran-2-carboxamide To a 50 mL two-neck flask were added 4-bromo-1-(cyclopropylsulfonyl)-2-methoxybenzene (46 mg, 0.16 mmol), N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (68 mg, 0.13 mmol), Pd(dppf)Cl$_2$·CH$_2$Cl$_2$ (10 mg, 0.012 mmol) and DMF (5 mL), then potassium carbonate solution (0.13 mL, 0.26 mmol) was added under nitrogen protection. The resulting mixture was stirred at 85° C. for 2 h. The reaction mixture was cooled to rt and the mixture was quenched with water (60 mL). The resulting mixture was extracted with EtOAc (50 mL×2). The combined organic layers were washed with water (80 mL×2) and saturated brine (80 mL), dried over anhydrous Na$_2$SO$_4$, and filtered. The filtrate was concentrated in vacuo, and the residue was purified by silica-gel column chromatography (DCM:EtOAc=10:1, V/V) to give a white solid (34 mg, 43%).

MS (ESI, pos. ion) m/z: 598.10 (M+1);

$^1$H NMR (600 MHz, CDCl$_3$) δ 8.14-8.01 (m, 2H), 7.72 (d, J=7.4 Hz, 2H), 7.55 (s, 1H), 7.40 (d, J=8.3 Hz, 1H), 7.06 (dd, J=8.9, 2.5 Hz, 1H), 6.89 (d, J=2.5 Hz, 1H), 6.78 (s, 1H), 3.92 (s, 3H), 2.37 (dd, J=29.3, 12.0 Hz, 4H), 2.27-2.12 (m, 4H), 2.05-1.92 (m, 3H), 1.56 (dd, J=8.0, 5.8 Hz, 2H), 1.04-0.98 (m, 2H), 0.78 (d, J=6.4 Hz, 2H).

Example 49: 6-(4-(cyano(morpholino)methyl)-3-methoxyphenyl)-N-(1-((1-cyano cyclopropyl)carbamoyl)-4,4-difluorocyclohexyl)benzofuran-2-carboxamide

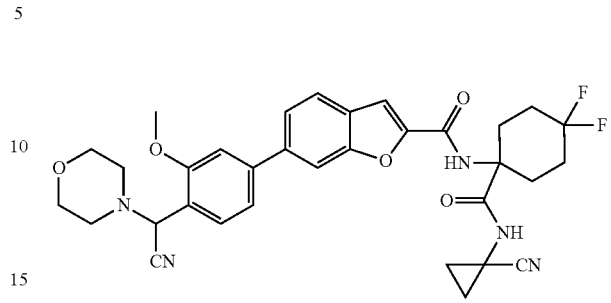

Step 1: 2-(4-bromo-2-methoxyphenyl)-2-morpholinoacetonitrile

To a stirred solution of 4-bromo-2-methoxybenzaldehyde (250 mg, 1.14 mmol), morpholine (100 mg, 1.14 mmol) and trimethylsilyl cyanide (115 mg, 1.14 mmol) in acetonitrile (15 mL) which was placed in a 100 mL round-bottom flask was added anhydrous lithium bromide (10 mg, 0.11 mmol), and the mixture was stirred at rt overnight. After the reaction monitored by TLC was completed, the mixture was concentrated in vacuo to remove acetonitrile. The residue was dissolved in ethyl ether (20 mL×3), and the mixture was washed with saturated aqueous sodium bicarbonate (20 mL×3) and pyridine (10 mL×2), dried over anhydrous sodium sulfate, filtered and concentrated. The residue was purified by silica-gel column chromatography (DCM) to give a white solid (142 mg, 40.05%).

MS (ESI, pos. ion) m/z: 313.1 (M+2);

Step 2: 6-(4-(cyano(morpholino)methyl)-3-methoxyphenyl)-N-(1-((1-cyanocyclopropyl) carbamoyl)-4,4-difluorocyclohexyl)benzofuran-2-carboxamide To a solution of 2-(4-bromo-2-methoxyphenyl)-2-morpholinoacetonitrile (51 mg, 0.16 mmol) and N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (70 mg, 0.13 mmol) in a mixed solvent of toluene (6 mL) and ethanol (2 mL) were added Pd(Ph$_3$P)$_4$ (16 mg, 0.014 mmol) and potassium carbonate (38 mg, 0.27 mmol). The reaction mixture was stirred at 90° C. for 1 h, and then cooled to rt, concentrated to remove solvent. The residue was added into water (100 mL), and the mixture was extracted with ethyl acetate (20 mL×3). The combined organic layers were dried over anhydrous sodium sulfate and concentrated to remove the solvent. The residue was purified by silica-gel column chromatography (EtOAc:DCM=1:6, V/V) to give a white solid (62 mg, 73.61%).

MS (ESI, pos. ion) m/z: 618.1 (M+1);

$^1$H NMR (400 MHz, DMSO-d$_6$) δ 8.77 (s, 1H), 8.51 (s, 1H), 8.07 (s, 1H), 7.90 (d, J=8.2 Hz, 1H), 7.75 (d, J=9.5 Hz, 1H), 7.68-7.41 (m, 3H), 5.76 (s, 1H), 5.33 (s, 1H), 3.97 (s, 2H), 3.60 (d, J=3.6 Hz, 3H), 2.39-1.93 (m, 5H), 1.23-1.16 (m, 8H).

Example 50: N-(1-((1-cyanocyclopropyl)carbamoyl)-4,4-difluorocyclohexyl)-6-(3-methoxy-4-(5-methyl-1H-1,2,4-triazol-1-yl)phenyl)benzofuran-2-carboxamide

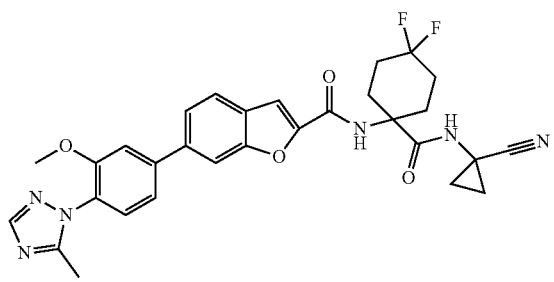 [SMILES: COc1cc(-c2ccc3cc(C(=O)NC4(C(=O)NC5(C#N)CC5)CCC(F)(F)CC4)oc3c2)ccc1-n1ncnc1C]

Step 1: 1-(2-methoxy-4-nitrophenyl)-5-methyl-1H-1,2,4-triazole

The title compound was prepared according to the procedure described in step 1 of example 42, using 3-methyl-1H-1,2,4-triazole (650 mg, 7.8 mmol), 1-fluoro-2-methoxy-4-nitrobenzene (1.2 g, 7.1 mmol), potassium carbonate (2.0 g, 14 mmol) and DMF (10 mL), and the title compound prepared was a white solid (530 mg, 30.2%).

$^1$H NMR (400 MHz, CDCl$_3$) 8.01 (dd, J=7.6, 3.2 Hz, 2H), 7.97 (d, J=2.3 Hz, 1H), 7.59 (d, J=8.5 Hz, 1H), 3.99 (s, 3H), 2.39 (s, 3H).

Step 2: 3-methoxy-4-(5-methyl-1H-1,2,4-triazol-1-yl)aniline

The title compound was prepared according to the procedure described in step 2 of example 42, using 1-(2-methoxy-4-nitrophenyl)-5-methyl-1H-1,2,4-triazole (530 mg, 2.18 mmol), methanol (5 mL), ethyl acetate (20 mL) and 10% Pd/C (100 mg), to give a light yellow solid (450 mg, 100%/).

MS (ESI, pos. ion) m/z: 205.1 (M+1);

Step 3: 1-(4-bromo-2-methoxyphenyl)-5-methyl-1H-1,2,4-triazole

The title compound was prepared according to the procedure described in step 3 of example 42, using a mixture of cuprous bromide (618 mg, 4.30 mmol), anhydrous acetonitrile (8 mL), tert-butyl nitrite (0.62 mL, 5.2 mmol) and 3-methoxy-4-(5-methyl-1H-1,2,4-triazol-1-yl)aniline (500 mg, 2.87 mmol) in acetonitrile (10 mL), to give a product (350 mg, 51.2%).

MS (ESI, pos. ion) m/z: 269.1 (M+2);

Step 4: N-(1-((1-cyanocyclopropyl)carbamoyl)-4,4-difluorocyclohexyl)-6-(3-methoxy-4-(5-methyl-1H-1,2,4-triazol-1-yl)phenyl)benzofuran-2-carboxamide The title compound was prepared according to the procedure described in step 4 of example 42 by using N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (70 mg, 0.13 mmol), DMF (6 mL), 1-(4-bromo-2-methoxyphenyl)-5-methyl-1H-1,2,4-triazole (42 mg, 0.17 mmol), Pd(dppf)Cl$_2$·CH$_2$Cl$_2$ (20 mg, 0.02 mmol) and aqueous potassium carbonate (0.2 mL, 2 mol/L) to give a white solid (45 mg, 68.2%).

MS (ESI, pos. ion) m/z: 575.2 (M+1);

$^1$H NMR (600 MHz, DMSO-d$_6$) δ 8.79 (s, 1H), 8.54 (s, 1H), 8.14 (s, 1H), 8.02 (s, 1H), 7.93 (d, J=8.2 Hz, 1H), 7.81 (d, J=8.3 Hz, 1H), 7.76 (s, 1H), 7.60 (s, 1H), 7.50 (s, 2H), 3.94 (s, 3H), 2.28 (s, 3H), 2.22 (s, 2H), 2.14-1.96 (m, 6H), 1.47 (dd, J=8.1, 5.4 Hz, 2H), 1.24 (s, 2H), 1.08 (dd, J=8.2, 5.5 Hz, 2H).

$^{19}$F NMR (565 MHz, DMSO-d$_6$) δ −92.67 (d, J=236.5 Hz), −98.26 (d, J=231.0 Hz).

Example 51: 6-(4-(3-cyano-1H-1,2,4-triazol-1-yl)-3-methoxyphenyl)-N-(1-((1-cyano cyclopropyl)carbamoyl)-4,4-difluorocyclohexyl)benzofuran-2-carboxamide

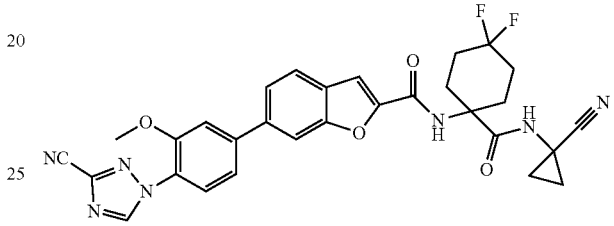

Step 1: ethyl 1-(4-bromo-2-methoxyphenyl)-1H-1,2,4-triazole-3-carboxylate

4-Bromo-2-methoxyaniline (2.00 g, 9.90 mmol) were dissolved in water (10 mL) and concentrated hydrochloric acid (3 mL). The mixture was cooled in ice-salt bath, then a solution of sodium nitrite (0.69 g, 9.8 mmol) in water (4 mL) was added dropwise slowly while maintaining the temperature at 0-5° C. After the addition, the mixture was stirred at 0° C. for 5 min. The mixture described above was added to a mixture of sodium acetate trihydrate (8.75 g, 64.3 mmol), ethyl isocyanoacetate (1.0 mL, 9.15 mmol) and MeOH/H$_2$O (22 mL, 10/1) while maintaining the temperature at 0-5° C. After the addition, the mixture was stirred at 0° C. for 30 min, then warmed to rt for further 3 h. After the reaction was completed, the mixture was concentrated to remove most of the solvent. The residue was filtered, and the filter cake was washed with cool water. The filter cake was dried in vacuo to give a reddish brown solid (2.65 g, 82.1%).

MS (ESI, pos. ion) m/z: 327.1 (M+2);

Step 2: 1-(4-bromo-2-methoxyphenyl)-1H-1,2,4-triazole-3-carboxamide

To a 50 mL sealed tube were added ethyl 1-(4-bromo-2-methoxyphenyl)-1H-1,2,4-triazole-3-carboxylate (1 g, 3.1 mmol) and a solution of ammonium in methanol (6 mL, 42 mmol, 7 mol/L). The mixture was stirred at 70° C. for 6 h, then cooled and concentrated to remove the solvent. The residue was purified by silica-gel column chromatography (EtOAc:DCM=1:1, V/V) to give a light yellow solid (0.34 g, 37%).

MS (ESI, pos. ion) m/z: 297.9 (M+2);

Step 3: 1-(4-bromo-2-methoxyphenyl)-1H-1,2,4-triazole-3-carbonitrile

To a 50 mL two-neck flask were added 1-(4-bromo-2-methoxyphenyl)-1H-1,2,4-triazole-3-carboxamide (0.33 g, 1.1 mmol) and DMF (8 mL), then thionyl chloride (0.40 mL, 5.5 mmol) was under nitrogen protection. The mixture was stirred at 0° C. for 1 h, then quenched with water (10 mL). To the mixture was added saturated aqueous sodium bicarbonate to adjust pH about 5, and the resulting mixture was extracted with ethyl acetate (50 mL×2). The combined organic layers were washed with saturated brine (20 mL), dried over anhydrous sodium sulfate and concentrated. The residue was purified by silica-gel column chromatography (EtOAc:PE=1:10, V/V) to give colourless oil (0.24 g, 77%).

MS (ESI, pos. ion) m/z: 280.10 (M+2);

Step 4: 6-(4-(3-cyano-1H-1,2,4-triazol-1-yl)-3-methoxyphenyl)-N-(1-((1-cyanocyclopropyl) carbamoyl)-4,4-difluorocyclohexyl)benzofuran-2-carboxamide To a 50 mL two-neck round-bottom flask were added 1-(4-bromo-2-methoxyphenyl)-1H-1,2,4-triazole-3-carbonitrile (43 mg, 0.15 mmol), N-(1-((1-cyanocyclopropyl)carbamoyl)4,4-difluorocyclohexyl)-6-(4,4,5,5-tetramethyl-1,3,2-dioxaborolan-2-yl)benzofuran-2-carboxamide (68 mg, 0.13 mmol), Pd(dppf)Cl$_2$.CH$_2$Cl$_2$ (11 mg, 0.013 mmol) and DMF (5 mL), then potassium carbonate solution (0.13 mL, 0.26 mmol, 2 mol/L) was added under nitrogen protection. The resulting mixture was stirred at 85° C. for 2 h. The reaction mixture was cooled to rt and the mixture was quenched with water (60 mL). The resulting mixture was extracted with EtOAc (50 mL×2). The combined organic layers were washed with water (80 mL×2) and saturated brine (80 mL), dried over anhydrous Na$_2$SO$_4$, and filtered. The filtrate was concentrated in vacuo, and the residue was purified by silica-gel column chromatography (DCM:MeOH=10:1, V/V) to give a white solid (48 mg, 62%).

MS (ESI, pos. ion) m/z: 586.2 (M+1); 1H NMR (600 MHz, DMSO-d$_6$) δ 9.38 (s, 1H), 8.79 (s, 1H), 8.55 (s, 1H), 8.16 (s, 1H), 7.93 (d, J=8.2 Hz, 1H), 7.80 (dd, J=15.7, 8.3 Hz, 2H), 7.76 (s, 1H), 7.67 (d, J=1.2 Hz, 1H), 7.57 (dd, J=8.3, 1.4 Hz, 1H), 4.04 (s, 3H), 2.22 (s, 2H), 2.06 (s, 6H), 1.47 (dd, J=8.1, 5.3 Hz, 2H), 1.09 (dd. J=8.1, 5.5 Hz, 2H).

Example 52: N-(1-((1-cyanocyclopropyl)carbamoyl)cycloheptyl)-6-(3-methoxy-4-(1H-1,2,4-triazol-1-yl)phenyl)benzofuran-2-carboxamide

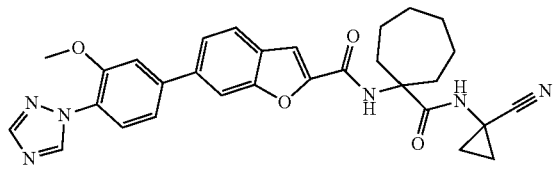 [SMILES: COc1cc(-c2ccc3cc(C(=O)NC4(C(=O)NC5(C#N)CC5)CCCCCC4)oc3c2)ccc1-n1cncn1]

Step 1: 1-amino-N-(1-cyanocyclopropyl)cycloheptanecarboxamide hydrochloride

To a 50 mL two-neck flask were added tert-butyl (1-((1-cyanocyclopropyl)carbamoyl)cycloheptyl)carbamate (1.00 g, 4.93 mmol) and ethyl acetate (5 mL), then a solution of hydrogen chloride in ethyl acetate (5 mL, 4 mol/L) was added. The mixture was stirred at rt for 15 min. The reaction mixture was concentrated in vacuo to give a white solid product (0.43 g, 100%).

Step 2: 6-bromo-N-(1-((1-cyanocyclopropyl)carbamoyl)cycloheptyl)benzofuran-2-carboxamide To a 50 mL two-neck flask were added 6-bromobenzofuran-2-carboxylic acid (0.34 g, 1.4 mmol), 1-amino-N-(1-cyanocyclopropyl)cycloheptanecarboxamide hydrochloride (0.43 g, 1.7 mmol), HATU (0.34 g, 1.4 mmol) and DMF (12 mL), then triethylamine (0.80 mL, 5.6 mmol) was added at 0° C. The mixture was stirred at rt for 3 h, and water (10 mL) was added to quench the reaction. The resulting mixture was extracted with EtOAc (50 mL×2). The combined organic layers were washed with water (80 mL×2) and saturated brine (80 mL), dried over anhydrous Na$_2$SO$_4$ and concentrated. The residue was purified by silica-gel column chromatography (PE:EtOAc=4:1, V/V) to give a white solid (0.12 g, 19%).

MS (ESI, pos. ion) m/z: 444.2 (M+1);

Step 3: 1-(2-methoxy-4-(4,4,5,5-tetramethyl-1,3,2-dioxaborolan-2-yl)phenyl)-1H-1,2,4-triazole To a 50 mL two-neck flask were added 1-(4-bromo-2-methoxyphenyl)-1H-1,2,4-triazole (0.15 g, 0.59 mmol), bis(pinacolato)diboron (0.18 g, 0.71 mmol), potassium acetate (0.18 g, 1.8 mmol), Pd(dppf)Cl$_2$.CH$_2$Cl$_2$ (50 mg, 0.060 mmol), then DMF (9 mL) was added under nitrogen protection. The resulting mixture was stirred at 85° C. for 2 h. The reaction mixture was cooled to rt and the mixture was quenched with water (80 mL). The resulting mixture was extracted with EtOAc (50 mL×2). The combined organic layers were washed with water (80 mL×2) and saturated aqueous NaCl solution (80 mL), dried over anhydrous Na$_2$SO$_4$, and filtered. The filtrate was concentrated in vacuo, and the residue was purified by silica-gel column chromatography (DCM:EtOAc=20:1, V/V) to give a yellow solid (38 mg, 21%).

MS (ESI, pos. ion) m/z: 302.10 (M+1);

Step 4: N-(1-((1-cyanocyclopropyl)carbamoyl)cycloheptyl)-6-(3-methoxy-4-(1H-1,2,4-triazol-1-yl)phenyl)benzofuran-2-carboxamide To a 50 mL two-neck flask were added 6-bromo-N-(1-((1-cyanocyclopropyl) carbamoyl)cycloheptyl)benzofuran-2-carboxamide (43 mg, 0.097 mmol), 1-(2-methoxy-4-(4,4,5,5-tetramethyl-1,3,2-dioxaborolan-2-yl)phenyl)-1H-1,2,4-triazole (36 mg, 0.12 mmol), Pd(dppf)Cl$_2$.CH$_2$Cl$_2$ (8 mg, 0.01 mmol) and DMF (5 mL), then aqueous potassium sulfate solution (0.10 mL, 0.2 mmol, 2 mol/L) was added under nitrogen protection. The resulting mixture was stirred at 85° C. for 2 h. The reaction mixture was cooled to rt and the mixture was quenched with water (60 mL). The resulting mixture was extracted with EtOAc (50 mL×2). The combined organic layers were washed with water (80 mL×2) and saturated brine (80 mL), dried over anhydrous Na$_2$SO$_4$, and filtered. The filtrate was concentrated in vacuo, and the residue was purified by silica-gel column chromatography (DCM:EtOAc=10:1, V/V) to give a white solid (36 mg, 69%).

MS (ESI, pos. ion) m/z: 539.10 (M+1);
$^1$HNMR (600 MHz, DMSO-d$_6$) δ 9.01 (s, 1H), 8.55 (s, 1H), 8.23 (s, 1H), 8.16 (s, 1H), 8.12 (s, 1H), 7.90 (d, J=8.2 Hz, 1H), 7.81-7.74 (m, 2H), 7.70 (d, J=0.6 Hz, 1H), 7.62 (d, J=1.7 Hz, 1H), 7.52 (dd, J=8.2, 1.8 Hz, 1H), 4.03 (s, 4H), 2.13-2.02 (m, 4H), 1.54 (s, 8H), 1.43 (dd, J=8.1, 5.3 Hz, 2H), 1.05 (dd, J=8.2, 5.4 Hz, 2H).

Example 53: N-(1-((1-cyanocyclopropyl)carbamoyl)-4,4-difluorocyclohexyl)-6-(3-(difluoromethoxy)-4-(1H-1,2,4-triazol-1-yl)phenyl)benzofuran-2-carboxamide

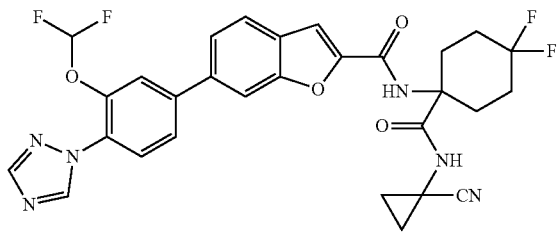 [SMILES: N#CC1(NC(=O)C2(NC(=O)c3cc4ccc(-c5ccc(-n6cncn6)c(OC(F)F)c5)cc4o3)CCC(F)(F)CC2)CC1]

Step 1: 1-fluoro-2-(methoxymethoxy)-4-nitrobenzene

To a 50 mL two-neck round-bottom flask were added 2-fluoro-5-nitrophenol (1.00 g, 6.36 mmol) and N,N-diisopropylethylamine (2.0 mL, 12 mmol), then a solution of chloro(methoxy)methane (0.8 mL, 10 mmol) in dichloromethane (20 mL) was added dropwise to the mixture. After the addition, the ice-bath was removed, and the mixture was stirred for 3 h. The reaction monitored by TLC was completed, and the mixture was diluted with water (50 mL). The resulting mixture was extracted with DCM (30 mL×2), and the combined organic layers were washed with water (100 mL×2) and pyridine (10 mL×2), dried over anhydrous sodium sulfate and filtered. The filtrate was concentrated in vacuo, and the residue was purified by silica-gel column chromatography (PE:EtOAc=20:1, V/V) to give yellow oil (1.14 g, 89.0%).

$^1$H NMR (600 MHz, CDCl$_3$) δ 8.13 (dd, J=7.1, 2.7 Hz, 1H), 7.93 (ddd, J=9.0, 3.9, 2.7 Hz, 1H), 7.26 (s, 1H), 7.24 (d, J=0.6 Hz, 1H), 7.22 (s, 1H), 5.32 (s, 2H), 3.56 (s, 3H).

Step 2: 1-(2-(methoxymethoxy)-4-nitrophenyl)-1H-1,2,4-triazole

To a 50 mL two-neck flask were added a solution of 1H-1,2,4-triazole (0.26 g, 3.7 mmol) in DMF (15 mL), then to the stirred solution was added dropwise 1-fluoro-2-(methoxymethoxy)-4-nitrobenzene (500 mg, 2.49 mmol). Then mixture was heated to 85° C. and stirred overnight under nitrogen protection. After the reaction monitored by TLC was completed, the mixture was cooled to rt and concentrated in vacuo to remove the solvent. The residue was poured into water (100 mL), and the mixture was extracted with ethyl acetate (50 mL). The organic layer was extracted with ethyl acetate (20 mL×2). The combined organic layers were dried over anhydrous sodium sulfate and filtered. The filtrate was concentrated in vacuo, and the residue was purified by silica-gel column chromatography (PE:EtOAc=5:1, V/V) to give a yellow solid (0.33 g, 53%).

MS (ESI, pos. ion) m/z: 251.2 (M+1);

Step 3: 3-(methoxymethoxy)-4-(1H-1,2,4-triazol-1-yl)aniline

To a 100 mL round-bottom flask were added 1-(2-(methoxymethoxy)-4-nitrophenyl)-1H-1,2,4-triazole (330 mg, 1.32 mmol) and methanol (15 mL). Then to the solution was added 10% Pd/C (0.28 g, 20%), and the mixture was stirred at rt overnight in a hydrogen atmosphere. After the reaction was completed, the mixture was filtered, and the filtrate was concentrated in vacuo to give brown oil (0.28 g, 96%).

MS (ESI, pos. ion) m/z: 221.1 (M+1);

Step 4: 1-(4-bromo-2-(methoxymethoxy)phenyl)-1H-1,2,4-triazole

Cuprous bromide (0.29 g, 2.0 mmol) was dissolved in anhydrous acetonitrile (3 mL) which was placed in a 100 mL round-bottom flask, then to the solution was added dropwise tert-butyl nitrite (0.29 mL, 2.4 mmol). The mixture was heated to 50° C. and stirred for 50 min. To the reaction flask was added dropwise a solution of 3-(methoxymethoxy)-4-(1H-1,2,4-triazol-1-yl)aniline (0.28 g, 1.3 mmol) in acetonitrile (5 mL). The mixture was heated to 80° C. and stirred for 8 h and the reaction was completed. The mixture was concentrated in vacuo to remove the solvent, and the residue was purified by silica-gel column chromatography (PE:EtOAc=3:1, V/V) to give a white solid (0.3 g, 80%).

MS (ESI, pos. ion) m/z: 285.0 (M+1);

Step 5: 5-bromo-2-(1H-1,2,4-triazol-1-yl)phenol 1-(4-Bromo-2-(methoxymethoxy)phenyl)-1H-1,2,4-triazole (280 mg, 0.98 mmol) was dissolved in a mixture of tetrahydrofuran (3.0 mL) and methanol (6.0 mL) which was placed in a 100 mL pear-shaped flask. Then hydrochloric acid (0.4 mL, 12 mol/L) was added, and the resulting mixture was stirred at 30° C. for 5 h. The reaction monitored by TLC was not completed. Then a solution of hydrogen chloride in ethyl acetate (2 mL, 6 mmol, 3 mol/L) was added, and the resulting mixture was stirred at 30° C. for 8 h. The starting material monitored by TLC was not consumed. Then concentrated hydrochloric acid (1.0 mL) was added into the mixture, and the mixture was stirred at 70° C. for 4 h. After the reaction was completed, the mixture was concentrated in vacuo to remove most of the solvent. To the residue was added water (100 mL), and the mixture was adjusted with saturated aqueous sodium bicarbonate to pH 6-7. The resulting mixture was extracted with ethyl acetate (50 mL×2). The combined organic layers were concentrated in vacuo, and the residue was purified by silica-gel column chromatography (DCM:EtOAc=6:1, V/V) to give a white solid (56 mg, 23.67%).

MS (ESI, pos. ion) m/z: 240.9 (M+2);

Step 6: 1-(4-bromo-2-(difluoromethoxy)phenyl)-1H-1,2,4-triazole

5-Bromo-2-(1H-1,2,4-triazol-1-yl)phenol (100 mg, 0.42 mmol) was dissolved in DMF (7 mL) which was placed in a 50 mL two-neck flask. To the stirred solution were added sodium chlorodifluoroacetate (164 mg, 1.04 mmol) and cesium carbonate (0.28 g, 0.83 mmol). The mixture was heated to 100° C. and stirred overnight under nitrogen protection. The reaction mixture was poured into water (50 mL), and the resulting mixture was extracted with EtOAc (10 mL×3). The combined organic layers were washed with water (20 mL×3), dried over anhydrous Na$_2$SO$_4$, and filtered. The filtrate was concentrated in vacuo, and the residue was purified by silica-gel column chromatography (PE:EtOAc=10:1, V/V) to give a yellow solid (70 mg, 57.9%).

MS (ESI, pos. ion) m/z: 291.9 (M+1);

Step 7: N-(1-((1-cyanocyclopropyl)carbamoyl)-4,4-difluorocyclohexyl)-6-(3-(difluoromethoxy)-4-(1H-1,2,4-triazol-1-yl)phenyl)benzofuran-2-carboxamide To a solution of 1-(4-bromo-2-(difluoromethoxy)phenyl)-1H-1,2,4-triazole (46 g, 158.59 mmol), N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (75 mg, 0.15 mol) in a mixture of toluene (6 mL) and ethanol (2 mL) were added Pd(Ph$_3$P)$_4$ (17 mg, 0.015 mmol) and potassium carbonate (41 mg, 0.29 mmol) in a 50 mL two-neck round-bottom flask. The mixture was stirred at 90° C. for 3 h under nitrogen protection, then the reaction was quenched with water (10 mL), and cooled to rt. The resulting mixture was extracted with EtOAc (30 mL×2). The combined organic layers were dried over anhydrous sodium sulfate, filtered and concentrated in vacuo. The residue was purified by silica-gel column chromatography (EtOAc:DCM=1:10, V/V) to give a white solid (50 mg, 57.37%).

MS (ESI, pos. ion) m/z: 597.3 (M+1);
$^1$H NMR (400 MHz, DMSO-d$_6$): δ: 8.97 (s, 1H), 8.77 (s, 1H), 8.52 (s, 1H), 8.30 (s, 1H), 8.13 (s, 1H), 7.95 (d, J=8.2 Hz, 1H), 7.86 (s, 2H), 7.84-7.77 (m, 2H), 7.76 (s, 1H), 7.36 (d, J=72.9, 1H), 2.28-2.00 (m, 8H), 1.47 (dd, J=8.1, 5.4 Hz, 2H), 1.00 (dd, J=8.2, 5.5 Hz, 2H).

Example 54: N-(1-((1-cyanocyclopropyl)carbamoyl)-4,4-difluorocyclohexyl)-6-(3-ethoxy-4-(1H-1,2,4-triazol-1-yl)phenyl)benzofuran-2-carboxamide

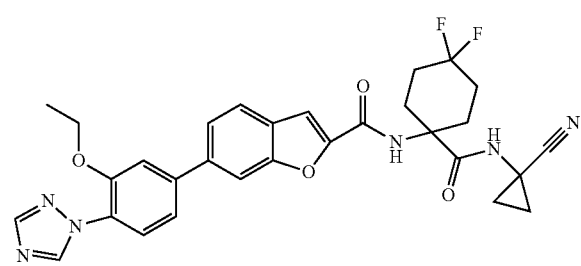 [SMILES: CCOc1cc(-c2ccc3cc(C(=O)NC4(C(=O)NC5(C#N)CC5)CCC(F)(F)CC4)oc3c2)ccc1-n1cncn1]

Step 1: 1-(2-fluoro-4-nitrophenyl)-1H-1,2,4-triazole

The title compound was prepared according to the similar synthetic procedure as described in step 1 of example 42 by using 1,2-difluoro-4-nitrobenzene (5.0 g, 31 mmol), 1H-1,2,4-triazole (2.28 g, 33.0 mmol), potassium carbonate (8.67 g, 62.8 mmol) and DMSO (20 mL) to give a light yellow solid (5.6 g, 86%).

MS (ESI, pos. ion) m/z: 209.1 (M+1);

Step 2: 3-fluoro-4-(1H-1,2,4-triazol-1-yl)aniline

The title compound was prepared according to the similar synthetic procedure as described in step 2 of example 42 by using 1-(2-fluoro-4-nitrophenyl)-1H-1,2,4-triazole (2.0 g, 9.6 mmol), ethyl acetate (20 mL) and 10% Pd/C (200 mg) to give a light yellow solid (1.6 g, 91.57%).

MS (ESI, pos. ion) m/z: 179.1 (M+1);

Step 3: 1-(4-bromo-2-fluorophenyl)-1H-1,2,4-triazole

The title compound was prepared according to the similar synthetic procedure as described in step 3 of example 42 by using the mixture of cuprous bromide (1.22 g, 8.50 mmol), anhydrous acetonitrile (15 mL), tert-butyl nitrite (1.2 mL, 10 mmol) and 3-fluoro-4-(1H-1,2,4-triazol-1-yl)aniline (1.6 g, 8.98 mmol) in acetonitrile (15 mL) to give the product (430 mg, 32%).

MS (ESI, pos. ion)/z: 243.1 (M+2);

Step 4: 1-(4-bromo-2-ethoxyphenyl)-1H-1,2,4-triazole

To a reaction flask were added 1-(4-bromo-2-fluorophenyl)-1H-1,2,4-triazole (260 mg, 1.07 mmol) and anhydrous DMF (10 mL), then sodium ethoxide (90 mg, 1.33 mmol) was added into the mixture under nitrogen protection. The mixture was stirred at 80° C. for 5 h, and the reagent monitored by TLC was disappeared. To the reaction mixture was added saturated brine (20 mL), and the resulting mixture was extracted with ethyl acetate (20 mL×3). The combined organic layers were dried over anhydrous sodium sulfate and filtered. The filtrate was concentrated in vacuo, and the residue was purified by silica-gel column chromatography (EtOAc:PE=1:3, V/V) to give a light yellow solid (180 mg, 62.5%).

MS (ESI, pos. ion) m/z: 269.1 (M+2);

Step 5: N-(1-((1-cyanocyclopropyl)carbamoyl)-4,4-difluorocyclohexyl)-6-(3-ethoxy-4-(1H-1,2,4-triazol-1-yl)phenyl)benzofuran-2-carboxamide The title compound was prepared according to the similar synthetic procedure as described in step 4 of example 1 by adding N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (86 mg, 0.16 mmol), DMF (6 mL) and 1-(4-bromo-2-ethoxyphenyl)-1H-1,2,4-triazole (43 mg, 0.16 mmol) to the reaction flask, and adding Pd(dppf)Cl$_2$.CH$_2$Cl$_2$ (20 mg, 0.02 mmol) and aqueous potassium carbonate (0.26 mL, 2 mol/L) to the mixture, and the title compound prepared was a white solid (50 mg, 63.1%).

MS (ESI, pos. ion) m/z: 575.2 (M+1);
$^1$H NMR (600 MHz, DMSO-d$_6$) 9.03 (s, 1H), 8.78 (s, 1H), 8.52 (s, 1H), 8.24 (s, 1H), 8.11 (s, 1H), 7.91 (d, J=8.2 Hz, 1H), 7.78 (d, J=8.3 Hz, 2H), 7.75 (d, J=0.6 Hz, 1H), 7.61 (d, J=1.7 Hz, 1H), 7.52 (dd, J=8.3, 1.8 Hz, 1H), 4.35 (q, J=7.0 Hz, 2H), 2.22 (s, 2H), 2.06 (dd, J=24.7, 16.6 Hz, 6H), 1.47 (dd, J=8.1, 5.4 Hz, 2H), 1.40 (t, J=6.9 Hz, 3H), 1.08 (dd, J=8.3, 5.5 Hz, 2H).

Example 55: N-(1-((1-cyanocyclopropyl)carbamoyl)-4,4-difluorocyclohexyl)-6-(4-(1,1-dioxidoisothiazolidin-2-yl)phenyl)benzofuran-2-carboxamide

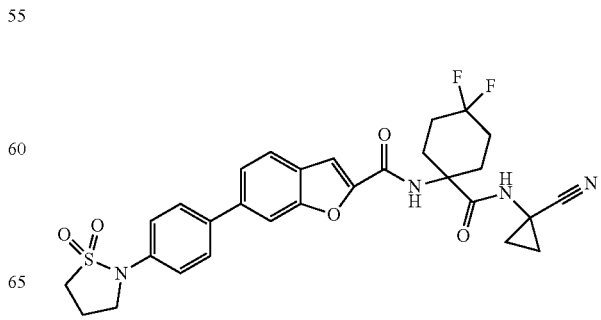

143

Step 1:
N-(4-bromophenyl)-N-(3-chloropropyl)sulfamide

To a solution of 4-bromoaniline (0.86 g, 5 mmol) and pyridine (0.5 mL) in anhydrous dichloromethane (15 mL) was added 3-chloropropanesulfonyl chloride (0.6 mL, 5.0 mmol) in an ice-bath. After the addition, the mixture was stirred at rt for 4 h, then extracted with DCM (20 mL×3). The combined organic layers were washed with water (15 mL) and hydrochloric acid (10 mL×1, 2 mol/L), dried over anhydrous sodium sulfate, and filtered. The filtrate was concentrated in vacuo, and the residue was purified by silica-gel column chromatography (PE:EtOAc=6:1, V/V) to give a yellow solid (1.8 g, 99%).

MS (ESI, pos. ion) m/z: 312.9 (M+2);

Step 2: 2-(4-bromophenyl)isothiazolidine 1,1-dioxide

To a solution of N-(4-bromophenyl)-N-(3-chloropropyl)sulfamide (1.8 g, 5.8 mmol) in anhydrous DMF (15 mL) was added potassium carbonate (2.0 g, 14 mmol). The mixture was heated to 50° C. and stirred for 2 h under nitrogen protection, then the reaction was completed. The reaction mixture was cooled to rt, and poured into ice-water (60 mL), then there was a solid precipitated out. The mixture was filtered, and the filter cake was dried in air to give a gray solid (1.3 g, 82%).

MS (ESI, pos. ion) m/z: 276.9 (M+2);

Step 3: N-(1-((1-cyanocyclopropyl)carbamoyl)-4,4-difluorocyclohexyl)-6-(4-(1,1-dioxidoisothiazolidin-2-yl)phenyl)benzofuran-2-carboxamide To a 50 mL two-neck flask were added N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (70 mg, 0.13 mmol), DMF (6 mL) and 2-(4-bromophenyl)isothiazolidine 1,1-dioxide (45 mg, 0.16 mmol), then Pd(dppf)Cl$_2$.CH$_2$Cl$_2$ (20 mg, 0.02 mmol) and aqueous potassium carbonate (0.2 mL, 2 mol/L) were added to the mixture. The mixture was stirred at 90° C. for 80 min. After the reaction was completed, to the mixture was added saturated brine (20 mL). The resulting mixture was extracted with EtOAc (20 mL×3). The combined organic layers were dried over anhydrous Na$_2$SO$_4$, and filtered. The filtrate was concentrated in vacuo, and the residue was purified by silica-gel column chromatography (PE:EtOAc=1:4, V/V) to give a white solid (40 mg, 50.3%).

MS (ESI, pos. ion) m/z: 583.1 (M+1);

$^1$H NMR (400 MHz, DMSO-d$_6$) δ 8.77 (s, 1H), 8.48 (s, 1H), 7.95 (s, 1H), 7.86 (d, J=8.2 Hz, 1H), 7.80 (d, J=8.6 Hz, 2H), 7.73-7.63 (m, 2H), 7.32 (d, J=8.5 Hz, 2H), 3.81 (t, J=6.5 Hz, 2H), 3.55 (t, J=7.3 Hz, 2H), 2.46-2.40 (m, 2H), 2.21 (s, 2H), 2.04 (dd, J=18.0, 11.3 Hz, 6H), 1.45 (d, J=7.3 Hz, 2H), 1.34 (d, J=5.9 Hz, 2H).

144

Example 56: N-(1-((1-cyanocyclopropyl)carbamoyl)-4,4-difluorocyclohexyl)-6-(4,4-dioxido-3,5-dihydro-2H-benzo[f][1,4]oxathiepin-8-yl)benzofuran-2-carboxamide

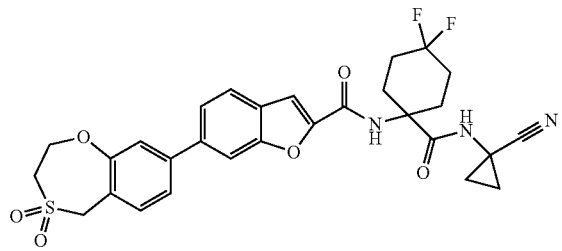 [SMILES: N#CC1(NC(=O)C2(NC(=O)c3cc4ccc(-c5ccc6c(c5)OCCS(=O)(=O)C6)cc4o3)CCC(F)(F)CC2)CC1]

Step 1: 4-bromo-2-(2-bromoethoxy)benzaldehyde

To a solution of 4-bromo-2-hydroxybenzaldehyde (3.0 g, 15 mmol) and 1,2-dibromoethane (7.8 g, 91 mmol) in anhydrous acetonitrile (20 mL) was added potassium carbonate (4.12 g, 29.9 mmol). The mixture was stirred at 65° C. for 10 h. The reaction mixture was cooled to rt and to the mixture was added water (50 mL). The resulting mixture was extracted with EtOAc (50 mL×3). The combined organic layers were dried over anhydrous Na$_2$SO$_4$, and filtered. The filtrate was concentrated in vacuo, and the residue was purified by silica-gel column chromatography (PE:EtOAc=10:1, V/V) to give a light yellow solid (3.8 g, 83%).

MS (ESI, pos. ion) m/z: 307.9 (M+2);

Step 2: (4-bromo-2-(2-bromoethoxy)phenyl)methanol

To a solution of 4-bromo-2-(2-bromoethoxy)benzaldehyde (1.6 g, 5.2 mmol) in methanol (15 mL) was added sodium borohydride (160 mg, 4.23 mmol) in an ice-bath, then the mixture was stirred for 10 min. The mixture was warmed to rt and stirred for 1 h, then the reaction was completed. The mixture was concentrated in vacuo, and dissolved in water (50 mL). The resulting mixture was extracted with ethyl acetate (20 mL×3). The combined organic layers were dried over anhydrous sodium sulfate and filtered. The filtrate was concentrated in vacuo, and the residue was purified by silica-gel column chromatography (PE:EtOAc=8:1, V/V) to give colourless oil (1.5 g, 93%).

MS (ESI, pos. ion) m/z: 309.9 (M+2)

Step 3: 4-bromo-2-(2-bromoethoxy)-1-(chloromethyl)benzene

To a solution of (4-bromo-2-(2-bromoethoxy)phenyl)methanol (1.0 g, 3.2 mmol) in anhydrous toluene (10 mL) was added dropwise thionyl chloride (0.3 mL, 4 mmol) in an ice-bath while maintaining the temperature below 35° C. After the addition, the mixture was stirred for 5 h at rt. The mixture was concentrated in vacuo to remove two thirds of the solvent, and the residue (1.1 g, 100%) was used directly in the next step without further purification.

Step 4: 4-bromo-2-(2-bromoethoxy)benzyl carbamimidothioate

To a reaction flask were added 4-bromo-2-(2-bromoethoxy)-1-(chloromethyl)benzene (1.1 g, 3.3 mmol) and anhydrous ethanol (15 mL), then thiourea (310 mg, 4.1 mmol) was added under nitrogen protection. The mixture was refluxed for 3 h. The reaction monitored by TLC was completed, and the mixture was cooled to rt, then filtered. The filter cake was washed with ethanol (20 mL) and dried to give a light yellow solid (1.23 g, 97%).

MS (ESI, pos. ion) m/z: 367.9 (M+2);

Step 5: 8-bromo-3,5-dihydro-2H-benzo[f][1,4]oxathiepine

A solution of sodium hydroxide (700 mg, 17.5 mmol) in water (30 mL) in a reaction flask was heated to 90° C., then a solution of 4-bromo-2-(2-bromoethoxy)benzyl carbamimidothioate (1.23 g, 3.34 mmol) in a mixture of ethanol (10 mL) and water (20 mL) was added dropwise slowly to the solution. After the addition, then mixture was stirred at 90° C. for 1 h, and cooled to rt. The mixture was extracted with ethyl ether (50 mL×3), and the combined organic layers were washed with water (20 mL×3), concentrated in vacuo and dried to give a gray solid (750 mg, 91.6%).

$^1$H NMR (400 MHz, CDCl$_3$) δ 7.30-7.24 (m, 1H), 7.18 (dd, J=8.0, 1.9 Hz, 1H), 7.04 (d, J=8.0 Hz, 1H), 4.26 (d, J=3.3 Hz, 2H), 3.78 (s, 2H), 3.12-2.97 (m, 2H).

Step 6: N-(1-((1-cyanocyclopropyl)carbamoyl)-4,4-difluorocyclohexyl)-6-(3,5-dihydro-2H-benzo[f][1,4]oxathiepin-8-yl)benzofuran-2-carboxamide

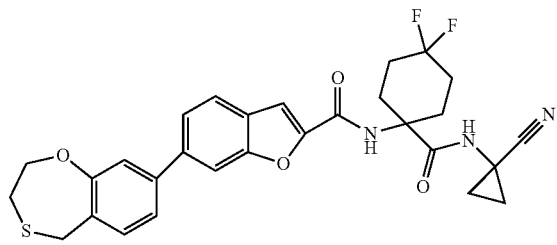 [SMILES: N#CC1(NC(=O)C2(NC(=O)c3cc4ccc(-c5ccc6c(c5)OCCSC6)cc4o3)CCC(F)(F)CC2)CC1]

To a 50 mL two-neck flask were added N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (70 mg, 0.13 mmol), DMF (6 mL) and 8-bromo-3,5-dihydro-2H-benzo[f][1,4]oxathiepine (40 mg, 0.16 mmol), then Pd(dppf)Cl$_2$.CH$_2$Cl$_2$ (20 mg, 0.02 mmol) and aqueous potassium carbonate (0.2 mL, 2 mol/L) were added to the mixture. The mixture was stirred at 90° C. for 80 min. After the reaction was completed, the reaction mixture was cooled to rt and to the mixture was added saturated brine (20 mL). The resulting mixture was extracted with EtOAc (20 mL×3). The combined organic layers were dried over anhydrous Na$_2$SO$_4$, and filtered. The filtrate was concentrated in vacuo, and the residue was purified by silica-gel column chromatography (DCM:EtOAc=10:1, V/V) to give a white solid (55 mg, 73.1%).

MS (ESI, pos. ion) m/z: 552.1 (M+1);

Step 7: N-(1-((1-cyanocyclopropyl)carbamoyl)-4,4-difluorocyclohexyl)-6-(4,4-dioxido-3,5-dihydro-2H-benzo[f][1,4]oxathiepin-8-yl)benzofuran-2-carboxamide To a mixture of N-(1-((1-cyanocyclopropyl)carbamoyl)-4,4-difluorocyclohexyl)-6-(3,5-dihydro-2H-benzo[f][1,4]oxathiepin-8-yl)benzofuran-2-carboxamide (55 mg, 0.1 mmol), sodium tungstate dihydrate (2 mg) and tetra-n-butylammonium hydrogen sulphate (0.01 g) in DCM (10 mL) added dropwise 30% H$_2$O$_2$ (0.1 mL) at 0° C. in an ice-bath. After the addition, the mixture was stirred at rt for 3 h, and the reaction monitored by TLC was completed. The reaction mixture was poured into ice-water (10 mL), and the resulting mixture was extracted with EtOAc (30 mL×3). The combined organic layers were dried over anhydrous Na$_2$SO$_4$, and filtered. The filtrate was concentrated in vacuo, and the residue was purified by silica-gel column chromatography (DCM:EtOAc=1:5, V/V) to give a white solid (33 mg, 56.7%).

MS (ESI, pos. ion) m/z: 584.1 (M+1);

$^1$H NMR (400 MHz, DMSO-d$_6$) 8.78 (s, 1H), 8.51 (s, 1H), 8.01 (s, 1H), 7.88 (d, J=8.2 Hz, 1H), 7.77-7.66 (m, 2H), 7.57 (d, J=8.0 Hz, 1H), 7.50 (d, J=10.0 Hz, 2H), 4.71 (s, 2H), 4.38 (s, 2H), 3.73 (s, 2H), 2.21 (s, 2H), 2.12-1.98 (m, 6H), 1.46 (dd, J=7.8, 5.5 Hz, 2H), 1.08 (dd, J=8.0, 5.6 Hz, 2H).

$^{19}$F NMR (376 MHz, DMSO-d$_6$) −92.78 (d, J=231.7 Hz), −98.19 (d, J=240.8 Hz).

Example 57: 6-(2-(1H-1,2,4-triazol-1-yl)thiazol-4-yl)-N-(1-((1-cyanocyclopropyl) carbamoyl)-4,4-difluorocyclohexyl)benzofuran-2-carboxamide

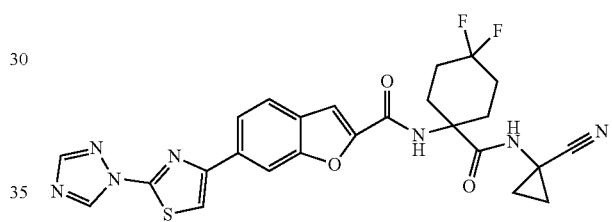

Step 1: 4-bromo-2-(1H-1,2,4-triazol-1-yl)thiazole

To a 50 mL two-neck flask were added 2,4-dibromothiazole (0.50 g, 2.1 mmol), 1H-1,2,4-triazole (0.22 g, 3.2 mmol) and anhydrous DMF (9 mL), then potassium carbonate (0.57 g, 4.0 mmol) was added. The mixture was stirred at 110° C. for 3 h. The reaction mixture was cooled to rt and quenched with water. The mixture was filtered by suction and the filtrate was concentrated in vacuo. The residue was purified by silica-gel column chromatography (DCM:EtOAc=25:1, V/V) to give a white solid (0.41 g, 86%).

MS (ESI, pos. ion) m/z: 232.1 (M+2);

Step 2: 6-(2-(1H-1,2,4-triazol-1-yl)thiazol-4-yl)-N-(1-((1-cyanocyclopropyl)carbamoyl)-4,4-difluorocyclohexyl)benzofuran-2-carboxamide To a 50 mL two-neck flask were added 4-bromo-2-(1H-1,2,4-triazol-1-yl)thiazole (30 mg, 0.13 mmol), N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (78 mg, 0.15 mmol), Pd(Ph$_3$P)$_4$ (15 mg, 0.013 mmol) and DMF (8 mL), then aqueous potassium carbonate solution (0.13 mL, 0.26 mmol, 2 mol/L) was added under nitrogen protection. The resulting mixture was stirred at 85° C. for 2 h. The reaction mixture was cooled to rt and the mixture was quenched with water (60 mL). The resulting mixture was extracted with EtOAc (50 mL×2). The combined organic layers were washed with water (80 mL×2) and saturated brine (80 mL), dried over anhydrous Na$_2$SO$_4$, and filtered. The filtrate was concentrated in vacuo, and the residue was purified by silica-gel column chromatography (DCM:MeOH=200:1, V/V) to give a white solid (51 mg, 73%).

MS (ESI, pos. ion) m/z: 538.0 (M+1);
$^1$H NMR (400 MHz, DMSO-d$_6$) δ 9.52 (s, 1H), 8.78 (s, 1H), 8.50 (s, 1H), 8.39 (s, 1H), 8.31 (s, 1H), 8.22 (s, 1H), 8.03 (d, J=8.2 Hz, 1H), 7.89 (d, J=8.2 Hz, 1H), 7.72 (s, 1H), 7.59 (dd, J=19.4, 8.9 Hz, 1H), 2.22 (s, 2H), 2.07 (d, J=14.4 Hz, 6H), 1.46 (t, J=6.5 Hz, 2H), 1.08 (t, J=6.6 Hz, 2H).

Example 58: N-(1-((1-cyanocyclopropyl)carbamoyl)-4,4-difluorocyclohexyl)-6-(2-(methylsulfonyl)thiazol-4-yl)benzofuran-2-carboxamide

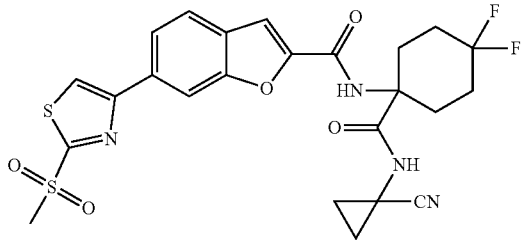 [SMILES: CS(=O)(=O)c1nc(-c2ccc3cc(C(=O)NC4(C(=O)NC5(C#N)CC5)CCC(F)(F)CC4)oc3c2)cs1]

Step 1: 4-bromo-2-(methylsulfonyl)thiazole

To a 25 mL sealed tube were added 2,4-dibromothiazole (800 mg, 3.29 mmol), methanesulfinic acid sodium salt (0.42 g, 4.0 mmol), cuprous iodide (128 mg, 0.66 mmol), sodium L-prolinate (186 mg, 1.32 mmol) and DMSO (10 mL). The mixture was stirred at 105° C. under nitrogen protection for 24 h. After the reaction was completed, the mixture was diluted with EtOAc (50 mL), and water (60 mL) was added. The resulting mixture was partitioned, and the aqueous layer was extracted with EtOAc (30 mL×2). The combined organic layers were washed with saturated aqueous NaCl solution (10 mL×2), dried over anhydrous Na$_2$SO$_4$, and filtered. The filtrate was concentrated in vacuo, and the residue was purified by silica-gel column chromatography (DCM:EtOAc=6:1, V/V) to give a white solid (0.51 g, 64%).

MS (ESI, pos. ion) m/z: 241.9 (M+1);

Step 2: N-(1-((1-cyanocyclopropyl)carbamoyl)-4,4-difluorocyclohexyl)-6-(2-(methylsulfonyl) thiazol-4-yl)benzofuran-2-carboxamide To a mixture of toluene (6 mL) and ethanol (2 mL) were added 4-bromo-2-(methylsulfonyl)thiazole (39 mg, 0.16 mmol), N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (75 mg, 0.15 mmol) and Pd(Ph$_3$P)$_4$ (17 mg, 0.0147 mmol) in a nitrogen atomosphere, then potassium carbonate (41 mg, 0.29 mmol) was added. The mixture was stirred at 90° C. for 3 h in a nitrogen atomosphere. The reaction monitored by TLC was completed, then cooled to rt. The mixture was diluted with water (100 mL×2) and ethyl acetate (50 mL×2), then partitioned. The organic layer was washed with brine (10 mL×2), dried over anhydrous sodium sulfate, and filtered. The filtrate was concentrated in vacuo to remove the solvent, and the residue was purified by silica-gel column chromatography (DCM:EtOAc=10:1, V/V) to give a white solid (56 mg, 69.86%).

MS (ESI, pos. ion) m/z: 549.9 (M+1);
$^1$H NMR (400 MHz, DMSO-d$_6$) δ 8.77 (d, J=4.5 Hz, 2H), 8.49 (s, 1H), 8.32 (s, 1H), 8.04 (d, J=8.2 Hz, 1H), 7.92 (d, J=8.2 Hz, 1H), 7.75 (s, 1H), 3.57 (s, 3H), 2.12 (t, J=34.4 Hz, 8H), 1.46 (dd, J=8.1, 5.4 Hz, 2H), 1.08 (dd, J=8.2, 5.5 Hz, 2H).

Example 59: N-(1-((1-cyanocyclopropyl)carbamoyl)-4,4-difluorocyclohexyl)-6-(5-methyl-2-(1H-1,2,4-triazol-1-yl)thiazol-4-yl)benzofuran-2-carboxamide Step 1: 4-bromo-5-methyl-2-(1H-1,2,4-triazol-1-yl)thiazole To a 50 mL two-neck flask were added 2,4-dibromo-5-methylthiazole (0.81 g, 3.2 mmol), 1H-1,2,4-triazole (0.22 g, 3.2 mmol) and anhydrous DMF (10 mL), then potassium carbonate (0.87 g, 6.2 mmol) was added. The mixture was stirred at 110° C. for 3 h. The reaction mixture was cooled to rt and to the mixture was added water (5 mL). The mixture was filtered by suction. The residue was purified by silica-gel column chromatography (DCM:EtOAc=2:1, V/V) to give a white solid (0.45 g, 58%).

MS (ESI, pos. ion) m/z: 245.9 (M+2);

Step 2: N-(1-((1-cyanocyclopropyl)carbamoyl)-4,4-difluorocyclohexyl)-6-(5-methyl-2-(1H-1,2,4-triazol-1-yl)thiazol-4-yl)benzofuran-2-carboxamide To a 50 mL two-neck flask were added 4-bromo-5-methyl-2-(1H-1,2,4-triazol-1-yl)thiazole (34 mg, 0.14 mmol), N-(1-((1-cyanocyclopropyl)carbamoyl)4,4-difluorocyclohexyl)-6-(4,4,5,5-tetramethyl-1,3,2-dioxaborolan-2-yl)benzofuran-2-carboxamide (78 mg, 0.15 mmol), Pd(Ph$_3$P)$_4$ (16 mg, 0.014 mmol) and DMF (8 mL), then aqueous potassium carbonate solution (0.14 mL, 0.28 mmol, 2 mol/L) was added under nitrogen protection. The resulting mixture was stirred at 85° C. for 2 h. The reaction mixture was cooled to rt and the mixture was quenched with water (60 mL). The resulting mixture was extracted with EtOAc (50 mL×2). The combined organic layers were washed with water (80 mL×2) and saturated brine (80 mL), dried over anhydrous Na$_2$SO$_4$, and concentrated in vacuo, and the residue was purified by silica-gel column chromatography (DCM:MeOH=200:1, V/V) to give a white solid (34 mg, 44%).

MS (ESI, pos. ion) m/z: 552.30 (M+1);
$^1$H NMR (600 MHz, DMSO-d$_6$) δ 9.41 (s, 1H), 8.79 (s, 1H), 8.52 (s, 1H), 8.36 (s, 1H), 8.01 (s, 1H), 7.91 (d, J=8.0

Hz, 1H), 7.82-7.69 (m, 2H), 2.65 (s, 3H), 2.22 (s, 2H), 2.15-1.98 (m, 6H), 1.50-1.41 (m, 2H), 1.08 (s, 2H).

Example 60: N-(1-((1-cyanocyclopropyl)carbamoyl)-4,4-difluorocyclohexyl)-6-(3-ethyl-4-(1H-1,2,4-triazol-1-yl)phenyl)benzofuran-2-carboxamide

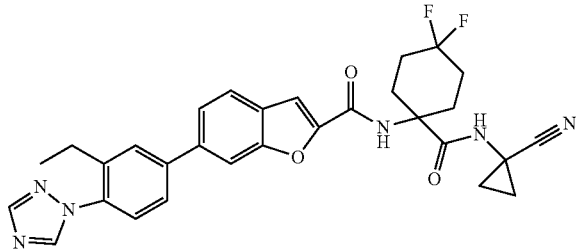 [SMILES: CCc1cc(-c2ccc3cc(C(=O)NC4(C(=O)NC5(C#N)CC5)CCC(F)(F)CC4)oc3c2)ccc1-n1cncn1]

Step 1:
5-bromo-2-(1H-1,2,4-triazol-1-yl)benzaldehyde

To a 50 mL two-neck flask were added 5-bromo-2-fluorobenzaldehyde (1.00 g, 4.93 mmol), DMSO (10 mL), 1H-1,2,4-triazole (510 mg, 7.38 mmol) and potassium carbonate (1.36 g, 9.86 mmol). The mixture was stirred at 80° C. for 1 h under nitrogen protection. The mixture was cooled to rt, and water (20 mL) was added. The resulting mixture was extracted with ethyl acetate (3×15 mL), dried and concentrated in vacuo, and the residue was purified by silica-gel column chromatography (n-hexane:EtOAc=1:1, V/V) to give a white solid (0.9 g, 70%).
MS (ESI, pos. ion) m/z: 252.9 (M+2);

Step 2: 1-(4-bromo-2-vinylphenyl)-1H-1,2,4-triazole

To a dried two-neck flask were added bromo(methyl)triphenylphosphorane (1.91 g, 5.35 mmol) and anhydrous tetrahydrofuran (20 mL), then t-BuOK (0.6 g, 5 mmol) was added under an ice-bath condition, and the mixture was stirred for 30 min under the ice-bath condition. To the reaction flask was added dropwise a solution of 5-bromo-2-(1H-1,2,4-triazol-1-yl)benzaldehyde (1.12 g, 4.45 mmol) in tetrahydrofuran (20 mL). After the addition, the mixture was stirred at rt overnight. The mixture was concentrated in vacuo and the residue was dissolved in ethyl acetate (50 mL). The resulting mixture was extracted with saturated brine (20 mL), dried over anhydrous sodium sulfate and filtered. The filtrate was concentrated in vacuo, and the residue was purified by silica-gel column chromatography (PE:EtOAc=4:1, V/V) to give a white solid (300 mg, 33.5%).
MS (ESI, pos. ion) m/z: 252.1 (M+2);

Step 3: 1-(4-bromo-2-ethylphenyl)-1H-1,2,4-triazole

To a solution of 1-(4-bromo-2-vinylphenyl)-1H-1,2,4-triazole (130 mg, 0.52 mmol) in THF (8 mL) was added 10% Pd(OH)$_2$ (90 mg). The mixture was stirred at rt for 3 h in a hydrogen atomosphere. After the reaction was completed, the mixture was filtered, and the filtrate was concentrated in vacuo to give a light yellow solid (120 mg, 91.57%).
MS (ESI, pos. ion) m/z: 253.1 (M+2);

Step 4: N-(1-((1-cyanocyclopropyl)carbamoyl)-4,4-difluorocyclohexyl)-6-(3-ethyl-4-(1H-1,2,4-triazol-1-yl)phenyl)benzofuran-2-carboxamide To a reaction flask were added N-(1-((1-cyanocyclopropyl)carbamoyl)-4,4-difluorocyclohexyl)-6-(4,4,5,5-tetramethyl-1,3,2-dioxaborolan-2-yl)benzofuran-2-carboxamide (86 mg, 0.16 mmol), DMF (6 mL) and 1-(4-bromo-2-ethylphenyl)-1H-1,2,4-triazole (50 mg, 0.2 mmol), then Pd(dppf)Cl$_2$.CH$_2$Cl$_2$ (20 mg, 0.02 mmol) and aqueous potassium carbonate (0.26 mL, 2 mol/L) were added to the mixture. The mixture was stirred at 90° C. for 1 h. After the reaction was completed, the reaction mixture was washed with saturated brine (20 mL). The resulting mixture was extracted with EtOAc (20 mL×3). The combined organic layers were dried over anhydrous Na$_2$SO$_4$, and filtered. The filtrate was concentrated in vacuo, and the residue was purified by silica-gel column chromatography (DCM:EtOAc=2:1, V/V) to give a white solid (40 mg, 36.1%).
MS (ESI, pos. ion) m/z: 559.2 (M+1);
$^1$H NMR (400 MHz, CDCl$_3$) δ 8.31 (s, 1H), 8.18 (d, J=10.5 Hz, 2H), 7.84-7.74 (m, 2H), 7.69-7.54 (m, 4H), 7.41 (d, J=8.1 Hz, 1H), 6.63 (s, 1H), 2.64 (q, J=7.5 Hz, 2H), 2.50-2.31 (m, 4H), 2.17 (s, 2H), 2.00 (d, J=5.1 Hz, 2H), 1.56 (dd, J=8.0, 6.0 Hz, 2H), 1.22 (dt, J=15.1, 6.6 Hz, 7H).
$^{19}$F NMR (376 MHz, CDCl$_3$) δ -96.11 (d, J=228.7 Hz), -100.44 (d, J=247.7 Hz).

Example 61-101

Compounds of examples 61-101 were prepared by using the corresponding reagents and intermediates according to the synthetic method, and the characteristic data were list as follows:

| Example | Structure of compound and characteristic data thereof |
|---|---|
| 61 | The compound was prepared according to the synthetic method of example 53:<br>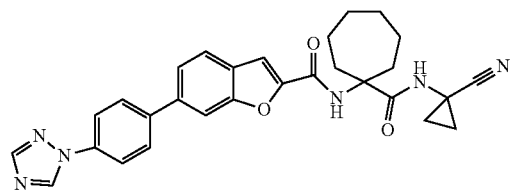 [SMILES: N#CC1(NC(=O)C2(NC(=O)c3cc4ccc(-c5ccc(-n6cncn6)cc5)cc4o3)CCCCCC2)CC1]<br>MS (ESI, pos.ion) m/z: 509.30 (M + 1). |

-continued

| Example | Structure of compound and characteristic data thereof |
|---|---|
| 62 | The compound was prepared according to the synthetic method of example 1:<br />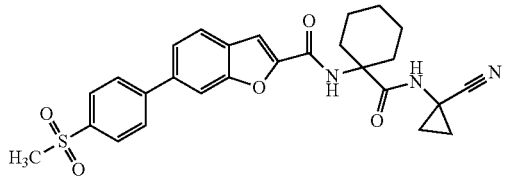 [SMILES: CS(=O)(=O)c1ccc(-c2ccc3cc(C(=O)NC4(C(=O)NC5(C#N)CC5)CCCCC4)oc3c2)cc1]<br />MS (ESI, pos.ion) m/z: 506.2 (M + 1). |
| 63 | The compound was prepared according to the synthetic method of example 58:<br />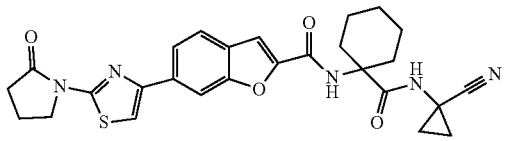 [SMILES: N#CC1(NC(=O)C2(NC(=O)c3cc4ccc(-c5csc(N6CCCC6=O)n5)cc4o3)CCCCC2)CC1]<br />MS (ESI, pos.ion) m/z: 518.2 (M + 1). |
| 64 | The compound was prepared according to the synthetic method of example 1:<br />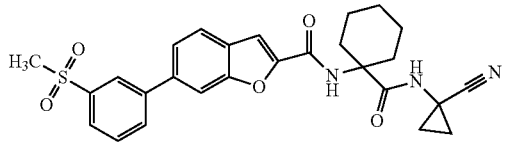 [SMILES: CS(=O)(=O)c1cccc(-c2ccc3cc(C(=O)NC4(C(=O)NC5(C#N)CC5)CCCCC4)oc3c2)c1]<br />MS (ESI, pos.ion) m/z: 506.2 (M + 1). |
| 65 | The compound was prepared according to the synthetic method of example 58:<br />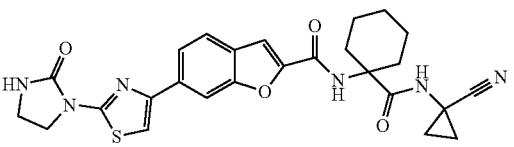 [SMILES: N#CC1(NC(=O)C2(NC(=O)c3cc4ccc(-c5csc(N6CCNC6=O)n5)cc4o3)CCCCC2)CC1]<br />MS (ESI, pos.ion) m/z: 519.2 (M + 1);<br />$^1$H NMR (400 MHz, DMSO-$d_6$) δ 8.58 (s, 1H), 8.19 (s, 1H), 7.97-7.89 (m, 2H), 7.80 (d, J = 8.2 Hz, 1H), 7.70 (s, 1H), 7.68-7.62 (m, 2H), 4.25-4.11 (m, 2H), 3.64-3.50 (m, 2H), 2.05 (d, J = 13.1 Hz, 2H), 1.79 (t, J = 10.8 Hz, 2H), 1.68-1.38 (m, 6H), 1.24 (s, 2H), 1.06 (dd, J = 8.3, 5.5 Hz, 2H). |
| 66 | The compound was prepared according to the synthetic method of example 58:<br />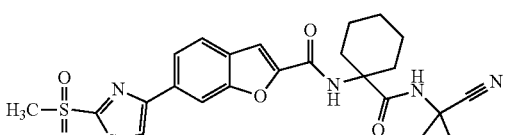<br />MS (ESI, pos.ion) m/z: 513.2 (M + 1). |
| 67 | The compound was prepared according to the synthetic method of example 58:<br />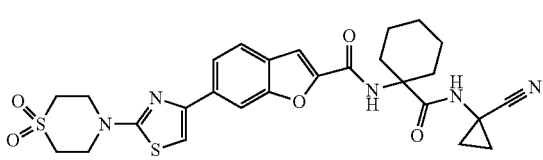 [SMILES: N#CC1(NC(=O)C2(NC(=O)c3cc4ccc(-c5csc(N6CCS(=O)(=O)CC6)n5)cc4o3)CCCCC2)CC1]<br />MS (ESI, pos.ion) m/z: 568.2 (M + 1). |

| Example | Structure of compound and characteristic data thereof |
|---|---|
| 68 | The compound was prepared according to the synthetic method of example 58:<br>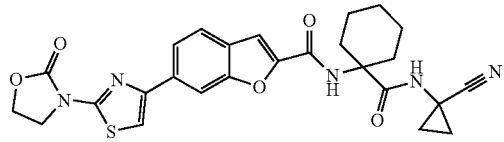 [SMILES: N#CC1(NC(=O)C2(NC(=O)c3cc4ccc(-c5csc(N6CCOC6=O)n5)cc4o3)CCCCC2)CC1]<br>MS (ESI, pos.ion) m/z: 520.2 (M + 1);<br>$^1$H NMR (400 MHz, DMSO-d$_6$) δ 8.57 (s, 1H), 8.22 (s, 1H), 7.98-7.91 (m, 2H), 7.89 (s, 1H), 7.82 (d, J = 8.3 Hz, 1H), 7.66 (s, 1H), 4.67-4.55 (m, 2H), 4.34 (t, J = 8.1 Hz, 2H), 2.05 (d, J = 13.2 Hz, 2H), 1.79 (t, J = 10.4 Hz, 2H), 1.62-1.41 (m, 6H), 1.24 (s, 2H), 1.06 (dd, J = 8.3, 5.5 Hz, 2H). |
| 69 | The compound was prepared according to the synthetic method of example 1:<br><br>MS (ESI, pos.ion) m/z: 508.1 (M + 1). |
| 70 | The compound was prepared according to the synthetic method of example 1:<br>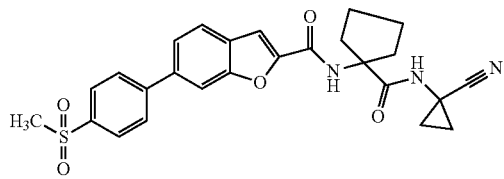 [SMILES: CS(=O)(=O)c1ccc(-c2ccc3cc(C(=O)NC4(C(=O)NC5(C#N)CC5)CCCC4)oc3c2)cc1]<br>MS (ESI, pos.ion) m/z: 492.1 (M + 1). |
| 71 | The compound was prepared according to the synthetic method of example 17:<br>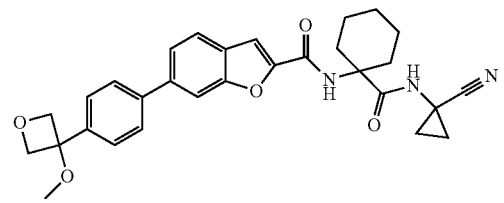 [SMILES: COC1(c2ccc(-c3ccc4cc(C(=O)NC5(C(=O)NC6(C#N)CC6)CCCCC5)oc4c3)cc2)COC1]<br>MS (ESI, pos.ion) m/z: 514.2 (M + 1). |
| 72 | The compound was prepared according to the synthetic method of example 17:<br>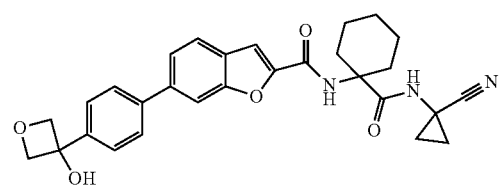 [SMILES: N#CC1(NC(=O)C2(NC(=O)c3cc4ccc(-c5ccc(C6(O)COC6)cc5)cc4o3)CCCCC2)CC1]<br>MS (ESI, pos.ion) m/z: 500.2 (M + 1). |

| Example | Structure of compound and characteristic data thereof |
|---|---|
| 73 | The compound was prepared according to the synthetic method of example 17:<br>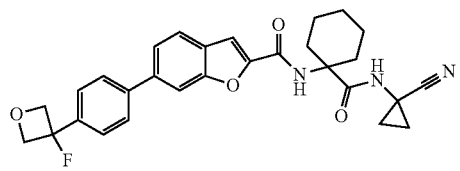 [SMILES: N#CC1(NC(=O)C2(NC(=O)c3cc4ccc(-c5ccc(C6(F)COC6)cc5)cc4o3)CCCCC2)CC1]<br>MS (ESI, pos.ion) m/z: 502.1 (M + 1). |
| 74 | The compound was prepared according to the synthetic method of example 13:<br>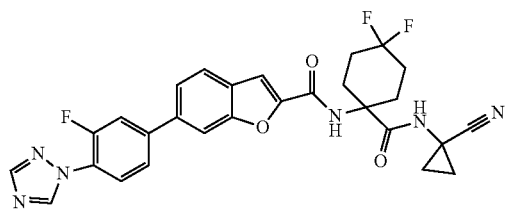 [SMILES: N#CC1(NC(=O)C2(NC(=O)c3cc4ccc(-c5ccc(-n6cncn6)c(F)c5)cc4o3)CCC(F)(F)CC2)CC1]<br>MS (ESI, pos.ion) m/z: 549.20 (M + 1). |
| 75 | The compound was prepared according to the synthetic method of example 17:<br>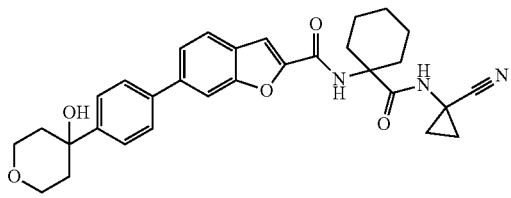 [SMILES: N#CC1(NC(=O)C2(NC(=O)c3cc4ccc(-c5ccc(C6(O)CCOCC6)cc5)cc4o3)CCCCC2)CC1]<br>MS (ESI, pos.ion) m/z: 528.2 (M + 1). |
| 76 | The compound was prepared according to the synthetic method of example 17:<br>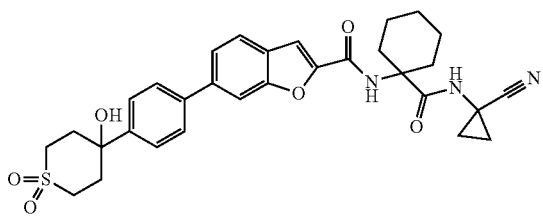 [SMILES: N#CC1(NC(=O)C2(NC(=O)c3cc4ccc(-c5ccc(C6(O)CCS(=O)(=O)CC6)cc5)cc4o3)CCCCC2)CC1]<br>MS (ESI, pos.ion) m/z: 576.2 (M + 1);<br>$^1$H NMR (600 MHz, DMSO-$d_6$) δ 8.59 (s, 1H), 7.99 (s, 1H), 7.95 (s, 1H), 7.86 (d, J = 8.2 Hz, 1H), 7.77 (d, J = 8.5 Hz, 2H), 7.72-7.65 (m, 2H), 7.62 (d, J = 8.5 Hz, 2H), 5.71 (s, 1H), 3.46-3.37 (m, 2H), 3.07 (d, J = 11.9 Hz, 2H), 2.06 (d, J = 11.7 Hz, 4H), 1.80 (s, 2H), 1.45 (dd, J = 8.1, 5.3 Hz, 7H), 1.17 (dd, J = 15.9, 8.7 Hz, 2H), 1.05 (d, J = 2.7 Hz, 2H), 0.92-0.76 (m, 2H). |

| Example | Structure of compound and characteristic data thereof |
|---|---|
| 77 | The compound was prepared according to the synthetic method of example 17:

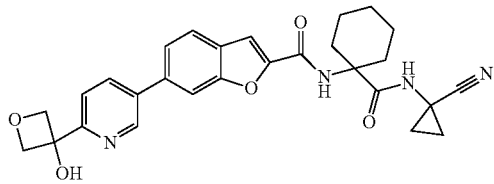 [SMILES: N#CC1(NC(=O)C2(NC(=O)c3cc4ccc(-c5ccc(C6(O)COC6)nc5)cc4o3)CCCCC2)CC1]

MS (ESI, pos.ion) m/z: 501.2 (M + 1);
$^1$H NMR (600 MHz, CDCl$_3$) δ 8.81 (s, 1H), 8.19-8.13 (m, 1H), 8.14-8.09 (m, 1H), 7.82 (d, J = 8.1 Hz, 1H), 7.78 (s, 1H), 7.59 (d, J = 8.1 Hz, 1H), 7.55 (s, 1H), 6.59 (s, 2H), 5.15 (d, J = 7.1 Hz, 2H), 4.79 (d, J = 7.1 Hz, 2H), 2.26 (d, J = 13.9 Hz, 2H), 2.13-1.94 (m, 2H), 1.74 (dd, J = 9.7, 4.2 Hz, 2H), 1.39 (ddd, J = 13.8, 8.2, 4.2 Hz, 4H), 0.95-0.78 (m, 2H). |
| 78 | The compound was prepared according to the synthetic method of example 58:

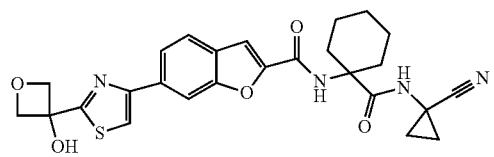 [SMILES: N#CC1(NC(=O)C2(NC(=O)c3cc4ccc(-c5csc(C6(O)COC6)n5)cc4o3)CCCCC2)CC1]

MS (ESI, pos.ion) m/z: 507.2 (M + 1). |
| 79 | The compound was prepared according to the synthetic method of example 17:

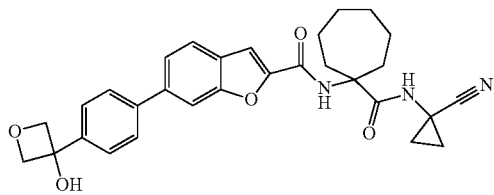 [SMILES: N#CC1(NC(=O)C2(NC(=O)c3cc4ccc(-c5ccc(C6(O)COC6)cc5)cc4o3)CCCCCC2)CC1]

MS (ESI, pos.ion) m/z: 514.2 (M + 1). |
| 80 | The compound was prepared according to the synthetic method of example 17:

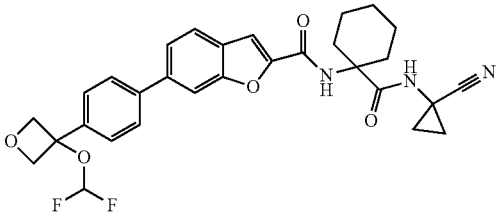 [SMILES: N#CC1(NC(=O)C2(NC(=O)c3cc4ccc(-c5ccc(C6(OC(F)F)COC6)cc5)cc4o3)CCCCC2)CC1]

MS (ESI, pos.ion) m/z: 550.2 (M + 1). |
| 81 | The compound was prepared according to the synthetic method of example 53:

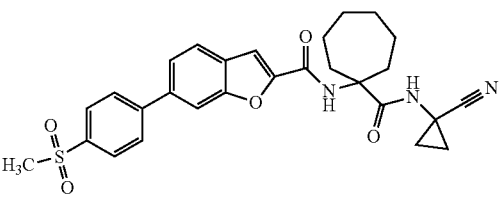 [SMILES: CS(=O)(=O)c1ccc(-c2ccc3cc(C(=O)NC4(C(=O)NC5(C#N)CC5)CCCCCC4)oc3c2)cc1]

MS (ESI, pos.ion) m/z: 520.2 (M + 1);
$^1$H NMR (600 MHz, CDCl$_3$) δ 8.04 (d, J = 8.0 Hz, 2H), 7.80 (m, 4H), 7.58 (d, J = 8.0 Hz, 1H), 7.52 (s, 1H), 6.67 (s, 1H), 3.12 (s, 3H), 2.41-2.28 (m, 2H), 2.25-2.12 (m, 2H), 1.79-1.11 (16H). |

| Example | Structure of compound and characteristic data thereof |
|---|---|
| 82 | The compound was prepared according to the synthetic method of example 1:<br>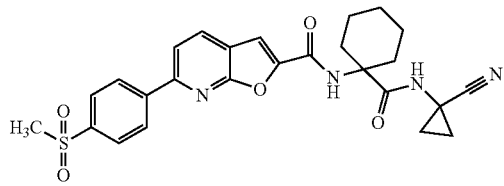 [SMILES: CS(=O)(=O)c1ccc(-c2ccc3cc(C(=O)NC4(C(=O)NC5(C#N)CC5)CCCCC4)oc3n2)cc1]<br>MS (ESI, pos.ion) m/z: 507.2 (M + 1);<br>$^1$H NMR (600 MHz, DMSO-d$_6$) δ 8.59 (s, 1H), 8.44 (dd, J = 8.3, 4.3 Hz, 2H), 8.26-8.16 (m, 2H), 8.09 (d, J = 8.5 Hz, 2H), 7.71 (s, 1H), 3.30 (s, 3H), 2.08 (d, J = 13.6 Hz, 2H), 1.81 (dd, J = 17.1, 6.8 Hz, 2H), 1.65-1.47 (m, 6H), 1.45 (dd, J = 8.1, 5.3 Hz, 2H), 1.06 (dd, J = 8.2, 5.5 Hz, 2H). |
| 83 | The compound was prepared according to the synthetic method of example 28:<br>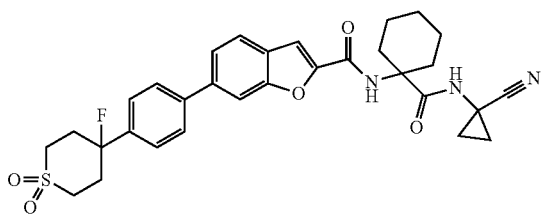 [SMILES: N#CC1(NC(=O)C2(NC(=O)c3cc4ccc(-c5ccc(C6(F)CCS(=O)(=O)CC6)cc5)cc4o3)CCCCC2)CC1]<br>MS (ESI, pos.ion) m/z: 578.2 (M + 1). |
| 84 | The compound was prepared according to the synthetic method of example 13:<br>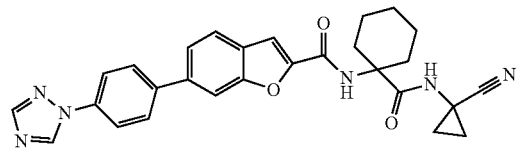 [SMILES: N#CC1(NC(=O)C2(NC(=O)c3cc4ccc(-c5ccc(-n6cncn6)cc5)cc4o3)CCCCC2)CC1]<br>MS (ESI, pos.ion) m/z: 495.2 (M + 1). |
| 85 | The compound was prepared according to the synthetic method of example 13:<br>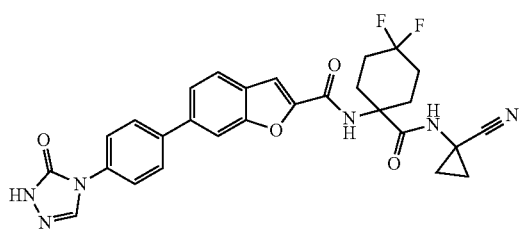 [SMILES: N#CC1(NC(=O)C2(NC(=O)c3cc4ccc(-c5ccc(-n6cn[nH]c6=O)cc5)cc4o3)CCC(F)(F)CC2)CC1]<br>MS (ESI, pos.ion) m/z: 547.2 (M + 1);<br>$^1$H NMR (400 MHz, DMSO-d$_6$) δ 8.90 (s, 1H), 8.80 (s, 1H), 8.53 (s, 1H), 8.07 (d, J = 7.4 Hz, 2H), 8.03 (d, J = 9.9 Hz, 4H), 7.92 (d, J = 8.1 Hz, 1H), 7.80-7.65 (m, 2H), 2.20 (d, J = 5.7 Hz, 2H), 2.07 (d, J = 15.2 Hz, 6H), 2.07 (s, 6H), 1.46 (dd, J = 8.1, 5.4 Hz, 2H), 1.08 (dd, J = 8.2, 5.5 Hz, 2H). |

| Example | Structure of compound and characteristic data thereof |
|---|---|
| 86 | The compound was prepared according to the synthetic method of example 1:<br>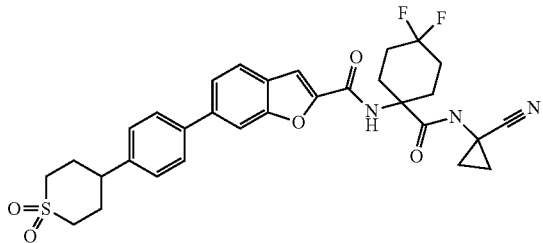 [SMILES: N#CC1(NC(=O)C2(NC(=O)c3cc4ccc(-c5ccc(C6CCS(=O)(=O)CC6)cc5)cc4o3)CCC(F)(F)CC2)CC1]<br>MS (ESI, pos.ion) m/z: 596.2 (M + 1);<br>$^1$H NMR (400 MHz, DMSO-d$_6$) δ: 8.90 (s, 1H), 8.80 (s, 1H), 8.53 (s, 1H), 8.07 (d, J = 7.4 Hz, 2H), 8.03 (d, J = 9.9 Hz, 4H), 7.92 (d, J = 8.1 Hz, 1H), 7.80-7.65 (m, 2H), 2.20 (d, J = 5.7 Hz, 2H), 2.07 (d, J = 15.2 Hz, 6H), 2.07 (s, 6H), 1.46 (dd, J = 8.1, 5.4 Hz, 2H), 1.08 (dd, J = 8.2, 5.5 Hz, 2H). |
| 87 | The compound was prepared according to the synthetic method of example 25:<br>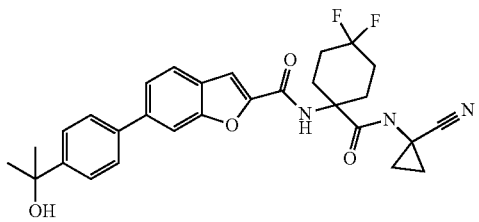 [SMILES: CC(C)(O)c1ccc(-c2ccc3cc(C(=O)NC4(C(=O)NC5(C#N)CC5)CCC(F)(F)CC4)oc3c2)cc1]<br>MS (ESI, pos.ion) m/z: 522.2 (M + 1). |
| 88 | The compound was prepared according to the synthetic method of example 13:<br>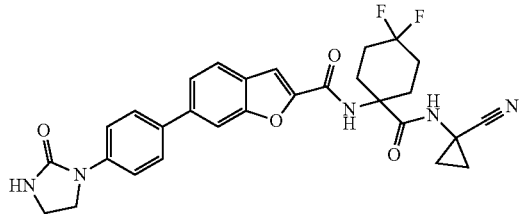 [SMILES: N#CC1(NC(=O)C2(NC(=O)c3cc4ccc(-c5ccc(N6CCNC6=O)cc5)cc4o3)CCC(F)(F)CC2)CC1]<br>MS (ESI, pos.ion) m/z: 548.2 (M + 1);<br>$^1$H NMR (400 MHz, DMSO-d$_6$) δ: 8.90 (s, 1H), 8.80 (s, 1H), 8.53 (s, 1H), 8.07 (d, J = 7.4 Hz, 2H), 8.03 (d, J = 9.9 Hz, 4H), 7.92 (d, J = 8.1 Hz, 1H), 7.80-7.65 (m, 2H), 2.20 (d, J = 5.7 Hz, 2H), 2.07 (d, J = 15.2 Hz, 6H), 2.07 (s, 6H), 1.46 (dd, J = 8.1, 5.4 Hz, 2H), 1.08 (dd, J = 8.2, 5.5 Hz, 2H);<br>$^{19}$F NMR (376 MHz, DMSO-d$_6$) δ: −92.78 (d, J = 233.4 Hz), −98.18 (d, J = 233.5 Hz). |
| 89 | The compound was prepared according to the synthetic method of example 13:<br>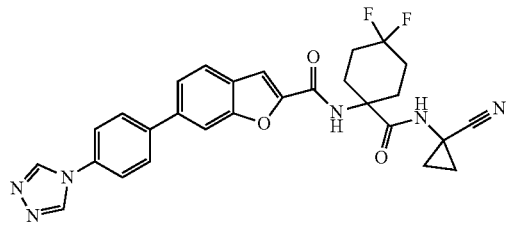 [SMILES: N#CC1(NC(=O)C2(NC(=O)c3cc4ccc(-c5ccc(-n6cnnc6)cc5)cc4o3)CCC(F)(F)CC2)CC1]<br>MS (ESI, pos.ion) m/z: 531.2 (M + 1). |

| Example | Structure of compound and characteristic data thereof |
|---|---|
| 90 | The compound was prepared according to the synthetic method of example 25: 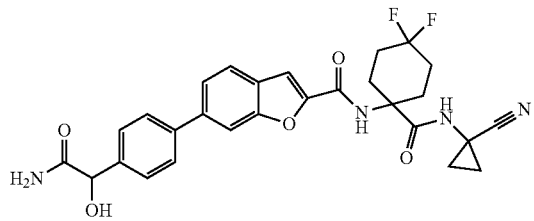 [SMILES: N#CC1(NC(=O)C2(NC(=O)c3cc4ccc(-c5ccc(C(O)C(N)=O)cc5)cc4o3)CCC(F)(F)CC2)CC1]<br><br>MS (ESI, pos.ion) m/z: 537.2 (M + 1);<br>¹H NMR (400 MHz, DMSO-d₆) δ 8.77 (s, 1H), 8.49 (s, 1H), 7.95 (s, 1H), 7.87 (d, J = 8.2 Hz, 1H), 7.73 (d, J = 8.5 Hz, 3H), 7.68 (d, J = 8.1 Hz, 1H), 7.55 (d, J = 8.2 Hz, 2H), 7.45 (s, 1H), 7.22 (s, 1H), 2.22 (s, 2H), 2.07 (d, J = 15.2 Hz, 6H), 1.46 (dd, J = 8.0, 5.4 Hz, 2H), 1.24 (s, 2H), 1.08 (dd, J = 8.1, 5.6 Hz, 2H). |
| 91 | The compound was prepared according to the synthetic method of example 1: <br><br>MS (ESI, pos.ion) m/z: 508.1 (M + 1). |
| 92 | The compound was prepared according to the synthetic method of example 50: 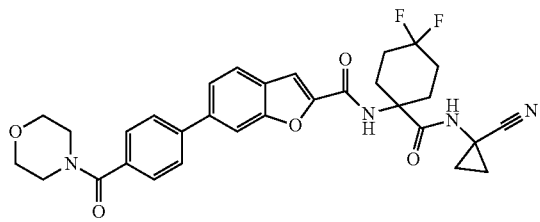 [SMILES: N#CC1(NC(=O)C2(NC(=O)c3cc4ccc(-c5ccc(C(=O)N6CCOCC6)cc5)cc4o3)CCC(F)(F)CC2)CC1]<br><br>MS (ESI, pos.ion) m/z: 577.3 (M + 1);<br>¹H NMR (400 MHz, DMSO-d₆) δ 8.78 (s, 1H), 8.52 (s, 1H), 7.97 ~ 7.85 (d, J = 8.1 Hz, 2H), 7.77 ~ 7.69 (m, 2H), 7.63 (dd, J = 11.8, 7.2 Hz, 2H), 7.55 (t, J = 7.5 Hz, 2H), 3.63 (d, J = 9.3 Hz, 4H), 3.34 (d, J = 9.3 Hz, 4H), 2.28 (d, J = 13.6 Hz, 4H), 2.07 (d, J = 14.6 Hz, 4H) 1.08 (d, J = 2.4 Hz, 2H), 0.94~0.66 (m, 2H). |
| 93 | The compound was prepared according to the synthetic method of example 6: 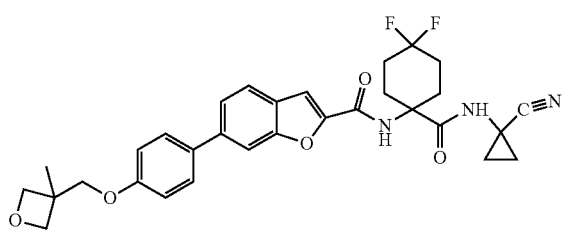 [SMILES: CC1(COc2ccc(-c3ccc4cc(C(=O)NC5(C(=O)NC6(C#N)CC6)CCC(F)(F)CC5)oc4c3)cc2)COC1]<br><br>MS (ESI, pos.ion) m/z: 564.2 (M + 1). |

| Example | Structure of compound and characteristic data thereof |
|---|---|
| 94 | The compound was prepared according to the synthetic method of example 54:<br>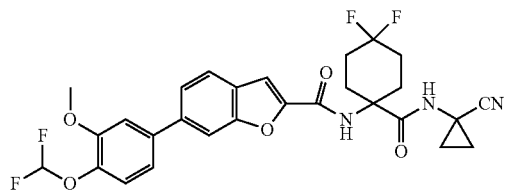 [SMILES: COc1cc(-c2ccc3cc(C(=O)NC4(C(=O)NC5(C#N)CC5)CCC(F)(F)CC4)oc3c2)ccc1OC(F)F]<br>MS (ESI, pos.ion) m/z: 560.2 (M + 1);<br>$^1$H NMR (400 MHz, DMSO-d$_6$) δ 8.77 (s, 1H), 8.50 (s, 1H), 8.03 (s, 1H), 7.88 (d, J = 8.1 Hz, 1H), 7.71 (d, J = 9.5 Hz, 2H), 7.49 (s, 1H), 7.35 (d, J = 8.3 Hz, 1H), 7.32-7.24 (m, 1H), 7.08 (t, J = 51.0 Hz, 1H), 3.96 (s, 3H), 2.22 (d, J = 5.7 Hz, 2H), 2.07 (d, J = 15.2 Hz, 6H), 1.46 (dd, J = 8.1, 5.4 Hz, 2H), 1.08 (dd, J = 8.2, 5.5 Hz, 2H). |
| 95 | The compound was prepared according to the synthetic method of example 1:<br>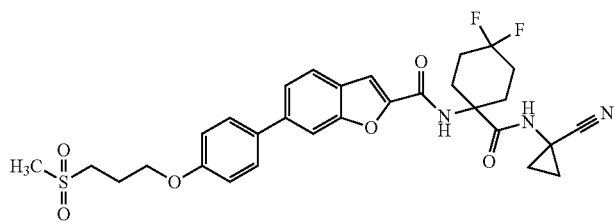 [SMILES: CS(=O)(=O)CCCOc1ccc(-c2ccc3cc(C(=O)NC4(C(=O)NC5(C#N)CC5)CCC(F)(F)CC4)oc3c2)cc1]<br>MS (ESI, pos.ion) m/z: 600.2 (M + 1). |
| 96 | The compound was prepared according to the synthetic method of example 1:<br>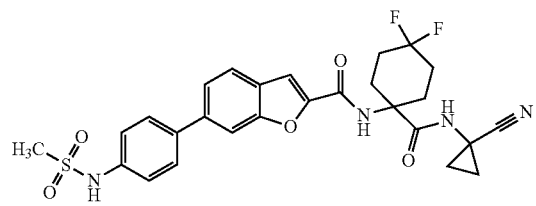 [SMILES: CS(=O)(=O)Nc1ccc(-c2ccc3cc(C(=O)NC4(C(=O)NC5(C#N)CC5)CCC(F)(F)CC4)oc3c2)cc1]<br>MS (ESI, pos.ion) m/z: 557.20 (M + 1);<br>$^1$H NMR (400 MHz, DMSO-d$_6$) δ 9.90 (s, 1H), 8.77 (s, 1H), 8.48 (s, 1H), 7.93 (s, 1H), 7.85 (d, J = 8.2 Hz, 1H), 7.76 (d, J = 8.7 Hz, 2H), 7.71 (s, 1H), 7.66 (dd, J = 8.3, 1.4 Hz, 1H), 7.33 (d, J = 8.7 Hz, 2H), 3.04 (s, 3H), 2.21 (s, 2H), 2.14-1.89 (m, 6H), 1.46 (dd, J = 8.2, 5.4 Hz, 2H), 1.07 (dd, J = 8.3, 5.6 Hz, 2H). |
| 97 | The compound was prepared according to the synthetic method of example 1:<br>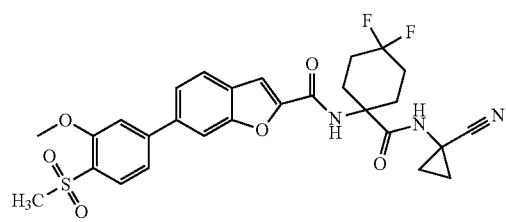 [SMILES: COc1cc(-c2ccc3cc(C(=O)NC4(C(=O)NC5(C#N)CC5)CCC(F)(F)CC4)oc3c2)ccc1S(C)(=O)=O]<br>MS (ESI, pos.ion) m/z: 572.20 (M + 1). |

| Example | Structure of compound and characteristic data thereof |
|---|---|
| 98 | The compound was prepared according to the synthetic method of example 1: 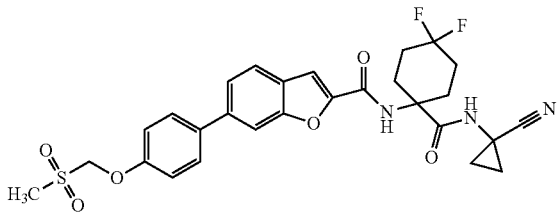 [SMILES: CS(=O)(=O)COc1ccc(-c2ccc3cc(C(=O)NC4(C(=O)NC5(C#N)CC5)CCC(F)(F)CC4)oc3c2)cc1] MS (ESI, pos.ion) m/z: 572.20 (M + 1); $^1$H NMR (600 MHz, DMSO-$d_6$) δ 8.78 (s, 1H), 8.49 (s, 1H), 7.94 (s, 1H), 7.85 (d, J = 8.2 Hz, 1H), 7.76 (d, J = 8.8 Hz, 1H), 7.76 (d, J = 8.8 Hz, 2H), 7.71 (s, 1H), 7.66 (d, J = 8.2 Hz, 1H), 7.28 (d, J = 8.8 Hz, 2H), 5.40 (s, 2H), 3.09 (s, 3H), 2.27-1.98 (m, 8H), 1.46 (dd, J = 8.0, 5.3 Hz, 2H), 1.07 (dd, J = 8.1, 5.5 Hz, 2H). |
| 99 | The compound was prepared according to the synthetic method of example 13: 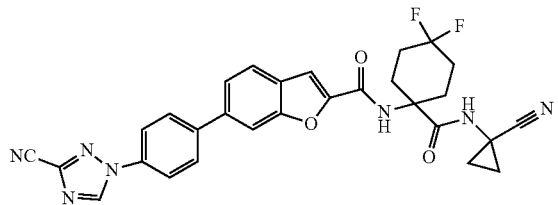 [SMILES: N#Cc1ncn(-c2ccc(-c3ccc4cc(C(=O)NC5(C(=O)NC6(C#N)CC6)CCC(F)(F)CC5)oc4c3)cc2)n1] MS (ESI, pos.ion) m/z: 556.20 (M + 1). |
| 100 | The compound was prepared according to the synthetic method of example 1: 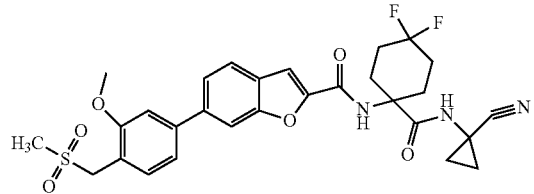 [SMILES: COc1cc(-c2ccc3cc(C(=O)NC4(C(=O)NC5(C#N)CC5)CCC(F)(F)CC4)oc3c2)ccc1CS(C)(=O)=O] MS (ESI, pos.ion) m/z: 586.20 (M + 1). |
| 101 | The compound was prepared according to the synthetic method of example 1: 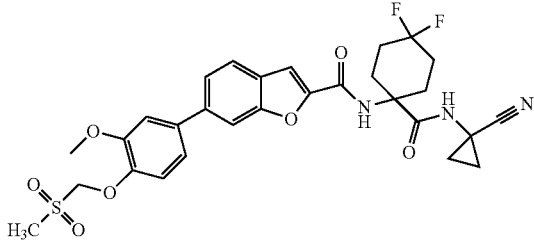 [SMILES: COc1cc(-c2ccc3cc(C(=O)NC4(C(=O)NC5(C#N)CC5)CCC(F)(F)CC4)oc3c2)ccc1OCS(C)(=O)=O] MS (ESI, pos.ion) m/z: 602.10 (M + 1). |

Biological Example 1 Assay Methods for Evaluating the Selectivity Towards Cathepsin Assay Method of Cathepsin K Inhibitory Activity In Vitro Using 45000-fold diluted cathepsin K solution and 10 μM Z-Phe-Arg-AMC as substrate, the test compound and cathepsin K solution were incubated at 25° C. for 15 min in a 15 μL reaction system according to the optimized experimental condition. Then the reaction kinetic slope in 15 min at 25° C. was determined, and IC$_{50}$ value of the compound against human cathepsin K was calculated.

Assay Method of Cathepsin B Inhibitory Activity In Vitro 0.01 ng/μL was the final concentration of Cathepsin B in the enzyme reaction, and Z-Phe-Arg-AMC with the final concentration of 10 μM was added into the reaction system as substrate, in the reaction system the test compound and enzyme had been incubated at 25° C. for 15 min. Then the reaction kinetic parameter in 10 min at 25° C. was determined, and $IC_{50}$ value of the test compound against human cathepsin B was calculated.

Assay Method of Cathepsin L Inhibitory Activity In Vitro 0.01 ng/μL was the final concentration of Cathepsin L in the enzyme reaction, and Z-Phe-Arg-AMC with the final concentration of 10 μM was added into the reaction system as substrate, in the reaction system the test compound and enzyme had been incubated at 25° C. for 15 min. Then the kinetic parameter in 10 min at 25° C. was determined, and $IC_{50}$ value of the test compound against human cathepsin L was calculated.

Assay Method of Cathepsin S Inhibitory Activity In Vitro 0.25 ng/L was the final concentration of Cathepsin S in the enzyme reaction, and Z-VVR-AMC with the final concentration of 20 μM was added into the reaction system as substrate, in the reaction system the test compound and enzyme had been incubated at 25° C. for 15 min. Then the reaction kinetic parameter in 10 min at 25° C. was determined, and $IC_{50}$ value of the test compound against human cathepsin S was calculated.

TABLE 2 the activity in vitro of the compound of the invention

| Example | Cat-K (nM) | Cat-B (nM) | Cat-L (nM) | Cat-S (nM) |
|---|---|---|---|---|
| Example 1 | 0.19 | 22 | 1500 | 1800 |
| Example 2 | 1.37 | 880 | >10000 | 4000 |
| Example 4 | 2.1 | 2500 | >10000 | >10000 |
| Example 5 | 1.1 | 78 | >10000 | 1600 |
| Example 6 | 3.1 | 750 | >10000 | 620 |
| Example 7 | 0.62 | 103 | >10000 | 2100 |
| Example 9 | 2.7 | 410 | >10000 | 3500 |
| Example 12 | 1.8 | 1400 | >10000 | 2500 |
| Example 14 | 0.38 | 86 | 3100 | 260 |
| Example 15 | 3.1 | 750 | >10000 | 620 |
| Example 18 | 2.2 | 806 | >10000 | 2800 |
| Example 19 | 2.0 | >10000 | >10000 | 2300 |
| Example 22 | 1.8 | 3100 | >10000 | 1800 |
| Example 27 | 0.83 | 2100 | >10000 | 400 |
| Example 28 | 1.2 | 2200 | >10000 | 1900 |
| Example 32 | 1.9 | 7600 | >10000 | 3300 |
| Example 33 | 2.95 | 2300 | >10000 | >10000 |
| Example 39 | 0.31 | 409 | >10000 | >10000 |
| Example 40 | 0.96 | 2222 | >10000 | >10000 |
| Example 43 | 0.69 | 440 | >10000 | 1337 |
| Example 44 | 2.35 | 7971 | >10000 | >10000 |
| Example 47 | 1.01 | >10000 | >10000 | >10000 |
| Example 53 | 1.4 | 2500 | >10000 | >10000 |
| Example 54 | 1.3 | 5000 | >10000 | >10000 |
| Example 57 | 1.3 | >10000 | >10000 | 416 |
| Example 61 | 1.26 | 423 | >10000 | >10000 |
| Example 62 | 1.37 | 880 | >10000 | 4000 |
| Example 63 | 1.6 | 1200 | >10000 | >10000 |
| Example 64 | 0.88 | 373 | >10000 | 637 |
| Example 65 | 1.3 | 697 | >10000 | >10000 |
| Example 66 | 0.81 | 540 | >10000 | 969 |
| Example 67 | 0.64 | 540 | >10000 | 990 |
| Example 68 | 0.79 | 360 | >10000 | 4075 |
| Example 70 | 8.6 | 530 | >10000 | 5056 |
| Example 71 | 2.1 | 290 | >10000 | >10000 |
| Example 72 | 0.50 | 727 | >10000 | >10000 |
| Example 73 | 3.04 | 1119 | >10000 | >10000 |
| Example 75 | 1.83 | 490 | >10000 | 4100 |
| Example 76 | 0.55 | 120 | >10000 | 340 |
| Example 77 | 0.67 | 178 | 10000 | 1047 |
| Example 78 | 0.95 | 282 | 10000 | 2067 |
| Example 79 | 0.72 | 330 | 7100 | 740 |
| Example 81 | 1.34 | 2400 | >10000 | 1600 |
| Example 82 | 2.7 | 200 | >10000 | 1500 |
| Example 83 | 2.2 | 1600 | >10000 | >10000 |
| Example 84 | 1.3 | 860 | >10000 | 9695 |

TABLE 2-continued the activity in vitro of the compound of the invention

| Example | Cat-K (nM) | Cat-B (nM) | Cat-L (nM) | Cat-S (nM) |
|---|---|---|---|---|
| Example 85 | 1.26 | 2200 | >10000 | 1500 |
| Example 86 | 1.1 | 6800 | >10000 | 4700 |
| Example 88 | 5.4 | 800 | >10000 | 2900 |
| Example 90 | 1.5 | 1200 | >10000 | 170 |
| Example 91 | 1.3 | 2500 | >10000 | >10000 |
| Example 92 | 1.4 | 6400 | >10000 | 2300 |
| Example 93 | 2.96 | 4300 | >10000 | >10000 |
| Example 94 | 2.4 | 4000 | >10000 | 6500 |
| Example 96 | 0.53 | 711 | >10000 | 2148 |
| Example 97 | 1.37 | 355 | >10000 | 2291 |
| Example 98 | 1.02 | ND | ND | ND |
| Example 100 | 0.56 | ND | ND | ND |
| Example 101 | 0.88 | ND | ND | ND |

ND denotes relevant assay test was not performed.

It is shown in table 2 that the compounds of the invention show the high inhibitory activity against cathepsin K, and the $IC_{50}$ values are in nM level, whereas the $IC_{50}$ values against other subtype of cathepsin such as cathepsin B, L and S are in μM level. The compounds of the invention show high selectivity on cathepsin K. The compounds of the invention not only show high inhibitory activity against cathepsin K, but also show high selectivity on cathepsin B, L and S, which are high homology to cathepsin K, and reduce the side effect of off-target resulting from the selectivity of the compounds, thereby it increases the possibility of developing cathepsin K inhibitors as drugs for the treatment of osteoporosis.

Biological Example 2 Pharmacokinetic Test of the Compounds of the Invention

1. Test Animal:

Healthy adult male SD rats were divided into groups with administration of compound by intravenous injection and oral gavage.

2. Preparation of the Test Compound Solution:

A certain amount of the test compound was weighed, and then mixed with 5% DMSO, 10% Kolliphor HS15 and 85% Saline to prepare a clarified solution.

3. Administration and Sample Collection:

All groups were fasted for 12 hours before administering, free drinking, and fed at 3 hours after administration. Each group was administered with test compound by vein intravenous (iv, 1 mg/kg) in the hind foot and oral gavage (po, 5 mg/kg) independently. The blood samples were collected from tail vein at the time point of 0 h, 0.083 h, 0.25 h, 0.5 h, 1 h, 2 h, 4 h, 6 h, 8 h and 24 h after administration and the amount of blood sample collected at each time point was about 200-400 μL. The blood samples collected at each time point were independently placed in K2EDTA anticoagulation tube and preserved in the incubator containing ice packs. The plasma of each blood sample above was separated by centrifugation at 4600 r/min at 4° C. for 5 min in 15 minutes after collecting. The plasma samples were preserved at −80° C. for measuring.

4. Analytical Method:

The content of the compound in plasma of rat after administration was determined by LC/MS/MS method. The test results were shown in table 3:

TABLE 3

| | | | | | | | | | |
|---|---|---|---|---|---|---|---|---|---|
| Pharmacokinetic activity the compound of the invention | | | | | | | | | |
| Example | administration route | F % | $T_{1/2}$ h | $T_{max}$ h | $C_{max}$ ng/ml | $AUC_{last}$ h * ng/ml | $AUC_{INF}$ h * ng/ml | Vss l/kg | CL ml/min/kg |
| 12 | iv | 60.56 | 7.84 | 0.08 | 1109.1 | 8150.1 | 9233 | 1.09 | 0.11 |
|  | po |  | 6.14 | 4.67 | 1886.2 | 25117 | 28409.68 | N/A | N/A |
| 43 | iv | 72.1 | 7.1 | 0.78 | 382 | 3800 | 4190 | 2.27 | 4.13 |
|  | po |  | 5.84 | 4.0 | 390 | 14300 | 15200 | N/A | N/A |
| 54 | iv | 46.87 | 5.59 | 0.33 | 1240 | 9280 | 9700 | 0.69 | 1.73 |
|  | po |  | 5.06 | 3 | 2260 | 21900 | 22700 | N/A | N/A |
| 18 | iv | 98.6 | 4.72 | 0.083 | 500 | 3210 | 3320 | 1.92 | 5.14 |
|  | po |  | 5.65 | 3.33 | 1380 | 18600 | 19900 | N/A | N/A |
| 53 | iv | 75.6 | 5.9 | 0.083 | 798 | 5470 | 5740 | 1.2 | 2.91 |
|  | po |  | 4.66 | 2.67 | 2230 | 21100 | 21700 | N/A | N/A |

CONCLUSION

It is shown from table 3 that compounds of the invention have high concentration in blood of rat, high exposure levels, high bioavailability and long half-life after oral administration, thereby that compounds of the invention have good pharmacokinetic proprieties.

What is claimed is:

1. A compound having Formula (I) or a stereoisomer, a tautomer, a geometric isomer, an N-oxide, or a pharmaceutically acceptable salt thereof,

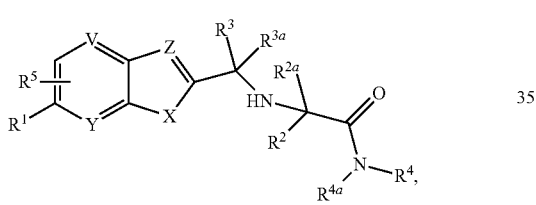

Formula (I)

wherein, $R^{4a}$ is H, $C_{1-6}$ alkyl or $C_{2-6}$ alkenyl, wherein each of the $C_{1-6}$ alkyl and $C_{2-6}$ alkenyl is independently and optionally substituted with 1, 2, 3, 4, 5 or 6 substituents selected from halogen, $C_{3-6}$ cycloalkyl, cyano, $C_{6-10}$ aryl, $C_{1-9}$ heteroaryl and $C_{2-9}$ heterocyclyl;

$R^4$ is $C_{1-6}$ alkyl, $-C(R^7)(R^{7a})-R^8$, $C_{3-9}$ heterocyclyl or $C_{2-6}$ alkenyl, wherein each of the $C_{1-6}$ alkyl and $C_{2-6}$ alkenyl is independently and optionally substituted with 1, 2, 3, 4, 5 or 6 substituents selected from halogen, $C_{3-6}$ cycloalkyl, cyano, $C_{6-10}$ aryl, $C_{1-9}$ heteroaryl or $C_{3-9}$ heterocyclyl;

or, $R^4$ and $R^{4a}$, together with the nitrogen atom to which they are attached, form a $C_{3-9}$ heterocyclyl group containing nitrogen, wherein the $C_{3-9}$ heterocyclyl is optionally substituted with 1, 2, 3, 4 or 5 substituents selected from $C_{1-6}$ alkyl, $C_{1-6}$ hydroxyalkyl, cyano, $-C(R^{10})(R^{10a})-C(=O)-N(R^{12})(R^{12a})$, $-C(=O)-OR^{8a}$, oxo (=O), $C_{1-6}$ haloalkyl and halogen;

each of $R^7$ and $R^{7a}$ is independently H, $C_{1-6}$ alkyl, $-C(R^{10})(R^{10a})-C(=O)-N(R^{12})(R^{12a})$, $-C(=O)-OR^{8a}$, $C_{2-9}$ heterocyclyl or $C_{2-6}$ alkenyl;

or, $R^7$ and $R^{7a}$, together with the carbon atom to which they are attached, form a $C_{3-6}$ carbocyclic ring or $C_{2-6}$ heterocyclic ring, wherein each of the $C_{3-6}$ carbocyclic ring and $C_{2-6}$ heterocyclic ring is independently and optionally substituted with 1, 2, 3, 4, 5 or 6 substituents selected from $C_{1-6}$ alkyl, $C_{1-6}$ hydroxyalkyl, $C_{1-6}$ haloalkyl, oxo (=O), cyano, $-C(=O)-OR^{8a}$ and halogen;

$R^8$ is H, $C_{1-6}$ alkyl, cyano, $-N(R^{12})(R^{12a})$, $-C(=O)-C(=O)-N(R^{12})(R^{12a})$, $-C(=O)-N(R^{12})(R^{12a})$, $-C(=O)-OR^{8a}$, $C_{3-6}$ heterocyclyl or $C_{2-6}$ alkenyl;

each $R^3$, $R^{3a}$, $R^2$, $R^{2a}$, $R^{8a}$, $R^{10}$, $R^{10a}$, $R^{12}$ and $R^{12a}$ is independently H or $C_{1-6}$ alkyl, wherein the $C_{1-6}$ alkyl is optionally substituted with 1, 2, 3, 4, 5 or 6 substituents selected from halogen, hydroxy, amino, carboxy, cyano, $C_{3-6}$ cycloalkyl, $C_{6-10}$ aryl, $C_{1-9}$ heteroaryl and $C_{2-9}$ heterocyclyl;

or, $R^2$ and $R^{2a}$, together with the carbon atom to which they are attached, form a $C_{3-9}$ carbocyclic ring or $C_{2-9}$ heterocyclic ring, wherein each of the $C_{3-9}$ carbocyclic ring and $C_{2-9}$ heterocyclic ring is independently and optionally substituted with 1, 2, 3, 4, 5 or 6 substituents selected from $C_{1-6}$ alkyl, $C_{2-6}$ alkenyl, $C_{1-6}$ hydroxyalkyl, $C_{1-6}$ haloalkyl, hydroxy, amino, carboxy, cyano and halogen;

or, $R^3$ and $R^{3a}$, together with the carbon atom to which they are attached, form a >C(=O), $C_{3-9}$ carbocyclic ring or $C_{2-9}$ heterocyclic ring, wherein each of the $C_{3-9}$ carbocyclic ring and $C_{2-9}$ heterocyclic ring is independently and optionally substituted with 1, 2, 3, 4, 5 or 6 substituents selected from $C_{1-6}$ alkyl, $C_{2-6}$ alkenyl, $C_{1-6}$ hydroxyalkyl, $C_{1-6}$ haloalkyl, hydroxy, amino, carboxy, cyano and halogen;

X is —O—, —S—, or —NH—;

each of V, Z and Y is independently $C(R^9)$ or N;

each $R^9$ is independently H, halogen, hydroxy, $C_{1-4}$ alkoxy, $C_{1-4}$ haloalkyl or $C_{1-4}$ alkyl, wherein each of the $C_{1-4}$ alkyl is optionally substituted with 1, 2, 3, 4, 5 or 6 substituents selected from halogen, $C_{3-6}$ cycloalkyl, $C_{6-10}$ aryl, $C_{1-9}$ heteroaryl and $C_{2-9}$ heterocyclyl;

$R^5$ is H, $C_{1-4}$ alkyl, $C_{2-6}$ alkenyl, $C_{2-6}$ alkynyl, $C_{1-6}$ alkoxy, F, Cl, Br, nitro, or $C_{1-4}$ haloalkyl;

$R^1$ is $C_{6-10}$ aryl, $C_{1-9}$ heteroaryl, $C_{3-12}$ cycloalkyl or $C_{2-12}$ heterocyclyl, wherein of the $R^1$ is independently and optionally substituted with 1, 2, 3, 4 or 5 $R^{1a}$ which are the same or different;

each $R^{1a}$ is independently H, $C_{1-6}$ alkyl, $C_{1-6}$ haloalkyl, halogen, cyano, oxo (=O), $C_{1-6}$ alkoxy, $C_{6-10}$ aryl, $C_{1-9}$ heteroaryl, $C_{3-12}$ cycloalkyl, $C_{2-12}$ heterocyclyl, $-OR^{14}$, $-SO_2-N(R^{13})(R^{13a})$, $-N(R^{13a})-SO_2-R^{11}$, $-N(R^{13})(R^{13a})$, $-C(=O)-C(=O)-N(R^{13})(R^{13a})$, $-C(=O)-N(R^{13})(R^{13a})$, $-C(=N-OH)(R^{14a})$, $-N(R^{13})-C(=O)R^{14a}$, $-C(=O)-OR^{14}$, $-C(=O)-R^{14a}$ or $-SO_2R^{14}$, wherein each of the $R^{1a}$ is independently and optionally substituted with 1, 2, 3, 4 or 5 $R^{1b}$ which are the same or different;

each $R^{1b}$ is independently H, $C_{1-6}$ alkyl, $C_{1-6}$ haloalkyl, $C_{2-6}$ alkenyl, $C_{2-6}$ alkynyl, $C_{1-6}$ alkoxy, halogen, nitro, cyano, hydroxy, oxo (=O), —$OR^{15}$, —$SO_2R^{15}$, —$N(R^{16})(R^{16a})$, —C(=O)—$N(R^{16})(R^{16a})$, $C_{6-10}$ aryl, $C_{1-9}$ heteroaryl, $C_{3-12}$ cycloalkyl or $C_{2-12}$ heterocyclyl, wherein each of the $R^{1b}$ is independently and optionally substituted with 1, 2, 3, 4 or 5 substituents selected from hydroxy, nitro, cyano, $C_{1-6}$ alkyl, $C_{1-6}$ haloalkyl, halogen, oxo (=O), $C_{1-6}$ alkoxy, $C_{6-10}$ aryl, $C_{1-9}$ heteroaryl, $C_{3-12}$ cycloalkyl, $C_{2-12}$ heterocyclyl and amino;

each $R^{16}$ and $R^{16a}$ is independently H, $C_{1-4}$ alkyl, $C_{2-6}$ alkenyl, $C_{2-6}$ alkynyl, $C_{6-10}$ aryl, $C_{1-9}$ heteroaryl, $C_{3-6}$ cycloalkyl, —$SO_2R^{17}$, —$N(R^{18})(R^{18a})$, $C_{1-4}$ haloalkyl or $C_{2-9}$ heterocyclyl;

each $R^{15}$, $R^{13}$, $R^{14}$, $R^{14a}$, $R^{17}$, $R^{18}$ and $R^{18a}$ is independently H, $C_{1-4}$ alkyl, $C_{1-4}$ haloalkyl, $C_{2-6}$ alkenyl, $C_{2-6}$ alkynyl, phenyl, 5- to 6-membered heteroaryl, $C_{3-6}$ cycloalkyl or 4- to 7-membered heterocyclyl, wherein each of the phenyl, 5- to 6-membered heteroaryl, $C_{3-6}$ cycloalkyl and 4- to 7-membered heterocyclyl is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

2. The compound of claim 1, wherein, $R^{4a}$ is H, methyl, ethyl, n-propyl, or isopropyl;

$R^4$ is methyl, ethyl, n-propyl, isopropyl, —$C(R^7)(R^{7a})$—$R^8$, 5- to 6-membered heterocyclyl or vinyl, wherein each of the methyl, ethyl, n-propyl, isopropyl and vinyl is independently and optionally substituted with 1, 2, 3, 4 or 5 substituents selected from halogen, $C_{3-6}$ cycloalkyl and cyano;

or, $R^4$ and $R^{42}$, together with the nitrogen atom to which they are attached, form one of the following sub-formulae:

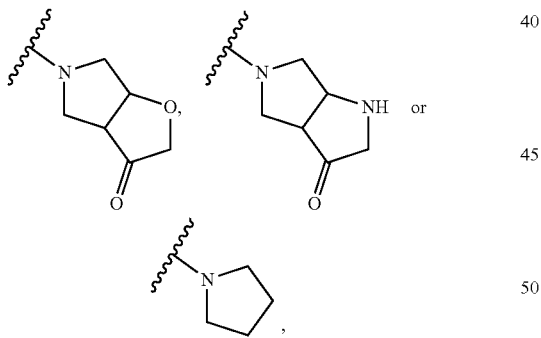

wherein each sub-formula is independently and optionally substituted with 1, 2, 3, 4 or 5 substituents selected from $C_{1-4}$ alkyl, $C_{1-4}$ hydroxyalkyl, oxo (=O), cyano, —$C(R^{10})(R^{10a})$—C(=O)—$N(R^{12})(R^{12a})$, —C(=O)—$OR^{8a}$, $C_{1-4}$ haloalkyl and halogen;

each of $R^7$ and $R^{7a}$ is independently H, $C_{1-4}$ alkyl, —$C(R^{10})(R^{10a})$—C(=O)—$N(R^{12})(R^{12a})$, —C(=O)—$OR^{8a}$, $C_{2-6}$ heterocyclyl or $C_{2-6}$ alkenyl;

or, $R^7$ and $R^{7a}$, together with the carbon atom to which they are attached, form a cyclopropyl, cyclopentyl, cyclobutyl, cyclohexyl, morpholinyl, piperidyl or pyrrolyl group, wherein each of the cyclopropyl, cyclopentyl, cyclobutyl, cyclohexyl, morpholinyl, piperidyl and pyrrolyl is independently and optionally substituted with 1, 2, 3, 4 or 5 substituents selected from $C_{1-4}$ alkyl, $C_{1-4}$ hydroxyalkyl, $C_{1-4}$ haloalkyl, oxo (=O), cyano, —C(=O)—$OR^{8a}$ and halogen;

$R^8$ is H, $C_{1-4}$ alkyl, cyano, —$N(R^{12})(R^{12a})$, —C(O)—C(=O)—$N(R^{12})(R^{12a})$, —C(=O)—$N(R^{12})(R^{12a})$, —C(=O)—$OR^{8a}$, $C_{3-6}$ heterocyclyl or $C_{2-6}$ alkenyl.

3. The compound of claim 1, wherein each $R^3$, $R^{3a}$, $R^2$, $R^{2a}$, $R^{8a}$, $R^{10}$, $R^{10a}$, $R^{12}$ and $R^{12a}$ is independently H, methyl, ethyl, n-propyl, isopropyl, 1-methylpropyl, 2-methylpropyl or tort-butyl, wherein each of the methyl, ethyl, n-propyl, isopropyl, 1-methylpropyl, 2-methylpropyl and text-butyl is independently and optionally substituted with 1, 2, 3, 4, 5 or 6 substituents selected from F, Cl, Br, hydroxy, amino, carboxy, cyano, cyclohexyl, cyclopentyl, cyclobutyl, cyclopropyl, phenyl, pyridyl, thiazolyl, diazolyl, piperidyl, furyl, tetrahydrofuryl, azetanyl, oxetanyl and morpholinyl;

or, $R^2$ and $R^{2a}$, together with the carbon atom to which they are attached, form a cyclohexyl, cyclopentyl, cyclobutyl, cyclopropyl, cycloheptyl, piperidyl, pyrrolidyl, piperazinyl, tetrahydropyranyl, morpholinyl or tetrahydrofuryl group, wherein each of the cyclohexyl, cyclopentyl, cyclobutyl, cyclopropyl, cycloheptyl, piperidyl, pyrrolidyl, piperazinyl, tetrahydropyranyl, morpholinyl and tetrahydrofuryl is independently and optionally substituted with 1, 2, 3, 4 or 5 substituents selected from $C_{1-4}$ alkyl, $C_{2-4}$ alkenyl, $C_{1-4}$ hydroxyalkyl, $C_{1-4}$ haloalkyl, hydroxy, amino, carboxy, cyano, F, Cl and Br;

or, $R^3$ and $R^{3a}$, together with the carbon atom to which they are attached, form a >C(=O), cyclohexyl, cyclopentyl, cyclobutyl, cyclopropyl, cycloheptyl, piperidyl, pyrrolidyl, piperazinyl, tetrahydropyranyl, morpholinyl or tetrahydrofuryl group, wherein each of the cyclohexyl, cyclopentyl, cyclobutyl, cyclopropyl, cycloheptyl, piperidyl, pyrrolidyl, piperazinyl, tetrahydropyranyl, morpholinyl and tetrahydrofuryl is independently and optionally substituted with 1, 2, 3, 4 or 5 substituents selected from $C_{1-4}$ alkyl, $C_{1-4}$ hydroxyalkyl, $C_{1-4}$ haloalkyl, hydroxy, amino, carboxy, cyano and halogen.

4. The compound of claim 1, $R^1$ is one of the following sub-formulae:

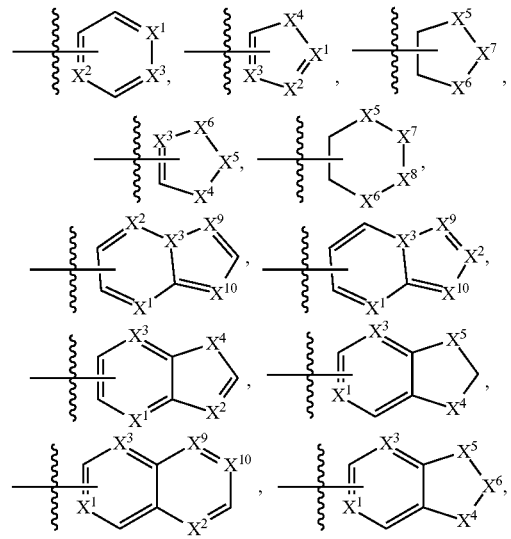

-continued

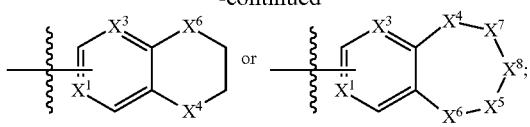

wherein each $X^1$, $X^2$, $X^3$, $X^9$ and $X^{10}$ is independently CH or N;

each $X^4$, $X^5$, $X^6$, $X^7$ and $X^8$ is independently —CH$_2$—, —C(=O)—, —O—, —S—, —S(=O)—, —S(=O)$_2$— or —NH—;

$R^1$ is independently and optionally substituted with 1, 2, 3, 4 or 5 $R^{1a}$ which are the same or different;

each $R^{1a}$ is independently H, C$_{1-4}$ alkyl, C$_{1-4}$ haloalkyl, halogen, cyano, oxo (=O), C$_{1-4}$ alkoxy, —SR$^{14}$, —OR$^{14}$, —SO$_2$—N(R$^{13}$)(R$^{13a}$), —N(R$^{13a}$)—SO$_2$—R$^{14}$, —N(R$^{13}$)(R$^{13a}$), —C(=O)—C(=O)—N(R$^{13}$)(R$^{13a}$), —C(=O)—N(R$^{13}$)(R$^{13a}$), —C(=N—OH)(R$^{14a}$), —N(R$^{13}$)—C(=O)R$^{14a}$, —C(=O)—OR$^{14}$, —C(=O)—R$^{14a}$ or —SO$_2$R$^{14}$, or one of the following sub-formulae:

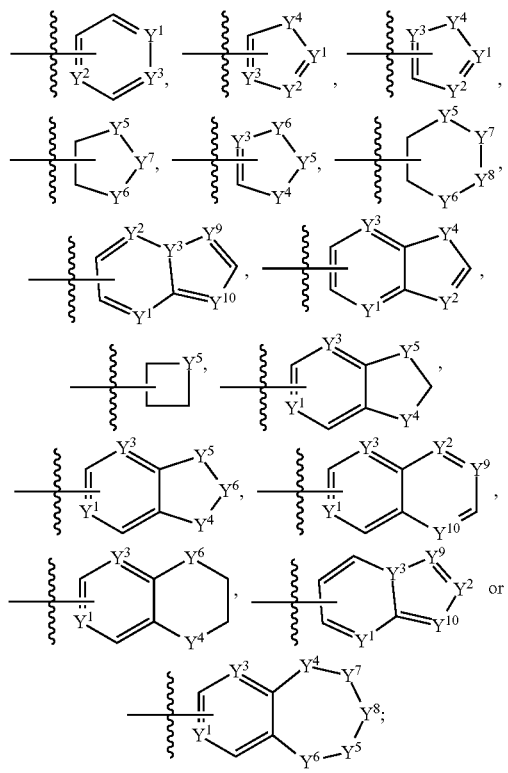

wherein each $Y^1$, $Y^2$, $Y^3$, $Y^9$ and $Y^{10}$ is independently CH or N;

each $Y^4$, $Y^5$, $Y^6$, $Y^7$ and $Y^8$ is independently —CH$_2$—, —C(=O)—, —O—, —S—, —S(=O)—, —S(=O)$_2$— or —NH—;

each $R^{1a}$ in independently and optionally substituted with 1, 2, 3, 4 or 5 $R^{1b}$ which are the same or different;

each $R^{1b}$ is independently H, C$_{1-4}$ alkyl, C$_{1-4}$ haloalkyl, C$_{2-6}$ alkenyl, C$_{2-6}$ alkynyl, C$_{1-4}$ alkoxy, halogen, nitro, cyano, hydroxy, oxo (=O), —OR$^{15}$, —SO$_2$R$^{15}$, —N(R$^{16}$)(R$^{16a}$), —C(=O)—N(R$^{16}$)(R$^{16a}$), or one of the following sub-formulae:

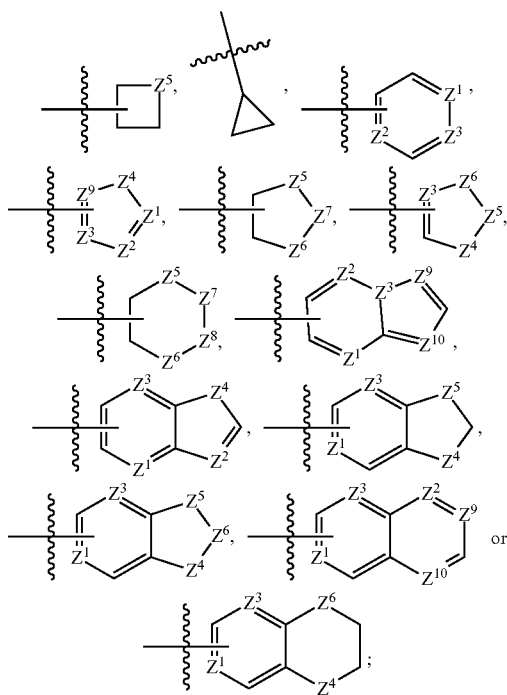

wherein each $Z^1$, $Z^2$, $Z^3$, $Z^9$ and $Z^{10}$ is independently CH or N;

each $Z^4$, $Z^5$, $Z^6$, $Z^7$ and $Z^8$ is independently —CH$_2$—, —C(=O)—, —O—, —S—, —S(=O)—, —S(=O)$_2$— or —NH—;

each $R^{1b}$ is independently and optionally substituted with 1, 2, 3, 4 or 5 substituents selected from hydroxy, nitro, cyano, C$_{1-4}$ alkyl, C$_{1-4}$ haloalkyl, halogen, oxo (=O), C$_{1-4}$ alkoxy, phenyl, 5- to 6-membered heteroaryl, 4- to 7-membered cycloalkyl, 4- to 7-membered heterocyclyl and amino;

each $R^{16}$ and $R^{16a}$ is independently H, C$_{1-4}$ alkyl, C$_{2-6}$ alkenyl, C$_{2-6}$ alkynyl, C$_{6-10}$ aryl, C$_{1-9}$ heteroaryl, C$_{3-6}$ cycloalkyl, —SO$_2$R$^{17}$, —N(R$^{18}$)(R$^{18a}$), C$_{1-4}$ haloalkyl or C$_{2-6}$ heterocyclyl;

each $R^{15}$, $R^{13}$, $R^{13a}$, $R^{14}$, $R^{14a}$, $R^{17}$, $R^{18}$ and $R^{18a}$ is independently H, C$_{1-4}$ alkyl, C$_{1-4}$ haloalkyl, C$_{2-6}$ alkenyl, C$_{2-6}$ alkynyl, phenyl, 5- to 6 membered heteroaryl, C$_{3-6}$ cycloalkyl or 4- to 6-membered heterocyclyl, wherein each of the phenyl, 5- to 6-membered heteroaryl, cycloalkyl and 4- to 6-membered heterocyclyl is independently and optionally substituted with 1, 2, 3, 4 or 5 substituents selected from F, Br, cyano, hydroxy, trifluoromethyl, C$_{1-4}$ alkyl, C$_{1-4}$ alkoxy and 2,2-difluoroethyl.

5. The compound of claim 1, wherein $R^1$ is one of the following sub-formulae:

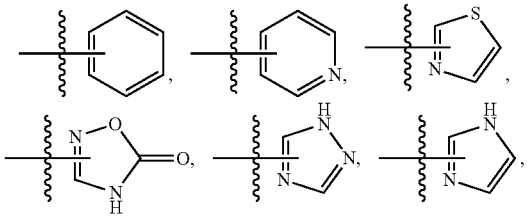

-continued

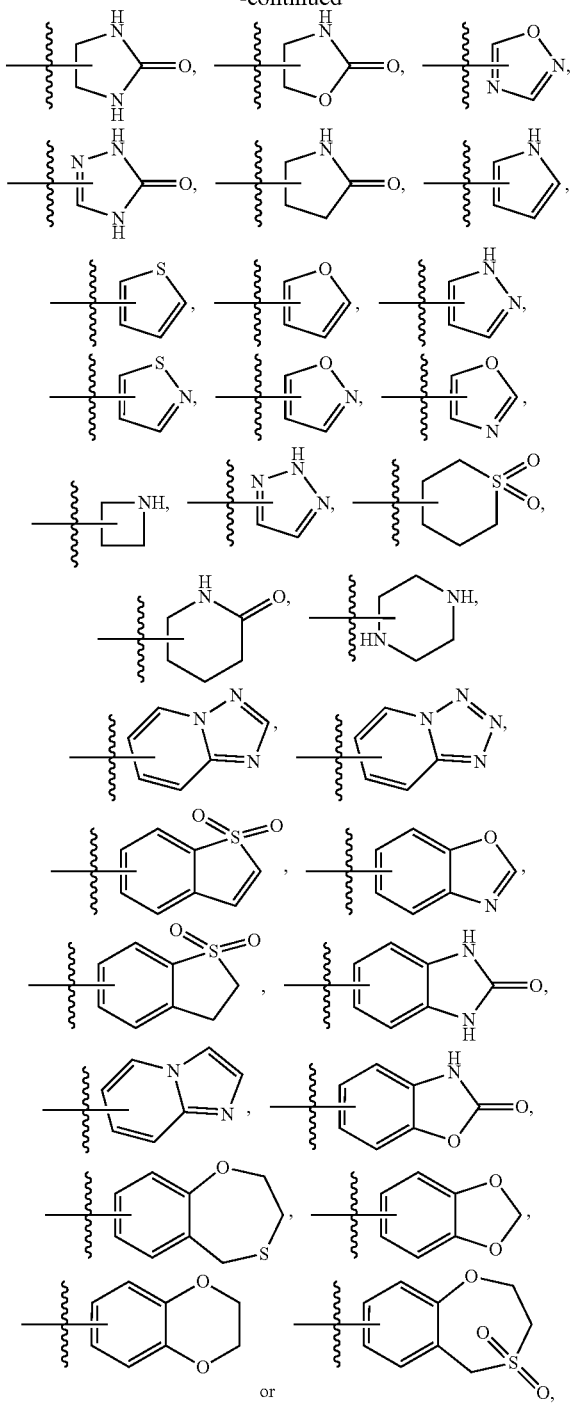

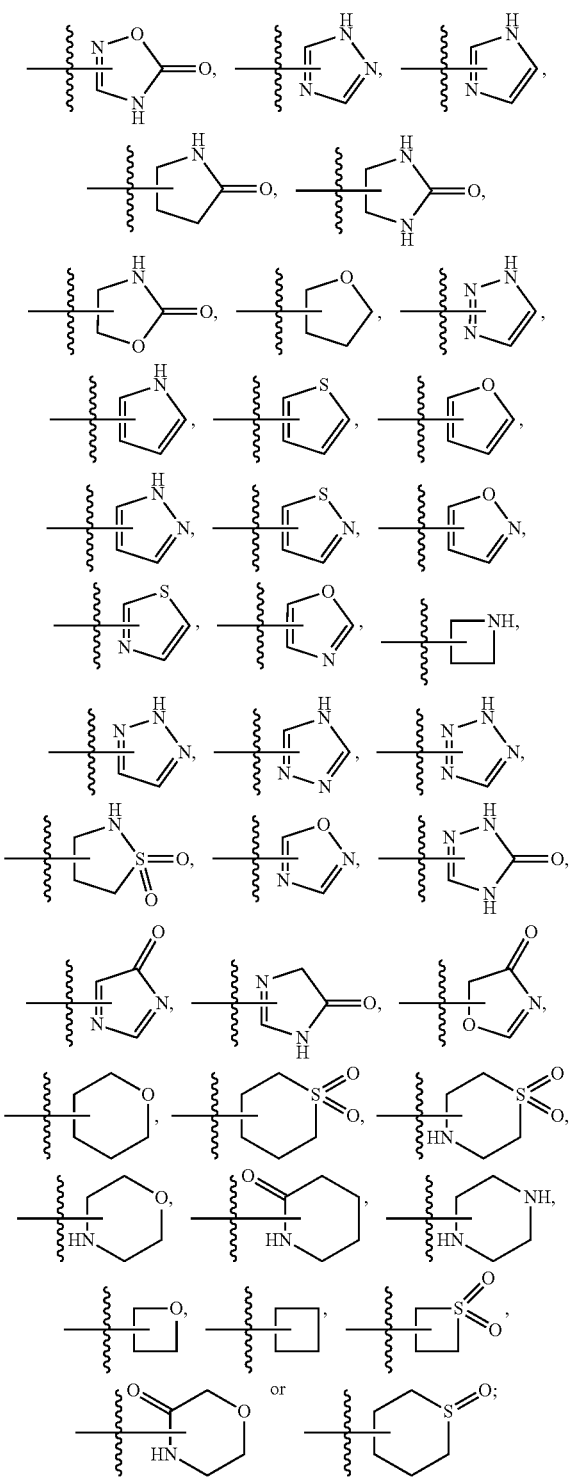

wherein each $R^1$ is independently and optionally substituted with 1, 2, 3, 4 or 5 $R^{1a}$ which are the same or different;

each $R^{1a}$ is independently H, ethyl, methyl, n-propyl, i-propyl, n-butyl, t-butyl, cyano, trifluoromethyl, 2,2-difluoroethyl, 3,3,3-trifluoropropyl, F, Cl, Br, oxo (=O), methoxy, n-propoxy, ethoxy, t-butoxy, 2-methylpropoxy, i-propoxy, —$SR^{14}$, —$OR^{14}$, —$SO_2$—N($R^{13}$)($R^{13a}$), —N($R^{13a}$)—$SO_2$—$R^{14}$, —N($R^{13}$)($R^{13a}$), —C(=O)—C(=O)—N($R^{13}$)($R^{13a}$), —C(=O)—N($R^{13}$)($R^{13a}$), —C(=N—OH)($R^{14a}$), —N($R^{13}$)—C(=O)$R^{14a}$, —C(=O)—$OR^{14}$, —C(=O)$R^{14a}$, —$SO_2R^{14}$, or one of the following sub-formulae:

wherein each $R^{1a}$ is independently and optionally substituted with 1, 2, 3, 4 or 5 $R^{1b}$ which are the same or different;

each $R^{1b}$ is independently H, methyl, ethyl, n-propyl, i-propyl, n-butyl, t-butyl, cyclobutyl, cyclopropyl, cyclohexyl, cyclopentyl, haloalkyl, $C_{2-6}$ alkenyl, $C_{2-6}$ alkenyl, methoxy, F, Cl, Br, nitro, cyano, hydroxy, oxo (=O), —$OR^{15}$, —$SO_2R^{15}$,

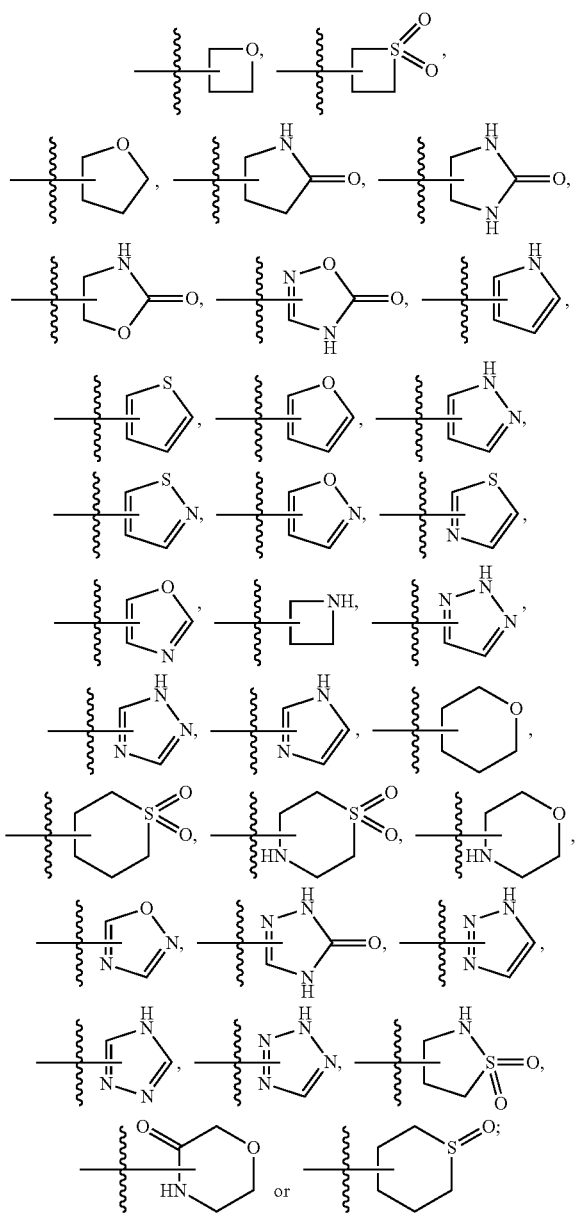

wherein each $R^{1b}$ is independently and optionally substituted with 1, 2, 3, 4 or 5 substituents selected from hydroxy, nitro, cyano, methyl, ethyl, n-propyl, i-propyl, n-butyl, t-butyl, $C_{1-4}$ haloalkyl, F, Cl, Br, oxo (=O), alkoxy, phenyl, pyridyl, thiazolyl, thienyl, diazolyl, triazolyl, tetrazolyl, epoxypropyl, tetrahydrofuryl, tetrahydropyranyl, morpholinyl, piperdyl, cyclobutyl, cyclopentyl, dioxanyl, cyclohexyl and amino;

each $R^{16}$ and $R^{16a}$ is independently H, $C_{1-4}$ alkyl, $C_{2-6}$ alkenyl, $C_{2-6}$ alkynyl, phenyl, $-SO_2R^{17}$, $-N(R^{18})(R^{18a})$, $C_{1-4}$ haloalkyl, cyclopropyl, cyclohexyl,

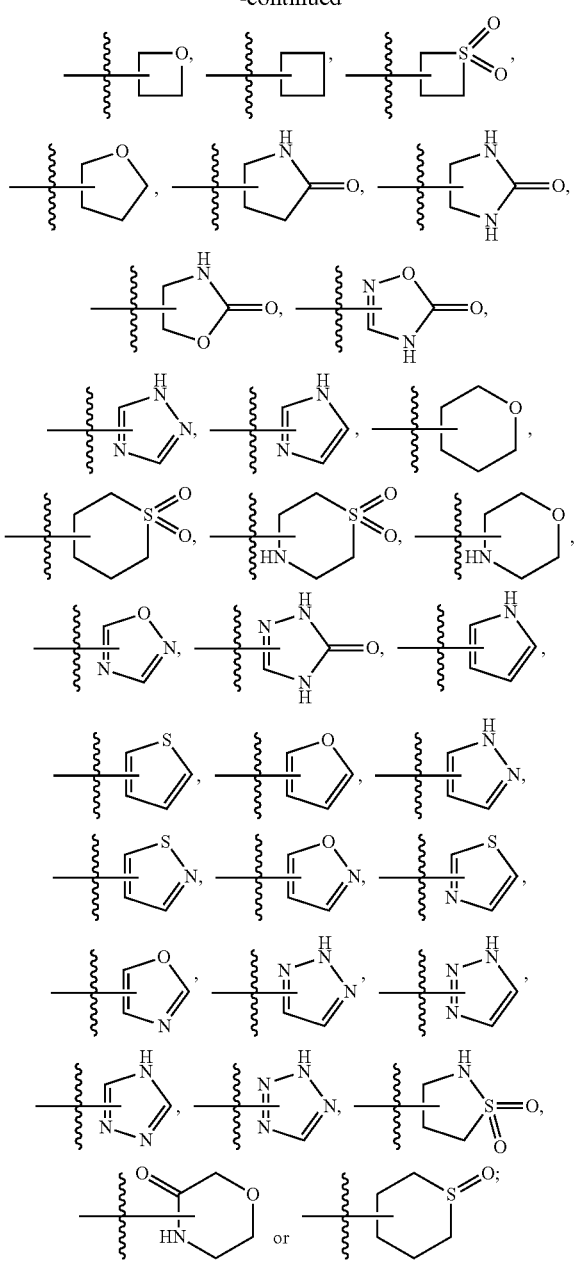

each $R^{15}$, $R^{13}$, $R^{13a}$, $R^{14}$, $R^{14a}$, $R^{17}$, $R^{18}$ and $R^{18a}$ is independently H, methyl, ethyl, n-propyl, i-propyl, n-butyl, 2-methylpropyl, t-butyl, trifluoromethyl, difluoromethyl, 2,2-difluoroethyl, 3,3,3-trifluoropropyl, phenyl, cyclopropyl, cyclohexyl,

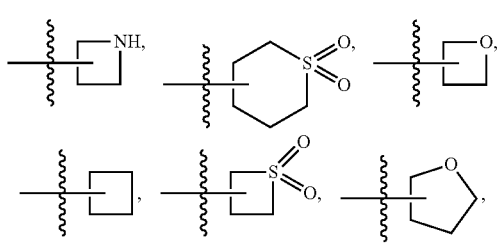

-continued

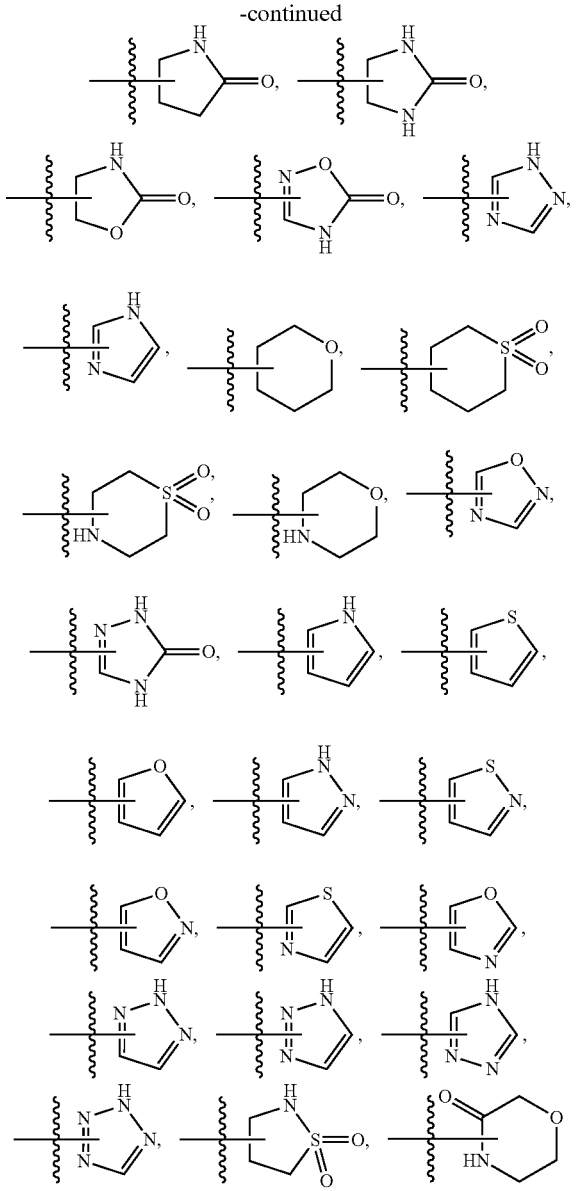

or 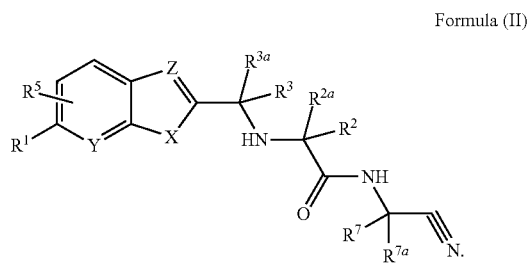

wherein each sub-formula is independently and optionally substituted with 1, 2, 3, 4 or 5 substituents selected from F, Cl, Br, cyano, hydroxy, trifluoromethyl, $C_{1-4}$ alkyl, $C_{1-4}$ alkoxy and 2,2-difluoroethyl.

6. The compound of claim 1 having Formula (II) or a stereoisomer, a tautomer, a geometric isomer, an N-oxide, or a pharmaceutically acceptable salt thereof,

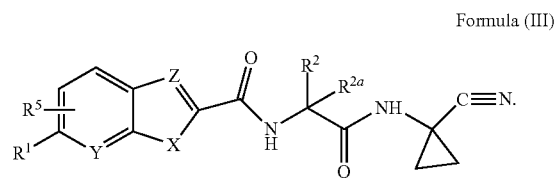

Formula (II)

7. The compound of claim 1 having Formula (III) or a stereoisomer, a tautomer, a geometric isomer, an N-oxide, or a pharmaceutically acceptable salt thereof,

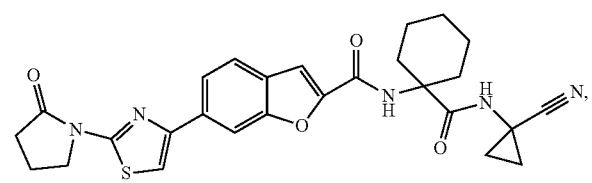

Formula (III)

8. The compound of claim 1 having one of the following structures or a stereoisomer, a tautomer, a geometric isomer, an N-oxide, or a pharmaceutically acceptable salt thereof, (1)

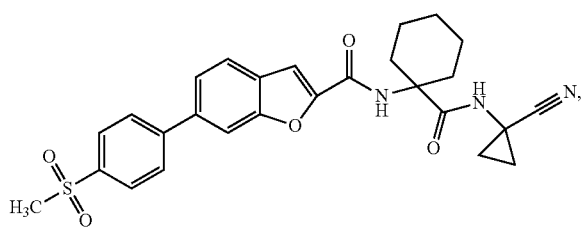

(2)

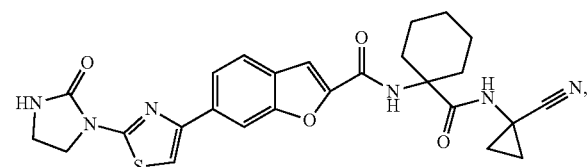

(3)

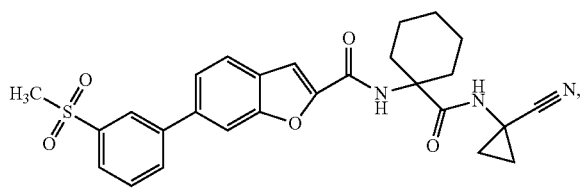

(4)

-continued
(5)
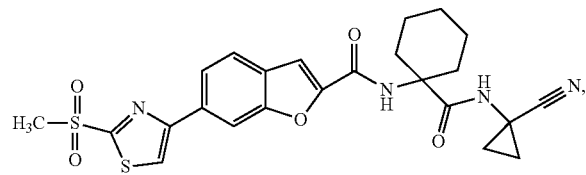
(6)
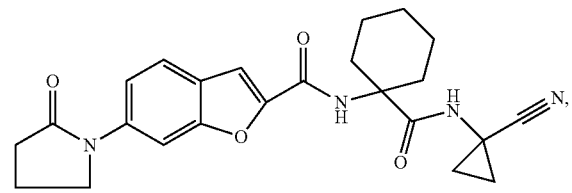
(7)
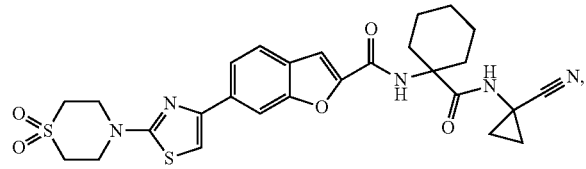
(8)
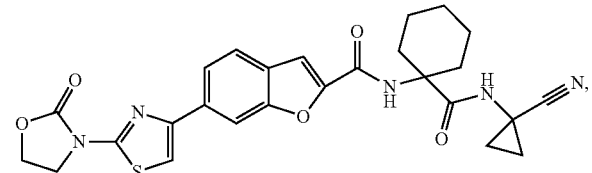
(9)
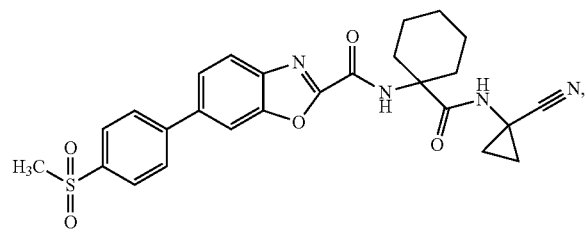
(10)
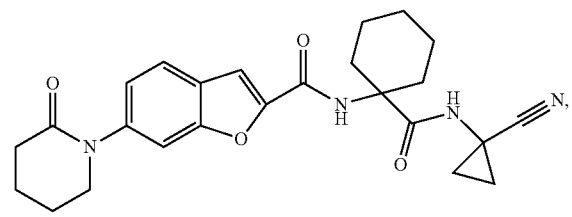
(11)
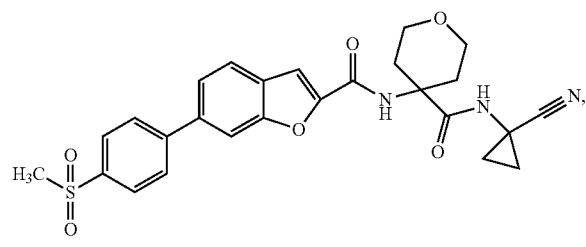
(12)
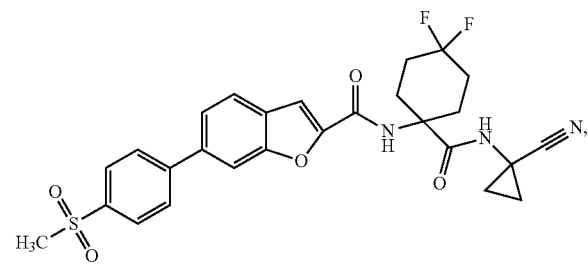
(13)
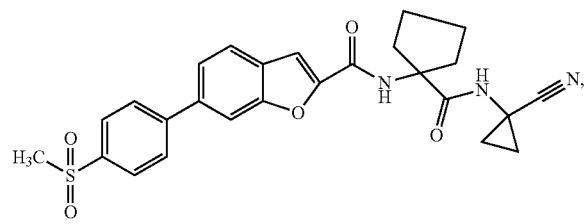
(14)
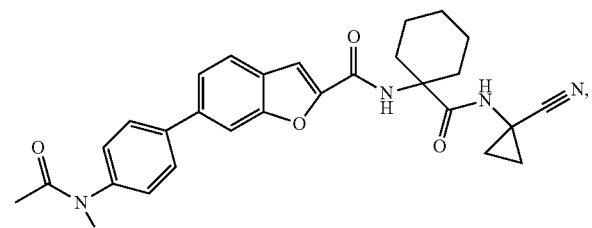
(15)
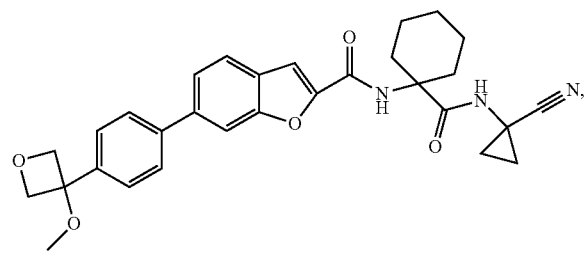
(16)
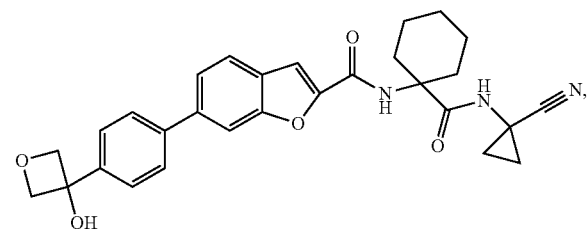

-continued
(17)
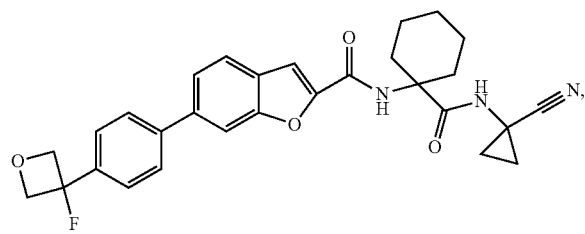
(18)
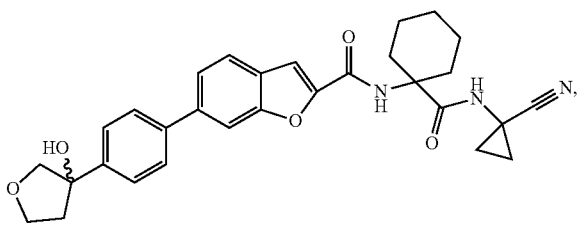
(19)
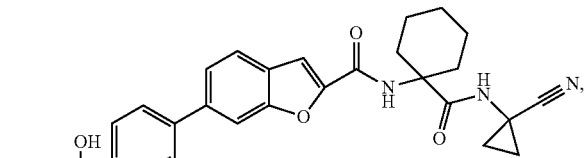
(20)
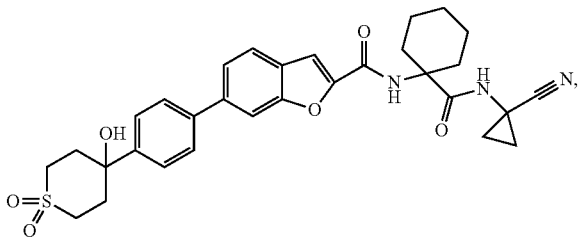
(21)
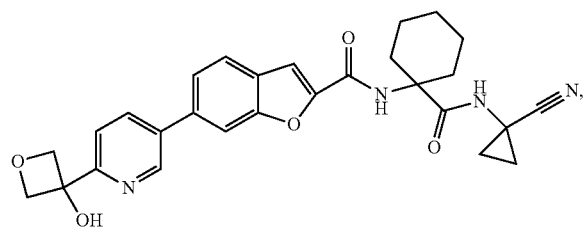
(22)
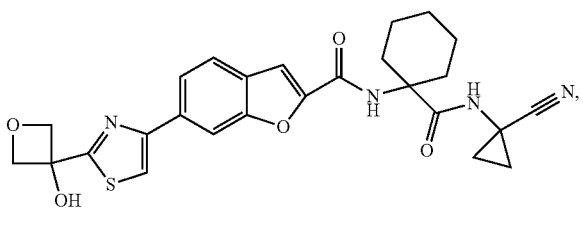
(23)
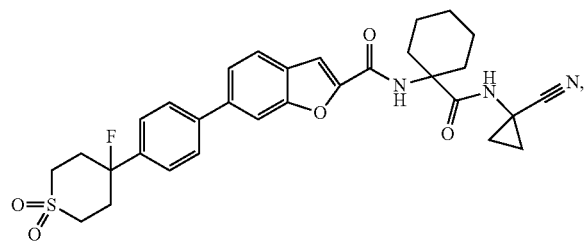
(24)
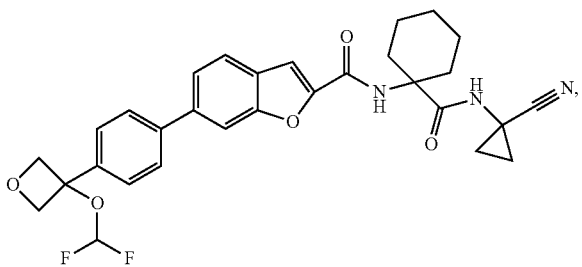
(25)
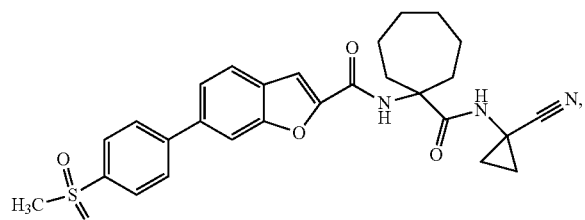
(26)
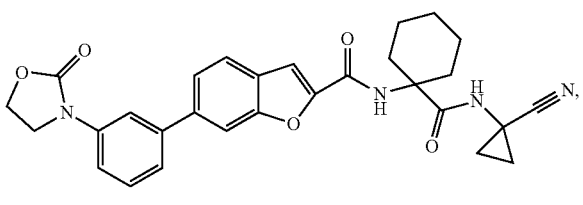
(27)
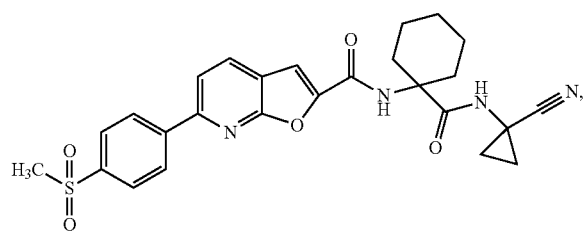
(28)
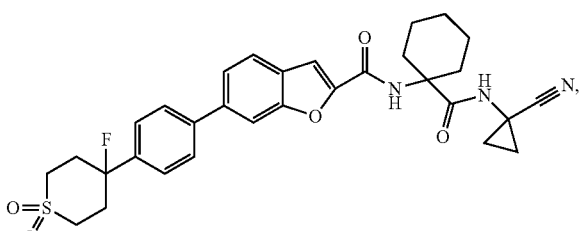

-continued
(29)
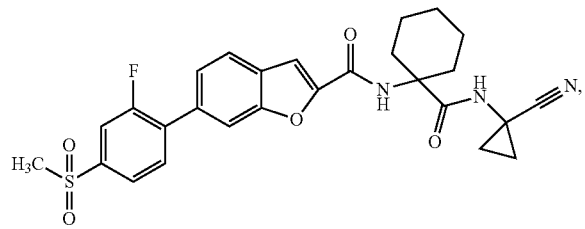
(30)
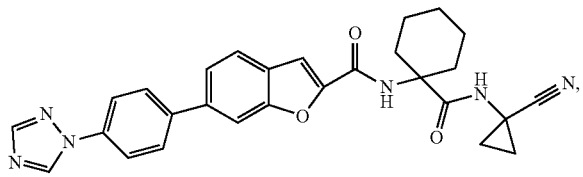
(31)
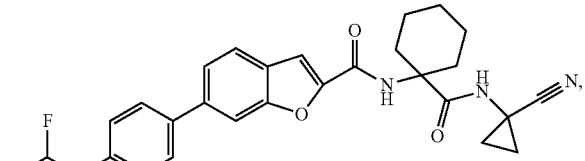
(32)
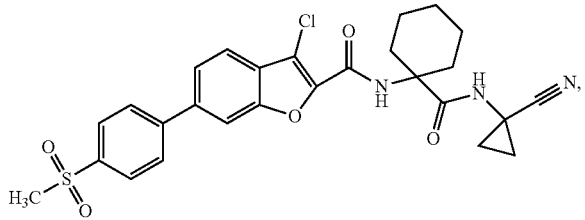
(33)
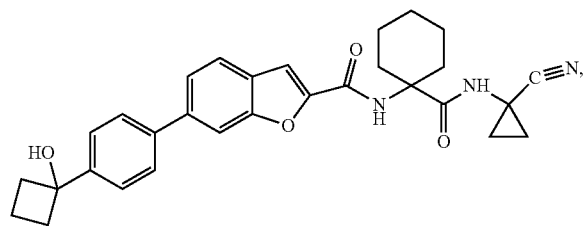
(34)
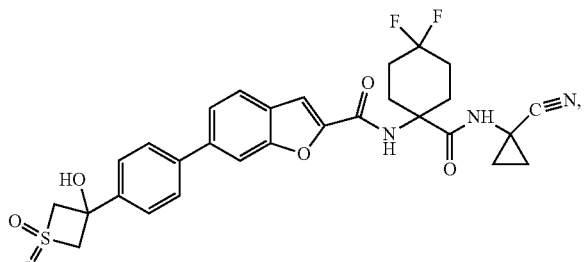
(35)
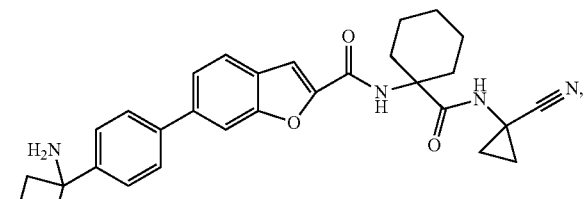
(36)
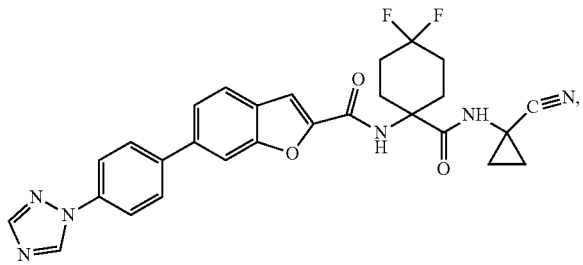
(37)
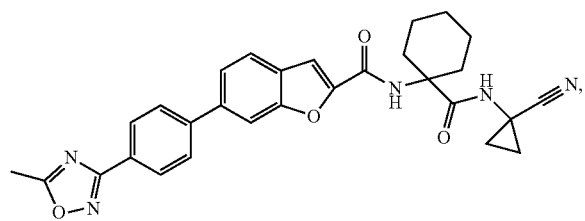
(38)
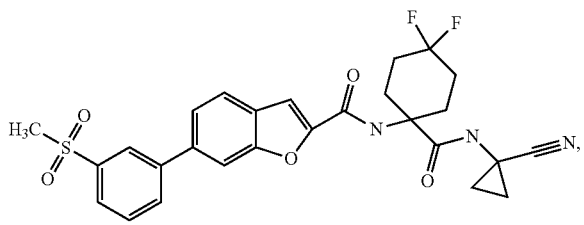
(39)
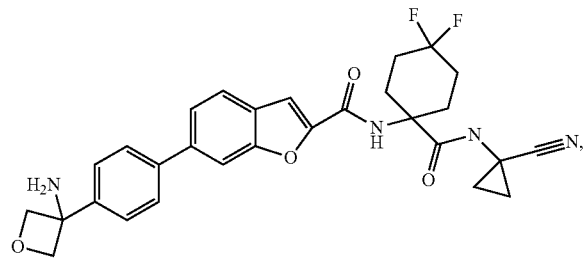
(40)
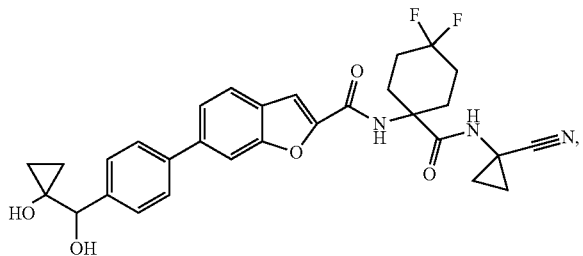

-continued
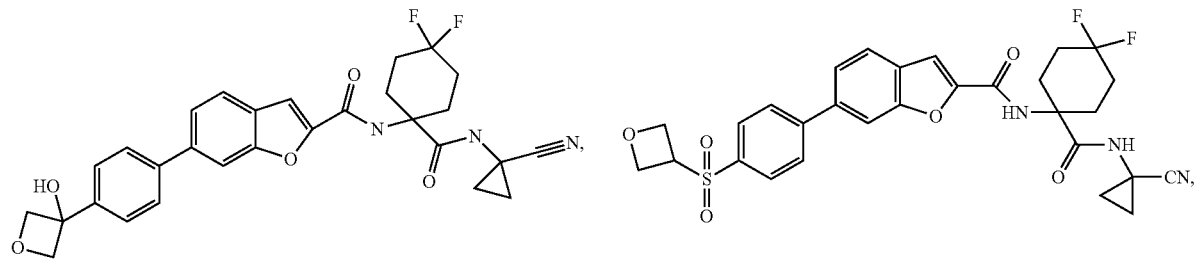
(41) (42)
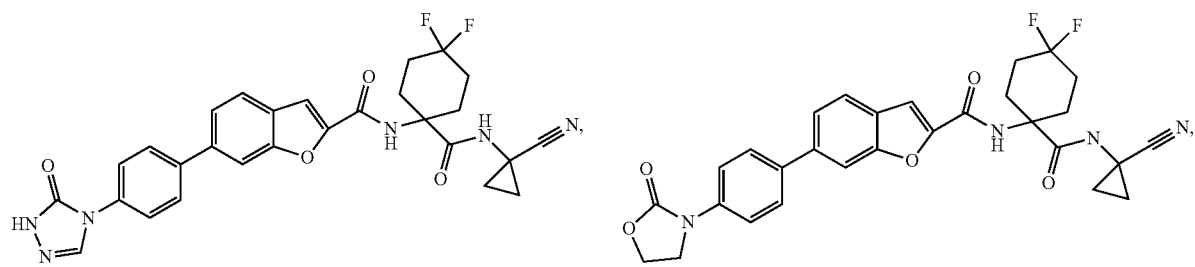
(43) (44)
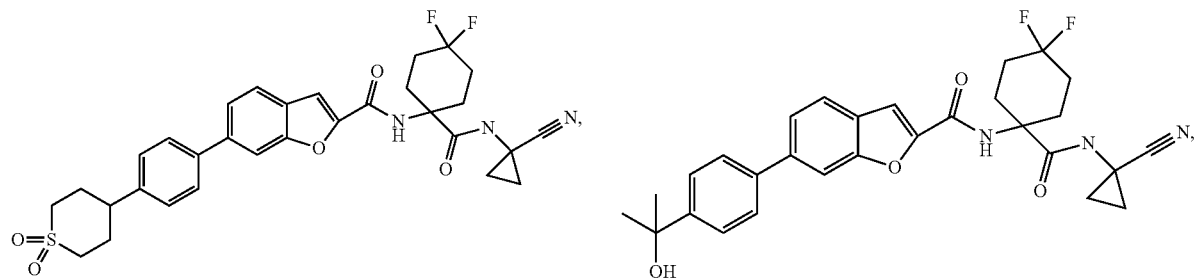
(45) (46)
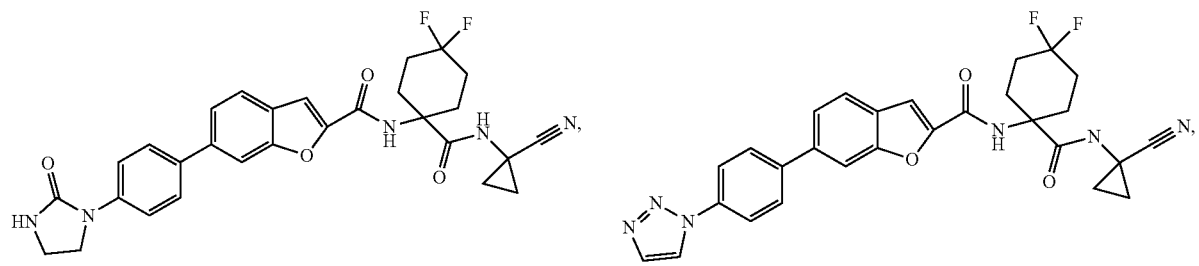
(47) (48)
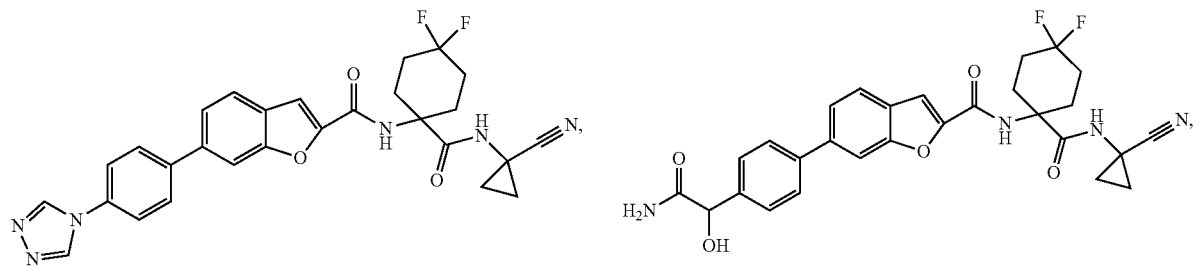
(49) (50)

-continued
(51)
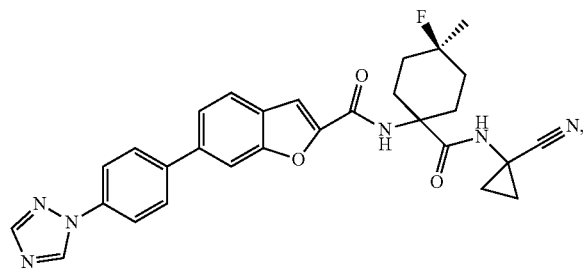
(52)
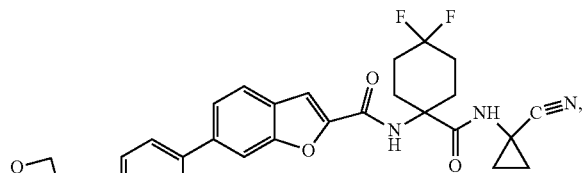
(53)
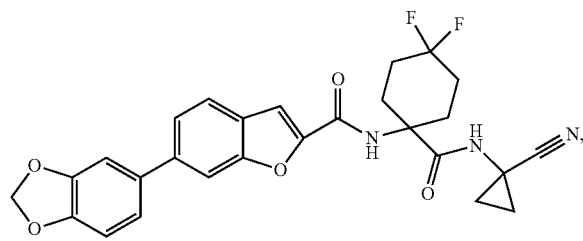
(54)
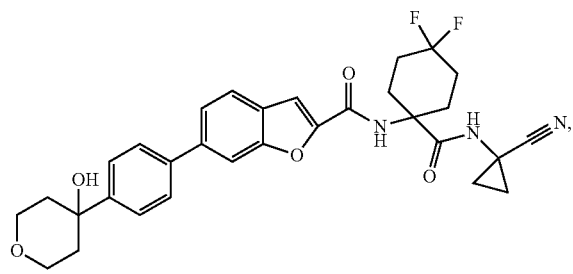
(55)
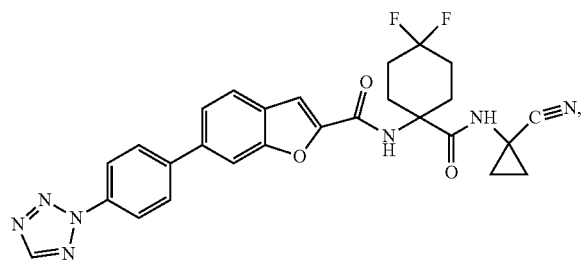
(56)
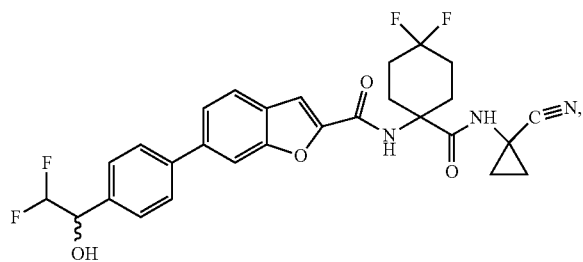
(57)
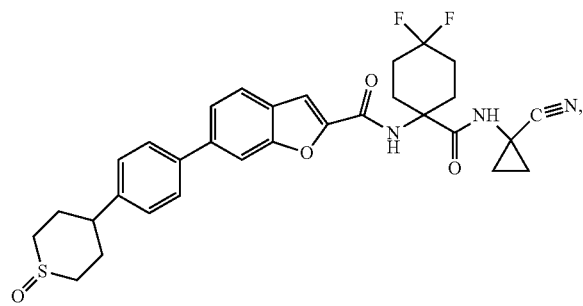
(58)
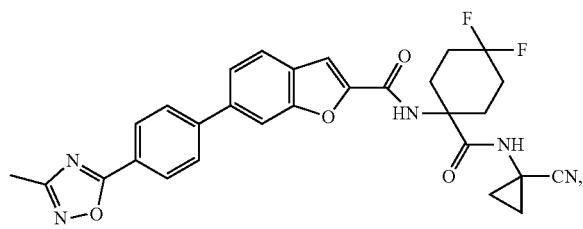
(59)
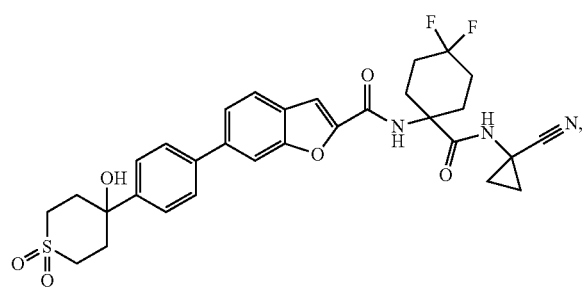
(60)
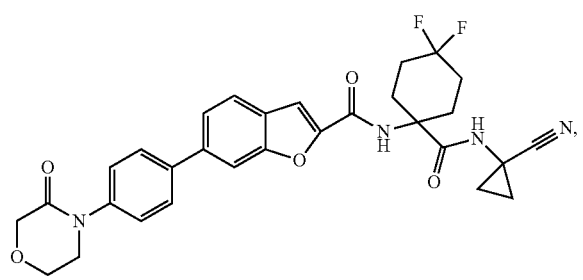

-continued
(61)
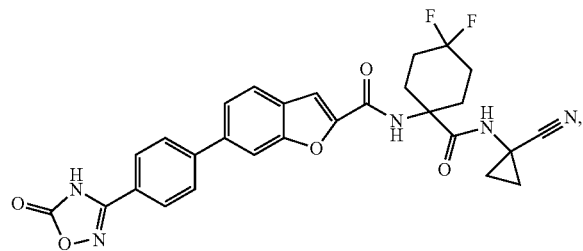
(62)
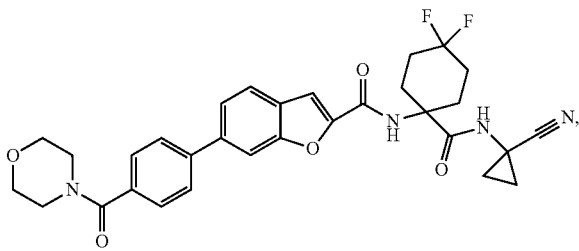
(63)
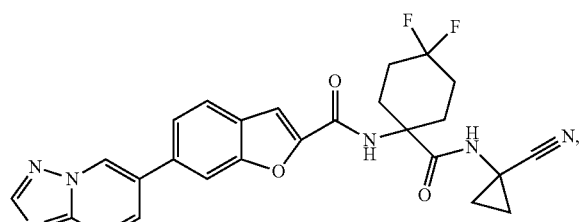
(64)
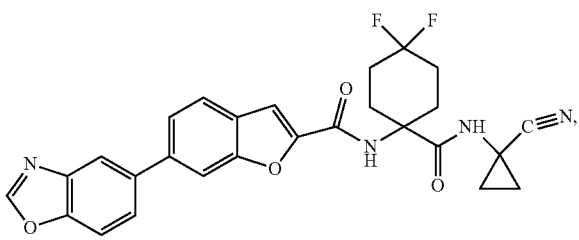
(65)
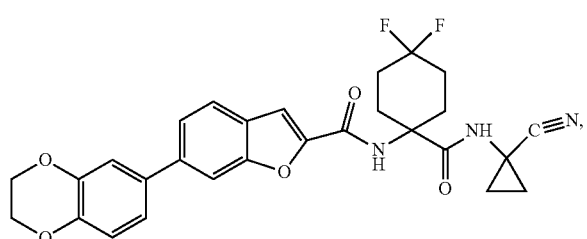
(66)
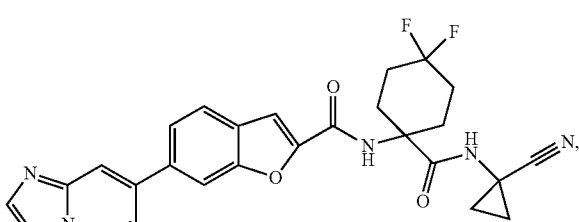
(67)
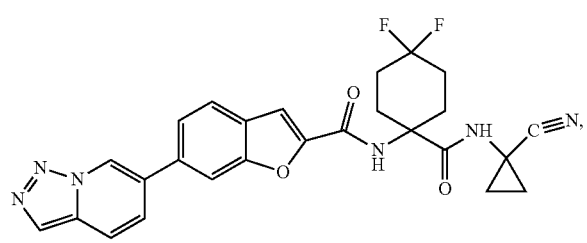
(68)
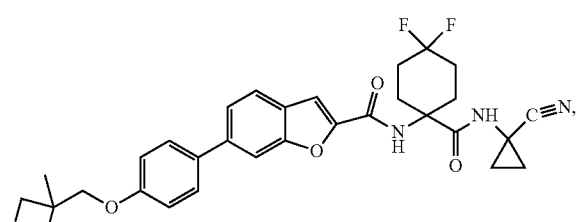
(69)
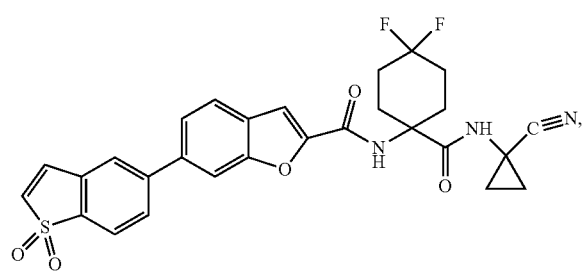
(70)
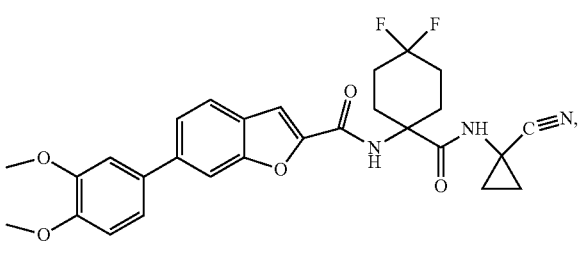
(71)
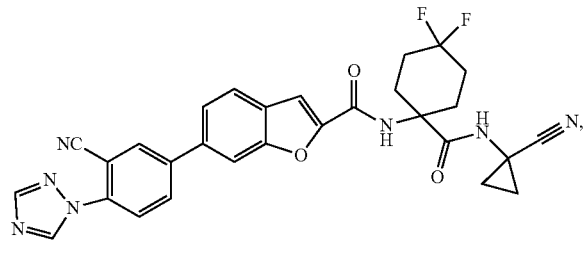
(72)
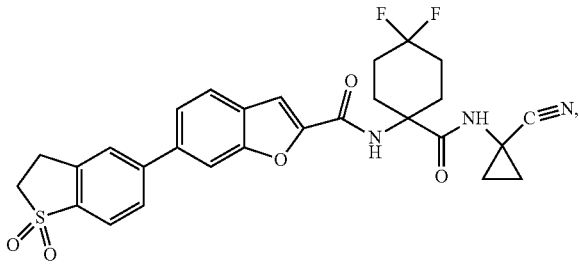

-continued
(73) 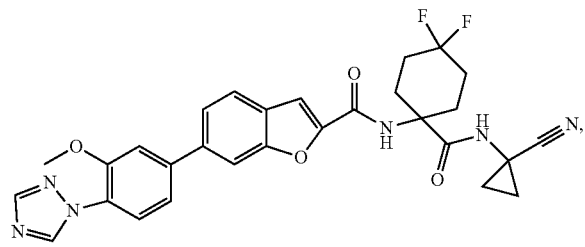
(74) 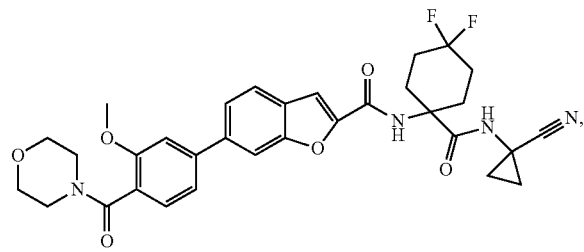
(75) 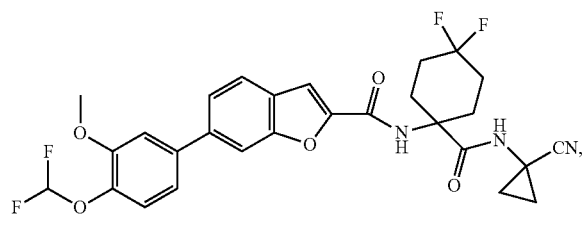
(76) 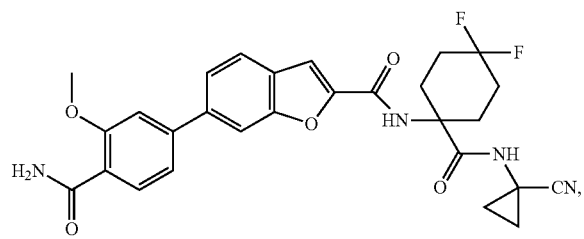
(77) 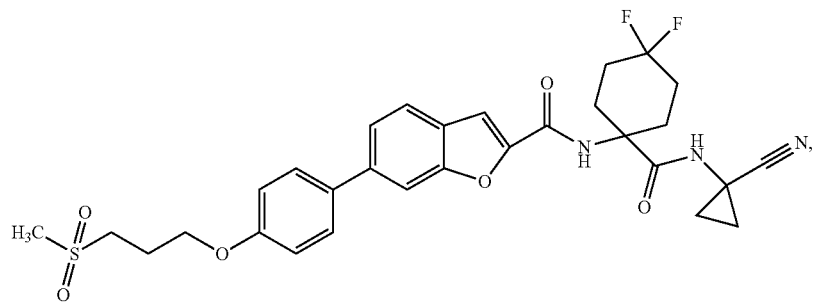
(78) 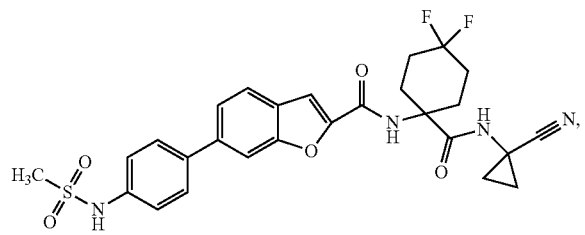
(79) 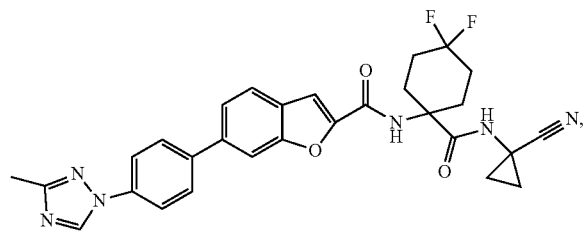
(80) 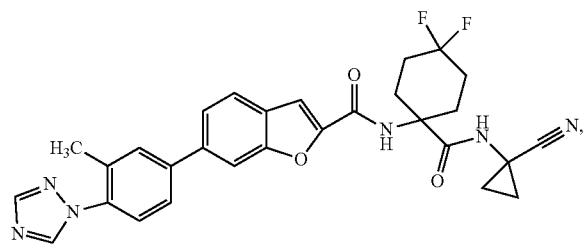
(81) 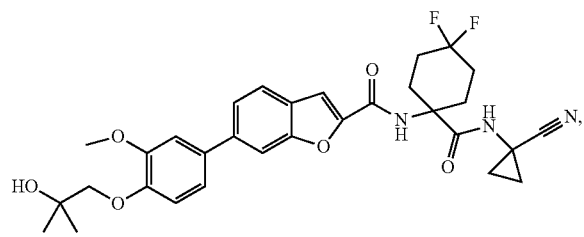

-continued
(82)
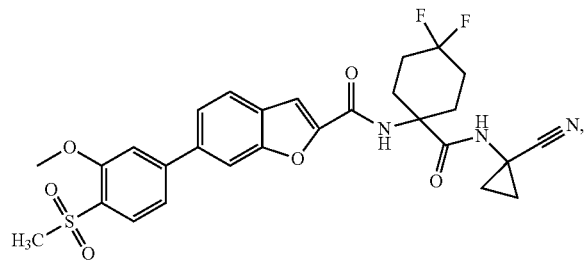
(83)
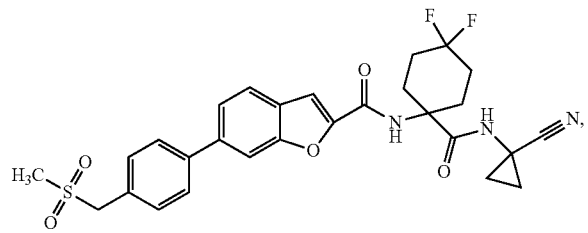
(84)
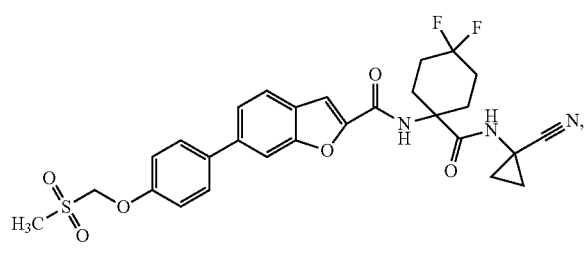
(85)
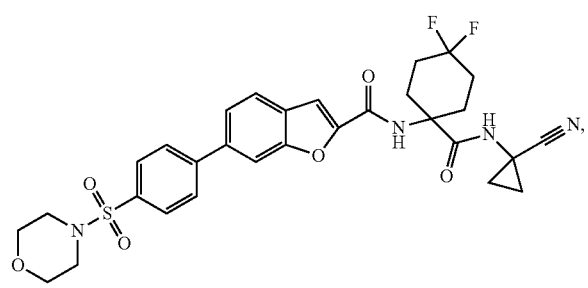
(86)
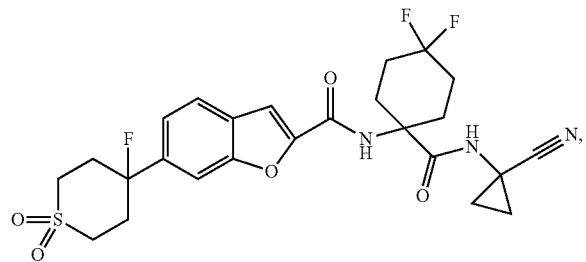
(87)
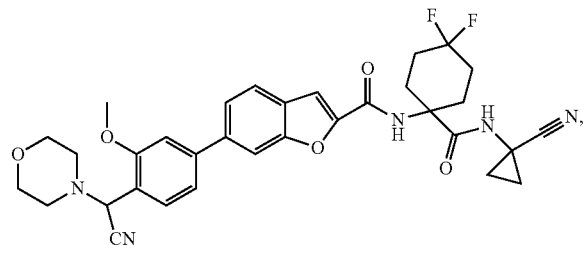
(88)
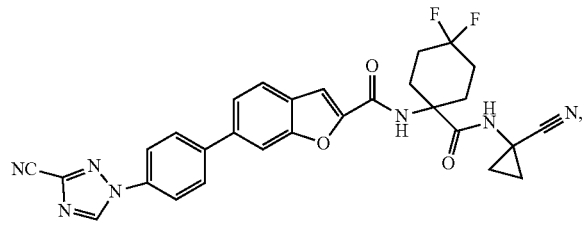
(89)
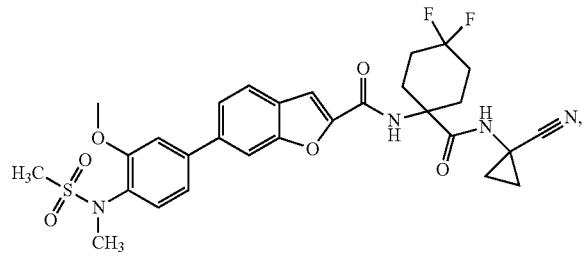
(90)
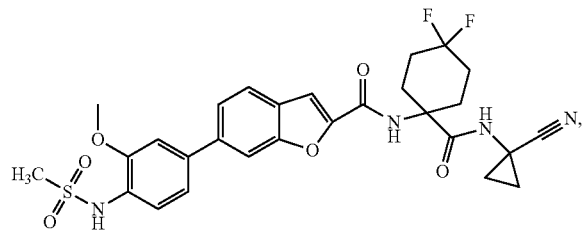
(91)
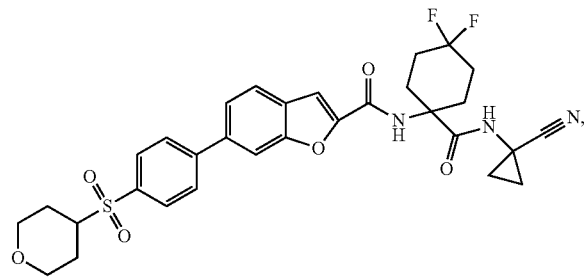

-continued
(92)
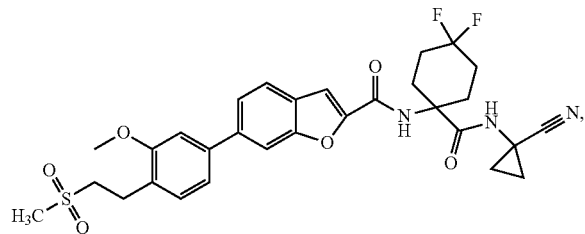
(93)
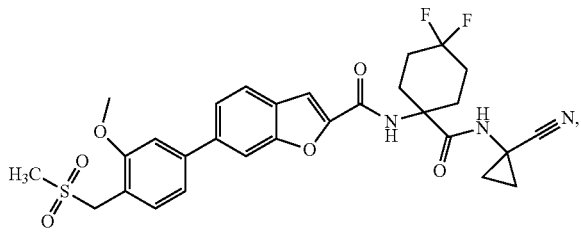
(94)
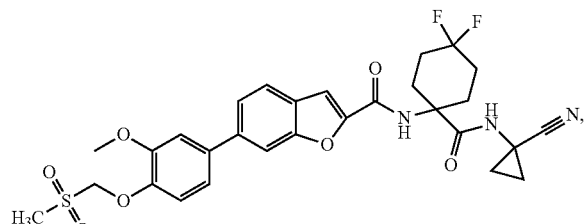
(95)
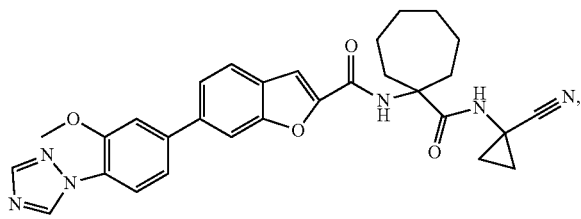
(96)
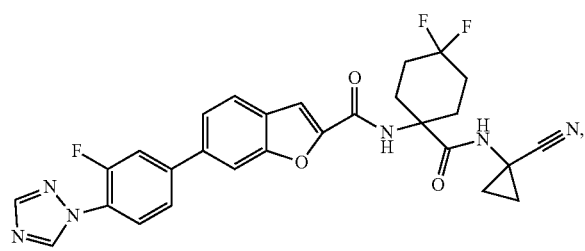
(97)
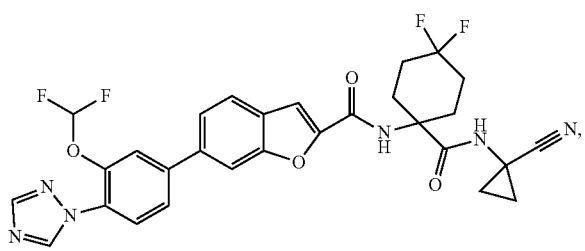
(98)
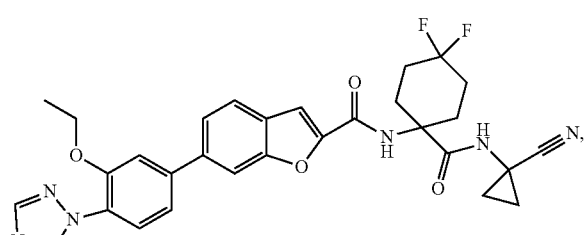
(99)
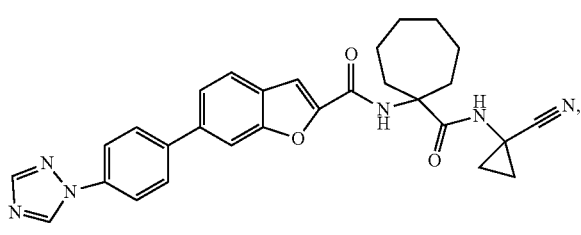
(100)
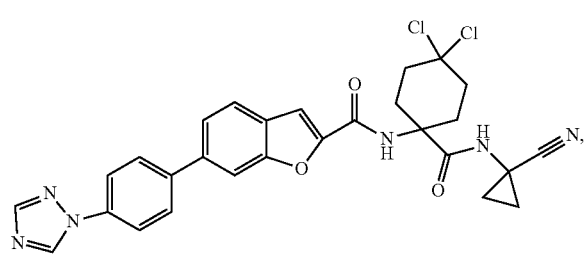
(101)
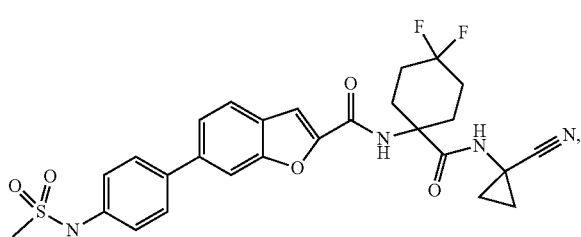
(102)
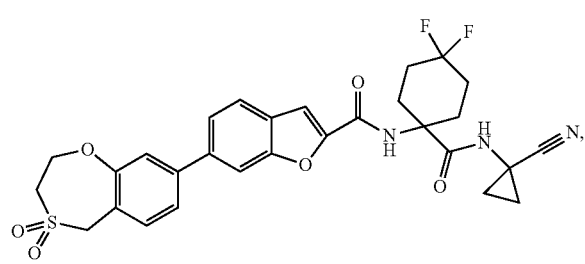
(103)
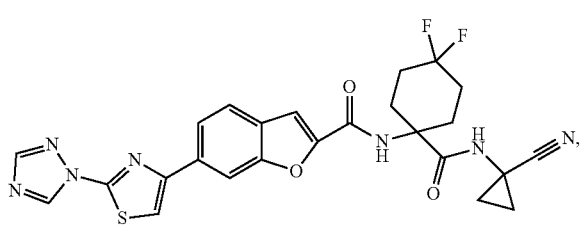

-continued
(104)
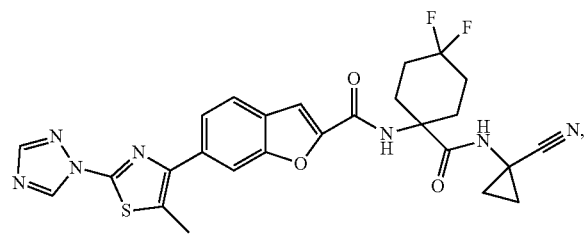
(105)
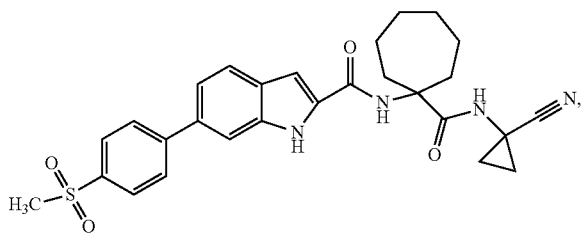
(106)
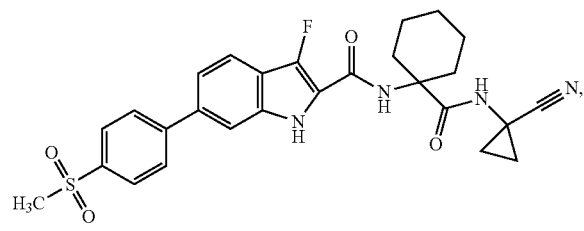
(107)
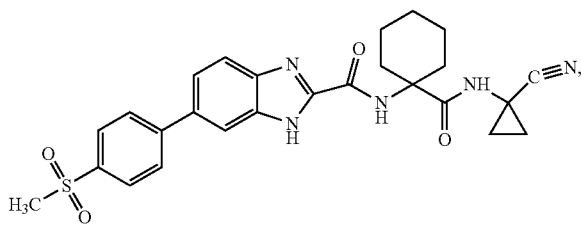
(108)
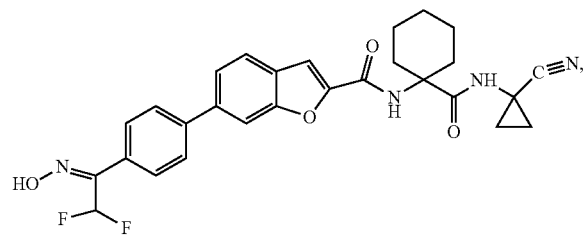
(109)
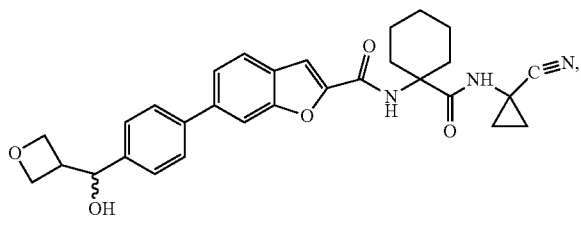
(110)
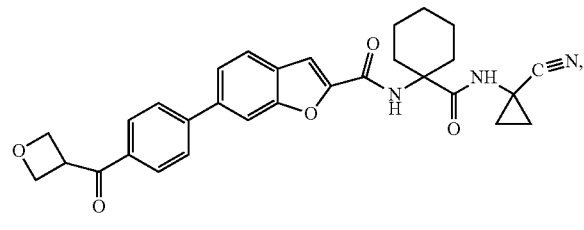
(111)
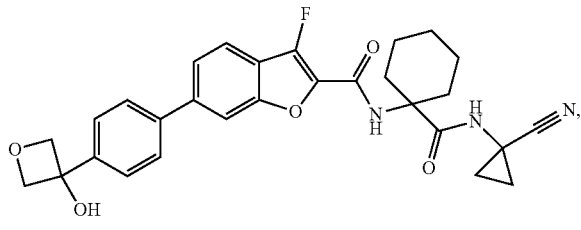
(112)
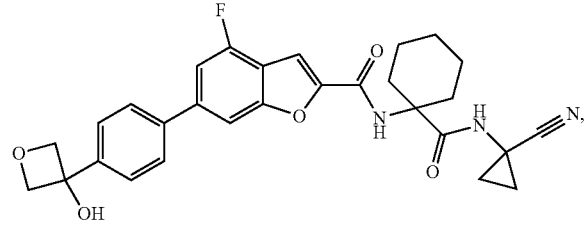
(113)
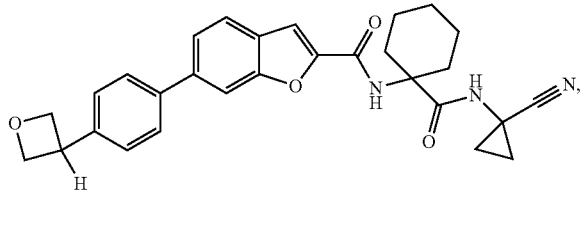
(114)
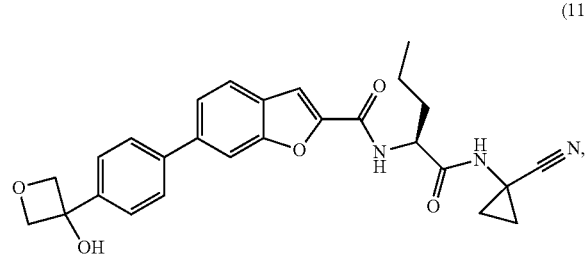
(115)
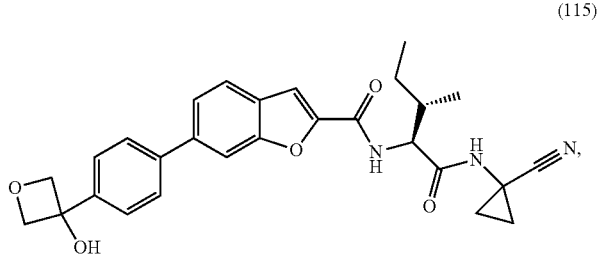

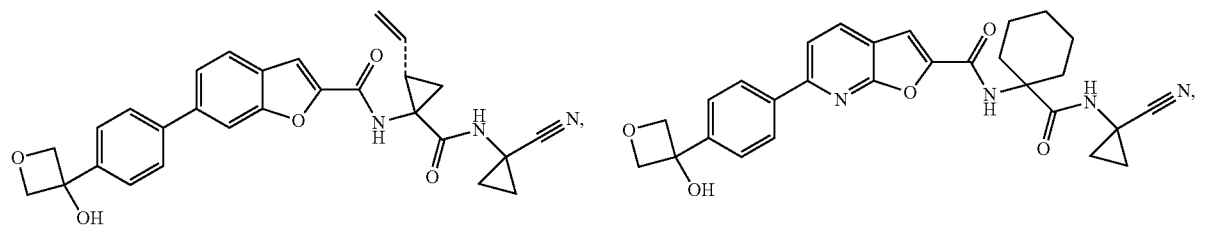
(116) (117)
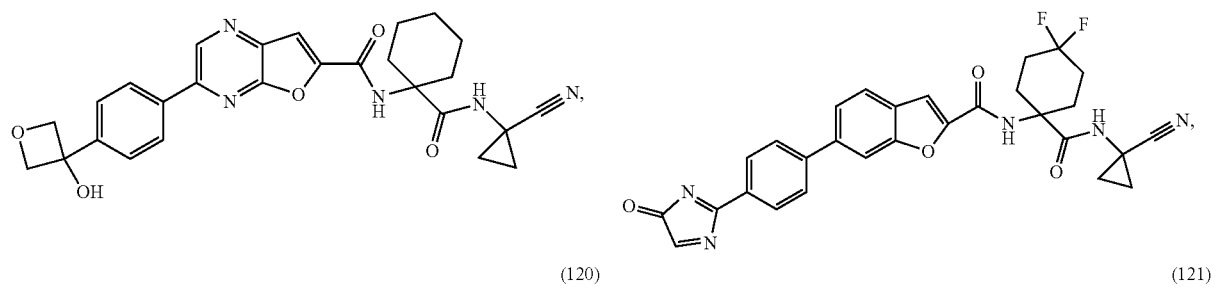
(118) (119)
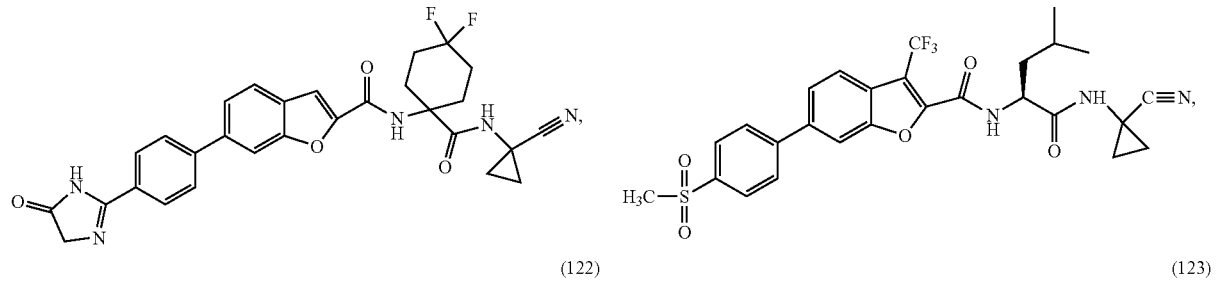
(120) (121)
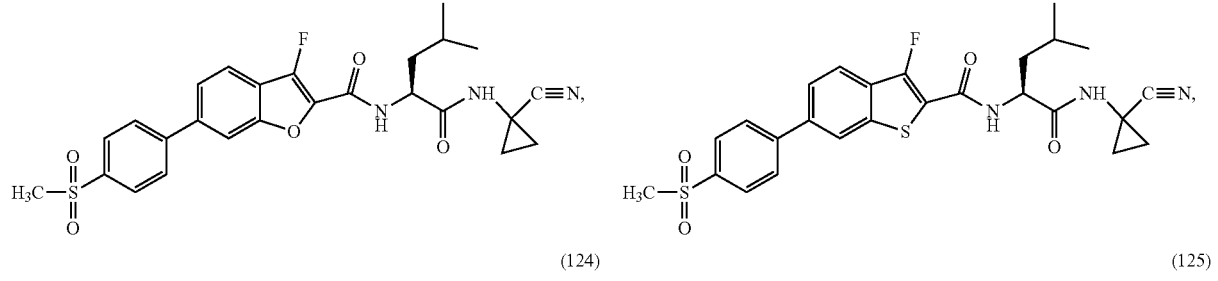
(122) (123)
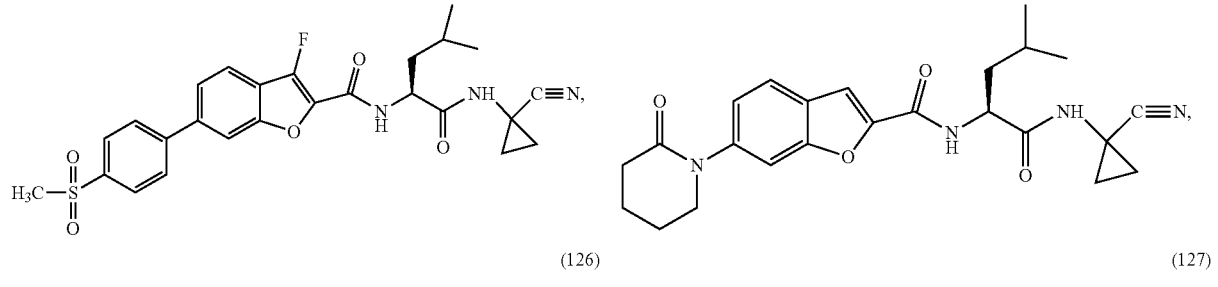
(124) (125)
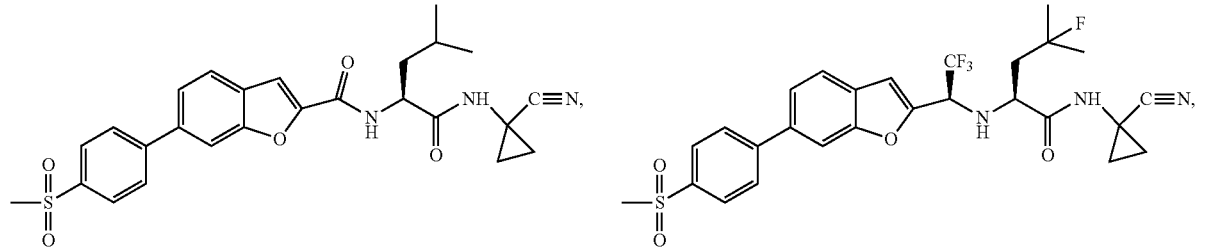
(126) (127)

-continued
(128)
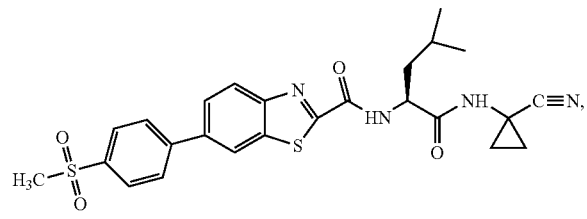
(129)
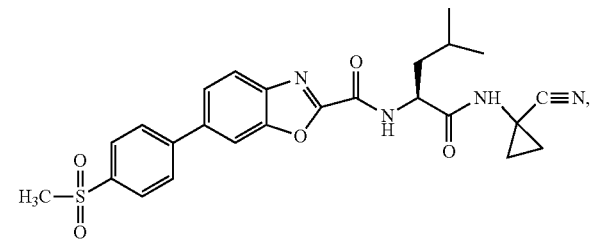
(130)
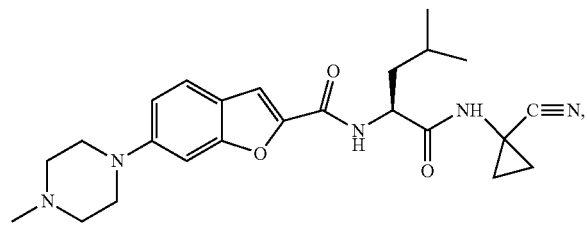
(131)
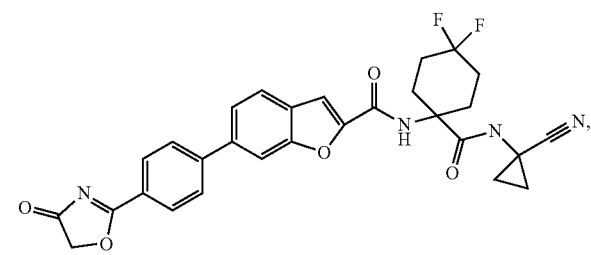
(132)
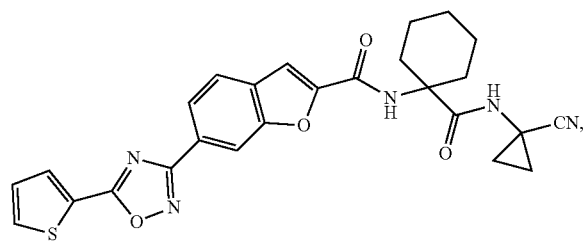
(133)
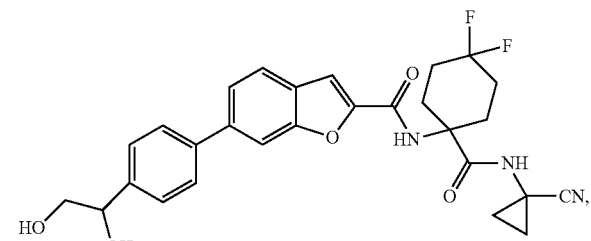
(134)
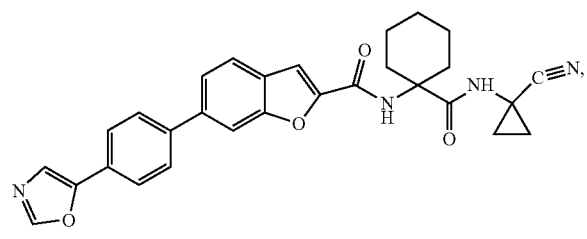
(135)
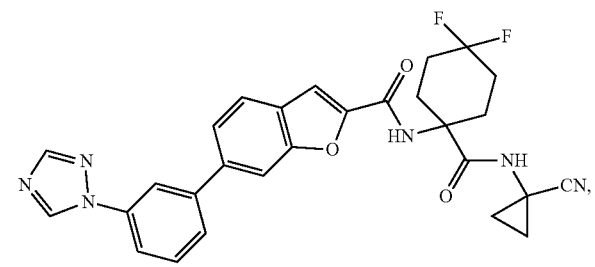
(136)
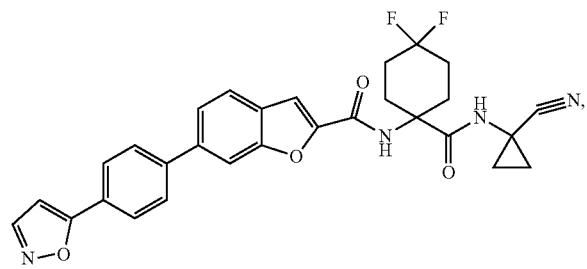
(137)
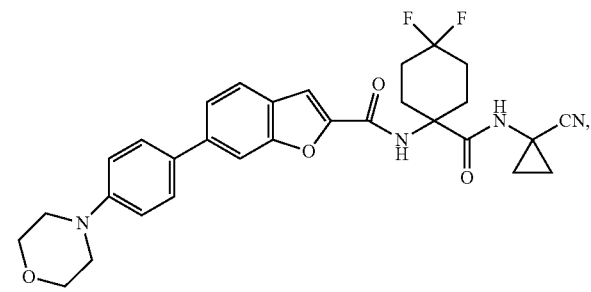

-continued
(138)
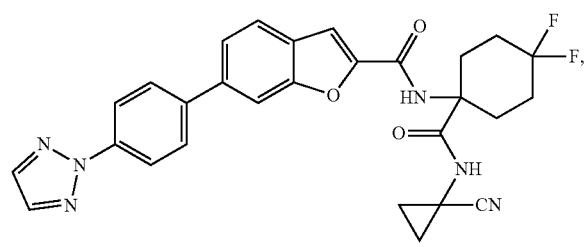
(139)
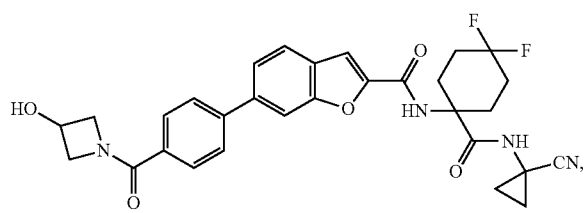
(140)
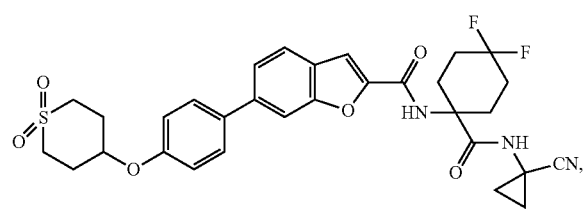
(141)
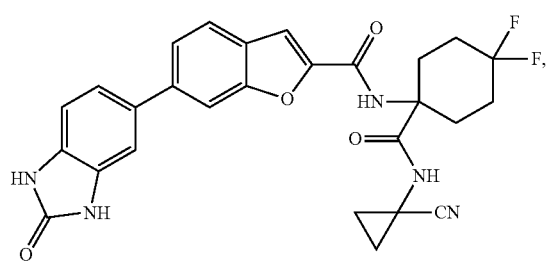
(142)
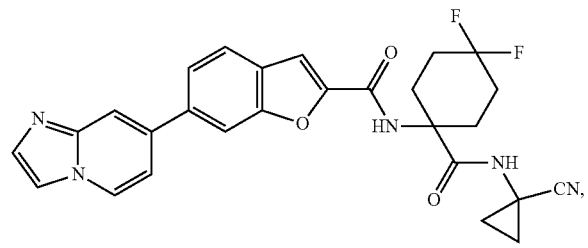
(143)
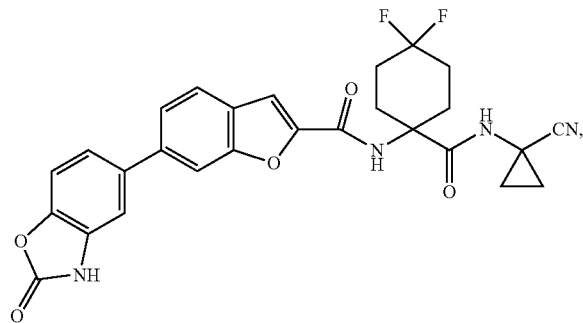
(144)
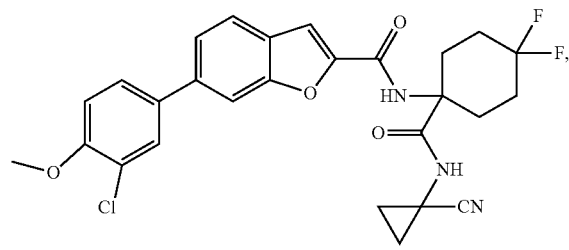
(145)
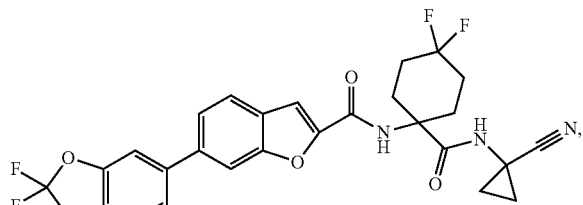
(146)
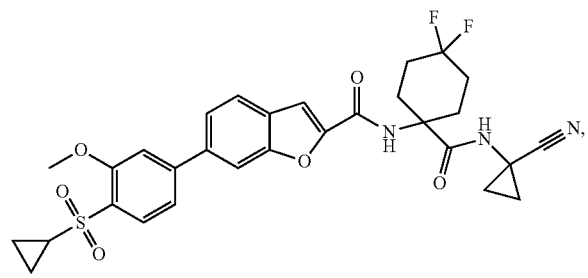
(147)
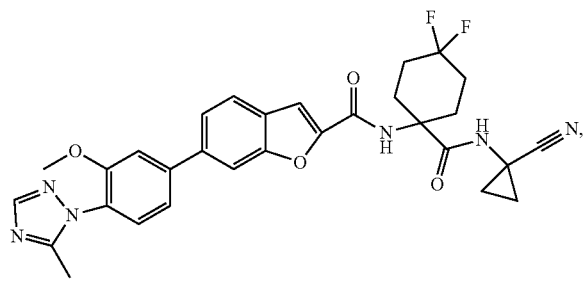

-continued (148)
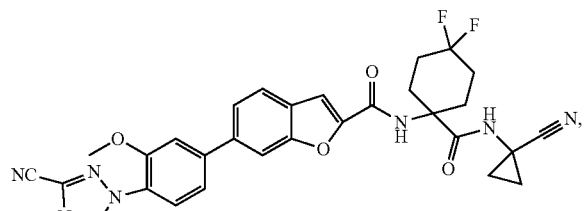

(149)
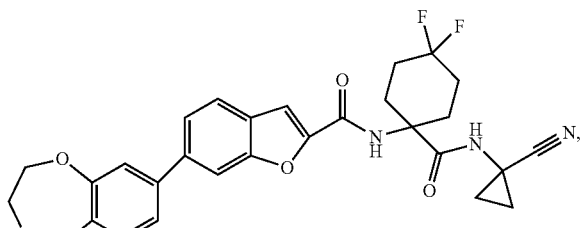

(150)
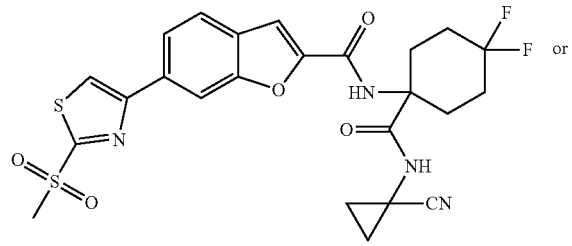

(151)
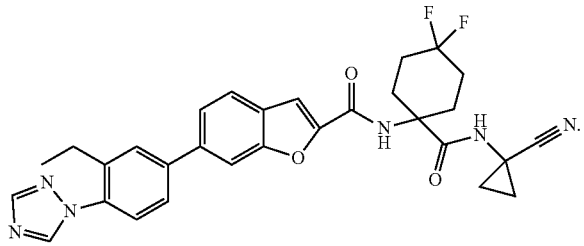

9. A pharmaceutical composition comprising the compound of claim 1 and a pharmaceutically acceptable carrier, excipient, diluent, adjuvant, vehicle, or a combination thereof.

10. The pharmaceutical composition of claim 9 further comprising an organic bisphosphonic acid compound, an estrogen receptor modulator, an estrogen receptor beta modulator, an androgen receptor modulator, an inhibitor of osteoclast proton ATPase, an inhibitor of HMG-CoA reductase, an integrin receptor antagonist, or an osteoblast anabolic agent, a non-steroidal anti-inflammatory drug, a selective cyclooxygenase-2 inhibitor, an interleukin-1β inhibitor, a LOX/COX inhibitor, vitamin D, phytoestrogen, calcitonin, strontium ranelate, odanacatib, ONO5334, MIV-711, MIV-710, and a pharmaceutically acceptable salt and a combination thereof.

11. A method of treating a cathepsin dependent disease in a patient comprising administering to the patient with a therapeutically effective amount of the compound of claim 1, wherein the cathepsin dependent disease is osteoporosis, glucocorticoid induced bone osteoporosis, Paget's disease, abnormally increased bone turnover, periodontal disease, tooth loss, bone fracture, rheumatoid arthritis, osteoarthritis, periprosthetic osteolysis, osteogenesis imperfecta, metastatic bone disease, hypercalcemia of malignancy and multiple myeloma.

12. A method of treating a cathepsin dependent disease in a patient comprising administering to the patient with a therapeutically effective amount of the pharmaceutical composition of claim 9, wherein the cathepsin dependent disease is osteoporosis, glucocorticoid induced bone osteoporosis, Paget's disease, abnormally increased bone turnover, periodontal disease, tooth loss, bone fracture, rheumatoid arthritis, osteoarthritis, periprosthetic osteolysis, osteogenesis imperfecta, metastatic bone disease, hypercalcemia of malignancy and multiple myeloma.

\* \* \* \* \*